US007223854B2

(12) United States Patent
Paul et al.

(10) Patent No.: US 7,223,854 B2

(45) Date of Patent: May 29, 2007

(54) POLYNUCLEIC ACIDS ISOLATED FROM A PORCINE REPRODUCTIVE AND RESPIRATORY SYNDROME VIRUS (PRRSV), PROTEINS ENCODED BY THE POLYNUCLEIC ACIDS, VACCINES BASED ON THE PROTEINS AND/OR POLYNUCLEIC ACIDS, A METHOD OF PROTECTING A PIG FROM A PRRSV AND A METHOD OF DETECTING A PRRSV

(75) Inventors: Prem S. Paul, Ames, IA (US); Xiang-Jin Meng, Ames, IA (US); Patrick Halbur, Ames, IA (US); Igor Morozov, Ames, IA (US); Melissa A. Lum, Mendota Heights, MN (US)

(73) Assignees: Wyeth Holdings Corporation, Madison, NJ (US); Iowa State University Research Foundation, Inc., Ames, IA (US)

( * ) Notice: Subject to any disclaimer, the term of this patent is extended or adjusted under 35 U.S.C. 154(b) by 45 days.

(21) Appl. No.: 09/810,501

(22) Filed: Mar. 19, 2001

(65) Prior Publication Data

US 2006/0029928 A1 Feb. 9, 2006

Related U.S. Application Data

(60) Division of application No. 08/301,435, filed on Sep. 1, 1994, which is a continuation-in-part of application No. 08/131,625, filed on Oct. 5, 1993, now Pat. No. 5,695,766, which is a continuation-in-part of application No. 07/969,071, filed on Oct. 30, 1992, now abandoned.

(51) Int. Cl.
*C07H 21/04* (2006.01)
*C12P 19/34* (2006.01)

(52) U.S. Cl. .............................. 536/23.72; 536/24.33; 435/91.2; 435/91.33

(58) Field of Classification Search .................... 435/5, 435/6, 91.2, 91.5; 536/23.72, 24.3, 24.33
See application file for complete search history.

(56) References Cited

U.S. PATENT DOCUMENTS

| | | | |
|---|---|---|---|
| 5,213,795 | A | 5/1993 | Carlson et al. |
| 5,419,907 | A | 5/1995 | Paul et al. |
| 5,476,778 | A | 12/1995 | Chladek et al. |
| 5,510,258 | A | 4/1996 | Sanderson et al. |
| 5,587,164 | A | 12/1996 | Sanderson et al. |
| 5,597,721 | A | 1/1997 | Brun et al. |
| 5,620,691 | A | 4/1997 | Wensvoort et al. |
| 5,674,500 | A | 10/1997 | Peeters et al. |
| 5,677,429 | A | 10/1997 | Benfield |
| 5,683,865 | A | 11/1997 | Collins et al. |
| 5,695,766 | A | 12/1997 | Paul et al. |
| 5,698,203 | A | 12/1997 | Visser et al. |
| 5,789,388 | A | 8/1998 | Visser et al. |
| 5,840,563 | A | 11/1998 | Chladek et al. |
| 5,846,805 | A | 12/1998 | Collins et al. |
| 5,858,729 | A | 1/1999 | Van Woensel et al. |
| 5,866,401 | A | 2/1999 | Hesse |
| 5,888,513 | A | 3/1999 | Plana Duran et al. |
| 5,910,310 | A | 6/1999 | Heinen et al. |
| 5,925,359 | A | 7/1999 | Van Woensel et al. |
| 5,976,537 | A | 11/1999 | Mengeling et al. |
| 5,989,563 | A | 11/1999 | Chladek et al. |
| 5,998,601 | A | 12/1999 | Murtaugh et al. |
| 6,001,370 | A | 12/1999 | Burch et al. |
| 6,015,663 | A | 1/2000 | Wesley et al. |
| 6,197,310 | B1 | 3/2001 | Wensvoort et al. |
| 6,455,245 | B1 | 9/2002 | Wensvoort et al. |
| 6,495,138 | B1 | 12/2002 | van Nieuwstadt et al. |

FOREIGN PATENT DOCUMENTS

| | | |
|---|---|---|
| CA | 2076744 | 8/1992 |
| EP | 0 595 436 A2 | 5/1994 |
| GB | 2282811 | 4/1995 |
| WO | WO 92/21375 | * 12/1992 |
| WO | WO 93/03760 | 3/1993 |
| WO | WO 93/06211 | 4/1993 |
| WO | WO 93/07898 | 4/1993 |
| WO | WO 94/18311 | 8/1994 |
| WO | WO 95/31550 | 11/1995 |
| WO | WO 96/04010 | 2/1996 |
| WO | 96 06619 | 3/1996 |
| WO | WO 96/40932 | 12/1996 |

OTHER PUBLICATIONS

Key et al. Veterinary Microbiology. 2001; 83: 249-263.*

(Continued)

*Primary Examiner*—Shanon Foley
(74) *Attorney, Agent, or Firm*—Sharon E. Crane; Bingham McCutchen LLP

(57) ABSTRACT

The present invention provides a purified preparation containing a polynucleic acid encoding at least one polypeptide selected from the group consisting of proteins encoded by one or more open reading frames (ORF's) of an Iowa strain of porcine reproductive and respiratory syndrome virus (PRRSV), proteins at least 80% but less than 100% homologous with those encoded by one or more of ORF 2, ORF 3, ORF 4 and ORF 5 of an Iowa strain of PRRSV, proteins at least 97% but less than 100% homologous with proteins encoded by one or both of ORF 6 and ORF 7 of an Iowa strain of PRRSV, antigenic regions of such proteins which are at least 5 amino acids in length and which effectively stimulate immunological protection in a porcine host against a subsequent challenge with a PRRSV isolate, and combinations thereof, in which amino acids non-essential for antigenicity may be conservatively substituted. The present invention also concerns a polypeptide encoded by such a polynucleic acid; a vaccine comprising an effective amount of such a polynucleic acid or protein; antibodies which specifically bind to such a polynucleic acid or protein; methods of producing the same; and methods of raising an effective immunological response against a PRRSV, treating a pig infected by a PRRSV, and detecting a PRRSV.

2 Claims, 40 Drawing Sheets

OTHER PUBLICATIONS

H. Mardassi et al., "Molecular analysis of the ORFs 3 to 7 of porcine reproductive and respiratory syndrome virus, Québec reference strain," Arch. Virol., 1995, pp. 1405-1418, vol. 140, Springer-Verlag, Austria.
R.W. Wills et al., "Transmission of PRRS Virus by Contact vs Airborne Exposures", Final Report of a grant, 1995, pp. 103-108, National Pork Producers Council, Des Moines, Iowa.
Samir Mounir et al, Expression and Characterization of PRRSV Envelope and ns4 Proteins, American Society for Virology, Annul Meeting, Jul. 9-12, 1994, Madison, WI.
Helmi Mardassi et al, Identification of Major Differences in the Nucleocapsid Protein Genes of a Quebec Strain and European Strains of Porcine Reproductive and Respiratory Syndrome Virus, Journal of General Virology, vol. 75, pp. 681-685 (1994).
H.S. Kim et al, Enhanced Replication of Porcine Reproductive and Respiratory Syndrome (PRRS) Virus in a Homogeneous Subpopulation of MA-104 Cell Line, Arch. Virol., vol. 133, pp. 477-483 (1993).
Janneke J.M. Meulenberg et al., "Lelystad Virus, the Causative Agent of Porcine Epidemic Abortion and Respiratory Syndrome (PEARS), is Related to LDV and EAV", Virology, vol. 192, No. 1, pp. 62-72, 1993.
Kuchler, Biochemical Methods in Cell Culture and Virology, Dowden, Hutchinson & Ross, Inc. (Stroudsburg, PA), p. 4-10 (1977).
Swenson et al., JAVMA, 204: 1943-1948 (1994).
A.A.S.P., Sep./Oct. (1991), pp. 7-11.
The Veterinary Record, Feb. 1, 1992, pp. 87-89.
The Veterinary Record, Nov. 30, 1991. p. 495-496.
The Veterinary Record, Oct. 26, 1991, p. 370.
The Veterinary Record, Oct. 19, 1991, pp. 367-368.
The Veterinary Record, Aug. 3, 1991, pp. 102-103.
The Veterinary Record, Jul. 6, 1991.
The Veterinary Record, Jun. 22, 1991, pp. 578.
The Veterinary Record, Jun. 15, 1991, p. 574.
The Veterinary Record, Jun. 8, 1991, p. 536.
The Veterinary Record, Jun. 1, 1991, p. 511.
The Veterinary Record, Mar. 2, 1991, p. 213.
Wensvoort et al, Vet. Quarterly, 13:121-130 (1991).
Wensvoort et al, Vet. Res., 24:117-124 (1993).
Paul et al, J. Clin. Vet. Med., 11:19-28 (1993).
Benfield et al, J. Vet. Diagn. Invest., 4:127-133 (1992).
Joo, PRRS: Diagnosis. Proc., Allen D. Leman Swine Conf., 20:53-55 (1993).
Kim et al, Arch. Virol., 133-477-483 (1993).
Bautista et al, J. Vet. Diagn. Invest., 5:163-165 (1993).
Conzelmann et al, Virology, 193:329-339 (1993).
Meulenberg et al, Virology, 192:62-72 (1993).
Goyal, J. Vet. Diagn. Invest., 5:656-664 (1993).
Pol et al, Veterinary Quarterly, 13:137-143 (1991).
Christianson et al, Am. J. Vet. Res., 53:485-488 (1992).
Collins et al, J. Vet. Diagn. Invest., 4:117-126 (1992).
Collins et al, Proc. Allen D. Leman Conference, pp. 47-48 (1993).
Murtaugh, Proc. Allen D. Leman Conference, pp. 43-45 (1993).
Mardassi et al, Abstract. Conf. Res. Workers in Animal Dis., Chicago, Illinois, p. 43 (1993).
Mardassi et al, J. Gen. Virol, 75:681-685 (1994).
Wensvoort et al, J. Vet. Diagn. Invest., 4:134-138 (1992).
Bautista et al, J. Vet. Diagn. Invest., 5:612-614 (1993).
Stevenson et al, J. Vet. Diagn. Invest., 5:432-434 (1993).
Animal Pharm., 264:11 (Nov. 13, 1992).
Vaughn et al, J. Clin. Micro., 32:1809-1812 (1994).
Hill et al, Am. Assoc. Swine Practitioner Newsletter., 4:47 (1992).
Hill et al, Proceedings Mystery Swine Disease Committee Meeting, Denver, Colorado., pp. 29-31 (1990).
Loula, Agri-Practice., 12:23-34 (1991).
Paton et al, Vet. Rec., 128:617 (1991).
Blaha, Proc. Am. Assoc. Swine Practitioners, pp. 313-315 (1993).
Collins et al, Proc., Minnesota Swine Conference for Veterinarians, pp. 200-205 (1991).
Woolen et al, J. Am. Vet. Med. Assoc., 197:600-601 (1990).
Plagemann, Proc. Am. Assoc. Swine Practitioners., 4:8-15 (1992).
Plagemann and Moennig, Adv. Virus Res., 41:99-192 (1992).
Spaan et al, J. Gen. Virol., 69:2939-2952 (1988).
Lai, Annu. Rev. Microbiol., 44;303-333 (1990).
Snijder et al, Nucleic Acid Res., 18:4535-4542 (1990).
Halbur et al, Proc. Central Veterinary Conference., pp. 750-759 (1993).
Nelson et al, J. Clin. Microbiol., 31:3184-3189 (1993).
Dalziel et al, J. Virol., 59-463-471 (1986).
Fleming et al, J. Virol., 58:869-875 (1986).
Fiscus et al, J. Virol., 61:2607-2613 (1987).
Parker et al, Virology., 173:664-673 (1989).
Laude et al, Vet. Res., 24:125-150 (1993).
Rasschaert et al, J. Gen. Virol., 71:2599-2607 (1990).
Magar et al, Can J. Vet. Res., 57:300-304 (1993).
Halbur et al, Proc. Am. Assoc. Swine Pract., 343-350 (1993).
Bautists et al, American Association of Swine Practitioners Newletter, 4:32 (1992).
Kohler et al, Nature, 256:495-497 (1975).
Godney et al, Virology, 177:768-771.
Hooper et al, J. Vet. Diagn. Invest., 6:13-25 (1994).
Koonin et al, Critical Rev. Biochem. Mol. Biol., 28:375-430 (1993).
Lai, Microbiol. Rev., 56:61-79 (1992).
Hahn et al, Proc. Natl. Acad. Sci. USA, 85:5997-6001 (1988).
Godeny et al, Virology, 194:585-596 (1993).
Mardassi, J. Gen. Virol., 75:681-685 (1994).
Kuo et al, Virus Res., 23:55-72 (1992).
Chen, J. Gen. Virol., 74:643-660 (1993).
Meng, J. Vet. Diagn. Invest., 5:254-258 (1993).
Den Boon et al, J. Virol., 65:2910-2920 (1990).
Keffaber, Am. Assoc. Swine Practitioner Newsletter, 1:1-9 (1989).
Meredith, Review of Porcine Reproductive and Respiratory Disease Syndrome, Pig Disease Information Centre, Department of Veterinary Medicine, Madingley Road, Cambridge CB3 OES, U.K. (1992).
Van Alstine et al, Swine Health & Production, vol. 1, No. 4, 24-28 (1993).
Christianson et al, Swine Health & Production, vol. 1, No. 2, 10-28 (1994).
Compiled By Sherwood et al. "International Reports on PRRS Status and Control: 1992". PDIC. pp. 1-58.
X.-J. Meng et al., *Arch Virol.* (1995) 140:745-55, Springer-Verlag, Austria.
X.-J. Meng et al., *J. Gen. Virol.* (1995) 76:3181-88, Society of General Microbiology, Great Britain.
Abstract Nos. 218-222, p. 43, Abstracts of Conf. of Research Workers in Animal Diseases, Chicago, IL (1993).
"'Mystery Pig Disease' Studies Needed", Animal Pharm., vol. 215, p. 12, publ. date: Nov. 2, 1990, Theta Reports, New York, NY.
"Mystery Virus in German Pig Herds", Animal Pharm., vol. 220, p. 8, publ. date: Jan. 25, 1991, Theta Reports, New York, NY.
"'Mystery Pig Disease' Still Unidentified", Animal Pharm., vol. 223, p. 3, publ. date: Mar. 8, 1991, Theta Reports, New York, NY.
"Dutch Team Isolates Mystery Pig Disease Agent", Animal Pharm., vol. 230, p. 21, publ. date: Jun. 21, 1991, Theta Reports, New York, NY.
"Dutch Scientists Confirm Porcine Reproductive and Respiratory Syndrome (PRRS) Agents is a Virus", Animal Pharm., vol. 238, p. 6, publ. date: Oct. 25, 1991, Theta Reports, New York, NY.
"Cyanamid Reports on Isolation of Porcine Reproductive and Respiratory Syndrome (PRRS) Virus", Animal Pharm., vol. 238, p. 20, publ. date: Oct. 25, 1991, Theta Reports, New York, NY.
"Pig Disease Mystery Solved by FRG Scientists", Animal Pharm., vol. 240, p. 7, publ. date: Nov. 22, 1991, Theta Reports, New York, NY.
"Bayer Prepare Cuts Mortality in PRRS Herds", Animal Pharm., vol. 240, p. 22, publ. date: Nov. 22, 1991, Theta Reports, New York, NY.
"Porcine Epidemic and Respiratory Syndrome (PEARS) Virus Isolated in France", Animal Pharm., vol. 244, p. 7, publ. date: Jan. 24, 1992, Theta Reports, New York, NY.

"No Immediate Prospect of a Procine Epidemic and Respiratory Syndrome (PEARS) Vaccine", Animal Pharm., vol. 244, p. 25, publ. date: Jan. 24, 1992, Theta Reports, New York, NY.
"US Market for Animal Health Products," Animal Pharm., vol. 247, Supplement, publ. date: Mar. 6, 1992, Theta Reports, New York, NY.
"Porcine Reproductive and Respiratory Syndrome (PRRS) Antibody Test Developed in France", Animal Pharm., vol. 253, p. 5, publ. date: Jun. 5, 1992, Theta Reports, New York, NY.
"IDEXX to Develop Procine Reproductive and Respiratory Syndrome (PRRS) Diagnostic", Animal Pharm., vol. 257, p. 20, publ. date: Jul. 31, 1992, Theta Reports, New York, NY.
"Procine Reproductive and Respiratory Syndrome (PRRS) Virus Identified in Japan", Animal Pharm., vol. 283, p. 11, publ. date: Aug. 27, 1993, Theta Reports, New York, NY.
"Porcine Reproductive and Respiratory Syndrome (PRRS): an Appraisal of Current Research", Animal Pharm., vol. 284, p. 20, publ. date: Sep. 10, 1993, Theta Reports, New York, NY.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell. Biol., 1990, pp. 2129-2138, vol. 111, The Rockefeller University Press, USA.
Cafruny et al., "Antibody response of mice to lactate dehydrogenase-elevating virus during infection and immunization with inactivated virus", Virus Research, 1986, pp. 357-375, vol. 5, Elsevier Science Publishers B.V., The Netherlands.
De Vries et al., "Structural Proteins of Equine Arteritis Virus", J. Virol., 1992, pp. 6294-6303, vol. 66, ASM Press, Washington, DC.
De Vries et al., "All subgenomic mRNAs of equine arteritis virus contain a common leader sequence", Nucleic Acids Res., 1990, pp. 3241-3247, vol. 18, Oxford University Press, United Kingdom.
Dea et al., "Antigenic Variant of Swine Influenza Virus Causing Proliferative and Necrotizing Pneumonia in Pigs", J. Vet. Diagn. Invest., 1992, pp. 380-392, vol. 4, American Assoc. of Vet. Lab. Diagnosticians, Columbia, MO.
Domingo et al., "New observations on antigenic diversification of RNA viruses. Antigenic variation is not dependent on immune selection", J. Gen. Virology, 1993, pp. 2039-2045, vol. 74, Society of General Microbiology, Great Britain.
Ellis, Ronald W., "New Technologies for Making Vaccines", Vaccines, Plotkin et al. (Eds.), W.B. Saunders Company, Chapter 29:568-575 (1988), USA.
Faaberg et al., "Disulfide Bonds Between Two Envelope Proteins of Lactate Dehydrogenase-Elevating Virus Are Essential for Viral Infectivity", J. Virol., 1995, pp. 613-617, vol. 69, ASM Press, Washington, DC.
Girard et al., "Experimentally Induced Porcine Proliferative and Necrotising Pneumonia With an Influenza A Virus", The Veterinary Record, 1992, pp. 206-207, vol. 130, British Veterinary Assoc., London, UK.
Kapur et al., "Genetic Variation in Porcine Reproductive and Respiratory Syndrome Virus Isolates in the Midwestern United States", J. Gen. Virol., 1996, pp. 1271-1276, vol. 77, Society of General Microbiology, Great Britain.
Kuo et al., "A Nested Set of Eight RNAs Is Formed in Macrophages Infected with Lactate Dehydrogenase-Elevating Virus", J. Virol., 1991, pp. 5118-5123, vol. 65, ASM Press, Washington, DC.
Lanza et al., "Pathogenicity of Concurrent Infection of Pigs With Porcine Respiratory Coronavirus and Swine Influenza", Res. Vet. Sci., 1992, pp. 309-314, vol. 53.
Lazar et al., "Transforming Growth Factor $\alpha$: Mutation of Aspartic Acid 47 and Leucine 48 Results in Different Biological Activities", Mol. Cell. Biol., 1988, pp. 1247-1252, vol. 8, ASM Press, Washington, DC.
Meng et al., "Molecular Cloning and Nucleotide Sequencing of the 3'-Terminal Genomic RNA of the Porcine Reproductive and Respiratory Syndrome Virus," Journal of General Virology, 1994, pp. 1795-1801, vol. 75, Society of General Microbiology, Great Britain.
Meulenberg et al., "Subgenomic RNAs of Lelystad virus contain a conserved leader-body junction sequence", J. Gen. Virology, 1993, pp. 1697-1701, vol. 74, Society of General Microbiology, Great Britain.
Meulenberg et al., "Characterization of Proteins Encoded by ORFs 2 to 7 of Lelystad Virus", Virology, 1995, pp. 155-163, vol. 206, Academic Press, Inc., Academic Press, USA.
Molitor, "Immune Responses to PRRS Virus", The Allen D. Leman Swine Conf., 1993, pp. 49-50.
Morin et al., "Severe Proliferative and Necrotizing Pneumonia in Pigs: a Newly Recognized Disease," Can. Vet. J., 1990, pp. 837-839, vol. 31, Canadian Veterinary Medical Assoc., Ontario, Canada.
Morozov et al., "Sequence Analysis of Open Reading Frames (ORFs) 2 to 4 of a U.S. Isolate of Porcine Reproductive and Respiratory Syndrome Virus", Arch. Virology, 1995, pp. 1313-1319, vol. 140, Springer-Verlag, Austria.
Morrison et al., "Serologic Evidence Incriminating a Recently Isolated Virus (ATCC VR-2332) as the Cause of Swine Infertility and Respiratory Syndrome (SIRS)," J. Vet. Diagn. Invest., 1992, pp. 186-188, vol. 4, American Assoc. of Vet. Lab. Diagnosticians, Columbia, MO.
Paton et al., "Isolation of a Lelystad Virus-like Agent From British Pigs and Scanning Electron Microscopy of Infected Macrophages," Vet. Microbiol., 1992, pp. 195-201, vol. 33, Elsevier Science Publishers B.V., Amsterdam.
Plana et al., "Porcine Epidemic Abortion and Respiratory Syndrome (Mystery Swine Disease), Isolation in Spain of the Causative Agent and Experimental Reproduction of the Disease", Vet. Microbiol., 1992, pp. 203-211, vol. 33, Elsevier Science Publishers B.V., The Netherlands.
Plotkin et al., "New Technologies for Making Vaccines", Vaccines, 1988, published by W.B. Saunders Co. (Phil.), see p. 571.
Sirinarumitr et al., A pneumo-virulent United States isolate of porcine reproductive and respiratory syndrome virus induces apoptosis in bystander cells both *in vitro* and *in vivo*, Journal of General Virology, 1998, pp. 2989-2995, vol. 79, Society of General Microbiology, Great Britain.
Swenson et al., "Porcine Reproductive and Respiratory Syndrome Virus in Experimentally Infected Boars: Isolation From Semen", Proc Am Assoc Swine Pract, 1993, pp. 719-720, American Assoc. of Swine Veterinarians, Perry, IA.
Swenson et al., "Porcine Reproductive and Respiratory Syndrome Virus in Experimentally Infectd Boars: Isolation From Semen", Proc Ann Meeting Livestock Conservation Institute, 1993, pp. 115-116.
Tizard, An Introduction to Vet Immunology, published in 1982 by W.B. Saunders Co. (Phil), see pp. 41-43.
Vaughn et al., "Three New Isolates of Porcine Respiratory Coronavirus With Various Pathogenicities and Spike (S) Gene Deletions," Journal of Clinical Microbiology, Jul. 1994, pp. 1809-1812, vol. 32, No. 7, ASM Press, Washington, DC.
Weiland et al., "Monoclonal antibodies to the $GP_5$ of porcine reproductive and respiratory syndrome virus are more effective in virus neutralization than monoclonal antibodies to the $GP_4$.", Veterinary Microbiology, 1999, pp. 171-186, vol. 66, Elsevier Science B.V., The Netherlands.
Zimmerman et al., "Susceptibility of Four Avian Species to PRRS Virus", Proc Ann Meeting Livestock Conservation Institute, 1993, pp. 107-108.
Zimmerman et al., "Transmission of PRRS Virus", The Allen D. Leman Swine Conf., 1993, pp. 51-52.
Zimmerman, "Mystery Swine Disease," USDA Abstracts, Dialog Computer Database, Jul. 1, 1990, pp. 501-504.
Y. Zhang et al., "Monoclonal antibodies against conformationally dependent epitopes on porcine reproductive and respiratory syndrome virus" Veterinary Microbiology, 1998m pp. 125-136, vol. 63, Elsevier Science B.V., The Netherlands.

* cited by examiner

```
GGCAGGCTTTGCTGTCCTCCAAGACATCAGTTGCCTTAGGCATCGCAACTCGGCCTCTGAGGCGATTCGCAAAGTCCCTCAGTGCCGCACGGCGATAGGG  100

ACACCCGTGTATATCACTGTCACAGCCAATGTTACCGATGAGAATTATTTGCATTCCTCTGATCTTCTCATGCTTTCTTCTTGCCTTTTCTATGCTTCTG  200

AGATGAGTGAAAAGGGATTTAAGGTGGTATTTGGCAATGTGTCAGGCATCGTGGCAGTGTGCGTCAACTTCACCAGTTACGTCCAACATGTCAAGGAATT  300

TACCCAACGTTCCTTGGTAGTTGACCATGTGCGGCTGCTCCATTTCATGACGCCCGAGACCATGAGGTGGGCAACTGTTTTAGCCTGTCTTTTTGGCATT  400
             ORF4 stop
             ***          +1>ORF5 start
CTGTTGGCAATTTGAATGTTTAAGTATGTTGGGGAAATGCTTGACCGCGGGCTGTTGCTCGCAATTGCTTTTTTTGTGGTGTATCGTGCCGTCTTGTTTT  500

GTTGCGCTCGTCAGCGCCAACGGGAACAGCGGCTCAAATTTACAGCTGATTTACAACTTGACGCTATGTGAGCTGAATGGCACAGATTGGCTAGCTAATA  600

AATTTGACTGGGCAGTGGAGTGTTTTGTCATTTTTCCTGTGTTGACTCACATTGTCTCTTATGGTGCCCTCACTACTAGCCATTTCCTTGACACAGTCGG  700

TCTGGTCACTGTGTCTACCGCTGGGTTTGTTCACGGGCGGTATGTTCTGAGTAGCATGTACGCGGTCTGTGCCCTGGCTGCGTTGATTTGCTTCGTCATT  800

AGGCTTGCGAAGAATTGCATGTCCTGGCGCTACTCATGTACCAGATATACCAACTTTCTTCTGGACACTAAGGGCAGACTCTATCGTTGGCGGTCGCCTG  900

TCATCATAGAGAAAAGGGGCAAAGTTGAGGTCGAAGGTCACCTGATCGACCTCAAAAGAGTTGTGCTTGATGGTTCCGCGGCTACCCCTGTAACCAGAGT  1000

             ORF6 start
             +1>           ***ORF5 stop
TTCAGCGGAACAATGGAGTCGTCCTTAGATGACTTCTGTCATGATAGCACGGCTCCACAAAAGGTGCTCTTGGCGTTTTCTATTACCTACACGCCAGTGA  1100
```

*FIG. 7A*

```
TGATATATGCCCTAAAGGTGAGTCGCGGCCGACTGCTAGGGCTTCTGCACCTTTTGGTCTTCCTGAATTGTGCTTTCACCTTCGGGTACATGACATTCGT   1200

GCACTTTCAGAGTACAAATAAGGTCGCGCTCACTATGGGAGCAGTAGTTGCACTCCTTTGGGGGGTGTACTCAGCCATAGAAACCTGGAAATTCATCACC   1300

TCCAGATGCCGTTTGTGCTTGCTAGGCCGCAAGTACATTCTGGCCCCTGCCCACCACGTTGAAAGTGCCGCAGGCTTTCATCCGATTGCGGCAAATGATA   1400

ACCACGCATTTGTCGTCCGGCGTCCCGGCTCCACTACGGTCAACGGCACATTGGTGCCCGGGTTAAAAAGCCTCGTGTTGGGTGGCAGAAAAGCTGTTAA   1500
                          ORF7 start
                          +1>      ***ORF6 stop
ACAGGGAGTGGTAAACCTTGTTAAATATGCCAAATAACACCGGCAAGCAGCAGAAGAGAAAGAAGGGGGATGGCCAGCCAGTCAATCAGCTGTGCCAGAT   1600

GCTGGGTAAGATCATCGCTCACCAAAACCAGTCCAGAGGCAAGGGACCGGGAAAGAAAAATAAGAAGAAAAACCCGGAGAAGCCCCATTTCCCTCTAGCG   1700

ACTGAAGATGATGTCAGACATCACTTTACCCCTAGTGAGCGTCAATTGTGTCTGTCGTCAATCCAGACCGCCTTTAATCAAGGCGCTGGGACTTGCACCC   1800
                                                                                          ***ORF7 stop
TGTCAGATTCAGGGAGGATAAGTTACACTGTGGAGTTTAGTTTGCCTACGCATCATACTGTGCGCCTGATCCGCGTCACAGCATCACCCTCAGCATGATG   1900

GGCTGGCATTCTTGAGGCATCCCAGTGTTTGAATTGGAAGAATGCGTGGTGAATGGCACTGATTGACATTGTGCCTCTAAGTCACCTATTCAATTAGGGC   2000

GACCGTGTGGGGGTAAGATTTAATTGGCGAGAACCACACGGCCGAAATTAAAAAAAAAAAAA                                         2062
```

*FIG. 7B*

```
LELYSTAD SEQ (13484-14089)      ATGAGATGTTCTCACAAATTGGGGCGTTTCTTGACTCCGCACTCTTGCTTCTGGTGGCTTTTTTTGCTGTGTA--   13556
ISU-12-3' TERMINAL (426-1028)   ---------------ATGTTGGGGAAATGCTTGACCGCGGCTGTTGCTCGCAATTGCTTTTTTTGTGGTGTATC     485

LELYSTAD SEQ (13484-14089)      ---CCGGCTTGTCCTGGT-CCTTTGCCGATGGCAACGGCGACAGCTCGACATACCAATA-C--ATATATAACTTG   13624
ISU-12-3' TERMINAL (426-1028)   GTGCCGTCTTGTTTTGTTGCGCTCGTCAGCGCCAACGGGAACAGCGGCTCAAATTTACAGCTGATTTACAACTTG     560

LELYSTAD SEQ (13484-14089)      ACGATATGCGAGCTGAATGGGACCGACTGGTTGTCCAGCCATTTTGGTTGGGCAGTCGAGACCTTTGTGCTTTAC   13699
ISU-12-3' TERMINAL (426-1028)   ACGCTATGTGAGCTGAATGGCACAGATTGGCTAGCTAATAAATTTGACTGGGCAGTGGAGTGTTTTGTCATTTTT     635

LELYSTAD SEQ (13484-14089)      CCGGTTGCCACTCATATCCTCTCACTGGGTTTTCTCACAACAAGCCATTTTTTTGACGCGCTCGGTCTCGGCGCT   13774
ISU-12-3' TERMINAL (426-1028)   CCTGTGTTGACTCACATTGTCTCTTATGGTGCCCTCACTACTAGCCATTTCCTTGACACAGTCGGTCTGGTCACT     710

LELYSTAD SEQ (13484-14089)      GTATCCACTGCAGGATTTGTTGGCGGGCGGTACGTACTCTGCAGCGTCTACGGCGCTTGTGCTTTCGCAGCGTTC   13849
ISU-12-3' TERMINAL (426-1028)   GTGTCTACCGCTGGGTTTGTTCACGGGCGGTATGTTCTGAGTAGCATGTACGCGGTCTGTGCCCTGGCTGCGTTG     785

LELYSTAD SEQ (13484-14089)      GTATGTTTTGTCATCCGTGCTGCTAAAAATTGCATGGCCTGCCGCTATGCCCGTACCCGGTTTACCAACTTCATT   13924
ISU-12-3' TERMINAL (426-1028)   ATTTGCTTCGTCATTAGGCTTGCGAAGAATTGCATGTCCTGGCGCTACTCATGTACCAGATATACCAACTTTCTT     860

LELYSTAD SEQ (13484-14089)      GTGGACGACCGGGGGAGAGTTCATCGATGGAAGTCTCCAATAGTGGTAGAAAAATTGGGCAAAGCCGAAGTCGAT   13999
ISU-12-3' TERMINAL (426-1028)   CTGGACACTAAGGGCAGACTCTATCGTTGGCGGTCGCCTGTCATCATAGAGAAAAGGGGCAAAGTTGAGGTCGAA     935

LELYSTAD SEQ (13484-14089)      GGCAACCTCGTCACCATCAAACATGTCGTCCTCGAAGGGGTTAAAGCTCAACCCT-TGACGAGGACTTCGGCTGA   14073
ISU-12-3' TERMINAL (426-1028)   GGTCACCTGATCGACCTCAAAAGAGTTGTGCTTGATGGTTCCGCGGCT-ACCCCTGTAACCAGAGTTTCAGCGGA    1009

LELYSTAD SEQ (13484-14089)      GCAATGGGAGGCCTAG----                                                          14089
ISU-12-3' TERMINAL (426-1028)   ACAAT-GGAGTCGTCCTTAG                                                           1028
```

FIG. 8

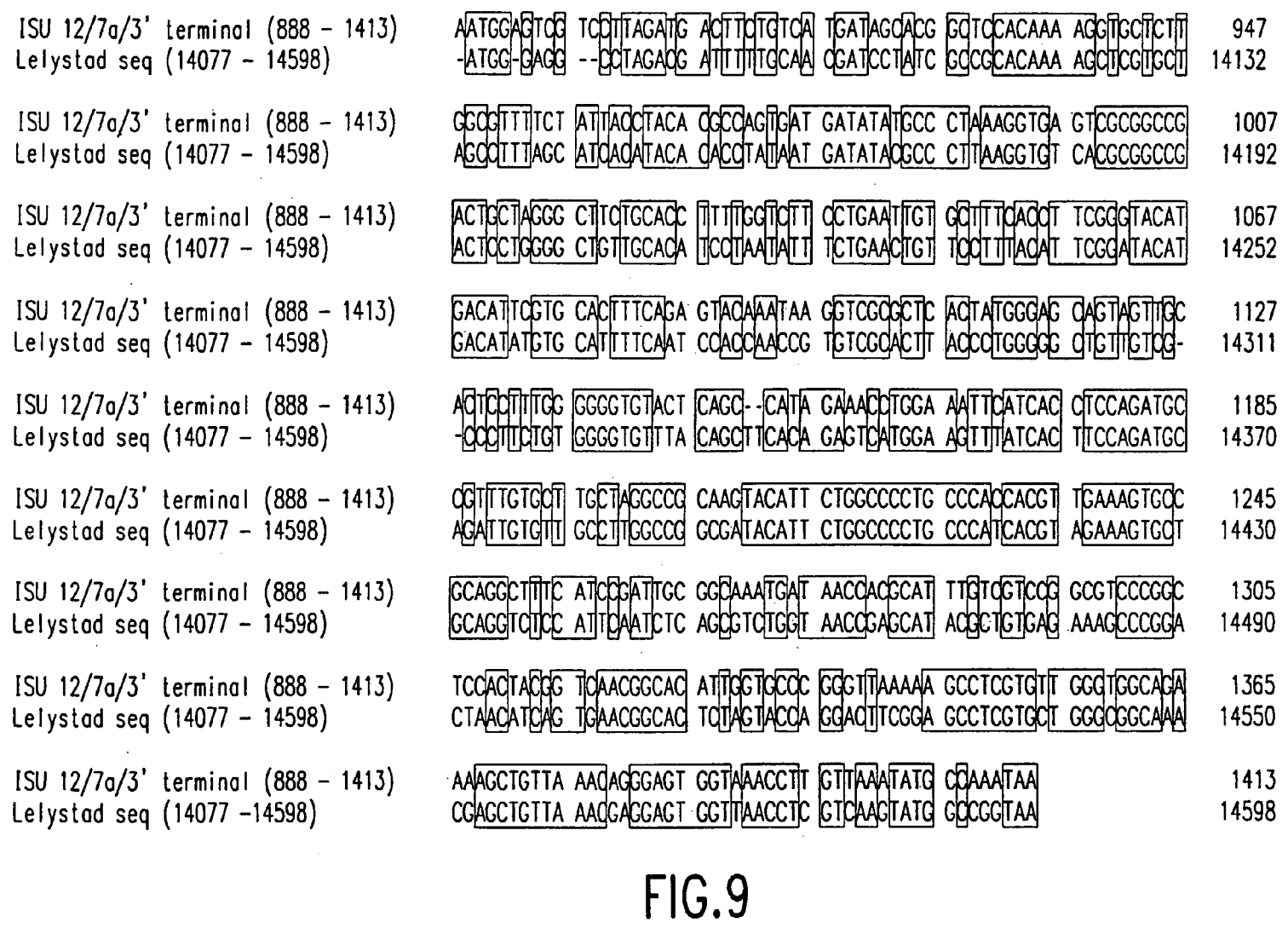

```
ISU 12/7a/3' terminal (888 - 1413)   AATGGAGTCG TCCTTAGATG ACTTCTGTCA TGATAGCACG GCTCCACAAA AGGTGCTCTT    947
Lelystad seq (14077 - 14598)         -ATGG-GAGG --CCTAGACG ATTTTTGCAA CGATCCTATC GCCGCACAAA AGCTCCGTGCT 14132

ISU 12/7a/3' terminal (888 - 1413)   GGCGTTTTCT ATTACCTACA CGCCAGTGAT GATATATGCC CTAAAGGTGA GTCGCGGCCG   1007
Lelystad seq (14077 - 14598)         AGCCTTTAGC ATCACATACA CACCTATAAT GATATACGCC CTTAAGGTGT CACGCGGCCG  14192

ISU 12/7a/3' terminal (888 - 1413)   ACTGCTAGCG CTTCTGCACC TTTTGGTCTT CCTGAATTGT GCTTTCACCT TCGGGTACAT   1067
Lelystad seq (14077 - 14598)         ACTCCTGGCG CTGTTGCACA TCCTAATATT TCTGAACTGT TCCTTTACAT TCGGATACAT  14252

ISU 12/7a/3' terminal (888 - 1413)   GACATTCGTG CACTTTCAGA GTACAAATAA GGTCGCGCTC ACTATGGCAG CAGTAGTTGC   1127
Lelystad seq (14077 - 14598)         GACATATGTG CATTTTCAAT CCACCAACCG TGTCGCACTT ACCCTGGCGG CTGTTGTCG-  14311

ISU 12/7a/3' terminal (888 - 1413)   ACTCCTTTGG GGGGTGTACT CAGC--CATA GAAACCTGGA AATTCATCAC CTCCAGATGC   1185
Lelystad seq (14077 - 14598)         -CCCTTCTGT GGGGTGTTTA CAGCTTCACA GAGTCATGGA AGTTTATCAC TTCCAGATGC  14370

ISU 12/7a/3' terminal (888 - 1413)   CGTTTGTGCT TGCTAGCCCG CAAGTACATT CTGGCCCCTG CCCACCACGT TGAAAGTGCC   1245
Lelystad seq (14077 - 14598)         AGATTGTGTT GCCTTGGCCG GCGATACATT CTGGCCCCTG CCCATCACGT AGAAAGTGCT  14430

ISU 12/7a/3' terminal (888 - 1413)   GCAGGCTTTC ATCCGATTGC GGCAAATGAT AACCACGCAT TTGTCGTCCG GCGTCCCGGC   1305
Lelystad seq (14077 - 14598)         GCAGGTCTCC ATTCAATCTC AGCGTCTGGT AACCGAGCAT ACGCTGTGAG AAAGCCCGGA  14490

ISU 12/7a/3' terminal (888 - 1413)   TCCACTACGG TCAACGGCAC ATTGGTGCCC GGGTTAAAAA GCCTCGTGTT GGGTGGCACA   1365
Lelystad seq (14077 - 14598)         CTAACATCAG TGAACGGCAC TCTAGTACCA GGACTTCGGA GCCTCGTGCT GGGCGGCAAA  14550

ISU 12/7a/3' terminal (888 - 1413)   AAAGCTGTTA AACAGGGAGT GGTAAACCTT GTTAAATATG CCAAATAA               1413
Lelystad seq (14077 -14598)          CGAGCTGTTA AACGACGAGT GGTTAACCTC GTCAAGTATG GCCCGTAA               14598
```

FIG.9

```
Lelystad seq (14588 - 14974)          ATGGCCGGTA AAAACCAGA- GCCAGAAGAA AAAGAAAAGT A-CAG----C 14632
ISU 12/7a/3' terminal (1403 - 1774)   ---------- --------AT GCCAAATAAC ACCGGCAAGC AGCAGAAGAG  1434

Lelystad seq (14588 - 14974)          TCCGATGGGG AATGGCCAGC CAGTCAATCA ACTGTGCCAG TTGCTGGGTG 14681
ISU 12/7a/3' terminal (1403 - 1774)   AAAGAAGGGG GATGGCCAGC CAGTCAATCA GCTGTGCCAG ATGCTGGGT-  1483

Lelystad seq (14588 - 14974)          CAATGATAAA GTCCCAGCGC CAGCAACCTA GGGG--A-GG ACAGGCCAAA 14728
ISU 12/7a/3' terminal (1403 - 1774)   -AA-GATCAT CGCTCACCAA AACCAGTCCA GAGGCAAGGG ACCGG---GA  1528

Lelystad seq (14588 - 14974)          AAGAAAAA-- ----G----- -CCTGAGAAG CCACATTTTC CCCTGGCTGC 14766
ISU 12/7a/3' terminal (1403 - 1774)   AAGAAAAATA AGAAGAAAAA CCCGGAGAAG CCCCATTTCC CTCTAGCGAC  1578

Lelystad seq (14588 - 14974)          TGAAGATGAC ATCCGGCACC ACCTCACCCA GACTGAACGC TCCCTCTGCT 14816
ISU 12/7a/3' terminal (1403 - 1774)   TGAAGATGAT GTCAGACATC ACTTTACCCC TAGTGAGCGT CAATTGTGTC  1628

Lelystad seq (14588 - 14974)          TGCAATCGAT CCAGACGGCT TTCAATCAAG GCGCAGGAAC -TGCGTCGCT 14865
ISU 12/7a/3' terminal (1403 - 1774)   TGTCGTCAAT CCAGACCGCC TTTAATCAAG GCGCTGGGAC TTGCACC-CT  1677

Lelystad seq (14588 - 14974)          TTCATCCAGC GGGAAGGTCA GTTTTCAGGT TGAGTTTATG CTGCCGGTTG 14915
ISU 12/7a/3' terminal (1403 - 1774)   GTCAGATTCA GGGAGGATAA GTTACACTGT GGAGTTTAGT TTGCCTACGC  1727

Lelystad seq (14588 - 14974)          CTCATACAGT GCGCCTGATT CGCGTGACTT CTACATCCGC CAGTCAGGGT 14965
ISU 12/7a/3' terminal (1403 - 1774)   ATCATACTGT GCGCCTGATC CGCGTCACAG CATCACCC-T CAG-CATGA-  1774

Lelystad seq (14588 - 14974)          GCAAGTTAA                                              14974
ISU 12/7a/3' terminal (1403 - 1774)                                                           1774
```

FIG.10

```
ISU 12/7a/3' terminal (1775 - 1938)   TGGGCTGGCA TTCTTGAGGC ATCCCAGTGT TTGAATTGGA    1814
Lelystad seq (14975 -15101)           ---------- ---------- ---------- --------TT   14976

ISU 12/7a/3' terminal (1775 - 1938)   AGAATGCGTG GTGAATGGCA CTGATTGACA TTGTGCCTCT    1854
Lelystad seq (14975 - 15101)          TGACAGTCAG GTGAATGGCC GCGATTGGCG TGTGGCCTCT   15016

ISU 12/7a/3' terminal (1775 - 1938)   AAGTCACCTA TTCAATTAGG GCGACCGTGT GGCGGTAAGA    1800
Lelystad seq (14975 - 15101)          GAGTCACCTA TTCAATTAGG GCGATCACAT GGCGGTCATA   15056

ISU 12/7a/3' terminal (1775 - 1938)   TTTAATT-GG CGAGAACCAC ACGGCCGAAA TTAAAAAAAA    1933
Lelystad seq (14975 - 15101)          CTTAATCAGG CAGGAACCAT GTGACCGAAA TTAAAAAAAA   15096

ISU 12/7a/3' terminal (1775 - 1938)   AAAAA                                          1938
Lelystad seq (14975 - 15101)          AAAAA                                         15101
```

FIG. 11

```
           ORF 6 start
           + 1>
VR 2385    ATGGAGTCGTCCTTAGATGACTTCTGTCATGATAGCACGGCTCCACAAAAGGTGCTCTTGGCGTTTTCTATTACCTACACGCCAGTGATGATATATGCCC  100
ISU-1894   ....G.....................C........T....................T...........................................  100
ISU-22     ....G...........................C.......................T...........................................  100
ISU-79     ....G......................T.......T....................T.....A.......................A.............  100
ISU-55     ....G.....................C.............................T........C..................................  100
ISU-3927   ....G.......C....C.....T..CA............................T..........................G..............T.  100
LV         ....G--A-G..C....C..T..T..CA.C...CCT.TC..CG........C.CG.GC.A..C...AGC..C..A.....A..TA.A........C....   97

VR 2385    TAAAGGTGAGTCGCGGCCGACTGCTAGGGCTTCTGCACCTTTTGGTCTTCCTGAATTGTGCTTTCACCTTCGGGTACATGACATTCGTGCACTTTCAGAG  200
ISU-1894   ............................................A.......................................................  200
ISU-22     .G..........................................A.......................................................  200
ISU-79     ............................................A.T........C..............................A.............  200
ISU-55     ....A..A....................................A.......A...............................................  200
ISU-3927   .......A....................................A.T..T..............T..T...........................G....  200
LV         .T......TCA...........C..G.....GT.....A.CCAA.A...T.....C...T.C..T..A.....A..........AT.....T.....ATC  197

VR 2385    TACAAATAAGGTCGCGCTCACTATGGGAGCAGTAGTTGCACTCCTTTGGGGGGTGTACTCAGC--CATAGAAACCTGGAAATTCATCACCTCCAGATGCC  298
ISU-1894   ...............................................................--...................................  298
ISU-22     ...............A...............................................--...................................  298
ISU-79     ...............................................................--...................................  298
ISU-55     C.....C........................................................--...................................  298
ISU-3927   C.......G...........................C.....T..C.................--...................................  298
LV         C..C..CCGT.....A..T..CC....G..T..T..C.--CCT..C..T.......TTA....TT..C...GT.A.....G..T.....T.........A  295
```

*FIG. 17A*

```
VR 2385    GTTTGTGCTTGCTAGGCCGCAAGTACATTCTGGCCCCTGCCCACCACGTTGAAAGTGCCGCAGGCTTTCATCCGATTGCGGCAAATGATAACCACGCATT  398
ISU-1894   ....................................................................................................  398
ISU-22     ....................................................................................................  398
ISU-79     ....................................................................................................  398
ISU-55     .............................T..............................................A.......................  398
ISU-3927   ....................................................G...............................................  398
LV         .A.....T.GC..T.....GCGA....................T......A.......T.....TC..C.T...A.CT..A..GTC..G.....GA...A  395

VR 2385    TGTCGTCCGGCGTCCCGGCTCCACTACGGTCAACGGCACATTGGTGCCCGGGTTAAAAAGCCTCGTGTTGGGTGGCAGAAAAGCTGTTAAACAGGGAGTG  498
ISU-1894   ......................................................G.............................................  498
ISU-22     ......T...............................................G.............................................  498
ISU-79     ......................................................G.............................................  498
ISU-55     ..............................T.......................G.................................C...........  498
ISU-3927   ..............................T.......................G.G.....................A............G........  498
LV         C.CT..GA.AAAG.....ACTA..AT.A..G........TC.A..A..A..AC.TCGG.........C....C....A.CG...........GA......  495

                          ORF 7 start
                          + 1>     *** ORF 6 stop
VR 2385    GTAAACCTTGTTAAATATGCCAAATAACACCGGCA-AGCAGCAGAAGAGAAAGAA---------------GGGGGATGGCCAGCCAGTCAATCAGCTGTG  582
ISU-1894   ...........C.................A.....-...................---------------..............................  582
ISU-22     ...........C.................A...T.-...................---------------..............................  582
ISU-79     ...........C.................A.....-...................---------------..............................  582
ISU-55     .............................A.....-............A......---------------..............................  582
ISU-3927   .............................A.....-............A......---------------...........................C..  582
LV         ..T.....C..C..G....G.CGG...A.A.--..G...--.......A......AAGTACAGCTCCGAT....A...................A.....  591
                                                                  ^^^^^^^^^^^^^^^
```

*FIG. 17B*

```
VR 2385   CCAGATGCTGGGT--AA-GATCATCGCTCACCAAAACCAGTCCAGAGGCAAGGGACCGGGAAAGAAAAATAAGAAGAAAAACCCGGAGAAGCCCCATTTC  679
ISU-1894  .............--..-............G......................................C.............................T  679
ISU-22    ............C--..-............G.....T..............................................................T  679
ISU-79    .............--..-.........C..G...........T........................................................T  679
ISU-55    .............--..-............G......................................C.............................T  679
ISU-3927  ...A.........--..-.........C..G.................T..................................................T  679
LV        ....T........GC..T...A.AGT.C..G.---G....--..-.CCT.G....---..C..---GCC..A........G..T........A......T  679

VR 2385   CCTCTAGCGACTGAAGATGATGTCAGACATCACTTTACCCCTAGTGAGCGTCAATTGTGTCTGTCGTCAATCCAGACCGCCTTTAATCAAGGCGCTGGGA  779
ISU-1894  ...................................C..............G.................................................  779
ISU-22    ..................................................G.................................................  779
ISU-79    ..................................................G.......................A..T......................  779
ISU-55    ...................................C...T..G.......G..........................A....................A.  779
ISU-3927  ...................................C.....C........G..........................T...........G..........  779
LV        ..C..G...TG.........CA..C.G..C...C.C....AG.C...A..CTCCC.C.CT...CAA..G........G..T..C...........A..A.  779
```

*FIG. 17C*

```
VR 2385    CTTGCACC-CTGTCAGATTCAGGGAGGATAAGTTACACTGTGGAGTTTAGTTTGCCTACGCATCATACTGTGCGCCTGATCCGCGTCACAGCATCACCC-  877
ISU-1894   ........-...............................................A..................T.......................-  877
ISU-22     ........-..........................................................................................-  877
ISU-79     ........-..................................................................T.......................-  877
ISU-55     ....T...-...............................................G...................................G......-  877
ISU-3927   .C..T.T.-..A............................................G.......................T........G...C.....-  877
LV         ..-..GT.G..T...TCCAGC....A.G.C....TTCAG..T.......TGC....GGTTGC......A...........T.....G..TT.TA..T..G  878

                            *** ORF 7 stop
VR 23 85   TCAG-CA----------TGA     886
ISU-1894   ....-..----------...     886
ISU-22     ....-..----------...     886
ISU-79     ....-..----------...     886
ISU-55     ....-..----------...     886
ISU-3927   ....-..----------...     886
LV         C...T..GGGTGCAAGT.A.     898
                  ^^^^^^^^^^
```

*FIG. 17D*

```
VR 2385 ORF6    MESSLDDFCHDSTAPQKVLLAFSITYTPVMIYALKVSRGRLLGLLHLLVFLNCAFTFGYMTFVHFQSTNKVALTMGAVVALLWGVYSAIETWKFITSRCR 100
ISU-1894 ORF6   .G..............................................I................................................... 100
ISU-22 ORF6     .G..............................................I................................................... 100
SIU-55 ORF6     .G..............................................I................................................... 100
ISU-79 ORF6     .G.......Y......................................I.............M..................................... 100
ISU-3927 ORF6   .G.......N......................................I................E...R.............................. 100
LV ORF6         .G-G.....N.PI.A..LV.........I.................I.I....S.......Y.......R....L............FT.S.........  99
PRRSV-10 ORF6   .G-G.....N.PI.A..LV.........I.................I.I....S.......Y.......R....L............FT.S.........  99
LDV-C ORF2      .G-G.-E..DQTSWY.-IFI...L....IA..S...F..T.A.IVNIFI.I..CVS.V.LMYH.-SV..TI..SL...I..V..I.TLVKIVDWLVI...  96
LDV-P ORF2      .G-G.-E..DQTSWY.-I.I...L....IA..S...F..T.A.IVNIFI.I..CVS.V.LMYH.-SV..T...SL...I..V..I.TLVKIVNWMVL...  96

VR 2385 ORF6    LCLLGRKYILAPAHHVESAAGFHPIAANDNH--------AFVVRRPGSTTVNGTLVPGLKSLVLGGRKAVKQGVVNLVKY-AK 183
ISU-1894 ORF6   ...............................--------.........................................-.. 174
ISU-22 ORF6     ...............................--------.........................................-.. 174
SIU-55 ORF6     ...............................--------.........................................-.. 174
ISU-79 ORF6     ...............................--------.........................................-.. 174
ISU-3927 ORF6   ...............................--------....................R......K.............-.. 174
LV ORF6         ..C...R..............L.S.S.SG.R--------.YA..K..L.S.........R......KR...R........-GR 173
PRRSV-10 ORF6   ..C...R..............L.S.S.SG.R--------.YA..K..L.S.........R......KR...R........-GR 173
LDV-C ORF2      ..F...S.....PS..D--------TSDGRQSLTTSLTT.....K....L...Q...DFQR.....K...SK.A...L..VS. 171
LDV-P ORF2      ..F...S.....PS..D--------TSDGRQSLTTSSTT.....K....L...Q...DFQR.....K...SK.A...L..VS. 171
```

*FIG. 18A*

```
VR 2385 ORF7     MPNNTGKQQKRKK-------GDGQPVNQLCQMLGKIIAHQNQSRGKGPGKKNKKKNPEKPHFPLATEDDVRHHFTPSERQLCLSSIQTAFNQGAGTCTLS 100
ISU-1894 ORF7    ....N........-------..................Q.............................................................  93
ISU-22 ORF7      ....N........-------..................Q.............................................................  93
ISU-79 ORF7      ....N........-------..................Q.............................................................  93
ISU-3927 ORF7    ....N.....K..-------..................Q..........................................................I..  93
ISU-55 ORF7      ....N.....K..-------..................Q...................................SG........................  93
VR2332 ORF7      ....N...TEE..-------..................Q.............................................................  93
LV ORF7          .---A..N.SQ..KKSTAPM.N.........L..AM.KS.R.---QPR.GQA...K.........A...I...L.QT..S...Q...........AS..  94
PRRSV-10 ORF7    .---A..N.SQ..KKSTAPM.N.........L..AM.KS.R.---QPR.GQA...K.........A...I...L.QT..S...Q...........PS..  94
LDV-C ORF1       .SQ.KK.GGQN.--------.AN.---..N.LISALLRNAG.--N..K.Q.K..-Q.-.L...M.GPS.L..VM..N.V.M.R..LV.L....G.Q...V  85
LDV-P ORF1       .SQ.KK.SGQN.--------.AN.---..N.LINALLRNAG.--N..K.Q.K..-Q.-.L...M.GPS.L..VM..N.V.M.R..LV.L....G.Q...V  85
EAV ORF7         .ASRRSRP.AASF-------RN.R--RRQPTSYNDLLRMFG.-------MRVR.PPAQPTQAII.EPG.L..DLNQQ..ATLS.NV.RF.MI.H.SL.-A  83
                              ^^^^^^^

VR 2385 ORF7     DSGRISYTVEFSLPTHHTVRLIRVTASP----SA  134
ISU-1894 ORF7    ............................----..  123
ISU-22 ORF7      ............................----..  123
ISU-79 ORF7      ............................----..  123
ISU-3927 ORF7    ..........................P.----..  123
ISU-55 ORF7      ............................----..  123
VR2332 ORF7      ............................----..  123
LV ORF7          S..KV.FQ...M..VA.........STSASQGAS  128
PRRSV-10 ORF7    S..KV.FQ...M..VA.........STSASQGAS  128
LDV-C ORF1       ...G.NF..S.M....A.....NAS.NS----..  115
LDV-P ORF1       ...G.NF..S.M....A.....NAS.NS----..  115
EAV ORF7         .A.GLT...SW-V..KQIQ.KVAPP.G.------  110
                                             ^^^^
```

*FIG. 18B*

+ Start ORF2
CCTGAATTGAGATGAAATGGGGTCTATGCAAAGCCTTTTTGACAAAATTGGCCAACTTTTTGTGGATGCTTTCACGGAGTTCTTGGTGTCCATTGTTGAT 100

ATCATTATATTTTTGGCCATTTTGTTTGGCTTCACCATCGCAGGTTGGCTGGTGGTCTTTTGCATCAGATTGGTTTGCTCCGCGATACTCCGTGCGCGCC 200

CTGCCATTCACTCTGAGCAATTACAGAAGATCCTATGAGGCCTTTCTCTCTCAGTGCCAGGTGGACATTCCCACCTGGGGAACTAAACATCCTTTGGGGA 300

TGCTTTGGCACCATAAGGTGTCAACCCTGATTGATGAAATGGTGTCGCGTCGAATGTACCGCATCATGGAAAAAGCAGGACAGGCTGCCTGGAAACAGGT 400

AGTGAGCGAGGCTACGCTGTCTCGCATTAGTAGTTTGGATGTGGTGGCTCATTTTCAGCATCTTGCCGCCATTGAAGCCGAGACCTGTAAATATCTGGCC 500

TCTCGGCTGCCCATGCTACACCACCTGCGCATGACAGGGTCAAATGTAACCATAGTGTATAATAGTACTTTGAATCAGGTGTTTGCTGTTTTCCCAACCC 600

+ Start ORF3
CTGGTTCCCGGCCAAAGCTTCATGATTTCCAGCAATGGCTAATAGCTGTACATTCCTCTATATTTTCCTCTGTTGCAGCTTCTTGTACTCTTTTTGTTGT 700

*** Stop ORF2
GCTGTGGTTGCGGGTTCCAATGCTACGTACTGTTTTTGGTTTCCGCTGGTTAGGGGCAATTTTTCTTTCGAACTCACGGTGAATTACACGGTGTGCCGC 800

CTTGCCTCACCCGGCAAGCAGCCGCAGAGGCCTACGAACCCGGCAGGTCCCTTTGGTGCAGGATAGGGCATGATCGATGTGGGGAGGACGATCATGATGA 900

ACTAGGGTTTGTGGTGCCGTCTGGCCTCTCCAGCGAAGGCCACTTGACCAGTGCTTACGCCTGGTTGGCGTCCCTGTCCTTCAGCTATACGGCCCAGTTC 1000

CATCCCGAGATATTCGGGATAGGGAATGTGAGTCGAGTCTATGTTGACATCAAGCACCAATTCATTTGCGCTGTTCATGATGGGCAGAACACCACCTTGC 1100

FIG. 20A

```
                                                                                                 + Start ORF4
CCCACCATGACAACATTTCAGCCGTGCTTCAGACCTATTACCAGCATCAGGTCGACGGGGGCAATTGGTTTCACCTAGAATGGGTGCGTCCCTTCTTTTC  1200

CTCTTGGTTGGTTTTAAATGTCTCTTGGTTTCTCAGGCGTTCGCCTGCAAGCCATGTTTCAGTTCGAGTCTTTCAGACATCAAGACCAACACCACCGCAG  1300

                                                                                                        *** Stop ORF3
CGGCAGGCTTTGCTGTCCTCCAAGACATCAGTTGCCTTAGGCATCGCAACTCGGCCTCTGAGGCGATTCGCAAAGTCCCTCAGTGCCGCACGGCGATAGG  1400

GACACCCGTGTATATCACTGTCACAGCCAATGTTACCGATGAGAATTATTTGCATTCCTCTGATCTTCTCATGCTTTCTTCTTGCCTTTTCTATGCTTCT  1500

GAGATGAGTGAAAAGGGATTTAAGGTGGTATTTGGCAATGTGTCAGGCATCGTGGCAGTGTGCGTCAACTTCACCAGTTACGTCCAACATGTCAAGGAAT  1600

TTACCCAACGTTCCTTGGTAGTTGACCATGTGCGGCTGCTCCATTTCATGACGCCCGAGACCATGAGGTGGGCAACTGTTTTAGCCTGTCTTTTTACCAT  1700

           *** Stop ORF4+Start ORF5
TCTGTTGGCAATTTGAATGTTTAAGTATGTTGGGGAAATGCTTGACCGCGGGCTGTTGCTCGCAATTGCTTTTTTTATGGTGTATCGTGCCGTCTTGTT   1799
```

FIG. 20B

```
Consensus     ATGMAATGGGGTCWMTGYRRAGCCTTTTTGAYAAAATYRGCCARCTKTTYGTGGAYGCYTTCACKGAGTTCYTKGTKWSYRTKGTTGATATYRYYATWTT  100
VR2385 ORF2   ...A.........TA..CAA...........C.....TG....A..T..T.....T..T.....G......T.G..GTCCA.T.........CATT..A..  100
LV ORF2       ...C.........AC..TGG..---------T.....CA....G..G..C.....C..C.....T......C.T..TAGTG.G.........TGCC..T..   91

Consensus     YYTKGCCATWYTGTTTGGSTTCACCRTCGCAGGWTGGYTRSTGGTCTTTYKYMTCAGAKTGGTTTGCTCCGCGMTWCTCCGTKCGCGCYCTGCCATTCAC  200
VR2385 ORF2   TT.G.....TT.......C......A.......T...C.GG........TGCA.....T..............A.A......G.....C...........  200
LV ORF2       CC.T.....AC.......G......G.......A...T.AC........CTTC.....G..............C.T......T.....T...........  191

Consensus     TCTSMSSAAYTAYMGAAGRTCCTATGARGSCTTKYTSYCYMASTGCMRRSYGGAYAKTCCCACAMTKKGSARYYAARCAYCCWTTGGGKATGYTTTGGCA  300
VR2385 ORF2   ...GAGC..T..CA....A.........G.C...TC.CT.TC.G...CAGGT...C.T.......-C.GG.G.ACT..A..T..T.....G...C.......  299
LV ORF2       ...CCCG..C..TC....G.........A.G...GT.GC.CA.C...AGACC...T-G.......A.TT.C.GTC..G..C..A.....T...T.......  290

Consensus     CCATRMGAGTKTCMMMCYTGATTGATGARATGGTSTCKCGTCGMATKTACCRSAYCATGGAAMAWKCAGGWCARGCKGCCTGGAARCAGGTRGTKRGYGA  400
VR2385 ORF2   ....AA.-..G..AAC.C..........A.....G..G.....A..G....GC.T.......A.AG....A..G..T.........A.....A..GA.C..  398
LV ORF2       .-..GC....T..CCA.T..........G.....C..T.....C..T....AG.C.......C.TT....T..A..G.........G.....G..TG.T..  389

Consensus     GGCYACGCTSTCWCGMAKYWGTCAGGKYTSGATRTRGTKRCTCATTTYCARCAYCTKGCCGCMRTKGARGCSGAKWCYTGYMRMTWTCTSRSCTCWCGRC  500
VR2385 ORF2   ...T.....G..T..C.TTA..-.-.TT.G...G.G..GG.......T..G..T..T.....CA.T..A..C..GA.C..TAAA.A...GGC...T..G.  496
LV ORF2       ...C.--..C..A..A.GCT......GC.C...A.A..TA.......C..A..C..G.....AG.G..G..G..TT.T..CCGC.T...CAG...A..A.  487
```

FIG. 21A

```
Consensus     TSSYSATGCTAMAMMAYCTGYGCAYGWYAGGGTCAAATGTRASCMTASWGTAYAAYASYACKTTGRAYCRSGTGTKWGCTCRTYTTCCCMACSCCWGGTW  600
VR2385 ORF2   .GCCC.....C.CC.C...C...T.AC............A.C.A..GT...T..T.GT..T...A.T.AG....TT...-G.T.....A..C..T...T  595
LV ORF2       .CGTG.....A.AA.T..-T..-C.TT--..-.-.....G.G.C..CA...C..C.CC..G...G.C.GC..-.GA....A.C.....C..G..A...A  580

Consensus     CSMGGCCMAAGYTKMMYGATTTCMRRCAATGGCTMATMRSTGTRCAYKCYTCYATWTTTTCCTCTGTKGCWKCWTCTKKTACYYTKTTYRTWGTGCTKTG  700
VR2385 ORF2   .CC...A...C.TCAT......CAG.........A..AGC...A..TT.C..T..A...........T..AG.T...TG...TC.T..TG.T.....G..  695
LV ORF2       .GA...C...T.GACC......AGA........C..CAG...G..CG.T..C..T...........G..TT.A...GT...CT.G..CA.A.....T..  680

Consensus     GYTKCGRRTTCCARYKCTACGYWMTGTTTTTGGTTTCCRYTGGYYMRSGGCAAYWYWTCWTTCGARCTSACGGTGA  776
VR2385 ORF2   .T.G..GG....ATG....TAC..............GC...TTAGG....TTTT..T.....A..C.......  771
LV ORF2       .C.T..AA....GCT....CTA..............AT...CCCAC....CACA..A.....G..G.------  750
```

*FIG. 21A.1*

```
Consensus    ATGGCTMATMRSTGTRCAYKCYTCYATWTTTTCCTCTGTKGCWKCWTCTKKTACYYTKTTYRTWGTGCTKTGGYTKCGRRTTCCARYKCTACGYWMTGTT  100
LV ORF3      ......C..CAG...G..CG.T..C..T...........G..TT.A...GT...CT.G..CA.A.....T...C.T..AA.....GCT.....CTA....  100
VR2385 ORF3  ......A..AGC...A..TT.C..T..A...........T..AG.T...TG...TC.T..TG.T.....G...T.G..GG.....ATG.....TAC....  100

Consensus    TTTGGTTTCCRYTGGYYMRSGGCAAYWYWTCWTTCGARCTSACSRTSAAYTACACSRTRTGCMYGCCYTGYYYYACCMGKCAAGCRGCTCGCMRARGSCT  200
LV ORF3      ..........AT...CCCAC.....CACA..A.....G..G..CA.C..C.....CA.A...AT...C..TTCT...A.T.....G......CA.A.G..  200
VR2385 ORF3  ..........GC...TTAGG.....TTTT..T.....A..C..GG.G..T.....GG.G...CC...T..CCTC...C.G.....A..-...AG.G.C..  199

Consensus    ACGARCCCGGYMGKWMCMTKTGGTGCARRATAGGGCATGAYMGRTGTGRGGAGSRYGAYCATGATGARYTAGKKWWTGTCSRTSCCGTCYGGSYWCKMCA  300
LV ORF3      -...G.....TC.TAA.A.G.......AA...........CA.G....A....CGT..C.........GT.-.TTAA....CA.C.....C..GTA.GA..  298
VR2385 ORF3  ....A.....CA.GTC.C.T.......GG...........TC.A....G....GAC..T.........AC...GGTT...-GG.G.....T..CCT.TC..  298

Consensus    sRCGAMKSMMACTTGACSRGTKMTTAYGCYTGGYTGGCKTYYYTGTCCTTYWSCTAYRCGGCCCARTTCCATCCSGAGWTRTTCGGGATAGGGAATGTGWS  400
LV ORF3      A.--CTCAA......-GG..TA...T..T...C....T.TTT.......TTC...CG.......A........G...T.G..................TC  395
VR2385 ORF3  G...AGGCC.......CA..GC...C..C...T....G.CCC.......CAG...TA.......G........C...A.A..................AG  398

Consensus    KCGMGTCTWYGTKGACAWSMRRCACCARTTCATTTGYGCYGWKCATGATGGRCASAAYWCMACCKTRYCYMMCSRWSACAACATYTCMGCMKTRYWTSMG  500
LV ORF3      G..C....TC..G....AGCGA.....G........T..C.AG........A..C..TT.A...G.AT.TAC.GGAC.......C..C..AT.ATA.GC.  495
VR2385 ORF3  T..A....AT..T....TCAAG.....A........C..T.TT........G..G..CA.C...T.GC.CCA.CATG.......T..A..CG.GCT.CA.  498
```

*FIG. 21B*

```
Consensus     RCMTATTACCASCAYCARRTMGACGGGGGCAATTGGTTYCAYYTRGAATGGSTGCGKCCMYTCTTTTCYTCYTGGYTGGTKYTMAAYRTMTCWTGGTTTC  600
LV ORF3       G.A.......C..C..AA.A................C..TT.G.....C...G..AC......T..C...C....GC.C..CA.A..A.......  595
VR2385 ORF3   A.C.......G..T..GG.C................T..CC.A.....G...T..CT......C..T...T....TT.A..TG.C..T.......  598

Consensus     TSAGGCGTTCGCCTGYAAGCCMTGTTTCWSKWCGMRTCTWTCAGAYATYRAGACCAACACSACCGCRGCKGCMGGYTTYRYKGTCCTYCARGACATCART  700
LV ORF3       .G............T.....C......TCGA..CA...A.....T..TG.........G.....G..T..C..T..CATG.....T..G.......A.  695
VR2385 ORF3   .C............C.....A......AGTT..AG...T.....C..CA.........C.....A..G..A..C..TGCT.....C..A.......G.  698

Consensus     TGYYTYMGRCMTCACGGSRWCTCRGCAGCKCAWGAGRMRATTTCCTTCGSAAAGTCGYCYCARTGYCGYGAMGSCGWYRGTACTCCCCAGTACATCACGA  800
LV ORF3       ..TT.CC.A.C......GGT...A.....G..A...AAA..........G.......T.C..A..T..T..A.C..TCG.....................  795
VR2385 ORF3   ..CC.TA.G.A..---.CAA...G..--.T.-T...GCG.-----....C......-C.T..G..C..C-.C.G..ATA.--------------------  765

Consensus     TAA  803
LV ORF3       ...  798
VR2385 ORF3   ---  765
```

*FIG. 21B.1*

```
Consensus     ATGGSTGCGKCCMYTCTTTTCYTCYTGGYTGGTKYTMAAYRTMTCWTGGTTTCTSAGGCGTTCGCCTGYAAGCCMTGTTTCWSKWCGMRTCTWTCAGAYA  100
VR2385 ORF4   ....G....T..CT.......C..T...T....TT.A..TG.C..T.........C.............C.....A......AGTT..AG...T.....C.  100
LV ORF4       ....C....G..AC.......T..C...C....GC.C..CA.A..A.........G.............T.....C......TCGA..CA...A.....T.  100

Consensus     TYRAGACCAACACSACCGCRGCKGCMGGYTTYRYKGTCCTYCARGACATCARTTGYYTYMGRCMTCACGGSRWCTCRGCAGCKCAWGAGRMRATTTCCTT  200
VR2385 ORF4   .CA..........C.....A..G..A..C..TGCT.....C..A.......G...CC.TA.G.A..---.CAA...G..--.T.-T...GCG.-----..  189
LV ORF4       .TG..........G.....G..T..C..T..CATG.....T..G.......A...TT.CC.A.C......GGT...A.....G..A...AAA........  200

Consensus     CGSAAAGTCGYCYCARTGYCGYRMRGCSRTMGGKACWCCCSWGTAYATCACKRTMACRGCYAAYGTKACCGAYGARWMWTAYTTGYAYWMCKCKGAYCTK  300
VR2385 ORF4   ..C......-C.T..G..C..CACG..GA.A..G..A...GT...T.....TG.C..A..C..T..T.....T..GAAT..T...C.TTC.T.T..T..T  288
LV ORF 4      ..G.......T.C..A..T..TGAA..CG.C..T..T...CA...C.....GA.A..G..T..C..G.....C..ATCA..C...T.CAA.G.G..C..G  300

Consensus     CTSATGCTTTCTKCKTGCCTTTTCTAYGCYTCWGARATGAGYGARAARGGMTTYAARGTSRTMTTTGGSAATGTSTCWGGCRTYGTKKCWGYKTGYGTCA  400
VR2385 ORF4   ..C.........T.T............T..T..T..G.....T..A..G..A..T..G..GG.A.....C.....G..A...A.C..GG.A.TG..C....  388
LV ORF4       ..G.........G.G............C..C..A..A.....C..G..A..C..C..A..CA.C.....G.....C..T...G.T..TT.T.CT..T....  400

Consensus     AYTTCACMRRTTAYGTSSMMCATGTCAAGGAATTTACCCAACATACCCAGCAGYATCAYYTGGTARTTGAYCAYRTKCGGYTGCTSCATTTCMTGACRCC  500
VR2385 ORF4   .C.....CAG...C..CCAA........................----------.T-..-CT.....G....C..TG.G...C....C......A....G..  476
LV ORF4       .T.....AGA...T..GGCC.....----.-----...................C....TC.....A....T..CA.T...T....G......C....A..  491

Consensus     MKMKRCMATGAGGTGGGCWACWRYYWTWGCYTGTYTKTTYRCCATTCTSTTGGCAATWTGA  561
VR2385 ORF4   CGAGA.C............A..TGTTT.A..C...C.T..TA.......G.........T...  537
LV ORF4       ATCTG.A............T..AACCA.T..T...T.G..CG.......C.........A...  552
```

*FIG. 21C*

| | | |
|---|---|---|
| Consensus | M.WG.C..K.........L.....W.........L..SL...P.CL.SPSQ.G.WSF.S.WFAPR.SVRALPFTL.NYRRSYE..L..C..D.P....KH | 100 |
| LV ORF2. | .Q..H.GV.SASCSWTPS.SSLLV.LI-------.PF..---.Y..G....D.Y...F.E.....F.........P.......GL.PN.RP.V.QFAV.. | 90 |
| VR2385 ORF2. | .K..L.--.----AFLTK.AN-FL.MLSRSSWCP.LI..YFW.F..A....V.W...A.D.....Y.........S.......AF.SQ.QV.I.TWGT.. | 93 |
| | | |
| Consensus | PLGM.WH..VS.LIDEMVSRR.Y..ME..GQAAWKQVV.EATL...S.LD.V.HFQHLAA.EA..C..L.SRL.ML..L.....NV...YN.TL..V... | 200 |
| LV ORF2. | ....F..MR..H.........I.QT..HS.........G....TKL.G..I.T.......V..DS.RF.S...V..KN.AV--G..SLQ..T..DR.ELI | 188 |
| VR2385 ORF2. | ....L..HK..T.........M.RI..KA.........S....SRI.S..V.A.......I..ET.KY.A...P..HH.RMTGS..TIV..S..NQ.FAV | 193 |
| | | |
| Consensus | FPTPG.RPKL.DF.QWLI.VH.SIFSSVA.S.TLF.VLWLR.P.LR.VFGF.W..A........ | 264 |
| LV ORF2. | .....T....T..R....S..A.......S.V...I.....I.A..Y....H.PT.---THHSS | 249 |
| VR2385 ORF2. | .....S....H..Q....A..S.......A.C...V.....V.M..T....R.LG.IFLSNSR- | 257 |

*FIG. 22A*

```
Consensus      MA..C.....FLC....Y....A....S..T.CFWFPL..GN.SFELT.NYT.C.PC.T.QAA....EPGR..WC.IGHDRC.E.DHDEL....PSG...   100
LV ORF3.       ..HQ.ARFHF...GFIC.LVHS.LASN.SS.L......AH..T.....I...I.M..S.S...RQRL....NM..K......E.R.....LMSI...YDN  100
VR2385 ORF3.    ..NS.TFLYI...CSFL.SFCC.VVAG.NA.Y......VR..F.....V...V.P..L.R...AEAY....SL..R......G.D.....GFVV...LSS  100

Consensus      ...L...YAWLA.LSFSY.AQFHPE.FGIGNVSRV.VD..HQFICA.HDG.N.T.....NISA....YY.HQ.DGGNWFHLEW.RP.FSSWLVLN.SWFL  200
LV ORF3.       L-K.EGY.....F.....A......L.........F..KR......E...H.S.VSTGH....LYAA..H..I..........L..L.........I....  199
VR2385 ORF3.   EGH.TSA.....S.....T......I.........Y..IK......V...Q.T.LPHHD....VLQT..Q..V..........V..F.........V....  200

Consensus      RRSP.S.VS.R..Q..RPT.P......S..TS....L.......R.F.........K.S.......              266
LV ORF3.       ....V.P..R.IY.IL...R.RLPVSW.FR..IVSD.TGSQQRK.K.PSESRPNVV.P.VLPSTSR             265
VR2385 ORF3.   ....A.H..V.VF.TS...P.QRQALL.SK..V--A.GIATRPL.R.A--------.-.LSAARR-             255
```

FIG. 22B

```
Consensus      M.A..LF.L.G.....VS.AFACKPCFS..LSDI.TNTTAAAGF.VLQDI.C.R......A.E.I...K..QCR.A.GTP.YIT.TANVTDE.YL...DL  100
LV ORF4.       .A.AT..F.A.AQHIM..E.........TH....E.........M.....N.F.PHGVSA.Q.K.SFG.SS...E.V...Q...I.......S..YNA..  100
VR2385 ORF4.   .G.SL..L.V.FKCLL..Q.........SS....K.........A.....S.L.HR--NS.S.A.R--.VP...T.I...V...V.......N..HSS..   96

Consensus      LMLS.CLFYASEMSEKGFKV.FGNVSG.V..CVNFT.YV.HV...TQ....V....RLLHF.TP..MRWAT..ACLF.ILLAI.   184
LV ORF4.       ....A...............I......V.SA.....D..A..TQH..QHHL.IDHI.....L..SA.....TI....A.....  183
VR2385 ORF4.   ....S...............V......I.AV.....S..Q..KEF..RSLV.DH-V.....M..ET.....VL....T.....  179
```

FIG. 22C

POLYNUCLEIC ACIDS ISOLATED FROM A PORCINE REPRODUCTIVE AND RESPIRATORY SYNDROME VIRUS (PRRSV), PROTEINS ENCODED BY THE POLYNUCLEIC ACIDS, VACCINES BASED ON THE PROTEINS AND/OR POLYNUCLEIC ACIDS, A METHOD OF PROTECTING A PIG FROM A PRRSV AND A METHOD OF DETECTING A PRRSV

The present application is a Divisional application of U.S. Ser. No. 08/301,435 filed Sep. 1, 1994, which is a Continuation-In-Part of U.S. Ser. No. 08/131,625 filed Oct. 5, 1993, now U.S. Pat. No. 5,695,766 which is a Continuation-In-Part of U.S. Ser. No. 07/969,071 filed Oct. 30, 1992 now abandoned.

BACKGROUND OF THE INVENTION

1. Field of the Invention

The present invention concerns DNA isolated from a porcine reproductive and respiratory virus (PRRSV), a protein and/or a polypeptide encoded by the DNA, a vaccine which protects pigs from a PRRSV based on the protein or DNA, a method of protecting a pig from a PRRSV using the vaccine, a method of producing the vaccine, a method of treating a pig infected by or exposed to a PRRSV, and a method of detecting a PRRSV.

2. Discussion of the Background

In recent years, North American and European swine herds have been susceptible to infection by new strains of reproductive and respiratory viruses (see A.A.S.P., September/October 1991, pp. 7–11*; The Veterinary Record*, Feb. 1, 1992, pp. 87–89; Ibid., Nov. 30, 1991, pp. 495–496; Ibid., Oct. 26, 1991, p. 370; Ibid., Oct. 19, 1991, pp. 367–368; Ibid., Aug. 3, 1991, pp. 102–103; Ibid., Jul. 6, 1991; Ibid., Jun. 22, 1991, p. 578; Ibid., Jun. 15, 1991, p. 574; Ibid., Jun. 8, 1991, p. 536; Ibid., Jun. 1, 1991, p. 511; Ibid., Mar. 2, 1991, p. 213). Among the first of the new strains to be identified was a virus associated with the so-called Mystery Swine Disease (MSD) or "blue-eared syndrome", now known as Swine Infertility and Respiratory Syndrome (SIRS) or Porcine Reproductive and Respiratory Syndrome (PRRS).

An MSD consisting of reproductive failure in females and respiratory disease in nursing and weaned pigs appeared in the Midwestern United States in 1987 (Hill et al., *Am. Assoc. Swine Practitioner Newsletter* 4:47 (1992); Hill et al., *Proceedings Mystery Swine Disease Committee Meeting*, Denver, Colo. 29–31 (1990); Keffaber, *Am. Assoc. Swine Practitioner Newsletter* 1:1–9 (1989); Loula, *Agri-Practice* 12:23–34 (1991)). Reproductive failure was characterized by abortions, stillborn and weak-born pigs. The respiratory disease in nursing and weaned pigs was characterized by fever, labored breathing and pneumonia. A similar disease appeared in Europe in 1990 (Paton et al., *Vet. Rec.* 128:617 (1991); Wensvoort et al., *Veterinary Quarterly* 13:121–130 (1991); Blaha, *Proc. Am. Assoc. Swine Practitioners, pp.* 313–315 (1993)), and has now been recognized worldwide.

This disease has also been called porcine epidemic abortion and respiratory syndrome (PEARS), blue abortion disease, blue ear disease (U.K.), abortus blau (Netherlands), seuchenhafter spatabort der schweine (Germany), Heko—Heko disease, and in the U.S., Wabash syndrome, mystery pig disease (MPD), and swine plague (see the references cited above and Meredith, *Review of Porcine Reproductive and Respiratory Disease Syndrome*, Pig Disease Information Centre, Department of Veterinary Medicine, Madingley Road, Cambridge CB3 OES, U.K. (1992); Wensvoort et al., *Vet. Res.* 24:117–124 (1993); Paul et al., *J. Clin. Vet. Med.* 11:19–28 (1993)). In Europe, the corresponding virus has been termed "Lelystad virus.".

At an international conference in May, 1992, researchers from around the world agreed to call this disease Porcine Reproductive and Respiratory Syndrome (PRRS). The disease originally appeared to be mainly a reproductive disease during its early phases, but has now evolved primarily into a respiratory disease.

Porcine reproductive and respiratory syndrome virus (PRRSV) is a relatively recently recognized swine pathogen associated with porcine reproductive and respiratory syndrome (PRRS). PRRSV is a significant pathogen in the swine industry. PRRSV infections are common in the U.S. swine herds. Outbreaks of PRRS in England have led to cancellation of pig shows.

The symptoms of PRRS include a reluctance to eat (anorexia), a mild fever (pyrexia), cyanosis of the extremities (notably bluish ears), stillbirths, abortion, high mortality in affected litters, weak-born piglets and premature farrowing. The majority of piglets born alive to affected sows die within 48 hours. PRRS clinical signs include mild influenza-like signs, rapid respiration ("thumping"), and a diffuse interstitial pneumonitis. PRRS virus has an incubation period of about 1–2 weeks from contact with a PRRSV-infected animal. The virus appears to be an enveloped RNA arterivirus (The Veterinary Record, Feb. 1, 1992). The virus has been grown successfully in pig alveolar macrophages and CL2621 cells (Benfield et al, *J. Vet. Diagn. Invest.,* 4:127–133, 1992; Collins et al, *Swine Infertility and Respiratory Syndrome/Mystery Swine Disease. Proc., Minn. Swine Conference for Veterinarians*, pp. 200–205, 1991), and in MARC-145 cells (Joo, PRRS: *Diagnosis, Proc.*, Allen D. Leman Swine Conference, Veterinary Continuing Education and Extension, University of Minnesota (1993), 20:53–55; Kim et al, *Arch. Virol.,* 133:477–483 (1993)). A successful culturing of a virus which causes SIRS has also been reported by Wensvoort et al (Mystery Swine Disease in the Netherlands: The Isolation of Lelystad Virus. Vet. Quart. 13:121–130, 1991).

Initially, a number of agents were incriminated in the etiology of this disease (Wensvoort et al., *Vet. Res.* 24:117–124 (1993); Woolen et al., *J. Am. Vet. Med. Assoc.* 197:600–601 (1990)). There is now a consensus that the causative agent of PRRS is an enveloped RNA virus referred to as Porcine Reproductive and Respiratory Syndrome Virus (PRRSV), reportedly of approximately 62 nm in diameter (Benfield et al., *J. Vet. Diagn. Invest.,* 4:127–133, 1992).

Virus isolates vary in their ability to replicate in continuous cell lines. Some grow readily, while others require several passages and some grow only in swine alveolar (SAM) cultures (Bautista et al., *J. Vet. Diagn. Invest.* 5:163–165, 1993; see also the Examples hereunder [particularly Table 1]).

PRRSV is a member of an Arterivirus group which includes equine arteritis virus (EAV), lactate dehydrogenase-elevating virus (LDV) and simian hemorrhagic fever virus (SHFV) (Benfield et al., 1992, supra; Plagemann, *Proc. Am. Assoc. Swine Practitioners,* 4:8–15 1992; Plagemann and Moennig, *Adv. Virus Res.* 41:99–192, 1992; Conzelmann et al., *Virology,* 193:329–339, 1993; Godney et al., *Virology,* 194:585–596, 1993; Meulenberg et al., *Virology,* 192:62–72, 1993). The positive-strand RNA viruses of this Arterivirus group resemble togaviruses morphologically, but are distantly related to coronaviruses and toroviruses on the basis of genome organization and gene expression (Plagemann et al., supra; Spaan et al., *J. Gen. Virol.* 69, 2939–2952 (1988); Strauss et al., *Annu. Rev. Biochem.* 42, 657–683 (1988); Lai, *Annu. Rev. Microbiol.* 44, 303–333 (1990); Snijder et al., *Nucleic Acid Res.* 18, 4535–4542 (1990)). The members of this group infect macrophages and contain a nested set of 5 to 7 subgenomic mRNAs in infected cells (Plagemann et al., supra; Meulenberg et al., *Virology,* 192, 62–72 (1993); Conzelmann et al., *Virology,* 193, 329–339 (1993); 15, 16, 17, 18, 19).

The viral genome of European isolates has been shown to be a plus stranded RNA of about 15.1 kb (Conzelmann et al., supra; Meulenberg et al., supra), and appears to be similar in genomic organization to LDV and EAV (Meulenberg et al., supra). However, no serological cross-reaction has been found among PRRSV, LDV and EAV (Goyal et al., *J. Vet. Diagn. Invest.,* 5, 656–664 (1993)).

PRRSV was initially cultivated in swine alveolar macrophage (SAM) cell cultures (Pol et al., *Veterinary Quarterly,* 13:137–143, 1991; Wensvoort et al., *Veterinary Quarterly,* 13:121–130, 1991) and then in continuous cell lines CL2621 (Benfield et al., supra), MA-104, and MARC-145 (Joo, *Proc. Allen D. Leman Swine Conference*, pp. 53–55, 1993). The reproductive and respiratory disease has been reproduced with cell free lung filtrates (Christianson et al., *Am. J. Vet. Res.,* 53:485–488, 1992; Collins et al., *J. Vet. Diagn. Invest.,* 4:117–126, 1992; Halbur et al., *Proc. Central Veterinary Conference*, pp. 50–59, 1993), and with cell culture-propagated PRRSV (Collins et al., supra, and *Proc. Allen D. Leman Swine Conference, pp.* 47–48, 1993).

Eight open reading frames (also referred to herein as "ORFs" or "genes") have been identified in a European PRRSV isolate. The genes of this European isolate are organized similarly to that in coronavirus (Meulenberg et al., supra). A 3'-end nested set of messenger RNA has been found in PRRSV-infected cells similar to that in coronaviruses (Conzelmann et al., supra; Meulenberg et al., supra).

The ORF 1a and 1b at the 5'-half of the European PRRSV genome are predicted to encode viral RNA polymerase. The ORF's 2–6 at the 3'-half of the genome likely encode for viral membrane-associated (envelope) proteins (Meulenberg et al., supra). ORF6 is predicted to encode the membrane protein (M) based on its similar characteristics with the ORF 6 of EAV, ORF 2 of LDV, and the M protein of mouse hepatitis virus and infectious bronchitis virus (Meulenberg et al., *Virology* 192, 62–72 (1993); Conzelmann et al., *Virology* 193, 329–339 (1993); Murtaugh, *Proc. Allen D. Leman Swine Conference*, Minneapolis, Minn., pp. 43–45 (1993); Mardassi et al., *Abstracts of Conference of Research Workers in Animal Diseases*, Chicago, Ill., pp. 43 (1993)). The product of ORF 7 is extremely basic and hydrophilic, and is predicted to be the viral nucleocapsid protein (N) (Meulenberg et al., supra; Conzelmann et al., supra; Murtaugh, supra; Mardassi et al., supra and *J. Gen. Virol.,* 75:681–685 (1994)).

Although conserved epitopes have been identified between U.S. and European PRRSV isolates using monoclonal antibodies (Nelson et al., *J. Clin. Microbiol.,* 31:3184–3189, 1993), there is extensive antigenic and genetic variation both among U.S. and European isolates of PRRSV (Wensvoort et al., *J. Vet. Diagn. Invest.,* 4:134–138, 1992). European isolates are genetically closely related, as the nucleotide sequence at the 3'-half of the genome from two European PRRSV isolates is almost identical (Conzelmann et al., supra; Meulenberg et al., supra).

Although the syndrome caused by PRRSV appears to be similar in the U.S. and Europe, several recent studies have described phenotypic, antigenic, genetic and pathogenic variations among PRRSV isolates in the U.S. and in Europe (Murtaugh, supra; Bautista et al., *J. Vet. Diagn. Invest.,* 5, 163–165 (1993); Bautista et al., *J. Vet. Diagn. Invest.,* 5, 612–614 (1993); Wensvoort et al., *J. Vet. Diagn. Invest.,* 4, 134–138 (1992); Stevenson et al., *J. Vet. Diagn. Invest.,* 5, 432–434 (1993)). For example, the European isolates grow preferentially in SAM cultures and replicate to a very low titer in other culture systems (Wensvoort, *Vet. Res.,* 24, 117–124 (1993); Wensvoort et al., *J. Vet. Quart.,* 13, 121–130 (1991); Wensvoort et al., *J. Vet. Diagn. Invest.,* 4, 134–138 (1992)). On the other hand, some of the U.S. isolates have been shown to replicate well in SAM as well as in the continuous cell line CL2621 (Benfield et al., *J. Vet. Diagn. Invest.,* 4, 127–133 (1992); Collins et al., *J. Vet. Diagn. Invest.,* 4, 117–126 (1992)). Thus, phenotypic differences among U.S. isolates are observed, as not all PRRSV isolates isolated on SAM can replicate on the CL2621 cell line (Bautista et al., *J. Vet. Diagn. Invest.,* 5, 163–165 (1993)).

A high degree of regional antigenic variation among PRRSV isolates may exist. Four European isolates were found to be closely related antigenically, but these European isolates differed antigenically from U.S. isolates. Further, three U.S. isolates were shown to differ antigenically from each other (Wensvoort et al., *J. Vet. Diagn. Invest.,* 4, 134–138 (1992)). Animals seropositive for European isolates were found to be negative for U.S. isolate VR 2332 (Bautista et al., *J. Vet. Diagn. Invest.,* 5, 612–614 (1993)).

U.S. PRRSV isolates differ genetically at least in part from European isolates (Conzelmann et al., supra; Meulenberg et al., supra; Murtaugh et al., *Proc. Allen D. Leman Conference*, pp. 43–45, 1993). The genetic differences between U.S. and European isolates are striking, especially since they are considered to be the same virus (Murtaugh, supra). Similar observations were also reported when comparing the Canadian isolate IAF-exp91 and another U.S. isolate VR 2332 with LV (Murtaugh, supra; Mardassi, supra). However, the 3' terminal 5 kb nucleotide sequences of two European isolates are almost identical (Conzelmann et al., supra; Meulenberg et al., supra).

The existence of apathogenic or low-pathogenic strains among isolates has also been suggested (Stevenson, supra). Thus, these studies suggest that the PRRSV isolates in North America and in Europe are antigenically and genetically heterogeneous, and that different genotypes or serotypes of PRRSV exist. However, prior to the present invention, the role of antigenic and genetic variation in the pathogenesis of PRRSV was not entirely clear.

The occurrence of PRRS in the U.S. has adversely affected the pig farming industry. Almost half of swine herds in swine-producing states in the U.S. are seropositive for PRRSV (*Animal Pharm.,* 264:11 (Nov. 11, 1992)). In Canada, PRRS has been characterized by anorexia and pyrexia in sows lasting up to 2 weeks, late-term abortions, increased stillbirth rates, weak-born pigs and neonatal deaths preceded by rapid abdominal breathing and diarrhea. Work on the isolation of the virus causing PRRS, on a method of diagnosing PRRS infection, and on the development of a vaccine-against the PRRS virus has been published (see Canadian Patent Publication No. 2,076,744; PCT International Patent Publication No. WO 93/03760; PCT International Patent Publication No. WO 93/06211; and PCT International Patent Publication No. WO 93/07898).

There is also variability in the virulence of PRRSV in herds. Recently, a more virulent form of PRRS has been occurring with increased incidence in 3–8 week old pigs in the midwestern United States. Typically, healthy 3–5 week old pigs are weaned and become sick 5–7 days later. Routine virus identification methods on tissues from affected pigs have shown that swine influenza virus (SIV), pseudorabies virus (PRV), and *Mycoplasma hyopneumoniae* are not associated with this new form of PRRS. Originally termed proliferative interstitial pneumonia (PIP; see U.S. patent application Ser. No. 07/969,071), this disease has been very recently linked with PRRS, and the virus has been informally named the "Iowa strain" of PRRSV (see U.S. patent application Ser. No. 08/131,625).

Pessimism and skepticism has been expressed in the art concerning the development of effective vaccines against these porcine viruses (The Veterinary Record, Oct. 26, 1991). A belief that human influenza vaccine may afford some protection against the effects of PRRS and PNP exists (*The Veterinary Record*, Jul. 6, 1991).

Viral envelope proteins are known to be highly variable in many coronaviruses, such as feline infectious peritonitis virus and mouse hepatitis virus (Dalziel et al: Site-specific alteration of murine hepatitis virus type 4 peplomer glycoprotein E2 results in reduced neurovirulence. *J. Virol.,* 59:464–471 (1986); Fleming et al: Pathogenicity of antigenic variants of murine coronavirus JHM selected with monoclonal antibodies. *J. Virol.,* 58:869–875 (1986); Fiscus et al: Antigenic comparison of the feline coronavirus isolates; Evidence for markedly different peplomer glycoproteins. *J. Virol.,* 61:2607–2613 (1987); Parker et al: Sequence analysis reveals extensive polymorphism and evidence of deletions within the E2 glycoprotein gene of several strains of murine hepatitis virus. *Virology,* 173:664–673 (1989)).

For example, a deletion or a mutation in the major envelope protein in coronaviruses can alter tissue tropism and in vivo pathogenicity. A mutation in a monoclonal antibody-resistant mutant of MHV has resulted in loss of its neurovirulence for mice (Fleming et al, 1986 supra). Porcine respiratory coronavirus (PRCV) is believed to be a deletion mutant of transmissible gastroenteritis virus (TGEV) in swine. The deletion in the PRCV genome may be in the 5'-end of the spike (S) gene of TGEV (Halbur et al, An overview of porcine viral respiratory disease. *Proc. Central Veterinary Conference*, pp. 50–59 (1993); Laude et al, Porcine respiratory coronavirus: Molecular features and virus-host interactions. Vet. Res., 24:125–150 (1993); Vaughn et al, Isolation and characterization of three porcine respiratory coronavirus isolates with varying sizes of deletions. *J. Clin. Micro.,* 32:1809–1812 (1994)).

PRCV has a selective tropism for the respiratory tract and does not replicate in the gastrointestinal tract (Rasschaert et al, Porcine respiratory coronavirus differs from transmissible gastroenteritis virus by a few genomic deletions. *J. Gen. Virol.,* 71:2599–2607 (1990); Laude et al, 1993 supra). In contrast, TGEV has a tropism for both respiratory and gastrointestinal tracts (Laude et al, 1993 supra).

Variation in antigenic and genetic relatedness among LDV isolates of varying pathogenicity is also known (Kuo et al, Lactate-dehydrogenase-elevating virus (LDV); subgenomic mRNAs, mRNA leader and comparison of 3'-terminal sequences of two LDV isolates. *Virus Res.,* 23:55–72 (1992); Plagemann, LDV, EAV, and SHFV: A new group of positive stranded RNA viruses. *Proc. Am. Assoc. Swine Practitioners,* 4:8–15 (1992); Chen et al, Sequences of 3' end of genome and of 5' end of open reading frame 1a of lactate dehydrogenase-elevating virus and common junction motifs between 5' leader and bodies of seven subgenomic mRNAs. *J. Gen. Virol.,* 74:643–660 (1993)).

However, the present invention provides the first insight into the relationships between the open reading frames of the PRRSV genome and their corresponding effects on virulence and replication.

Further, a diagnosis of porcine reproductive and respiratory syndrome (PRRS) relies on compiling information from the clinical history of the herd, serology, pathology, and ultimately on isolation of the PRRS virus (PRRSV). Three excellent references reviewing diagnosis of PRRSV have been published in the last year (Van Alstine et al, "Diagnosis of porcine reproductive and respiratory syndrome," *Swine Health and Production*, Vol. 1, No. 4 (1993), p. 24–28; Christianson et al, "Porcine reproductive and respiratory syndrome: A review." *Swine Health and Production*, Vol. 1, No. 2 (1994), pp. 10–28 and Goval, "Porcine reproductive and respiratory syndrome," *J. Vet. Diagn. Invest.* 5:656–664 (1993)). PRRSV has also recently been shown to replicate in pulmonary alveolar macrophages by gold colloid immunohistochemistry (Magar et al (1993): Immunohistochemical detection of porcine reproductive and respiratory syndrome virus using colloidal gold. *Can. J. Vet. Res.,* 57:300–304).

Clinical signs vary widely between farms, and thus, are not the most reliable evidence of a definitive diagnosis, except in the case of a severe acute outbreak in naive herds which experience abortion storms, increased numbers of stillborn pigs, and severe neonatal and nursery pig pneumonia. Presently, the most common clinical presentation is pneumonia and miscellaneous-bacterial problems in 3–10 week old pigs. However, many PRRSV-positive herds have no apparent reproductive or respiratory problems.

Some herds evidence devastating reproductive failure, characterized by third-trimester abortions, stillborn pigs and weak-born pigs. Many of these herds also experience severe neonatal respiratory disease. Respiratory disease induced by PRRSV in 4–10 week-old pigs is also common and can be quite severe (Halbur et al, Viral contributions to the porcine respiratory disease complex. *Proc. Am. Assoc. Swine Pract.* (1993), pp. 343–350). Clinical PRRSV outbreaks are frequently followed by bacterial pneumonia, septicemia, or enteritis. Thus, it has been difficult to obtain an acceptably rapid and reliable diagnosis of infection by PRRSV, prior to the present invention.

The pig farming industry has been and will continue to be adversely affected by these porcine reproductive and respiratory diseases and new variants thereof, as they appear. PRRSV is a pathogen of swine that causes economic losses from reproductive and respiratory diseases. Economic losses from PRRS occur from loss of pigs from abortions, stillborn pigs, repeat breeding, pre-weaning and postweaning mortality, reduced feed conversion efficiency, increased drug and labor cost and have been estimated to cost approximately $236 per sow in addition to loss of profits (Polson et al., Financial implications of mystery swine disease (MSD), *Proc. Mystery Swine Disease Committee Meeting*, Denver, Co., 1990, pp. 8–28). This represents a loss of $23,600 for a 100 sow herd or $236,000 for a 1000 sow herd.

PRRSV causes additional losses from pneumonia in nursery pigs. However, the exact economic losses from PRRSV-associated pneumonia are not known. PRRSV is an important cause of pneumonia in nursery and weaned pigs. Reproductive disease was the predominant clinical outcome of PRRSV infections during the past few years. Respiratory disease has now become the main problem associated with PRRSV.

Surprisingly, the market for animal vaccines in the U.S. and worldwide is larger than the market for human vaccines. Thus, there exists an economic incentive to develop new veterinary vaccines, in addition to the substantial public health benefit which is derived from protecting farm animals from disease.

SUMMARY OF THE INVENTION

Accordingly, one object of the present invention is to provide a polynucleic acid isolated from a porcine reproductive and respiratory virus (PRRSV).

It is a further object of the present invention to provide an isolated polynucleic acid which encodes a PRRSV protein.

It is a further object of the present invention to provide a PRRSV protein, either isolated from a PRRSV or encoded by a PRRSV polynucleic acid.

It is a further object of the present invention to provide a protein- or polynucleic acid-based vaccine which protects a pig against PRRS.

It is a further object of the present invention to provide a method of raising an effective immunological response against a PRRSV using the vaccine.

It is a further object of the present invention to provide a method of producing a protein- or polynucleic acid-based vaccine which protects a pig against a PRRSV infection.

It is a further object of the present invention to provide a method of treating a pig infected by or exposed to a PRRSV.

It is a further object of the present invention to provide a method of detecting PRRSV.

It is a further object of the present invention to provide an immunoperoxidase diagnostic assay for detection of PRRSV antigen in porcine tissues.

It is a further object of the present invention to provide an antibody which immunologically binds to a PRRSV protein or to an antigenic region of such a protein.

It is a further object of the present invention to provide an antibody which immunologically binds to a protein- or polynucleic acid-based vaccine which protects a pig against a PRRSV.

It is a further object of the present invention to provide a method of treating a pig exposed to or infected by a PRRSV.

It is a further object of the present invention to provide a method of detecting and a diagnostic kit for assaying a PRRSV.

It is a further object of the present invention to provide the above objects, where the PRRS virus is the Iowa strain of PRRSV.

These and other objects which will become apparent during the following description of the preferred embodiments, have been provided by at least one purified polypeptide selected from the group consisting of proteins encoded by one or more open reading frames (ORF's) of an Iowa strain of porcine reproductive and respiratory virus (PRRSV), proteins at least 80% but less than 100% homologous with those encoded by one or more of ORF 2, ORF 3, ORF 4 and ORF 5 of an Iowa strain of PRRSV, proteins at least 97% but less than 100% homologous with proteins encoded by one or both of ORF 6 and ORF 7 of an Iowa strain of PRRSV, antigenic regions of said proteins which are at least 5 amino acids in length and which effectively stimulate immunological protection in a porcine host against a subsequent challenge with a PRRSV isolate, and combinations thereof; an isolated polynucleic acid which encodes such a polypeptide or polypeptides; a vaccine comprising an effective amount of such a polynucleotide or polypeptide(s); antibodies which specifically bind to such a polynucleotide or polypeptide; methods of producing the same; and methods of raising an effective immunological response against a PRRSV, treating a pig exposed to or infected by a PRRSV, and detecting a PRRSV using the same.

BRIEF DESCRIPTION OF THE FIGURES

FIGS. 7A and 7B shows the 2062-bp 3'-terminal sequence (SEQ ID NO:13) and the amino acid sequences encoded by ORF's 5, 6 and 7 (SEQ ID NOS:15, 17 and 19, respectively) of VR 2385;

FIG. 8 compares the ORF-5 regions of the genomes of VR 2385 and Lelystad virus;

FIG. 9 compares the ORF-6 regions of the genomes of VR 2385 and Lelystad virus;

FIG. 10 compares the ORF-7 regions of the genomes of VR 2385 and Lelystad virus;

FIG. 11 compares the 3'-nontranslational regions of the genomes of VR 2385 and Lelystad virus;

FIGS. 17A, B, C and D compares the ORF 6 and ORF 7 nucleotide sequences of six U.S. PRRSV isolates and of LV, in which the VR 2385 nucleotide sequence is shown first, and in subsequent sequences, only those nucleotides which are different are indicated;

FIGS. 18(A)–(B) show the alignment of amino acid sequences of the putative M (FIG. 18(A)) and N (FIG. 18(B)) genes of the proposed arterivirus group, performed with a GENEWORKS program (IntelliGenetics, Inc.);

FIGS. 20A and B shows the nucleotide sequence of a region of the genome of PRRSV isolate VR 2385 containing ORF's 2, 3 and 4;

FIGS. 21(A)–(C) compare the nucleotide sequences of ORF 2, ORF 3 and ORF 4 of PRRSV VR 2385 with the corresponding ORF's of Lelystad virus (LV);

FIGS. 22(A)–(C) show alignments of the predicted amino acid sequences encoded by ORF's 2, 3 and 4 of PRRSV VR 2385 and LV;

DETAILED DESCRIPTION OF THE PREFERRED EMBODIMENTS

Figure 1:
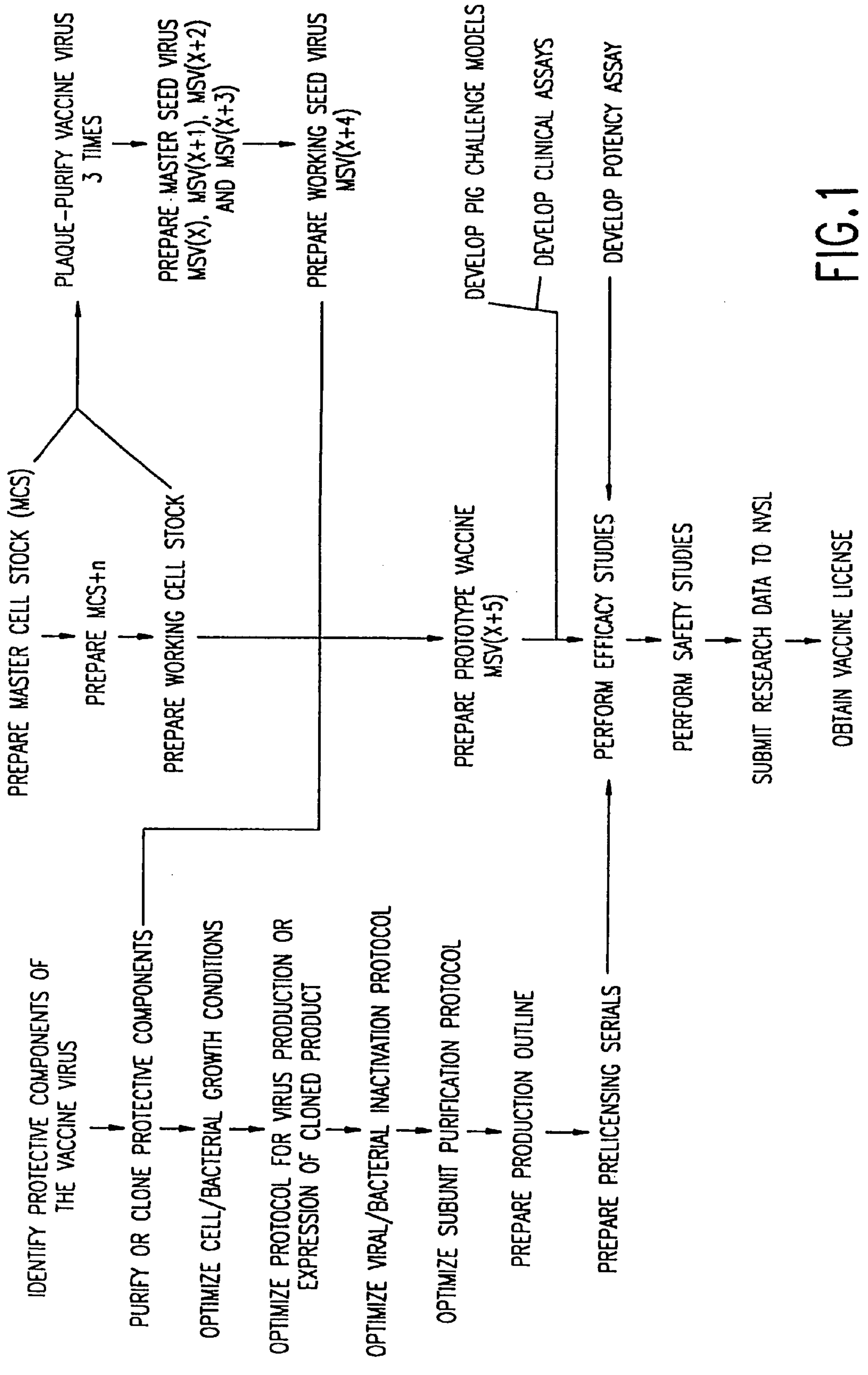
FIG. 1 is a flowchart outlining a procedure for producing a subunit vaccine.

In the present invention, a "porcine reproductive and respiratory syndrome virus" or "PRRSV" refers to a virus which causes the diseases PRRS, PEARS, SIRS, MSD and/or PIP (the term "PIP" now appears to be disfavored), including the Iowa strain of PRRSV, other strains of PRRSV found in the United States (e.g., VR 2332), strains of PRRSV found in Canada (e.g., IAF-exp91), strains of PRRSV found in Europe (e.g., Lelystad virus, PRRSV-10), and closely-related variants of these viruses which may have appeared and which will appear in the future.

The present vaccine is effective if it protects a pig against infection by a porcine reproductive and respiratory syndrome virus (PRRSV). A vaccine protects a pig against infection by a PRRSV if, after administration of the vaccine to one or more unaffected pigs, a subsequent challenge with a biologically pure virus isolate (e.g., VR 2385, VR 2386, or other virus isolate described below) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control) More particularly, the present vaccine may be shown to be effective by administering the vaccine to one or more suitable pigs in need thereof, then after an appropriate length of time (e.g., 1–4 weeks), challenging with a large sample ($10^{3-7}$ $TCID_{50}$) of a biologically pure PRRSV isolate. A blood sample is then drawn from the challenged pig after about one week, and an attempt to isolate the virus from the blood sample is then performed (e.g., see the virus isolation procedure exemplified in Experiment VIII below). Isolation of the virus is an indication that the vaccine may not be effective, and failure to isolate the virus is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoperoxidase assay method [described below], etc.). The symptoms of the porcine reproductive and respiratory disease may be evaluated quantitatively (e.g., temperature/fever), semi-quantitatively (e.g., severity of respiratory distress [explained in detail below], or qualitatively (e.g., the presence or absence of one or more symptoms or a reduction in severity of one or more symptoms, such as cyanosis, pneumonia, heart and/or brain lesions, etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one which shows symptoms of PRRS or from which PRRSV can be isolated.

The clinical signs or symptoms of PRRS may include lethargy, respiratory distress, "thumping" (forced expiration), fevers, roughened haircoats, sneezing, coughing, eye edema and occasionally conjunctivitis. Lesions may include gross and/or microscopic lung lesions, myocarditis, lymphadenitis, encephalitis and rhinitis. The infectious agent may be a single virus, or may be combined with one or more additional infectious agents (e.g., other viruses or bacteria). In addition, less virulent and non-virulent forms of the PRRSV and of Iowa strain have been found, which may cause either a subset of the above symptoms or no symptoms at all. Less virulent and non-virulent forms of PRRSV can be used according to the present invention to provide protection against porcine reproductive and respiratory diseases nonetheless.

Histological lesions in the various porcine diseases are different. Table I below compares physiological observations and pathology of the lesions associated with a number of diseases caused by porcine viruses:

TABLE I

| | Swine Viral Pneumonia Comparative Pathology | | | | | | |
|---|---|---|---|---|---|---|---|
| Lesion | PRRS(p) | PRRS(o) | SIV | PNP | PRCV | PPMV | Iowa |
| Type II | + | +++ | + | +++ | ++ | ++ | ++++ |
| Inter. thickening | ++++ | + | + | + | ++ | ++ | + |
| Alveolar exudate | + | +++ | ++ | ++ | ++ | ++ | +++ |
| Airway necrosis | – | – | ++++ | ++++ | +++ | + | – |
| Syncytia | – | ++ | +/– | ++ | + | + | +++ |
| Encephalitis | + | +++ | – | – | – | ++ | + |
| Myocarditis | +/– | ++ | – | – | – | – | +++ |

wherein "PRRS(p)" represents the published pathology of the PRRS virus, "PRRS(O)" represents the pathology of PRRS virus observed by the present Inventors, "SIV" represents swine influenza A virus, "PRCV" represents porcine respiratory coronavirus, "PPMV" represents porcine paramyxovirus, "Iowa" refers to the strain of PRRSV discovered by the present Inventors, "Type II" refers to Type II pneumocytes (which proliferate in infected pigs), "Inter." refers to interstitial septal infiltration by mononuclear cells, "Airway necrosis" refers to necrosis in terminal airways, and the symbols (–) and (+) through (++++) refer to a comparative severity scale as follows:

(–): negative (not observed)

(+): mild (just above the threshold of observation)

(++): moderate (+++): severe (++++): most severe

A "porcine reproductive and respiratory virus" or "PRRSV" causes a porcine reproductive and respiratory disease defined by one or more of the clinical signs, symptoms, lesions and histopathology as described above, and is characterized as being an enveloped RNA arterivirus, having a size of from 50 to 80 nm in diameter and from 250 to 400 nm in length. "North American strains of PRRSV" refer to those strains of PRRSV which are native to North America. "U.S. strains of PRRSV" refer to strains of PRRSV native to the U.S., and "European strains of PRRSV" refer to strains native to Europe, such as Lelystad virus (deposited by the CDI [Lelystad, Netherlands] in the depository at the Institut Pasteur, Paris, France, under the deposit number I-1102; see International Patent Publication No. WO 92/21375, published on Dec. 10, 1992).

The "Iowa strain" of PRRSV refers to (a) those strains of PRRSV isolated by the presented Inventors, (b) those strains having at least a 97% sequence identity (or homology) in the seventh open reading frame (ORF 7) with at least one of VR 2385, VR 2430 and VR 2431; (c) strains which, after no more than 5 passages, grow to a titer of at least $10^4$ $TCID_{50}$ in CRL 11171 cells, MA-104 cells or PSP-36 cells, (d) those strains having at least 80% and preferably at least 90% homology with one or more of ORF's 2–5 of VR 2385, and (e) those strains which cause a greater percentage consolidation of lung tissue than Lelystad virus (e.g., at 10 days post-infection, infected pigs exhibit at least 20% and preferably at least 40% lung consolidation). Preferably, the Iowa strain of PRRSV is characterized by at least two of the above characteristics (a)–(e).

The present invention is primarily concerned with polynucleic acids (segments of genomic RNA and/or DNA, mRNA, cDNA, etc.) isolated from or corresponding to a porcine reproductive and respiratory syndrome virus (PRRSV), proteins encoded by the DNA, methods of producing the polynucleic acids and proteins, vaccines which protect pigs from a PRRSV, a method of protecting a pig from a PRRSV using the vaccine, a method of producing the vaccine, a method of treating a pig infected by or exposed to a PRRSV, and a method of detecting a PRRSV. More particularly, the present invention is concerned with a vaccine which protects pigs from North American strains of PRRSV, a method of producing and administering the vaccine, and polynucleic acids and proteins obtained from an Iowa strain of PRRSV. However, it is believed that the information learned in the course of developing the present invention will be useful in developing vaccines and methods of protecting pigs against any and/or all strains of porcine reproductive and respiratory syndrome. Therefore, the present invention is not necessarily limited to polynucleic acids, proteins, vaccines and methods related to the Iowa strain of PRRS virus (PRRSV).

The phrase "polynucleic acid" refers to RNA or DNA, as well as mRNA and cDNA corresponding to or complementary to the RNA or DNA isolated from the virus or infectious agent. An "ORF" refers to an open reading frame, or polypeptide-encoding segment, isolated from a viral genome, including the PRRSV genome. In the present polynucleic acid, an ORF can be included in part (as a fragment) or in whole, and can overlap with the 5'- or 3'-sequence of an adjacent ORF (see FIGS. 7 and 21, and Experiments I and IV below). A "polynucleotide" is equivalent to a polynucleic acid, but may define a distinct molecule or group of molecules (e.g., as a subset of a group of polynucleic acids).

Figure 2:
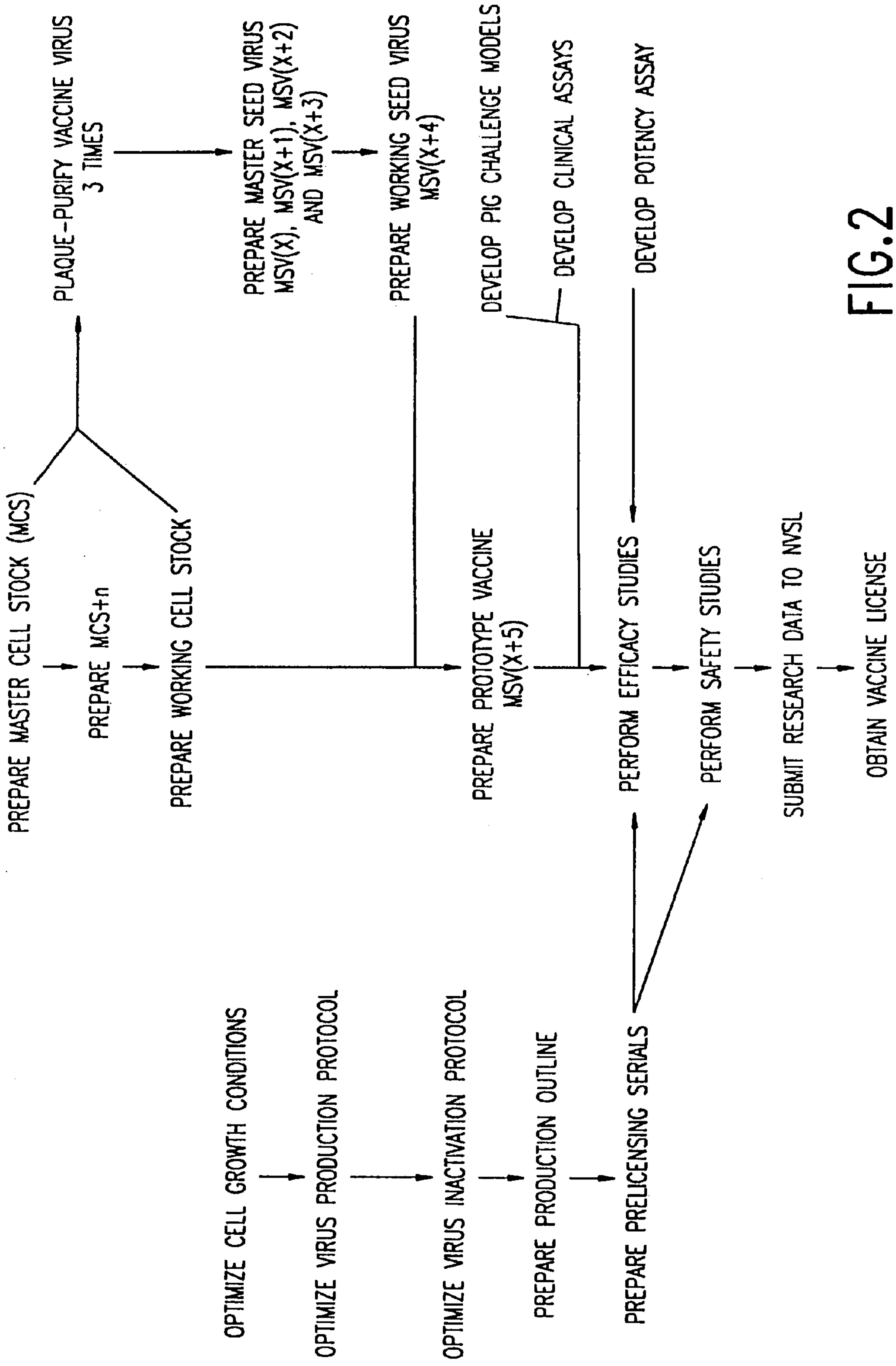
FIG. 2 is a flowchart outlining a procedure for producing a genetically engineered vaccine.

Referring now to FIGS. 1–2, flowcharts of procedures are provided for preparing types of vaccines encompassed by the present invention. The flowcharts of FIGS. 1–2 are provided as exemplary methods of producing the present vaccines, and are not intended to limit the present invention in any manner.

The first step in each procedure detailed in FIGS. 1–2 is to identify a cell line susceptible to infection with a porcine reproductive and respiratory virus or infectious agent. (To simplify the discussion concerning preparation of the vaccine, the term "virus" refers to a virus and/or other infectious agent associated with a porcine reproductive and respiratory disease.) A master cell stock (MCs) of the susceptible host cell is then prepared. The susceptible host cells continue to be passaged beyond MCS. Working cell stock (Wcs) is prepared from cell passages between MCS and MCS+n.

A master seed virus is propagated on the susceptible host cell line, between MCS and MCS+n, preferably on WCS. The raw virus is isolated by methods known in the art from appropriate, preferably homogenized, tissue samples taken from infected pigs exhibiting disease symptoms corresponding to those caused by the virus of interest. A suitable host cell, preferably a sample of the WCS, is infected with the raw virus, then cultured. Vaccine virus is subsequently isolated and plaque-purified from the infected, cultured host cell by methods known in the art. Preferably, the virus to be used to prepare the vaccine is plaque-purified three times.

Master seed virus (MSV) is then prepared from the plaque-purified virus by methods known in the art. The MSV(X) is then passaged in WCS at least four times through MSV(X+1), MSV(X+2), MSV(X+3) and MSV(X+4) virus passages. The MSV(X+4) is considered to be the working seed virus. Preferably, the virus passage to be used in the pig studies and vaccine product of the present invention is MSV(X+5), the product of the fifth passage.

In conjunction with the working cell stock, the working seed virus is cultured by known methods in sufficient amounts to prepare a prototype vaccine, preferably MSV (X+5). The present prototype vaccines may be of any type suitable for use in the veterinary medicine field. The primary types of vaccines on which the present invention focuses include a subunit vaccine (FIG. 1) and a genetically engineered vaccine (FIG. 2). However, other types of vaccines recognized in the field of veterinary vaccines, including live, modified live, attenuated and killed virus vaccines, are also acceptable. A killed vaccine may be rendered inactive through chemical treatment or heat, etc., in a manner known to the artisan of ordinary skill.

An attenuated virus may be obtained by repeating serial passage of the virus in a suitable host cell a sufficient number of times to obtain an essentially non-virulent virus. For example, a PRRSV may be serially passaged from 1 to 20 times (or more, if desired), in order to render it sufficiently attenuated for use as an attenuated vaccine. MSV(X+5) may be such an attenuated vaccine.

In the procedures outlined by each of FIGS. 1–2, following preparation of a prototype vaccine, pig challenge models and clinical assays are conducted by methods known in the art. For example, before performing actual vaccination/challenge studies, the disease to be prevented and/or treated must be defined in terms of its symptoms, clinical assay results, conditions, etc. As described herein, the Iowa strain of PRRSV has been defined in terms of its histopathology and the clinical symptoms which it causes. Clinical analyses of the Iowa strain of PRRSV are described in detail in the Experiments below.

One then administers a prototype vaccine to a pig, then exposes the pig to the virus which causes the disease. This is known as "challenging" the pig and its immunological system. After observing the response of the challenged pig to exposure to the virus or infectious agent and analyzing the ability of the prototype vaccine to protect the pig, efficacy studies are then performed by conventional, known methods. A potency assay is then developed in a separate procedure by methods known in the art, and prelicensing serials are then produced.

Prior to preparation of the prototype subunit vaccine (FIG. 1), the protective or antigenic components of the vaccine virus should be identified. Such protective or antigenic components include certain amino acid segments or fragments of the viral proteins (preferably coat proteins) which raise a particularly strong protective or immunological response in pigs; such antigenic protein fragments fused to non-PRRSV proteins which act as a carrier and/or adjuvant; single or multiple viral coat proteins themselves, oligomers thereof, and higher-order associations of the viral coat proteins which form virus substructures or identifiable parts or units of such substructures; oligoglycosides, glycolipids or glycoproteins present on or near the surface of the virus or in viral substructures such as the nucleocapsid; lipoproteins or lipid groups associated with the virus, etc.

Antigenic amino acid segments or fragments are preferably at least 5 amino acids in length, particularly preferably at least 10 amino acids in length, and can be up to but not including the entire length of the native protein. In the present invention, the binding affinity (or binding constant or association constant) of an antigenic fragment is preferably at least 1% and more preferably at least 10% of the binding affinity of the corresponding full-length protein (i.e., which is encoded by the same ORF) to a monoclonal antibody which specifically binds the full-length protein. The monoclonal antibody which specifically binds to the full-length protein encoded by an ORF of a PRRSV is preferably deposited under the Budapest Treaty at an acceptable depository, or is sequenced or otherwise characterized in terms of its physicochemical properties (e.g., antibody type [IgG, IgM, etc.], molecular weight, number of heavy and light chains, binding affinities to one or more known or sequenced proteins [e.g., selected from SEQ ID NOS:15, 17, 19, 21, 24, 26, 43, 45, 47, 49, 51, 53, 55, 57, 59, 61, 67, 69, 71, 73, 75 and 77], etc.).

Antigenic fragments of viral proteins (e.g., those encoded by one or more of ORF's 2–6 of a PRRSV virus) are identified by methods known in the art. For example, one can prepare polynucleic acids having a truncated ORF encoding a polypeptide with a predetermined number of amino acid residues deleted from the N-terminus, C-terminus, or both. The truncated ORF can be expressed in vitro or in vivo in accordance with known methods, and the corresponding truncated polypeptide can then be isolated in accordance with known methods. The immunoprotective properties of the polypeptides may be measured directly (e.g., in vivo). Alternatively, the antigenic region(s) of the full-length polypeptide can be determined indirectly by screening a series of truncated polypeptides against, for example, suitably deposited or characterized monoclonal antibodies. (If the alternative, indirect method is performed, the failure of a truncated polypeptide to bind to a neutralizing monoclonal antibody is a strong indication that the portion of the full-length polypeptide deleted in the truncated polypeptide contains an antigenic fragment.) Once identified, the antigenic or immunoprotective portion (s) (the "subunit(s)") of the viral proteins or of the virus itself may be subsequently cloned and/or purified in accordance with known methods. (The viral/bacterial inactivation and subunit purification protocols recited in FIG. 1 are optional.)

Genetically engineered vaccines (FIG. 2) begin with a modification of the general procedure used for preparation of the other vaccines. After plaque-purification, the PRRS virus may be isolated from a suitable tissue homogenate by methods known in the art, preferably by conventional cell culture methods using PSP-36, ATCC CRL 11171 or macrophage cells as hosts.

The RNA is extracted from the biologically pure virus by a known method, preferably by the guanidine isothiocyanate method using a commercially available RNA isolation kit (for example, the kit available from Stratagene, La Jolla, Calif.), and purified by one or more known methods, preferably by ultracentrifugation in a CsCl gradient. Messenger RNA may be further purified or enriched by oligo (dT)-cellulose column chromatography.

The viral genome is then cloned into a suitable host by methods known in the art (see Maniatis et al, "Molecular Cloning: A Laboratory Manual," Cold Spring Harbor Laboratory (1989), Cold Spring Harbor, Mass.). The virus genome is then analyzed to determine essential regions of the genome for producing antigenic portions of the virus. Thereafter, the procedure for producing a genetically engineered vaccine is essentially the same as for a modified live vaccine, an inactivated-vaccine or a subunit vaccine (see FIG. 1 of the present application and FIGS. 1–3 of U.S. application Ser. No. 08/131,625). During prelicensing serials, expression of the cloned, recombinant subunit of a subunit vaccine may be optimized by methods known to those in the art (see, for example, relevant sections of Maniatis et al, cited above).

The present vaccine protects pigs against a virus or infectious agent which causes a porcine reproductive and respiratory disease. Preferably, the present vaccine protects pigs against infection by PRRSV. However, the present vaccine is also expected to protect a pig against infection by closely related variants of various strains of PRRSV as well.

Subunit virus vaccines may also be prepared from semi-purified virus subunits by the methods described above in the discussion of FIG. 1. For example, hemagglutinin isolated from influenza virus and neuraminidase surface antigens isolated from influenza virus have been prepared, and shown to be less toxic than the whole virus. Subunit vaccines can also be prepared from highly purified subunits of the virus. An example in humans is the 22-nm surface antigen of human hepatitis B virus. Human herpes simplex virus subunits and many other examples of subunit vaccines for use in humans are known. Thus, methods of preparing purified subunit vaccines from PRRSV cultured in a suitable host cell may be applicable to the present subunit vaccine.

Attenuated virus vaccines can be found in nature and may have naturally-occurring gene deletions (see Experiments VIII and IX below). Alternatively, attenuated vaccines may be prepared by a variety of known methods, such as serial passage (e.g., 5–25 times) in cell cultures or tissue cultures. However, the attenuated virus vaccines preferred in the present invention are those attenuated by recombinant gene deletions or gene mutations (as described above).

Genetically engineered vaccines are produced by techniques known to those in the art. Such techniques include those using recombinant DNA and those using live viruses. For example, certain virus genes can be identified which code for proteins responsible for inducing a stronger immune or protective response in pigs. Such identified genes can be cloned into protein expression vectors, such (but not limited to) as the baculovirus vector (see, for example, O'Reilly et al, "Baculovirus Expression Vectors: A Lab Manual," Freeman & Co. (1992)). The expression vector containing the gene encoding the immunogenic virus protein can be used to infect appropriate host cells. The host cells are cultured, thus expressing the desired vaccine proteins, which can be purified to a desired extent, then used to protect the pigs from a reproductive and respiratory disease.

Genetically engineered proteins may be expressed, for example, in insect cells, yeast cells or mammalian cells. The genetically engineered proteins, which may be purified and/or isolated by conventional methods, can be directly inoculated into animals to confer protection against porcine reproductive and respiratory diseases. One or more envelope proteins from a PRRSV (i.e., those encoded by ORF's 2–6) or antigenic portions thereof may be used in a vaccine to induce neutralizing antibodies. Nucleoproteins from a PRRSV may be used in a vaccine to induce cellular immunity.

Preferably, the present invention transforms an insect cell line (HI-FIVE) with a transfer vector containing polynucleic acids obtained from the Iowa strain of PRRSV. Preferably, the present transfer vector comprises linearized baculovirus DNA and a plasmid containing one or more polynucleic acids obtained from the Iowa strain of PRRSV. The host cell line may be co-transfected with the linearized baculovirus DNA and a plasmid, so that a recombinant baculovirus is made. Particularly preferably, the present polynucleic acid encodes one or more proteins of the Iowa strain of PRRSV.

Alternatively, RNA or DNA from a PRRSV encoding one or more viral proteins (e.g., envelope and/or nucleoproteins) can be inserted into live vectors, such as a poxvirus or an adenovirus, and used as a vaccine.

Thus, the present invention further concerns a purified preparation of a polynucleic acid isolated from the genome of a PRRS virus, preferably a polynucleic acid isolated from the genome of the Iowa strain of PRRSV. The present polynucleic acid has utility (or usefulness) in the production of the present vaccine, in screening or identifying infected or exposed animals, in identifying related viruses and/or infectious agents, and as a vector for transforming cells and/or immunizing animals (e.g., pigs) with heterologous genes.

In the Experiments described hereinbelow, the isolation, cloning and sequencing of ORF's 2–7 of plaque-purified PRRSV isolate ISU-12 (deposited on Oct. 30, 1992, in the American Type Culture Collection, 1080 University Blvd., Manassas, Va. 20110-2209, U.S.A., under the accession numbers VR 2385 [3 ×plaque-purified] and VR 2386 [non-plaque purified]) and ORF's 6–7 of PRRSV isolates ISU-22, ISU-55 and ISU-3927 (deposited on Sep. 29, 1993, in the American Type Culture Collection under the accession numbers VR 2429, VR 2430 and VR 2431, respectively), ISU-79 and ISU-1894 (deposited on Aug. 31, 1994, in the American Type Culture Collection under the accession numbers VR 2484 and VR 2475, respectively) are described in detail. However, the techniques used to isolate, clone and sequence these genes can be also applied to the isolation, cloning and sequencing of the genomic polynucleic acids of any PRRSV. Thus, the present invention is not limited to the specific sequences disclosed in the Experiments below.

For example, primers for making relatively large amounts of DNA by the polymerase chain reaction (and if desired, for making RNA by transcription and/or protein by translation in accordance with known in vivo or in vitro methods) can be designed on the basis of sequence information where more than one sequence obtained from a PRRSV genome has been determined (e.g., ORF's 2–5 of VR 2385 and Lelystad virus, or ORF's 6–7 of VR 2385, VR 2429, VR 2430, ISU-79, ISU-1894, VR 2431 and Lelystad virus). A region from about 15 to 50 nucleotides in length having at least 80% and preferably at least 90% identity is selected from the determined sequences. A region where a deletion occurs in one of the sequences (e.g., of at least 5 nucleotides) can be used as the basis for preparing a selective primer for selective amplification of the polynucleic acid of one strain or type of PRRSV over another (e.g., for the differential diagnosis of North American and European PRRSV strains).

Once the genomic polynucleic acid is amplified and cloned into a suitable host by known methods, the clones can be screened with a probe designed on the basis of the sequence information disclosed herein. For example, a region of from about 50 to about 500 nucleotides in length is selected on the basis of either a high degree of identity (e.g., at least 90%) among two or more sequences (e.g., in ORF's 6–7 of the Iowa strains of PRRSV disclosed in Experiment III below), and a polynucleotide of suitable length and sequence identity can be prepared by known methods (such as automated synthesis, or restriction of a suitable fragment from a polynucleic acid containing the selected region, PCR amplification using primers which hybridize specifically to the polynucleotide, and isolation by electrophoresis). The polynucleotide may be labeled with, for example, $^{32}$p (for radiometric identification) or biotin (for detection by fluorometry). The probe is then hybridized with the polynucleic acids of the clones and detected according to known methods.

The present Inventors have discovered that ORF 4 appears to be related to the virulence of PRRSV. For example, at least one isolate of PRRSV which shows relatively low virulence also appears to have a deletion in ORF 4 (see, for example, Experiments VIII–XI below). Accordingly, in a preferred embodiment, the present invention is concerned with a polynucleic acid obtained from a PRRSV isolate which confers immunogenic protection directly or indirectly against a subsequent challenge with a PRRSV, but in which ORF 4 is deleted or mutated to an extent which would render a PRRSV containing the polynucleic acid either low-virulent (i.e., a "low virulence" (lv) phenotype; see the explanation below) or non-virulent (a so-called "deletion mutant"). Preferably, ORF 4 is deleted or mutated to an extent which would render a PRRS virus non-virulent. However, it may be desirable to retain regions of a PRRSV ORF 4 in the present polynucleic acid which (i) encode an antigenic, immunoprotective peptide fragment and (ii) would not confer virulence to a PRRS virus containing the polynucleic acid.

The present invention also encompasses a PRRSV per se in which ORF 4 is deleted or mutated to an extent which renders it either low-virulent or non-virulent (e.g., VR 2431). Such a virus is useful as a vaccine or as a vector for transforming a suitable host (e.g., MA-104, PSP 36, CRL 11171, MARC-145 or porcine alveolar macrophage cells) with a heterologous gene. Preferred heterologous genes which may be expressed using the present deletion mutant may include those encoding a protein or an antigen other than a porcine reproductive and respiratory syndrome virus antigen (e.g., pseudorabies and/or swine influenza virus proteins and/or polypeptide-containing antigens, a porcine growth hormone, etc.) or a polypeptide-based adjuvant (such as those discussed below for the present vaccine composition).

It may also be desirable in certain embodiments of the present polynucleic acid which contain, for example, the 3'-terminal region of ORF 3 (e.g., from 200 to 700 nucleotides in length), at least part of which may overlap with the 5'-region of ORF 4. Similarly, where the 3'-terminal region of ORF 4 may overlap with the 5'-terminal region of ORF 5, it may be desirable to retain the 5'-region of ORF 4 which overlaps with ORF 5.

The present Inventors have also discovered that ORF 5 in the PRRSV genome appears to be related to replication of the virus in mammalian host cells capable of sustaining a culture while infected with PRRSV. Accordingly, the present invention is also concerned with polynucleic acids obtained from a PRRSV genome in which ORF 5 may be present in multiple copies (a so-called "overproduction mutant"). For example, the present polynucleic acid may contain at least two, and more preferably, from 2 to 10 copies of ORF 5 from a high-replication (hr) phenotype PRRSV isolate.

Interestingly, the PRRSV isolate ISU-12 has a surprisingly large number of potential start codons (ATG/AUG sequences) near the 5'-terminus of ORF 5, possibly indicating alternate start sites of this gene (see SEQ ID NO:13). Thus, alternate forms of the protein encoded by ORF 5 of a PRRSV isolate may exist, particularly where alternate ORF's encode a protein having a molecular weight similar to that determined experimentally (e.g., from about 150 to about 250 amino acids in length). The most likely coding region for ORF 5 of ISU-12 (SEQ ID NO:14) is indicated in FIG. 7.

One can prepare deletion and overproduction mutants in accordance with known methods. For example, one can prepare a mutant polynucleic acid which contains a "silent" or degenerate change in the sequence of a region encoding a polypeptide. By selecting and making an appropriate degenerate mutation, one can substitute a polynucleic acid sequence recognized by a known restriction enzyme. For example, if such a silent, degenerate mutation is made at one or two of the 3'-end of ORF 3 and the 5'- and 3'-ends of ORF 4 and ORF 5, one can insert a synthetic polynucleic acid (a so-called "cassette") which may contain multiple copies of ORF 5, multiple copies of a viral envelope protein or an antigenic fragment thereof. The "cassette" may be preceded by a suitable initiation codon (ATG), and may be suitably terminated with a termination codon at the 3'-end (TAA, TAG or TGA).

Of course, an oligonucleotide sequence which does not encode a polypeptide may be inserted, or alternatively, no cassette may be inserted. By doing so, one may provide a so-called deletion mutant.

Thus, in one embodiment of the present invention, the polynucleic acid encodes one or more proteins, or antigenic regions thereof, of a PRRSV. Preferably, the present nucleic acid encodes at least one antigenic region of a PRRSV membrane (envelope) protein. More preferably, the present polynucleic acid contains at least one copy of the ORF-5 gene from a high virulence (hv) phenotype isolate of PRRSV (see the description of "hv phenotype" below) and a sufficiently long fragment, region or sequence of at least one of ORF-2, ORF-3, ORF-4, ORF-5 and/or ORF-6 from the genome of a PRRSV isolate to encode an antigenic region of the corresponding protein(s) and effectively stimulate immunological protection against a subsequent challenge with an hv phenotype PRRSV isolate. Even more preferably, at least one entire envelope protein encoded by ORF-2, ORF-3, ORF-5 and/or ORF-6 of a PRRSV is contained in the present polynucleic acid, and the present polynucleic acid excludes a sufficiently long portion of ORF 4 from an hv PRRSV to render a PRRSV containing the same either low-virulent or non-virulent. Particularly preferably, the present polynucleic acid excludes the entire region of an hv PRRSV ORF 4 which does not overlap with the 3'-end of ORF 3 and the 5'-end of ORF 5.

Most preferably, the polynucleic acid is isolated from the genome of an isolate of the Iowa strain of PRRSV (for example, VR 2385 (3×plaque-purified ISU-12), VR 2386 (non-plaque-purified ISU-12), VR 2428 (ISU-51), VR 2429 (ISU-22), VR 2430 (ISU-55), VR 2431 (ISU-3927), ISU-79 and/or ISU-1894.

A preferred embodiment of the present invention concerns a purified preparation which may comprise, consist essentially of or consist of a polynucleic acid having a sequence of the formula (I):

$$5'\text{-}\alpha\text{-}\beta\text{-}\gamma\text{-}3' \qquad (I)$$

wherein α encodes at least one polypeptide or antigenic fragment thereof encoded by a polynucleotide selected from the group consisting of ORF 2 and ORF 3 of an Iowa strain of PRRSV and regions thereof encoding the antigenic fragments; and β is either a covalent bond or a linking polynucleic acid which excludes a sufficiently long portion of ORF 4 from an hv PRRSV to render the hv PRRSV either low-virulent or non-virulent; and γ is at least one copy of an ORF 5 from an Iowa strain of PRRSV, preferably from a high replication (hr) phenotype.

Alternatively, the present invention may concern a purified preparation which may comprise, consist essentially of or consist of a polynucleic acid having a sequence of the formula (II):

$$5'\text{-}\gamma\text{-}\delta\text{-}\epsilon\text{-}3' \quad \text{(II)}$$

where $\gamma$ is at least one copy of an ORF 5 from an Iowa strain of PRRSV, preferably from an hv PRRSV isolate; $\delta$ is either a covalent bond or a linking polynucleic acid which does not materially affect transcription and/or translation of the polynucleic acid; and $\epsilon$ encodes at least one polypeptide or antigenic fragment thereof encoded by a polynucleotide selected from the group consisting of ORF 6 and ORF 7 of an Iowa strain of PRRSV and regions thereof encoding the antigenic fragments; and when $\delta$ is a covalent bond, $\gamma$ may have a 3'-end which excludes the region overlapping with the 5'-end of a corresponding ORF 6. Preferably, $\epsilon$ is a polynucleotide encoding at least an antigenic region of a protein encoded by an ORF 6 of an Iowa strain of PRRSV, and more preferably, encodes at least a protein encoded by an ORF 6 of an Iowa strain of PRRSV.

The present invention may also concern a purified preparation which may comprise, consist essentially of or consist of a polynucleic acid having a sequence of the formula (III):

$$5'\text{-}\alpha\text{-}\beta\text{-}\gamma\text{-}\delta\text{-}\epsilon\text{-}3' \quad \text{(III)}$$

where $\alpha$, $\beta$, $\gamma$, $\delta$ and $\epsilon$ are as defined in formulas (I) and (II) above. Thus, the present polynucleic acid may be selected from the group consisting of, from 5' to 3':

| | |
|---|---|
| $(\text{ORF 5})_n$ | (IV) |
| $\zeta$ - $(\text{ORF 5})_n$ | (V) |
| $(\text{ORF 5})_n$-$\eta$ | (VI) |
| $\zeta$ - $(\text{ORF 5})_n$-$\eta$ | (VII) |

where:

$\zeta$ is selected from the group consisting of ORF 2-, ORF 3-, ORF 4*-, ORF 2-ORF 3-, ORF 2-ORF 4*-, ORF 3-ORF 4*- and ORF 2-ORF 3-ORF 4*-; and $\eta$ is selected from the group consisting of -ORF 5*, -ORF 6, -ORF 7, -ORF 5*-ORF 6, -ORF 5*-ORF 7, -ORF 6-ORF 7 and -ORF 5*-ORF 6-ORF 7;

wherein ORF 2, ORF 3, ORF 6 and ORF 7 each encode a protein encoded by the second, third, sixth and seventh open reading frames of an Iowa strain of PRRSV, respectively; ORF 4* is a region of a fourth open reading frame of an Iowa strain of PRRSV which (i) encodes an antigenic, immunoprotective peptide fragment and which (ii) does not confer virulence to a PRRSV containing the polynucleic acid; ORF 5 is a fifth open reading frame of an hv PRRSV isolate; ORF 5* is a region of a fifth open reading frame of an Iowa strain of PRRSV which (i) encodes an antigenic, immunoprotective peptide fragment and (ii) does not confer virulence to a PRRSV containing the polynucleic acid, and which may have a 3'-end which excludes the portion overlapping with the 5'-end of a corresponding ORF 6; and $n \geqq 1$.

The present polynucleic acid may also comprise, consist essentially of or consist of combinations of the above sequences, either as a mixture of polynucleotides or covalently linked in either a head-to-tail (sense-antisense) or head-to-head fashion. Polynucleic acids complementary to the above sequences and combinations thereof (antisense polynucleic acid) are also encompassed by the present invention. Thus, in addition to possessing multiple or variant copies of ORF 5, the present polynucleic acid may also contain multiple or variant copies of one or more of ORF's 1–3 and 6–7 and regions of ORF's 4–5 of Iowa strain PRRSV's.

The present invention may also concern polynucleic acids comprising, consisting essentially of or consisting of the open reading frame 1a and 1b from a PRRSV isolate. Based on information regarding viruses evolutionally related to PRRSV, ORF 1a and 1b of PRRSV are believed to encode an RNA polymerase. ORF 1a and 1b are translated into a single protein by frameshifting. Preferably, the polynucleic acid from ORF 1a and 1b of a PRRSV isolate is obtained from an Iowa strain of PRRSV.

Similar to the methods described above and in the following Experiments for ORF's 2–7, one can prepare a library of recombinant clones (e.g., using *E. coli* as a host) containing suitably prepared restriction fragments of a PRRSV genome (e.g., inserted into an appropriate plasmid expressible in the host). The clones are then screened with a suitable probe (e.g, based on a conserved sequence of ORF's 2–3; see, for example, FIG. 22). Positive clones can then be selected and grown to an appropriate level. The polynucleic acids can then be isolated from the positive clones in accordance with known methods. A suitable primer for PCR can then be designed and prepared as described above to amplify the desired region of the polynucleic acid. The amplified polynucleic acid can then be isolated and sequenced by known methods.

The present purified preparation may also contain a polynucleic acid selected from the group consisting of sequences having at least 97% sequence identity (or homology) with at least one ORF 7 of VR 2385, VR 2430 and/or VR 2431; and sequences having at least 80% and preferably at least 90% sequence identity (or homology) with at least one of ORF's 1–6 of VR 2385, VR 2428, VR 2429, VR 2430 and/or VR 2431. Preferably, the polynucleic acid excludes a sufficiently long region or portion of ORF 4 of the hv PRRSV isolates VR 2385, VR 2429, ISU-28, ISU-79 and/or ISU-984 to render the isolate low-virulent or non-virulent.

In the context of the present application, "homology" refers to the percentage of identical nucleotide or amino acid residues in the sequences of two or more viruses, aligned in accordance with a conventional method for determining homology (e.g., the MACVECTOR or GENEWORKS computer programs, aligned in accordance with the procedure described in Experiment III below).

Accordingly, a further aspect of the present invention encompasses an isolated polynucleic acid at least 90% homologous to a polynucleotide which encodes a protein, polypeptide or fragment thereof encoded by ORF's 1–7 from an Iowa strain of PRRSV (e.g., SEQ ID NOS:15, 17, 19, 43, 45, 47, 49, 51, 53, 55, 57, 59, 61, 63, 65 and 67). Preferably, the present isolated polynucleic acid encodes a protein, polypeptide, or antigenic fragment thereof which is at least 10 amino acids in length and in which amino acids non-essential for antigenicity may be conservatively substituted. An amino acid residue in a protein, polypeptide, or antigenic fragment thereof is conservatively substituted if it is replaced with a member of its polarity group as defined below:

Basic amino acids:
lysine (Lys), arginine (Arg), histidine (His)
Acidic amino acids:
aspartic acid (Asp), glutamic acid (Glu), asparagine (Asn), glutamine (Gln)
Hydrophilic, nonionic amino acids:
serine (Ser), threonine (Thr), cysteine (Cys), asparagine (Asn), glutamine (Gln)

-continued

| |
|---|
| Sulfur-containing amino acids: |
| cysteine (Cys) , methionine (Met) |
| Hydrophobic, aromatic amino acids: |
| phenylalanine (Phe), tyrosine (Tyr), tryptophan (Trp) |
| Hydrophobic, nonaromatic amino acids: |
| glycine (Gly), alanine (Ala), valine (Val), |
| leucine (Leu), isoleucine (Ile), proline (Pro) |

More particularly, the present polynucleic acid encodes one or more of the protein(s) encoded by the second, third, fourth, fifth, sixth and/or seventh open reading frames (ORF's 2–7) of the PRRSV isolates VR 2385, VR 2386, VR 2428, VR 2429, VR 2430, VR 2431, VR 2432, ISU-79 and/or ISU-1894 (e.g., SEQ ID NOS:15, 17, 19, 43, 45, 47, 49, 51, 53, 55, 57, 59, 61, 63 and 65).

Relatively short segments of polynucleic acid (about 20 bp or longer) in the genome of a virus can be used to screen or identify tissue and/or biological fluid samples from infected animals, and/or to identify related viruses, by methods described herein and known to those of ordinary skill in the fields of veterinary and viral diagnostics and veterinary medicine. Accordingly, a further aspect of the present invention encompasses an isolated (and if desired, purified) polynucleic acid consisting essentially of a fragment of from 15 to 2000 bp, preferably from 18 to 1000 bp, and more preferably from 21 to 100 bp in length, derived from ORF's 2–7 of a PRRSV genome (preferably the Iowa strain of PRRSV). Particularly preferably, the present isolated polynucleic acid fragments are obtained from a terminus of one or more of ORF's 2–7 of the genome of the Iowa strain of PRRSV, and most preferably, are selected from the group consisting of SEQ ID NOS:1–12, 22 and 28–34.

The present invention also concerns a diagnostic kit for assaying a porcine reproductive and respiratory syndrome virus, comprising (a) a first primer comprising a polynucleotide having a sequence of from 10 to 50 nucleotides in length which hybridizes to a genomic polynucleic acid from an Iowa strain of porcine reproductive and respiratory syndrome virus at a temperature of from 25 to 75° C., (b) a second primer comprising a polynucleotide having a sequence of from 10 to 50 nucleotides in length, said sequence of said second primer being found in said genomic polynucleic acid from said Iowa strain of porcine reproductive and respiratory syndrome virus and being downstream from the sequence to which the first primer hybridizes, and (c) a reagent which enables detection of an amplified polynucleic acid. Preferably, the reagent is an intercalating dye, the fluorescent properties of which change upon intercalation into double-stranded DNA.

ORF's 6 and 7 are not likely candidates for controlling virulence and replication phenotypes of PRRSV, as the nucleotide sequences of these genes are highly conserved among high virulence (hv) and low virulence (lv) isolates (see Experiment III below). However, ORF 5 in PRRSV isolates appears to be less conserved among high replication (hr) and low replication (lr) isolates. Therefore, it is believed that the presence of an ORF 5 from an hr PRRSV isolate in the present polynucleic acid will enhance the production and expression of a recombinant vaccine produced from the polynucleic acid.

Accordingly, it is preferred that the present polynucleic acid, when used for immunoprotective purposes (e.g., in the preparation of a vaccine), contain at least one copy of ORF 5 from a high-replication isolate (i.e., an isolate which grows to a titer of $10^6$–$10^7$ $TCID_{50}$ in, for example, CRL 11171 cells; also see the discussions in Experiments VIII–XI below).

On the other hand, the lv isolate VR 2431 appears to be a deletion mutant, relative to hv isolates (see Experiments III and VIII–XI below). The deletion appears to be in ORF 4, based on Northern blot analysis. Accordingly, when used for immunoprotective purposes, the present polynucleic acid preferably does not contain a region of ORF 4 from an hv isolate responsible for its high virulence, and more preferably, excludes the region of ORF 4 which does not overlap with the adjacent ORF's 3 and 5 (where ORF 4 overlaps with the adjacent-ORF's 3 and 5).

It is also known (at least for PRRSV) that neither the nucleocapsid protein nor antibodies thereto confer immunological protection against the virus (e.g., PRRSV) to pigs. Accordingly, the present polynucleic acid, when used for immunoprotective purposes, contains one or more copies of one or more regions from ORF's 2, 3, 4, 5 and 6 of a PRRSV isolate encoding an antigenic region of the viral envelope protein, but which does not result in the symptoms or histopathological changes associated with PRRS. Preferably, this region is immunologically cross-reactive with antibodies to envelope proteins of other PRRSV isolates. Similarly, the protein encoded by the present immunoprotective polynucleic acid confers immunological protection to a pig administered a composition comprising the protein, and antibodies to this protein are immunologically cross-reactive with the envelope proteins of other PRRSV isolates. More preferably, the present immunoprotective polynucleic acid encodes the entire envelope protein of a PRRSV isolate or a protein at least 80% homologous thereto and in which non-homologous residues are conservatively substituted, or a protein at least 90% homologous thereto.

The present isolated polynucleic acid fragments can be obtained by digestion of the cDNA corresponding to (complementary to) the viral polynucleic acids with one or more appropriate restriction enzymes, can be amplified by PCR and cloned, or can be synthesized using a commercially available automated polynucleotide synthesizer.

Another embodiment of the present invention concerns one or more proteins or antigenic fragments thereof from a PRRS virus, preferably from the Iowa strain of PRRSV. As described above, an antigenic fragment of a protein from a PRRS virus (preferably from the Iowa strain of PRRSV) is at least 5 amino acids in length, particularly preferably at least 10 amino acids in length, and provides or stimulates an immunologically protective response in a pig administered a composition containing the antigenic fragment.

Methods of determining the antigenic portion of a protein are known to those of ordinary skill in the art (see the description above). In addition, one may also determine an essential antigenic fragment of a protein by first showing that the full-length protein is antigenic in a host animal (e.g., a pig). If the protein is still antigenic in the presence of an antibody which specifically binds to a particular region or sequence of the protein, then that region or sequence may be non-essential for immunoprotection. On the other hand, if the protein is no longer antigenic in the presence of an antibody which specifically binds to a particular region or sequence of the protein, then that region or sequence is considered to be essential for antigenicity.

The present invention also concerns a protein or antigenic fragment thereof encoded by one or more of the polynucleic acids defined above, and preferably by one or more of the ORF's of a PRRSV, more preferably of the Iowa strain of PRRSV. The present proteins and antigenic fragments are useful in immunizing pigs against PRRSV, in serological tests for screening pigs for exposure to or infection by PRRSV (particularly the Iowa strain of PRRSV), etc.

For example, the present protein may be selected from the group consisting of the proteins encoded by ORF's 2–7 of VR 2385, ISU-22 (VR 2429), ISU-55 (VR 2430), ISU-1894, ISU-79 and ISU-3927 (VR 2431) (e.g., SEQ ID NOS:15, 17, 19, 43, 45, 47, 49, 51, 53, 55, 57, 59, 61, 67, 69 and 71); antigenic regions of at least one of the proteins of SEQ ID SEQ ID NOS:15, 17, 19, 43, 45, 47, 49, 51, 53, 55, 57, 59, 61, 67, 69 and 71 having a length of from 5 amino acids to less than the full length of the polypeptides of SEQ ID NOS:15, 17, 19, 43, 45, 47, 49, 51, 53, 55, 57, 59, 61, 67, 69 and 71; polypeptides at least 80% homologous with a protein encoded by one of the ORF's 2–5 of VR 2385 (SEQ ID NOS:15, 67, 69 and 71); and polypeptides at least 97% homologous with a protein encoded by one of the ORF's 6–7 of VR 2385, VR 2429, VR 2430, ISU-1894, ISU-79 and VR 2431 (e.g., SEQ ID NOS:17, 19, 43, 45, 47, 49, 51, 53, 55, 57, 59 and 61). Preferably, the present protein has a sequence selected from the group consisting of SEQ ID NOS:15, 17, 19, 43, 45, 47, 49, 51, 53, 55, 57, 59, 61, 67, 69 and 71; variants thereof which provide effective immunological protection to a pig administered the same and in which from 1 to 100 (preferably from 1 to 50 and more preferably from 1 to 25) deletions or conservative substitutions in the amino acid sequence exist; and antigenic fragments thereof at least 5 and preferably at least 10 amino acids in length which provide effective immunological protection to a pig administered the same.

More preferably, the present protein variant or protein fragment has a binding affinity (or association constant) of at least 1% and preferably at least 10% of the binding affinity of the corresponding full-length, naturally-occurring protein to a monoclonal antibody which specifically binds to the full-length, naturally-occurring protein (i.e., the protein encoded by a PRRSV ORF). Most preferably, the present protein has a sequence selected from the group consisting of SEQ ID NO:15, SEQ ID NO:17, SEQ ID NO:19, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:67, SEQ ID NO:69 and SEQ ID NO:71.

The present invention may also concern a biologically pure virus, characterized in that it contains the present polynucleic acid and/or that it causes a porcine reproductive and respiratory disease which may include one or more of the following histological lesions: gross and/or microscopic lung lesions (e.g., lung consolidation), Type II pneumocytes, myocarditis, encephalitis, alveolar exudate formation and syncytia formation. The phrase "biologically pure" refers to a sample of a virus or infectious agent in which all progeny are derived from a single parent. Usually, a "biologically pure" virus sample is achieved by 3×plaque purification in cell culture.

In particular, the present biologically pure virus or infectious agent is an isolate of the Iowa strain or porcine reproductive and respiratory syndrome virus, samples of which have been deposited under the terms of the Budapest Treaty at the American Culture Collection, 10801 University Blvd., Manassas, Va. 20110-2209, U.S.A., under the accession numbers VR 2385, VR 2386, VR 2428, VR 2429, VR 2430, VR 2431, VR 2484 and VR 2475.

In addition to the characteristics (a)–(e) described above, the Iowa strain of PRRSV may also be characterized by Northemmblots of its mRNA. For example, the Iowa strain of PRRSV may contain either 7 or 9 mRNA's, and may also have deletions or variations in their size. In particular, as will be described in the Experiments below, the mrRNA's of the Iowa strain of PRRSV may contain up to four deletions, relative to VR 2385/VR 2386.

The present invention further concerns a composition for protecting a pig from viral infection, comprising an amount of the present vaccine effective to raise an immunological response to a virus which causes a porcine reproductive and respiratory disease in a physiologically acceptable carrier.

An effective amount of the present vaccine is one in which a sufficient immunological response to the vaccine is raised to protect a pig exposed to a virus which causes a porcine reproductive and respiratory disease or related illness. Preferably, the pig is protected to an extent in which from one to all of the adverse physiological symptoms or effects (e.g., lung lesions) of the disease to be prevented are found to be significantly reduced.

The composition can be administered in a single dose, or in repeated doses. Dosages may contain, for example, from 1 to 1,000 micrograms of virus-based antigen (vaccine), but should not contain an amount of virus-based antigen sufficient to result in an adverse reaction or physiological symptoms of infection. Methods are known in the art for determining suitable dosages of active antigenic agent.

The composition containing the present vaccine may be administered in conjunction with an adjuvant or with an acceptable carrier which may prolong or sustain the immunological response in the host animal. An adjuvant is a substance that increases the immunological response to the present vaccine when combined therewith. The adjuvant may be administered at the same time and at the same site as the vaccine or at a different time, for example, as a booster. Adjuvants also may advantageously be administered to the animal in a manner or at a site or location different from the manner, site or location in which the vaccine is administered. Adjuvants include aluminum hydroxide, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete adjuvant, Freund's complete adjuvant, and the like. Toxin-based adjuvants, such as diphtheria toxin, tetanus toxin and pertussis toxin, may be inactivated prior to use, for example, by treatment with formaldehyde.

The present invention also concerns a method of protecting a pig from infection against a virus which causes a porcine reproductive and respiratory disease, comprising administering an effective amount of a vaccine which raises an immunological response against such a virus to a pig in need of protection against infection by such a virus. By "protecting a pig from infection" against a porcine reproductive and respiratory syndrome virus or infectious agent, it is meant that after administration of the present vaccine to a pig, the pig shows reduced (less severe) or no clinical symptoms (such as fever) associated with the corresponding disease, relative to control (infected) pigs. The clinical symptoms may be quantified (e.g., fever, antibody count, and/or lung lesions), semi-quantified (e.g., severity of respiratory distress), or qualified.

The present invention concerns a system for measuring respiratory distress in affected pigs. The present clinical respiratory scoring system evaluates the respiratory distress of affected pigs by the following scale:

| | |
|---|---|
| 0 = | no disease; normal breathing |
| 1 = | mild dyspnea and polypnea when the pigs are stressed (forced to breathe in larger volumes and/or at an accelerated rate) |
| 2 = | mild dyspnea and polypnea when the pigs are at rest |
| 3 = | moderate dyspnea and polypnea when the pigs are stressed |
| 4 = | moderate dyspnea and polypnea when the pigs are at rest |
| 5 = | severe dyspnea and polypnea when the pigs are stressed |
| 6 = | severe dyspnea and polypnea when the pigs are at rest |

In the present clinical respiratory scoring system, a score of "0" is normal, and indicates that the pig is unaffected by a porcine reproductive and respiratory disease. A score of "3" indicates moderate respiratory disease, and a score of "6" indicates very severe respiratory disease. An amount of the present vaccine or composition may be considered effective if a group of challenged pigs given the vaccine or composition show a lower average clinical respiratory score than a group of identically challenged pigs not given the vaccine or composition. (A pig is considered "challenged" when exposed to a concentration of an infectious agent sufficient to cause disease in a non-vaccinated animal.)

Preferably, the present vaccine composition is administered directly to a pig not yet exposed to a virus which causes a reproductive or respiratory disease. The present vaccine may be administered orally or parenterally. Examples of parenteral routes of administration include intradermal, intramuscular, intravenous, intraperitoneal, subcutaneous and intranasal routes of administration.

When administered as a solution, the present vaccine may be prepared in the form of an aqueous solution, a syrup, an elixir, or a tincture. Such formulations are known in the art, and are prepared by dissolution of the antigen and other appropriate additives in the appropriate solvent systems. Such solvents include water, saline, ethanol, ethylene glycol, glycerol, A1 fluid, etc. Suitable additives known in the art include certified dyes, flavors, sweeteners, and antimicrobial preservatives, such as thimerosal (sodium ethylmercurithiosalicylate). Such solutions may be stabilized, for example, by addition of partially hydrolyzed gelatin, sorbitol, or cell culture medium, and may be buffered by methods known in the art, using reagents known in the art, such as sodium hydrogen phosphate, sodium dihydrogen phosphate, potassium hydrogen phosphate and/or potassium dihydrogen phosphate.

Liquid formulations may also include suspensions and emulsions. The preparation of suspensions, for example using a colloid mill, and emulsions, for example using a homogenizer, is known in the art.

Parenteral dosage forms, designed for injection into body fluid systems, require proper isotonicity and pH buffering to the corresponding levels of porcine body fluids. Parenteral formulations must also be sterilized prior to use.

Isotonicity can be adjusted with sodium chloride and other salts as needed. Other solvents, such as ethanol or propylene glycol, can be used to increase solubility of ingredients of the composition and stability of the solution. Further additives which can be used in the present formulation include dextrose, conventional antioxidants and conventional chelating agents, such as ethylenediamine tetraacetic acid (EDTA).

The present invention also concerns a method of producing the present vaccine, comprising the steps of synthesizing or isolating a polynucleic acid of a PRRS virus (preferably the Iowa strain) encoding an antigenic protein or portion thereof (preferably the viral coat protein), infecting a suitable host cell with the polynucleic acid, culturing the host cell, and isolating the antigenic protein or portion thereof from the culture. Alternatively, the polynucleic acid itself can confer immunoprotective activity to a host animal to which it is administered.

Preferably, the vaccine is collected from a culture medium by the steps of (i) precipitating transfected, cultured host cells, (ii) lysing the precipitated cells, and (iii) isolating the vaccine. Particularly preferably, the host cells infected with the virus or infectious agent are cultured in a suitable medium prior to collecting.

Preferably, after culturing infected host cells, the infected host cells are precipitated by adding a solution of a conventional poly(ethylene glycol) (PEG) to the culture medium, in an amount sufficient to precipitate the infected cells. The precipitated infected cells may be further purified by centrifugation. The precipitated cells are then lysed by methods known to those of ordinary skill in the art. Preferably, the cells are lysed by repeated freezing and thawing (three cycles of freezing and thawing is particularly preferred). Lysing the precipitated cells releases the virus, which may then be collected, preferably by centrifugation. The virus may be isolated and purified by centrifuging in a CsCl gradient, then recovering the appropriate virus-containing band from the CsCl gradient.

Alternatively, the infected cell culture may be frozen and thawed to lyse the cells. The frozen and thawed cell culture material may be used directly as a live vaccine. Preferably, however, the frozen and thawed cell culture material is lyophilized (for storage), then rehydrated for use as a vaccine.

The culture media may contain buffered saline, essential nutrients and suitable sources of carbon and nitrogen recognized in the art, in concentrations sufficient to permit growth of virus-infected cells. Suitable culture media include Dulbecco's minimal essential medium (DMEM), Eagle's minimal essential medium (MEM), Ham's medium, medium 199, fetal bovine serum, fetal calf serum, and other equivalent media which support the growth of virus-infected cells. The culture medium may be supplemented with fetal bovine serum (up to 10%) and/or L-glutamine (up to 2 mM), or other appropriate additives, such as conventional growth supplements and/or antibiotics. A preferred medium is DMEM.

Preferably, the present vaccine is prepared from a virus or infectious agent cultured in an appropriate cell line. The cell line is preferably PSP-36 or an equivalent cell line capable of being infected with the virus and cultured. An example of a cell line equivalent to PSP-36 is the cell line PSP-36-SAH, which was deposited under the terms of the Budapest Treaty at the American Type Culture Collection, 12301 Parklawn Drive, Rockville, Md. 20852, U.S.A., on Oct. 28, 1992, under the deposit number CRL 11171. Another equivalent cell line is MA-104, available commercially from Whittaker Bioproducts, Inc. (Walkersville, Md.). Preliminary results indicate that the Iowa strain of PRRSV can also be cultured in porcine turbinate cells.

There also appears to be a relationship between the severity of histopathology caused by a challenge with a standard amount of a particular isolate and the titer to which the isolate can be grown in a mammalian host cell (e.g., CRL 11171, MA-104 cells [from African green monkey kidney], etc.).

Accordingly, the present invention also concerns a method of culturing a PRRS virus, comprising infecting cell line PSP-36, CRL 11171 or an equivalent cell line and culturing the infected cell line in a suitable medium. An "equivalent cell line" to PSP-36 or CRL 11171 is one which is capable of being infected with the virus and cultured, thereby producing culturable infected cells. Equivalent cell lines include MA-104, PSP-36-SAH and MARC-145 cells (available from the National Veterinary Services Laboratory, Ames, Iowa), for example.

Preferably, the virus cultured is at least one isolate of the Iowa strain of PRRSV. Particularly preferably, the present vaccine is prepared from such a culture of the Iowa strain of PRRSV, cultivated in PSP-36 cells, and plaque-purified at least three times.

The cell line MA-104 is obtained from monkey kidney cells, and is epithelial-like. MA-104 cells form a confluent monolayer in culture flasks containing Dulbecco's minimal essential medium and 10% FBS (fetal bovine serum). When the monolayer is formed, the cells are inoculated with a sample of 10% homogenized tissue, taken from an appropriate tissue (such as lung and/or heart) in an infected pig. Preferably, appropriate antibiotics are present, to permit growth of virus and host cells and to suppress growth and/or viability of cells other than the host cells (e.g., bacteria or yeast).

Both PSP-36 and MA-104 cells grow some isolates of the PRRS virus to high titers (over 107 $TCID_{50}$/ml). PSP-36 and MA-104 cells will also grow the infectious agent associated with the Iowa strain of PRRSV. MA-104 cells also are able to grow rotaviruses, polioviruses, and other viruses.

CL2621 cells are believed to be of non-porcine origin and are epithelial-like, and are proprietary (Boehringer-Ingelheim). By contrast to PSP-36 and MA-104, some samples of the virus which causes PRRS have been unsuccessfully cultured in CL2621 cells (Bautista et al, *American Association of Swine Practitioners Newsletter,* 4:32, 1992).

The primary characteristics of CL2621 are that it is of non-swine origin, and is epithelial-like, growing in MEM medium. However, Benfield et al (*J. Vet. Diagn. Invest.,* 1992; 4:127–133) have reported that CL2621 cells were used to propagate PRRS virus, but MA-104 cells were used to control polio virus propagation, thus inferring that CL2621 is not the same as MA-104, and that the same cell may not propagate both viruses.

The Iowa strain of PRRSV generally cannot grow in cell lines other than PSP-36, PSP-36-SAH and MA-104. As described above, however, some viruses which cause PRRS have been reported to grow in both CL2621 and primary swine alveolar macrophages, although some strains of PRRS virus do not grow in PSP-36, MA-104 or CL2621 cells.

The present vaccine, virus isolates, proteins and polynucleic acids can be used to prepare antibodies which may provide immunological resistance to a patient (in this case, a pig) exposed to a virus or infectious agent. Antibodies encompassed by the present invention immunologically bind either to (1) a vaccine which protects a pig against a PRRS virus or (2) to the PRRS virus itself. The present antibodies also have the following utilities: (1) as a diagnostic agent for determining whether a pig has been exposed to a PRRS virus or infectious agent, and (2) in the preparation of the present vaccine. The present antibody may be used to prepare an immunoaffinity column by known methods, and the immunoaffinity column can be used to isolate the virus or infectious agent, or a protein thereof.

To raise antibodies to such vaccines or viruses, one immunizes an appropriate host animal, such as a mouse, rabbit, or other animals used for such inoculation, with the protein used to prepare the vaccine. The host animal is then immunized (injected) with one of the types of vaccines described above, optionally administering an immune-enhancing agent (adjuvant), such as those described above. The host animal is preferably subsequently immunized from 1 to 5 times at certain intervals of time, preferably every 1 to 4 weeks, most preferably every 2 weeks. The host animals are then sacrificed, and their blood is collected. Sera is then separated by known techniques from the whole blood collected. The sera contains antibodies to the vaccines. Antibodies can also be purified by known methods to provide immunoglobulin G (IgG) antibodies.

The present invention also encompasses monoclonal antibodies to the present vaccines and/or viruses. Monoclonal antibodies may be produced by the method of Kohler et al (*Nature, vol.* 256 (1975), pages 495–497). Basically, the immune cells from a whole cell preparation of the spleen of the immunized host animal (described above) are fused with myeloma cells by a conventional procedure to produce hybridomas. Hybridomas are cultured, and the resulting culture fluid is screened against the fluid or inoculum carrying the infectious agent (virus or vaccine). Introducing the hybridoma into the peritoneum of the host animal produces a peritoneal growth of the hybridoma. Collection of the ascites fluid of the host animal provides a sample of the monoclonal antibody to the infectious agent produced by the hybridoma. Also, supernatant from the hybridoma cell culture can be used as a source of the monoclonal antibody, which is isolated by methods known to those of ordinary skill in the art. Preferably, the present antibody is of the IgG or IgM type of immunoglobulin.

The present invention also concerns a method of treating a pig suffering from a reproductive and respiratory disease, comprising administering an effective amount of an antibody which immunologically binds to a virus which causes a porcine reproductive and respiratory disease or to a vaccine which protects a pig against infection by a porcine reproductive and respiratory virus in a physiologically acceptable carrier to a pig in need thereof.

The present method also concerns a method of diagnosing infection of a pig by or exposure of a herd to a porcine reproductive and respiratory syndrome virus and a diagnostic kit for assaying the same, comprising the present antibody (preferably a monoclonal antibody) and a diagnostic agent which indicates a positive immunological reaction with said antibody (preferably comprising peroxidase-conjugated streptavidin, a biotinylated antibody to a PRRSV protein or antigen and a peroxidase). The present kit may further comprise aqueous hydrogen peroxide, a protease which digests the porcine tissue sample, a fluorescent dye (e.g., 3,3'-diaminobenzidine tetrahydrochloride), and a tissue stain (e.g., hematoxylin).

A diagnosis of PRRS relies on compiling information from the clinical history of the herd being diagnosed, from serology and pathology of infected pigs, and ultimately, on isolation of the PRRS virus (PRRSV) from the infected herd. Thus, the present method of detecting PRRSV is useful in diagnosing infection by and/or exposure to the virus in a herd.

Clinical signs vary widely between farms, and thus, are not the most reliable evidence of a definitive diagnosis, except in the case of a severe acute outbreak in naive herds which experience abortion storms, increased numbers of stillborn pigs, and severe neonatal and nursery pig pneumonia. Presently, the most common clinical presentation is pneumonia and miscellaneous bacterial problems in 3–10 week old pigs. However, many PRRSV-positive herds have no apparent reproductive or respiratory problems.

There are some gross lesions that are very suggestive of PRRSV infection in growing pigs. The most consistent experimentally reproducible gross lesion in 3–10 week-old pigs inoculated with several different PRRSV strains is lymphadenopathy. In particular, iliac and mediastinal lymph nodes are often 3–10 times normal size, tan in color, and sometimes cystic. The lymph nodes are not normally hyperemic, such as the lesion/conditions seen in bacterial septicemia.

Three histologic lesions are consistent with PRRSV infection. Interstitial pneumonia is commonly observed and is characterized by septal infiltration with mononuclear cells, type 2 pneumocyte proliferation, and the presence of necrotic cells in the alveolar spaces. Nonsuppurative perivascular myocarditis and hyperplastic lymph nodes are commonly observed in the subacute stages of disease.

The degree of grossly visible pneumonia is strain dependent. In general, the lungs fail to collapse and have a patchy distribution of 10–80% tan-colored consolidation with irregular borders. Encephalitis is less often observed. Lesions in the fetus and placenta are rarely observed by light microscopy.

However, the percentage of consolidation in the lungs provides a particularly reliable test for infection by PRRSV (i.e., $\geqq$10% consolidation at any time from 3 to 10 days post-infection (DPI) is a positive indication of infection), particularly by a high virulence phenotype (hv) virus ($\geqq$40% consolidation at any time from 3 to 10 days DPI is a positive indication of infection by an hv PRRSV isolate).

In contrast to histopathology on lung tissue(s), most laboratories are routinely using either an indirect-fluorescent antibody (IFA) test or immunoperoxidase monolayer assay (IPMA) for serum antibody detection. With both the IFA and IPMA, one must subjectively determine endpoints and thus the tests are not automatable. Serum virus (SVN) neutralization tests have also been developed, and ELISA tests are currently used in some research laboratories. Antibodies detected by the IFA test usually appear with 10 days of exposure but may be relatively short-lived, sometimes disappearing within 3 months.

Antibodies detected by ELISA usually appear within 3 weeks, but their duration is unknown. SVN antibodies usually are not detected until 4–5 weeks post exposure. The SVN test is considered less sensitive in acute disease, but improvements have been made in the SVN test using seronegative porcine serum supplementation. SVN titers reportedly are measurable longer than titers in IFA and IPMA, and thus, may be better suited for detection of positive animals in chronically infected herds.

In IFA, infected cells are fixed with acetone and methanol solutions, and antibodies for the convalescent sera of infected pigs are incubated with the infected cells, preferably for about 30 min. at 37° C. A positive immunological reaction is one in which the antibody binds to the virus-infected cells, but is not washed out by subsequent washing steps (usually 3× with PBS buffer). A second antibody (an anti-antibody) labeled with a fluorescent reagent (FITC) is then added and incubated, preferably for anther 30 min. A positive immunological reaction results in the second antibody binding to the first, being retained after washing, and resulting in a fluorescent signal, which can be detected and semi-quantified. A negative immunological reaction results in little or no binding of the antibody to the infected cell. Therefore, the second, fluorescently-labeled antibody fails to bind, the fluorescent label is washed out, and little or no fluorescence is detected, compared to an appropriate positive control.

IPA and ELISA kits are similar to the IFA kit, except that the second antibody is labeled with a specific enzyme, instead of a fluorescent reagent. Thus, one adds an appropriate substrate for the enzyme bound to the second antibody which results in the production of a colored product, which is then detected and quantified by colorimetry, for example.

Clinicians use antibody titers to determine the appropriate time for vaccination and/or implementation of management or control strategies. Prior to the present invention, serology tests did not provide antibody titer levels adequate or reliable enough to make animal health care decisions. It may have been appropriate to look for a change from seronegative to seropositive status, or for at least a 4-fold increase in titer, as a positive indication of PRRSV infection/exposure. Looking for an increasing percentage of seropositive pigs in a particular age group over time in a herd can be useful to determine where the virus is maintained and actively spreading. Sows infected in the early 3rd trimester and aborting near term will likely not show increasing titers, however.

Virus isolation (VI) provides a definitive diagnosis, but has some limitations. Virus is rarely isolated from stillborn or autolyzed aborted fetuses. Sows infected early in the last trimester may have transient viremia and not abort until late term. Dead pigs of any age are not the best samples for VI, because the virus does not survive well at room temperature. Tissues should be removed from the carcass, packaged separately, and refrigerated as soon as possible to obtain a viable virus sample.

The best tissues for virus isolation are tonsil, lung, lymph nodes, and spleen. Serum is also an excellent sample for virus isolation, since (a) viremia is often prolonged in growing pigs, (b) the sample is easy to handle, and (c) the sample can be quickly chilled and processed.

Variation between laboratories in the ability to isolate PRRSV is high because the tests, reagents, cell lines, and media used to detect/screen for PRRSV have not been standardized. The efficacy of isolation varies because not all North American strains will grow on each cell line. Frozen tissue-section IFA tests have been used with limited success.

Serum virus neutralization (SVN) tests have also been developed, and ELISA tests are currently used in some research laboratories. Antibodies detected by ELISA usually appear within 3 weeks, but their duration is unknown. SVN antibodies usually are not detected until 4–5 weeks post-exposure. The SVN test is considered less sensitive in acute disease, but improvements have been made in the SVN test using seronegative porcine serum supplementation. SVN titers reportedly are measurable for a longer period of time than titers in IFA and IPMA. Thus, SVN titers may be better suited for detection of positive animals in chronically infected herds.

Prior to the present invention, however, serology tests did not provide antibody titer levels adequate or reliable enough to make animal health care decisions. Looking for an increasing percentage of seropositive pigs in a particular age group over time in a herd can also be useful to determine where the virus is maintained and actively spreading. Sows infected in the early third trimester and aborting near term will likely not show increasing titers, however. Thus, although it may have been appropriate to look for a change from seronegative to seropositive status or for at least a 4-fold increase in titer as a positive indication of PRRSV infection and/or exposure, a need for a more reliable titer-based assay is felt.

Thus, the present invention also concerns a method for detecting PRRSV antigen in tissues. The present diagnostic method, employing an immunoperoxidase test (IPT) preferably on formalin-fixed tissue, appears to be quite useful to confirm the presence of active infection, and may provide a significant and meaningful increase in the reliability of titer-based assays. A section of lungs, tonsils, mediastinal lymph nodes, and tracheobronchial lymph nodes from 26 pigs experimentally inoculated with ATCC VR 2385 PRRSV was examined (see Experiment V below). The virus was detected in 18/26 lungs, 26/26 tonsils, 15/26 mediastinal lymph nodes, and 14/26 tracheobronchial lymph nodes. The pigs in this study were killed over a 28 day period (post-inoculation). The virus was detected in at least one tissue in every pig necropsied up to 10 days post inoculation.

A complete technique for the present immunoperoxidase technique for PRRSV antigen detection in porcine tissues, based on a streptavidin-biotin assay, is described in Example V hereinunder. Briefly, the present method for detecting PRRSV comprises removing endogenous peroxidase from an isolated porcine tissue sample with aqueous hydrogen peroxide (preferably, a 0.1–5%, and more preferably, 0.1–1.0% solution), then digesting the tissue with sufficient amount of an appropriate protease to expose viral antigens (for example, Protease XIV, Sigma Chemical Company, St. Louis, Mo., and more preferably, a 0.001–0.25% aqueous solution thereof). Thereafter, the method further comprises incubating primary monoclonal antibody ascites fluid (preferably diluted in TRIS/PBS by an amount of from 1:10 to 1:100,000, and more preferably, from 1:100 to 1:10,000) with the protease-treated tissue sections in a humidified chamber for a sufficient length of time and at an appropriate temperature to provide essentially complete immunological binding to occur, if it can in fact occur (e.g., 16 hours at 4° C.).

One suitable monoclonal antibody for use in the present diagnostic assay is SDOW-17 (available from Dr. David Benfield, South Dakota State-Univ.), which recognizes a conserved epitope of the PRRSV nucleocapsid protein (Nelson et al, "Differentiation of U.S. and European isolates of porcine reproductive and respiratory syndrome virus by monoclonal antibodies," *J. Clin. Micro.,* 31:3184–3189 (1993)).

The present method for detecting PRRSV then further comprises incubating biotinylated goat anti-mouse linking antibody (available from Dako Corporation, Carpintera, Calif.) with the tissue, followed by incubating peroxidase-conjugated streptavidin with the biotinylated antibody-treated tissue (Zymed Laboratories, South San Francisco, Calif.). The method then further comprises incubating the peroxidase-conjugated streptavidin-treated tissue with a chromagen, such as 3,3'-diaminobenzidine tetrahydrochloride (available from Vector Laboratories Inc., Burlingame, Calif.), and finally, staining the treated tissue with hematoxylin.

Particularly when combined with the further diagnostic techniques of histopathology, virus isolation procedures and serology, the present tissue immunoperoxidase antigen detection technique offers a rapid and reliable diagnosis of PRRSV infection.

Other features of the invention will become apparent in the course of the following descriptions of exemplary embodiments, which are given for illustration of the invention, and are not intended to be limiting thereof.

EXPERIMENT I

Molecular Cloning and Nucleotide Sequencing of the 3'-Terminal Region of VR 2385 (Plaque-Purified ISU-12)

(I) Materials and Methods (A) Virus Propagation and Purification

A continuous cell line, PSP-36, was used to isolate and propagate ISU-12. The ISU-12 virus was plaque-purified 3 times on PSP-36 cells (plaque-purified ISU-12 virus was deposited under the terms and conditions of the Budapest Treaty at the American Type Culture Collection, 12301 Parklawn Drive, Rockville, Md. 20852, U.S.A., under Accession No. VR 2385). The PSP-36 cells were then infected with the plaque-purified virus. When more than 70% of the infected cells showed cytopathic changes, the culture was frozen and thawed three times. The culture medium was then clarified by low-speed centrifugation at 5,000×g for 15 min. at 4° C. The virus was then precipitated with 7% PEG-8000 and 2.3% NaCl at 4° C. overnight with stirring, and the precipitate was pelleted by centrifugation. The virus pellets were then resuspended in 2 ml of tris-EDTA buffer, and layered on top of a CsCl gradient (1.1245–1.2858 g/ml). After ultracentrifugation at 28,000 rpm for about 8 hours at 20° C., a clear band with a density of 1.15–1.18 g/ml was observed and harvested. The infectivity titer of this band was determined by IFA, and the titer was found to be $10^6$ $TCID_{50}$/ml. Typical virus particles were also observed by negative staining electron microscopy (EM).

(B) Isolation of Viral RNA

Total RNA was isolated from the virus-containing band in the CsCl gradient with a commercially available RNA isolation kit (obtained from Stratagene). Poly(A) RNA was then enriched by oligo (dT)-cellulose column chromatography according to the procedure described by the manufacturer of the column (Invitrogen).

(c) Construction of VR 2385 cDNA λ library

Figure 3A:
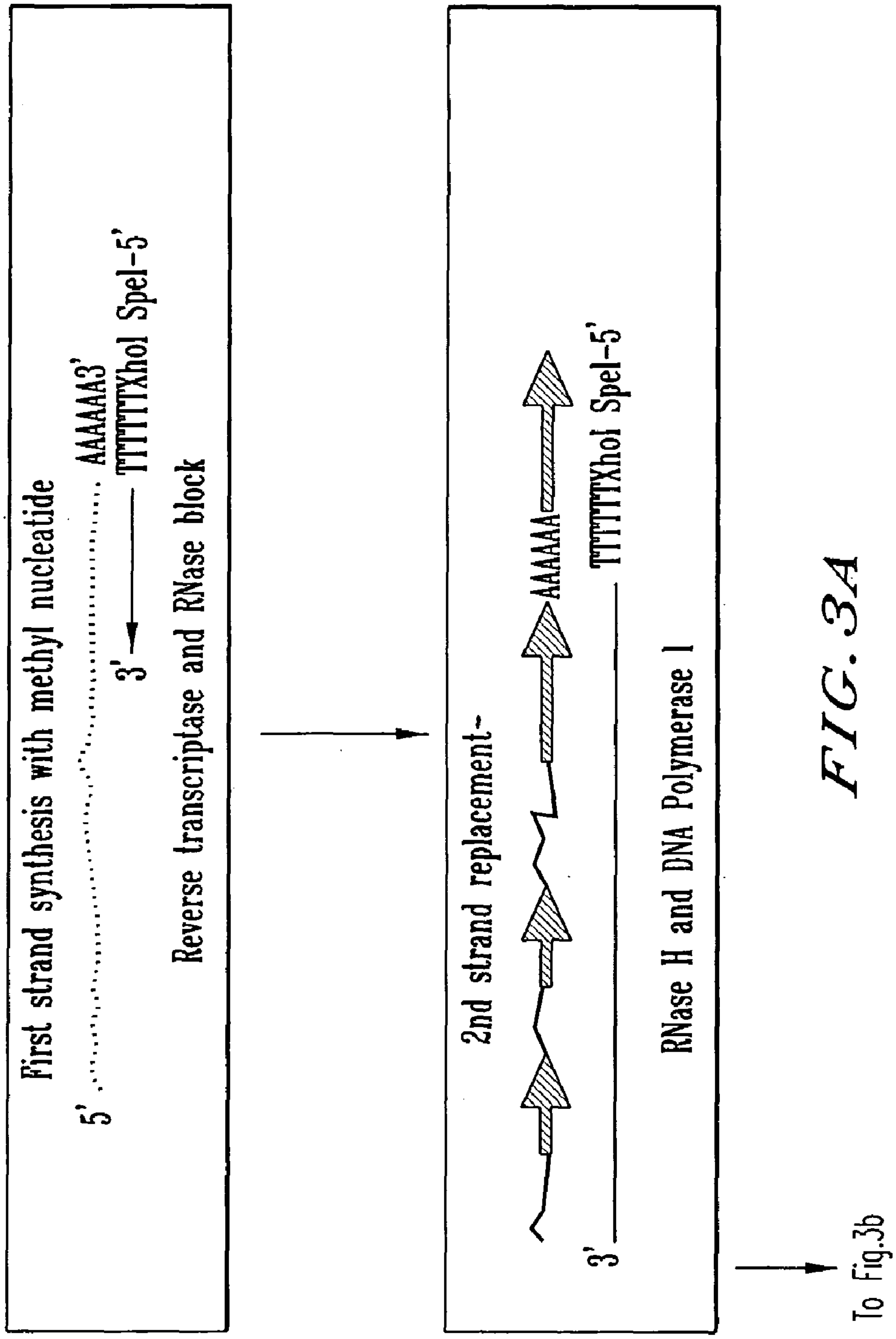
FIGS. 3A, B and C shows a general schematic procedure for the construction of a cDNA λ library as described by the manufacturer (Stratagene)
Figure 3B:
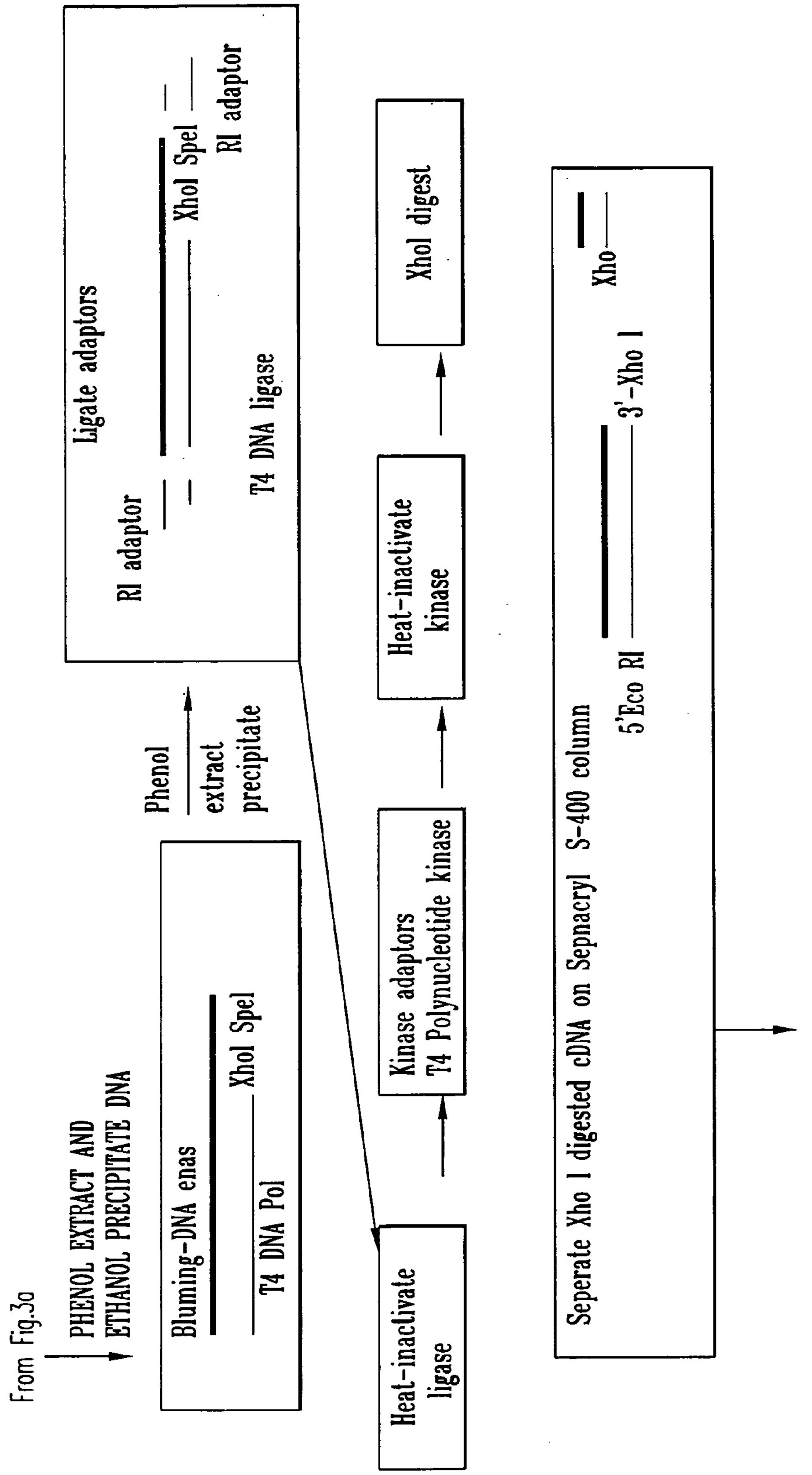
Figure 3C:
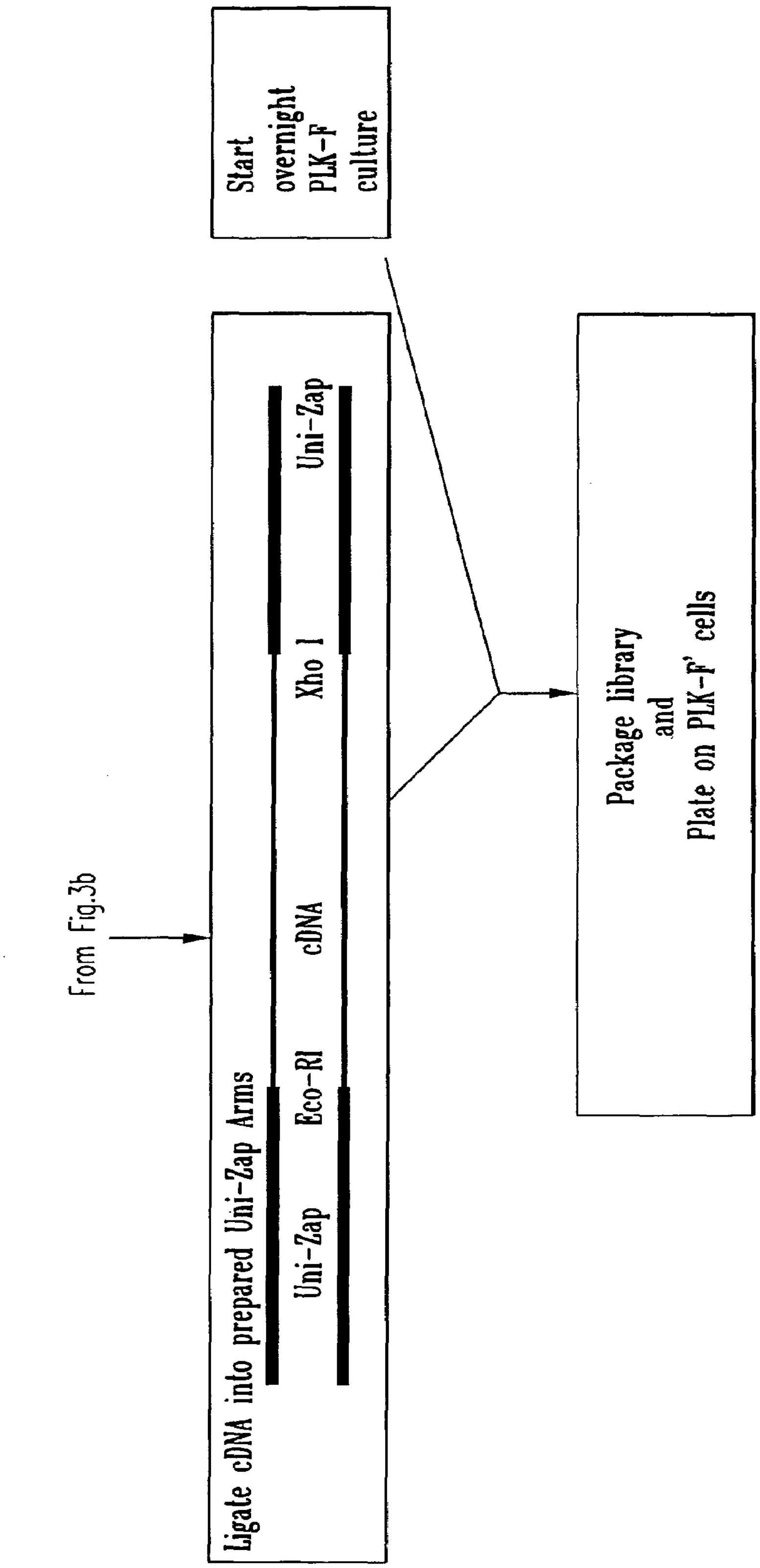

A general schematic procedure for the construction of a cDNA λ library is shown in FIG. 3. First strand cDNA synthesis from mRNA was conducted by reverse transcription using an oligo (dT) primer having a Xho I restriction site. The nucleotide mixture contained normal dATP, dGTP, dTTP and the analog 5-methyl dCTP, which protects the cDNA from restriction enzymes used in subsequent cloning steps.

Second strand cDNA synthesis was then conducted with RNase H and DNA polymerase I. The cDNA termini were blunted (blunt-ended) with T4 DNA polymerase, ligated to EcoR I adaptors with T4 DNA ligase, and subsequently phosphorylated with T4 polynucleotide kinase. The cDNA was digested with Xho I, and the digested cDNA were size-selected on an agarose gel. Digested cDNA larger than 1 kb in size were selected and purified by a commercially available DNA purification kit (GENECLEAN, available from BIO 101, Inc., La Jolla, Calif.).

The purified cDNA was then ligated into lambda phage vector arms, engineered with Xho I and EcoR I cohesive ends. The ligated vector was packaged into infectious lambda phages with lambda extracts. The SURE strain (available from Stratagene) of *E. coli* cells were used for transfection, and the lambda library was then amplified and titrated in the XL-1 blue cell strain.

(D) Screening the λ Library by Differential Hybridization

Figure 4:
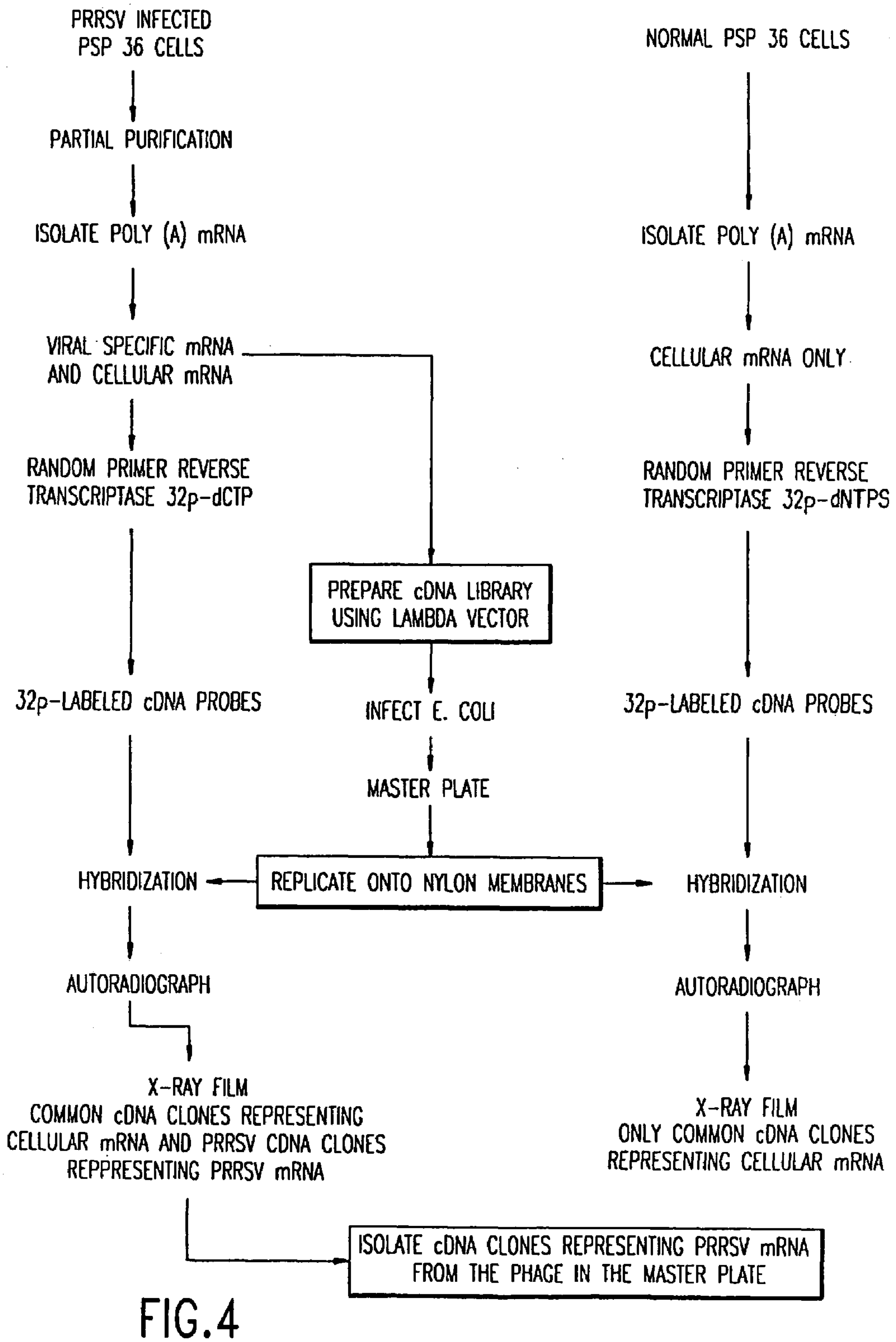
FIG. 4 shows a general schematic procedure for identifying authentic clones of the PRRS virus isolate ISU-12 (VR 2385) by differential hybridization (modified from "Recombinant DNA," 2nd ed., Watson, J. D., et al., eds. (1992), p. 110)

A general schematic procedure for identifying authentic clones of the PRRS virus VR 2385 strain by differential hybridization is shown in FIG. 4, and is described hereunder. The λ library was plated on XL-1 blue cells, plaques were lifted onto nylon membranes in duplicates, and denatured with 0.5 N NaOH by conventional methodology. Messenger RNA's from both virus-infected PSP-36 cells and non-infected PSP-36 cells were isolated by oligo (dT) cellulose column chromatography as described by the manufacturer of the column (Invitrogen).

Complementary DNA probes were synthesized from mRNA's isolated from virus-infected PSP-36 cells and normal PSP-36 cells using random-primers in the presence of $^{32}$P-dCTP according to the procedure described by the manufacturer (Amersham). Two probes (the first synthesized from virus-infected PSP-36 cells, the other from normal, uninfected PSP-36 cells) were then purified individually by Sephadex G-50 column chromatography. The probes were hybridized with the duplicated nylon membranes, respectively, at 42° C. in 50% formamide. Plaques which hybridized with the probe prepared from virus infected cells, but not with the probe prepared from normal cells, were isolated. The phagemids containing viral cDNA inserts were rescued by in vitro excision with the help of G408 helper phage. The rescued phagemids were then amplified on XL-1 blue cells. The plasmids containing viral cDNA inserts were isolated by Qiagen column chromatography, and were subsequently sequenced.

(E) Nucleotide Sequencing and Sequence Analysis

Plasmids containing viral cDNA inserts were purified by Qiagen column chromatography, and sequenced by Sanger's dideoxy method with universal and reverse primers, as well as a variety of internal oligonucleotide primers. Sequences were obtained from at least three separate clones. Additional clones or regions were sequenced when ambiguous sequence data were obtained. The nucleotide sequence data were assembled and analyzed independently using two computer software programs, GENEWORKS (IntelliGenetics, Inc., Mountain View, Calif.) and MACVECTOR (International Biotechnologies, Inc., New Haven, Conn.).

(F) Oligonucleotide Primers

Oligonucleotides were synthesized as single-stranded DNA using an automated DNA synthesizer (Applied Biosystems) and purified by HPLC. Oligonucleotides PP284 (5'-CGGCCGTGTG GTTCTCGCCA AT-3'; SEQ ID NO:1) and PP285 (5'-CCCCATTTCC CTCTAGCGAC TG-3'; SEQ ID NO:2) were synthesized for PCR amplification. A DNA probe was generated with these two primers from the extreme 3' end of the viral genome for Northern blot analysis (see discussion below). Oligonucleotides PP286 (5'-GCCGCGGAAC CATCAAGCAC-3'; SEQ ID NO:3) and PP287 (5'-CAACTTGACG CTATGTGAGC-3'; SEQ ID NO:4) were synthesized for PCR amplification. A DNA probe generated by these two primers was used to further screen the λ library. Oligonucleotides PP288 (5'-GCGGTCTGGA TTGACGACAG-3'; SEQ ID NO:5), PP289 (5'-GACTGCTAGG GCTTCTGCAC-3'; SEQ ID NO:6), PP386 (5'-GCCATTCAGC TCACATAGCG-3'; SEQ ID NO:7), PP286 and PP287 were used as sequencing primers to obtain internal sequences.

(G) Northern Blot Analysis

Figure 5:
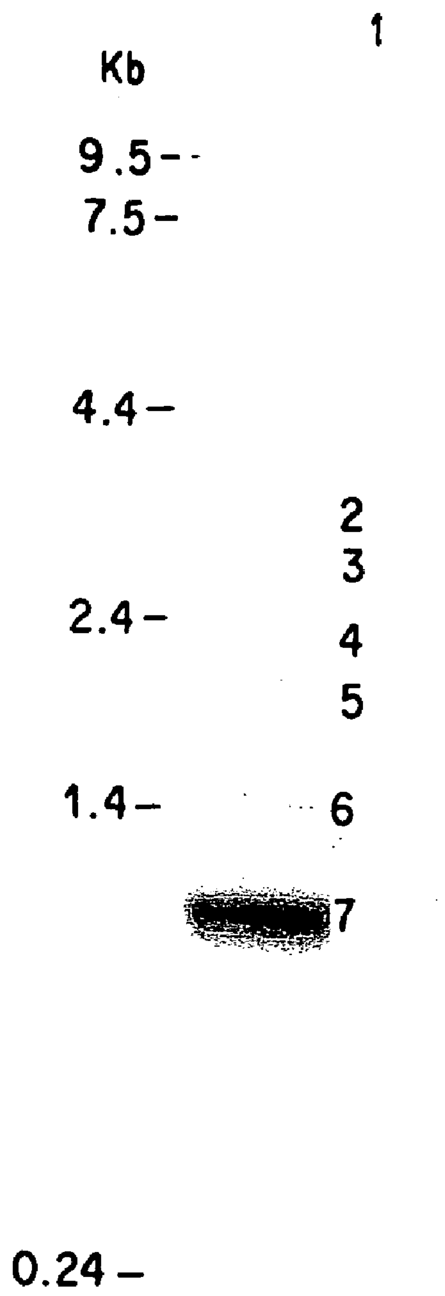
FIG. 5 is a Northern blot showing the VR 2385 subgenomic mRNA species, denatured with 6 M glyoxal and DMSO, and separated on a 1.5% agarose gel.

A specific DNA fragment from the extreme 3' end of the VR 2385 cDNA clone was amplified by PCR with primers PP284 and PP285. The DNA fragment was excised from an agarose gel with a commercially available DNA purification kit (GENECLEAN, obtained from Bio 101), and labeled with $^{32}$P-dCTP by random primer extension (using a kit available from Amersham). Total RNA was isolated from VR 2385-infected PSP-36 cells at 36 hours post-infection, using a commercially available kit for isolation of total RNA according to the procedure described by the manufacturer (Stratagene). VR 2385 subgenomic mRNA species were denatured with 6 M glyoxal and DMSO, and separated on a 1% agarose gel. (Results from a similar procedure substituting a 1.5% agarose gel are described in Experiment II below and are shown in FIG. 5.) The separated subgenomic mRNA's were then transferred onto nylon membranes using a POSIBLOT pressure blotter (Stratagene). Hybridization was carried out in a hybridization oven with roller bottles at 42° C. and 50% formamide.

RESULTS (A) Cloning, Identification and Sequencing of VR 2385 3' Terminal Genome An oligo (dT)-primed cDNA λ library was constructed from a partially purified virus, obtained from VR 2385-infected PSP-36 cells. Problems were encountered in screening the cDNA λ library with probes based on the Lelystad virus sequence. Three sets of primers were prepared. The first set (PP105 and PP106; SEQ ID NOS:8–9) correspond to positions 14577 to 14596 and 14977 to 14995 of the Lelystad genomic sequence, located in the nucleocapsid gene region. The second set (PP106 and PP107, SEQ ID NOS:9–10) correspond to positions 14977 to 14995 and 14054 to 14072 of the Lelystad genomic sequence, flanking ORF's 6 and 7. The third set (PM541 and PM542; SEQ ID NOS:11–12) correspond to positions 11718 to 11737 and 11394 to 11413 of the Lelystad genomic sequence, located in the ORF-1b region.

| | | |
|---|---|---|
| PP105: | 5'-CTCGTCAAGT ATGGCCGGT-3' | (SEQ ID NO:8) |
| PP106: | 5'-GCCATTCGCC TGACTGTCA-3' | (SEQ ID NO:9) |
| PP107: | 5'-TTGACGAGGA CTTCGGCTG-3' | (SEQ ID NO:10) |
| PM541: | 5'-GCTCTACCTG CAATTCTGTG-3' | (SEQ ID NO:11) |
| PM542: | 5'-GTGTATAGGA CCGGCAACCG-3' | (SEQ ID NO:12) |

All attempts to generate probes by PCR from the VR 2385 infectious agent using these three sets of primers were unsuccessful. After several attempts using the differential hybridization technique, however, the authentic plaques representing VR 2385-specific cDNA were isolated using probes prepared from VR 2385-infected PSP-36 cells and normal PSP-36 cells. The procedures involved in differential hybridization are described and set forth in FIG. 4.

Figure 6:
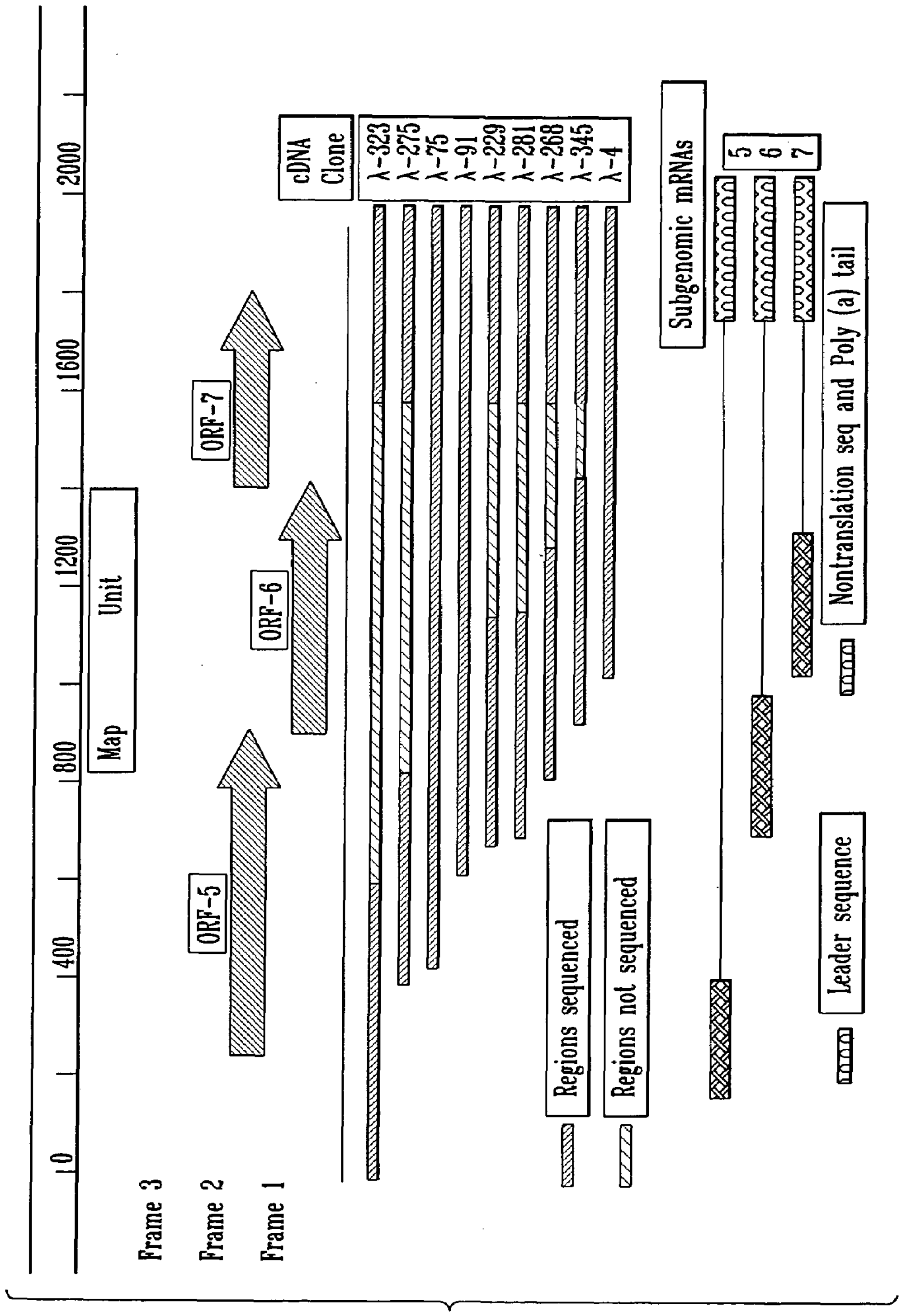
FIG. 6 shows the λ cDNA clones used to obtain the 3'-terminal nucleotide sequence of VR 2385.

Three positive plaques (λ-4, λ-75 and λ-91) were initially identified. Phagemids containing viral cDNA inserts within the λ phage were rescued by in vitro excision with the help of G408 helper phages. The inserts of the positive clones were analyzed by restriction enzyme digestion and terminal sequencing. The specificity of the cDNA clones was further confirmed by hybridization with RNA is from PSP-36 cells infected with the Iowa strain of PRRSV, but not with RNA from normal PSP-36 cells. A DNA probe was then generated from the 5'-end of clone λ-75 by PCR with primers PP286 and PP287. Further positive plaques (λ-229, λ-268, λ-275, λ-281, λ-323 and λ-345) were identified using this probe. All λ cDNA clones used to obtain the 3'-terminal nucleotide sequences are presented in FIG. 6. At least three separate clones were sequenced to eliminate any mistakes. In the case of any ambiguous sequence data, additional clones and internal primers (PP288, PP289, PP286, PP287 and PP386) were used to determine the sequence. The 2062-bp 3'-terminal sequence (SEQ ID NO:13) and the amino acid sequences encoded by ORF's 5, 6 and 7 (SEQ ID NOS:15, 17 and 19, respectively) are presented in FIG. 7.

(B) A Nested Set of Subgenomic mRNA

Total RNA from virus-infected PSP-36 cells was separated on 1% glyoxal/DMSO agarose gel, and blotted onto nylon membranes. A cDNA probe was generated by PCR with a set of primers (PP284 and PP285) flanking the extreme 3'-terminal region of the viral genome. The probe contains a 3'-nontranslational sequence and most of the ORF-7 sequence. Northern blot hybridization results show that the pattern of mRNA species from PSP-36 cells infected with the Iowa strain of PRRSV is very similar to that of Lelystad virus (LV), equine arteritis virus (EAV), lactate dehydrogenase-elevating virus (LDV) and coronavirus, in that virus replication required the formation of subgenomic mRNA's.

The results also indicate that VR 2385-specific subgenomic mRNA's represent a 3'-nested set of mRNA's, because the Northern blot probe represents only the extreme 3' terminal sequence. The size of VR 2385 viral genomic RNA (14 kb) and 6 subgenomic mRNA's (RNA 2 (3.0 kb), RNA 3 (2.5 kb), RNA 4 (2.2 kb), RNA 5 (1.8 kb), RNA 6 (1.3 kb) and RNA 7 (0.98 kb)) resemble those of LV, although there are differences in both the genome and in subgenomic RNA species. Differences were also observed in the relative amounts of the subgenomic mRNA's, RNA 7 being the most predominant subgenomic mRNA.

(C) Analysis of Open Reading-Frames Encoded by Subgenomic RNA

Three large ORF's have been found in SEQ ID NO:13: ORF-5 (nucleotides [nt] 426–1025; SEQ ID NO:14), ORF 6 (nt 1013–1534; SEQ ID NO:16) and ORF 7 (nt 1527–1895; SEQ ID NO:18). ORF 4, located at the 5' end of the resulting sequence, is incomplete in the 2062-bp 3'-terminal sequence of SEQ ID NO:13. ORF'S 5, 6 AND 7 each have a coding capacity of more than 100 amino acids. ORF 5 and ORF 6 overlap each other by 13 bp, and ORF 6 and ORF 7 overlap each other by 8 bp. Two smaller ORF's located entirely within ORF 7 have also been found, coding for only 37 aa and 43 aa, respectively. Another two short ORF's overlap fully with ORF 5. The coding capacity of these two ORF's is only 29 aa and 44 aa, respectively. No specific subgenomic mrRNA's were correlated to these smaller ORF's by Northern blot analysis. ORF 6 and ORF 7 are believed to encode the viral membrane protein and capsid protein, respectively.

(D) Consensus Sequence for Leader Junction

Sequence analysis shows that a short sequence motif, AACC, may serve as the site in the subgenomic mRNA's where the leader is added during transcription (the junction site). The junction site of ORF 6 is found 21 bp upstream from the ATG start codon, and the junction site of ORF 7 is found 13 bp upstream from the ATG start codon, respectively. No AACC consensus sequence has been identified in ORF 5, although it has been found in ORF 5 of LV. Similar junction sequences have been found in LDV and EAV.

(E) 3'-Nontranslational Sequence and Poly (A) Tail

A 151 nucleotide-long (151 nt) nontranslational sequence following the stop codon of ORF 7 has been identified in the genome of VR 2385, compared to 114 nt in LV, 80 nt in LDV and 59 nt in EAV. The length of the poly (A) tail is at least 13 nucleotides. There is a consensus sequence, CCGG/AAATT-poly (A) among PRRS virus VR 2385, LV and LDV in the region adjacent to the poly (A) tail.

(F) Sequence Comparison of VR 2385 and LV Genomes Among ORF's 5, 6 and 7, and Among the Nontranslational Sequences A comparison of the ORF-5 regions of the genomes of VR 2385 and of the Lelystad virus (SEQ ID NO:20) is shown in FIG. 8. The corresponding comparisons of the ORF-6 region, the ORF-7 region, and the nontranslational sequences of VR 2385 (SEQ ID NOS:16, 18 and 22, respectively) with the corresponding regions of LV (SEQ ID NOS:23, 25 and 27, respectively) are shown in FIGS. 9, 10 and 11, respectively.

The results of the comparisons are presented in Table 1 below. The nucleotide sequence homologies between LV and VR 2385 of the ORF 5, ORF 6, ORF 7 and the nontranslational sequences are 53%, 78%, 58% and 58%, respectively.

The size of ORF 7 in LV is 15 nt larger than that in VR 2385. Also, the 3'-terminal nontranslational sequence is different in length (150 nt in VR 2385, but only 114 nt in LV). Like LV, the junction sequence, AACC, has also been identified in the genome of the Iowa strain of PRRS virus isolate VR 2385, except for ORF 5. The junction sequence of ORF 6 in VR 2385 is 21 nt upstream from the ATG start codon, whereas the junction sequence of ORF 6 is 28 nt upstream from ATG in LV.

TABLE 1

Comparison of genes of U.S. PRRSV isolate ATCC VR 2385 with those of European isolate Lelystad virus*

| | | | | VR 2385 | | | Lelystad | | | |
|---|---|---|---|---|---|---|---|---|---|---|
| Gene | RNA | Estimated RNA size (in Kb) | ORF's | Size amino acids | N-glyco-sylation sites | Pred. protein size (kd) | Size amino acids | N-glyco-sylation sites | Pred. protein size (kd) | Homology between VR 2385 & Lelystad |
| 5 | 5 | 1.9 | 5 | 200 | 2 | 22.2 | 201 | 2 | 22.4 | 53 |
| 6 | 6 | 1.4 | 6 | 174 | 1 | 19.1 | 173 | 2 | 18.9 | 78 |
| 7 | 7 | 0.9 | 7 | 123 | 2 | 13.6 | 128 | 1 | 13.8 | 58 |
| NTR | — | — | — | 151 (nt) | — | NA | 114 (nt) | 0 | NA | 58 (nt) |

*Based on data presented by Conzelmann et al, Virology, 193, 329–339 (1993), Meulenberg et al, Virology, 192, 62–72 (1993), and the results presented herein.

EXPERIMENT II

The Expression OF VR 2385 Genes in Insect Cells (A) Production of Recombinant Baculovirus The ORF-5, ORF-6 and ORF-7 sequences were individually amplified by PCR using primers based on the VR 2385 (ISU-12) genomic nucleotide sequence. ORF-5 was amplified using the following primers:

```
5'-GGGGATCCGG TATTTGGCAA TGTGTC-3'  (SEQ ID NO:28)
3'-GGGAATTCGC CAAGAGCACC TTTTGTGG-5' (SEQ ID NO:29)
```

ORF-6 was amplified using the following primers:

```
5'-GGGGATCCAG AGTTTCAGCG G-3'   (SEQ ID NO:30)
3'-GGGAATTCTG GCACAGCTGA TTGAC-5'  (SEQ ID NO:31)
```

ORF-7 was amplified using the following primers:

```
5'-GGGGATCCTT GTTAAATATG CC-3'   (SEQ ID NO:32)
3'-GGGAATTCAC CACGCATTC-5'     (SEQ ID NO:33)
```

The amplified DNA fragments were cloned into baculovirus transfer vector pVL1393 (available from Invitrogen). One μg of linearized baculovirus ACMNPV DNA (commercially available from Pharmingen, San Diego, Calif.) and 2 μg of PCR-amplified cloned cDNA-containing vector constructs were mixed with 50 μl of lipofectin (Gibco), and incubated at 22° C. for 15 min. to prepare a transfection mixture.

One hour after seeding HI-FIVE cells, the medium was replaced with fresh Excell 400 insect cell culture medium (available from JR Scientific Co.), and the transfection mixture was added drop by drop. The resulting mixture was incubated at 28° C. for six hours. Afterwards, the transfection medium was removed, and fresh Excell 400 insect cell culture medium was added. The resulting mixture was then incubated at 28° C.

Five days after transfection, the culture medium was collected and clarified. Ten-fold dilutions of supernatants were inoculated onto HI-FIVE cells, and incubated for 60 min. at room temperature. After the inoculum was discarded, an overlay of 1.25% of agarose was applied onto the cells. Incubation at 28° C. was conducted for four days. Thereafter, clear plaques were selected and picked using a sterile Pasteur pipette. Each plaque was mixed with 1 ml of Grace's insect medium into a 5 ml snap cap tube, and placed in a refrigerator overnight to release the virus from the agarose. Tubes were centrifuged for 30 minutes at 2000×g to remove agarose, and the supernatants were transferred into new sterile tubes. Plaque purification steps were repeated three times to avoid possible wild-type virus contamination. Pure recombinant clones were stored at −80° C. for further investigation.

(B) Expression of Recombinant Iowa Strain Infectious Agent Proteins

Indirect immunofluorescence assay and radioimmunoprecipitation tests were used to evaluate expression.

Figure 12:
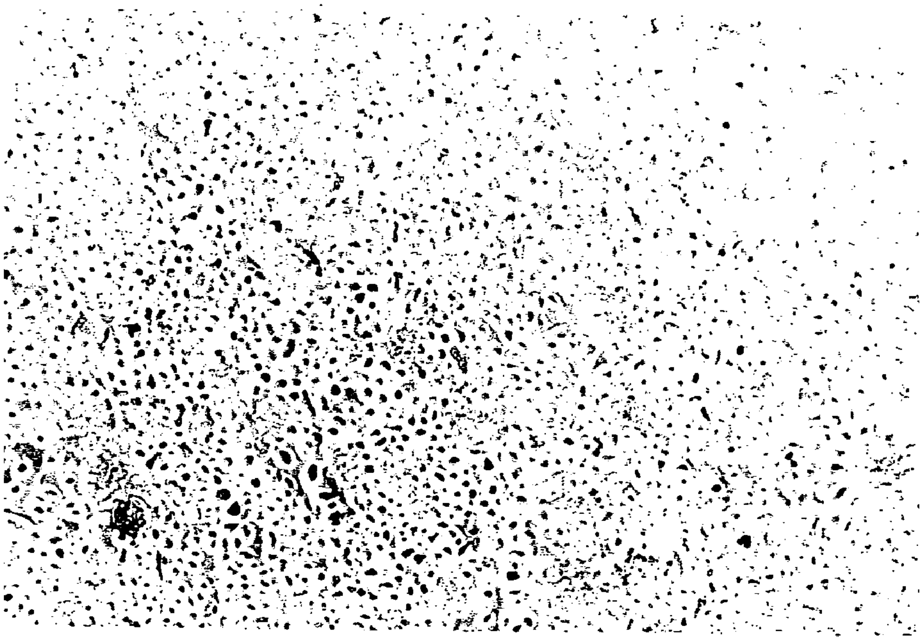
FIG. 12 shows a cytopathic effect in HI-FIVE cells infected with a recombinant baculovirus containing the VR 2385 ORF-7 gene (Baculo.PRRSV.7)
Figure 13:
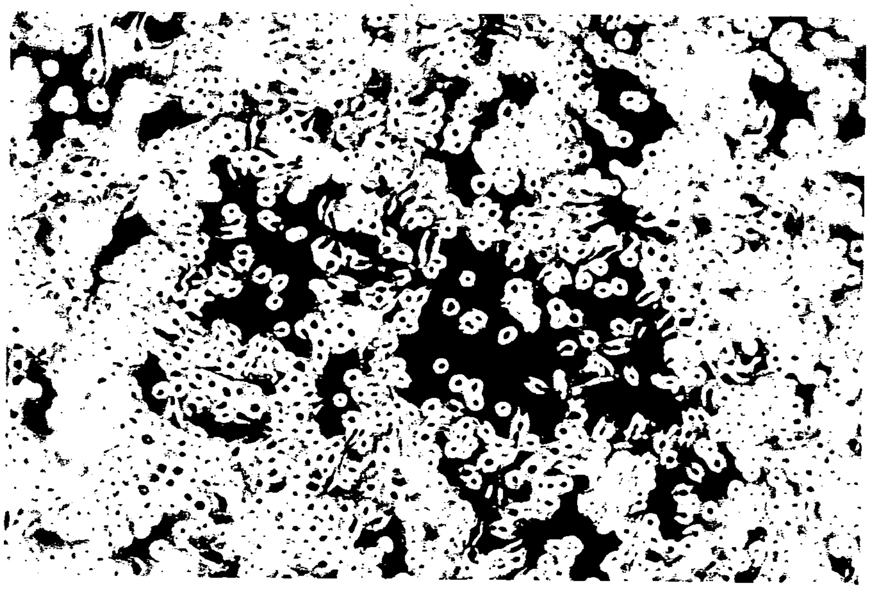
FIG. 13 shows HI-FIVE cells infected with a recombinant baculovirus containing the VR 2385 ORF-6 gene, stained with swine antisera to VR 2385, followed by fluorescein-conjugated anti-swine IgG.
Figure 14:
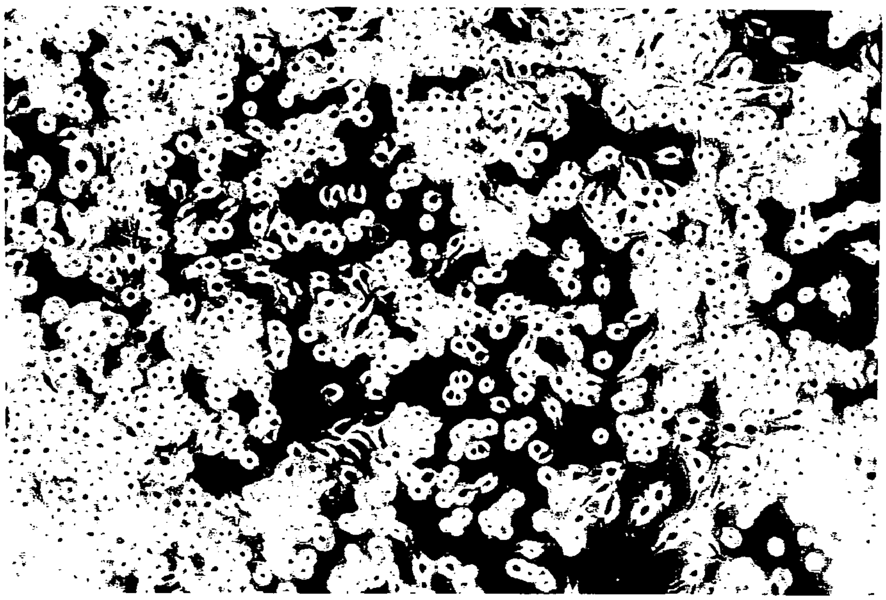
FIG. 14 shows HI-FIVE cells infected with a recombinant baculovirus containing the VR 2385 ORF-7 gene, respectively, stained with swine antisera to VR 2385, followed by fluorescein-conjugated anti-swine IgG.

Indirect immunofluorescence assay: Hi-five insect cells in a 24-well cell culture cluster plate were infected with wild-type baculovirus or recombinant baculovirus, or were mock-infected. After 72 hours, cells were fixed and stained with appropriate dilutions of swine anti-VR 2385 polyclonal antibodies, followed by fluorescein isothiocyanate-labelled (FITC-labelled) anti-swine IgG. Immunofluorescence was detected in cells infected with the recombinant viruses, but not in mock-infected cells or cells inoculated with wild-type baculovirus. For example, FIG. 12 shows HI-FIVE cells infected with the recombinant baculovirus containing the VR 2385 ORF-7 gene (Baculo.PRRSV.7), which exhibit a cytopathic effect. Similar results were obtained with recombinant baculovirus containing ORF-5 (Baculo.PRRSV.5) and ORF-6 (Baculo.PRRSV.6; data not shown). FIGS. 13 and 14 show HI-FIVE cells infected with a recombinant baculovirus containing the VR 2385 ORF-6 gene and VR 2385 ORF-7 gene, respectively, stained with swine antisera to VR 2385, followed by fluorescein-conjugated anti-swine IgG, in which the insect cells are producing recombinant Iowa strain viral protein. Similar results were obtained with recombinant baculovirus containing ORF-5.

Figure 15:
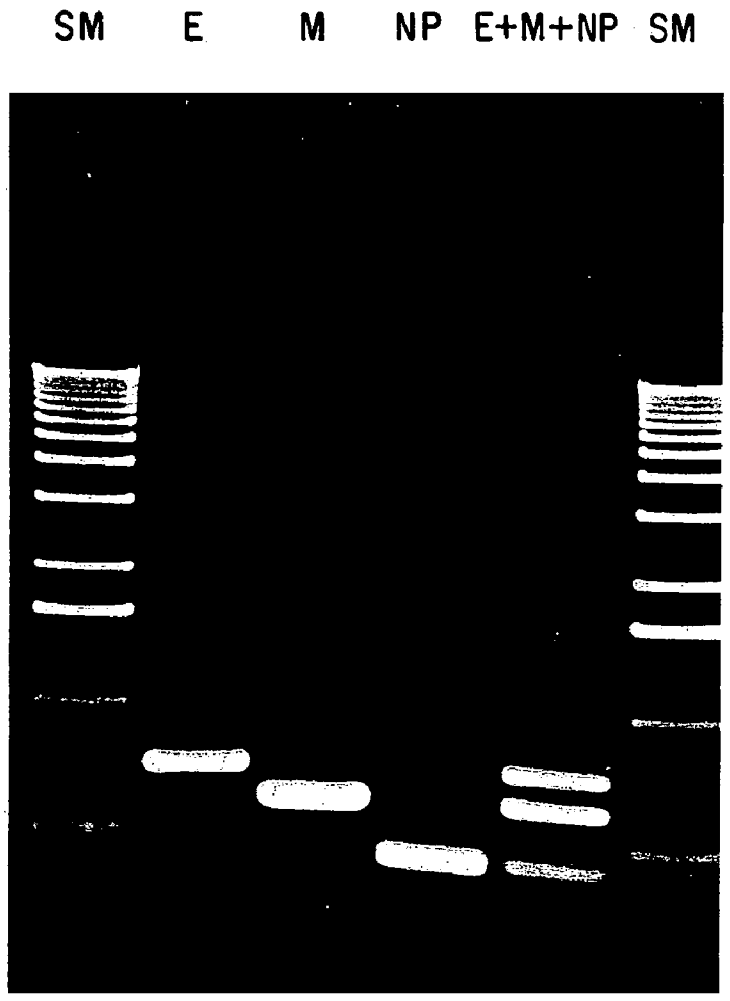
FIG. 15 shows a band of expected size for the VR 2385 ORF-6 product, detected by a radioimmunoprecipitation technique (see Experiment II(B) below)
Figure 16:
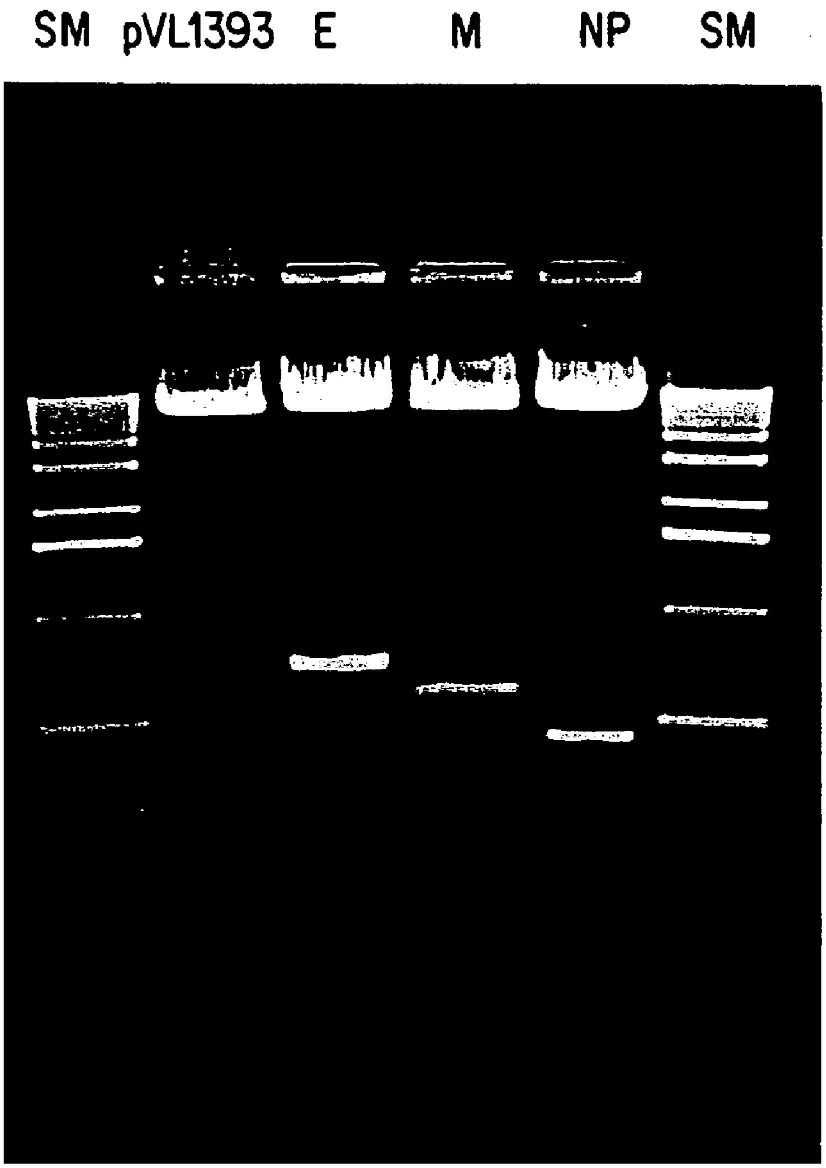
FIG. 16 shows a band of expected size for the VR 2385 ORF-7 product, detected by a radioimmunoprecipitation technique (see Experiment II(B) below)

Radioimmunoprecipitation: Radioimmunoprecipitation was carried out with each recombinant virus (Baculo-.PRRSV.5, Baculo.PRRSV.6 and Baculo.PRRSV.7) to further determine the antigenicity and authenticity of the recombinant proteins. HI-FIVE insect cells were mock-infected, or alternatively, infected with each of the recombinant baculoviruses. Two days after infection, methionine-free medium was added. Each mixture was incubated for two hours, and then proteins labeled with $^{35}$S-methionine (Amersham) were added, and the mixture was incubated for four additional hours at 28° C. Radiolabeled cell lysates were prepared by three cycles of freezing and thawing, and the cell lysates were incubated with preimmune or immune anti-VR 2385 antisera. The immune complexes were precipitated with Protein A agarose and analyzed on SDS-PAGE after boiling. X-ray film was exposed to the gels at −80° C., and developed. Bands of expected size were detected with ORF-6 (FIG. 15) and ORF-7 (FIG. 16) products.

EXPERIMENT III

SUMMARY

The genetic variation and possible evolution of porcine reproductive and respiratory syndrome virus (PRRSV) was determined by cloning and sequencing the putative membrane protein (M, ORF 6) and nucleocapsid (N, ORF 7) genes of six U.S. PRRSV isolates with differing virulence. The deduced amino acid sequences of the putative M and N proteins from each of these isolates were aligned with the corresponding sequences (to the extent known) of one other U.S. isolate, two European isolates, and other members of the proposed arterivirus group, including lactate dehydrogenase-elevating virus (LDV) and equine arteritis virus (EAV).

The putative M and N genes displayed 96–100% amino acid sequence identity among U.S. PRRSV isolates with differing virulence. However, their amino acid sequences varied extensively from those of European PRRSV isolates, and displayed only 57–59% and 78–81% identity, respectively. The U.S. PRRSV isolates were more closely related to LDV than were the European PRRSV isolates. The N protein of the U.S. isolates and European isolates shared about 50% and 40% amino acid-sequence identity with that of LDV, respectively.

The phylogenetic dendrograms constructed on the basis of the putative M and N genes of the proposed arterivirus group were similar and indicated that both U.S. and European PRRSV isolates were related to LDV and were distantly related to EAV. The U.S. and European PRRSV isolates fell into two distinct groups with slightly different genetic distance relative to LDV. The results suggest that U.S. and European PRRSV isolates represent two different genotypes, and that they may have evolved from LDV at different time periods and have existed separately in U.S. and Europe before their association with PRRS was recognized in swine.

ORF 6 encodes the membrane protein (M) of PRRSV, based on the similar characteristics of the ORF 6 of EAV, ORF 2 of LDV, and the M protein of mouse hepatitis virus and infectious bronchitis virus (Meulenberg et al, *Virology,* 192, 62–72 (1993); Conzelmann et al, *Virology,* 193, 329–339 (1993); Mardassi et al, *Abstr. Conf. Res. Workers in Animal Diseases*, Chicago, Ill., p. 43 (1993)). The product of ORF 7, the viral nucleocapsid protein (N), is extremely basic and hydrophilic (Meulenberg et al, *Virology,* 192, 62–72 (1993); Conzelmann et al, *Virology,* 193, 329–339 (1993); Murtaugh et al, *Proc. Allen D. Leman Swine Conference*, Minneapolis, Minn., pp. 43–45 (1993); Mardassi et al, *Abstr. Conf. Res. Workers in Animal Diseases*, Chicago, Ill., p. 43 (1993)).

The amino acid sequences encoded by ORF's 5, 6 and 7 of U.S. isolate VR 2385 and of the European isolate Lelystad virus (LV) have been compared, and the identity (i.e., the percentage of amino acids in sequence which are the same) between the two viruses is only 54%, 78% and 58%, respectively. Thus, striking genetic differences exist between the U.S. isolate VR 2385 and the European isolate LV (see U.S. application Ser. No. 08/131,625, filed Oct. 5, 1993).

However, the U.S. isolate VR 2385 is highly pathogenic compared to European LV. Thus, PRRSV isolates in North America and in Europe appear to be antigenically and genetically heterogeneous, and different genotypes or serotypes of PRRSV may exist.

To further determine the genetic variation among the PRRSV isolates, the putative M and N genes of five additional U.S. PRRSV isolates with differing virulence were cloned and sequenced. Phylogenetic trees based on the putative M and N genes of seven U.S. PRRSV isolates, two European PRRSV isolates and other members of the proposed arterivirus group, including LDV and EAV, have been constructed.

PRRSV isolates (ISU-12 (VR 2385/VR 2386), ISU-22 (VR 2429), ISU-55 (VR 2430), ISU-79, ISU-1894 and ISU-3927 (VR 2431), each of which is disclosed and described in U.S. application Ser. No. 08/131,625, filed Oct. 5, 1993) were isolated from pig lungs obtained from different farms in Iowa during PRRS outbreaks, according to the procedure described in U.S. application Ser. No. 08/131,625. A continuous cell line, ATCC CRL 11171, was used to isolate and propagate these viruses. All viruses were biologically cloned by three cycles of plaque purification prior to polynucleic acid sequencing.

Pathogenicity studies in caesarean-derived colostrum-deprived (CDCD) pigs, described in U.S. application Ser. No. 08/131,625, showed that VR 2385, VR 2429 and ISU-79 were highly pathogenic, whereas VR 2430, ISU-1894 and VR 2431 were not as pathogenic. For example, VR 2385, VR 2429 and ISU-79 produced from 50 to 80% consolidation of the lung tissues in experimentally-infected five-week-old CDCD pigs necropsied at 10 days post inoculation, whereas VR 2430, ISU-1894 and VR 2431 produced only 10 to 25% consolidation of lung tissues in the same experiment.

EXPERIMENTAL SECTION

Monolayers of ATCC CRL 11171 cells were infected with each of the PRRSV isolates at the seventh passage at an m.o.i. of 0.1. Total cellular RNA was isolated from infected cells by the guanidine isothiocyanate method (Sambrook et al, "Molecular Cloning: A Laboratory Manual," 2nd ed., Cold Spring Harbor Laboratory, Cold Spring Harbor, N.Y. (1989)). The quality of RNA from each isolate was determined by Northern blot hybridization (data not shown) with a cDNA probe generated from the extreme 3'-end of the VR 2385 genome by the polymerase chain reaction (PCR) with primers PP284 and PP285 (SEQ ID NOS:1 AND 2), as described in U.S. application Ser. No. 08/131,625. cDNA was synthesized from total cellular RNA with random primers using reverse transcriptase. The synthesized cDNA was amplified by polymerase chain reaction (PCR) as described previously (Meng et al, *J. Vet. Diagn. Invest.*, 5, 254–258 (1993)). Primers for RT-PCR were designed on the basis of a sequence in the genome of VR 2385 which resulted in amplification of the entire protein coding regions of the putative M and N genes (5' primer: 5'-GGGGATCCAGAGTTTCAGCGG-3' (SEQ ID NO:30); 3' primer: 5'-GGGAATTCACCACGCATTC-3' (SEQ ID NO:33)). Unique restriction sites (EcoR I and BamH I) at the termini of the PCR products were introduced by conventional methods. A PCR product with the expected size of about 900 bp was obtained from each of the virus isolates. Southern blot hybridization was then used to confirm the specificity of the amplified products.

The $^{32}P$-labelled cDNA probe from VR 2385 hybridized with the RT-PCR products from each of the above virus isolates. The PCR products of the putative M and N genes from each of the PRRSV isolates were purified and cloned into vector pSK+ (Meng et al, *J. Vet. Diagn. Invest.* 5, 254–258 (1993)). Plasmids containing the full length putative M and N genes were sequenced with an automated DNA Sequencer (obtained from Applied Biosystems, Inc., Foster City Calif.). Three to four cDNA clones from each virus isolate were sequenced with universal and reverse primers, as well as other virus specific sequencing primers (PP288: 5'-GCGGTCTGGATTGACGAC-3' (SEQ ID NO:5) and PP289: 5'-GACTGCTAGGGCTTCTGC-3' (SEQ ID NO:6), each of which is described in application Ser. No. 08/131, 625, and DP966: 5'-AATGGGGCTTCTCCGG-3' (SEQ ID NO:34)). The sequences were combined and analyzed by the MACVECTOR (International Biotechnologies, Inc.) and GENEWORKS (IntelliGenetics, Inc.) computer programs.

Analysis of the nucleotide sequences encoding the putative M and N proteins of the 5 U.S. PRRSV isolates indicated that, like LV (Meulenberg et al, *Virology,* 192, 62–72 (1993)) and VR 2385, the putative M and N genes of each of the five additional U.S. isolates overlapped by 8 base pairs (bp). FIG. 17 shows the nucleotide sequence of ORF's 6 and 7 of six U.S. PRRSV isolates and of LV, in which the ISU-12 (VR 2385 and VR 2386) nucleotide sequence (SEQ ID NO:35) is shown first, and in subsequent sequences (SEQ ID NOS:36–41), only those nucleotides which are different are indicated. Start codons are underlined and indicated by (+1>), stop codons are indicated by asterisks (*), are indicated by (–), and the two larger deletions in the putative N gene are further indicated by (^).

FIGS. 18(A)–(B) show the alignment of amino acid sequences of the putative M (FIG. 18(A)) and N (FIG. 18(B)) genes of the proposed arterivirus group, performed with a GENEWORKS program (IntelliGenetics, Inc.), using the following parameters (default values): cost to open a gap is 5, cost to lengthen a gap is 25, minimum diagonal length is 4, and maximum diagonal offset is 10. The EAV M gene sequence was omitted because the relatively low sequence identity with PRRSV and LDV requires gaps in the alignments. The VR 2385/VR 2386 sequences (SEQ ID NOS:17 and 19) are shown first, and in subsequent sequences (SEQ ID NOS:43, 45, 47, 49, 51, 24, 53, 55, 57, 59, 61 and 26, respectively), only the differences are indicated. Deletions are indicated by (–), and the two larger deletions in the putative N gene are further indicated by (^).

Numerous substitutions in the nucleotide sequence were distributed randomly throughout the M and N genes in each of the five isolates, as compared to VR 2385. Most of the substitutions are third base silent mutations when converted to amino acid sequences (see FIG. 18). Insertions and deletions are found in the nucleotide sequences of the putative M and N genes when comparing the U.S. isolates to LV, but not found among the U.S. isolates (FIG. 17). For example, there are two larger deletions, 15 and 10 nucleotides each, in the putative N gene of the U.S. isolates as compared to the LV N genome (FIG. 17).

The deduced amino acid sequences of the putative M and N genes from the six Iowa strain PRRSV isolates are aligned with the corresponding N sequence of another U.S. isolate, VR 2332 (Murtaugh et al, *Proc. Allen D. Leman Swine Conference*, Minneapolis, Minn., pp. 43–45 (1993)); two European PRRSV isolates, LV (Meulenbera et al, *Virology* 192, 62–72 (1993)) and PRRSV isolate 10 (PRRSV-10) (Conzelmann et al, *Virology,* 193, 329–339 (1993)); two LDV strains, LDV-C (Godney et al, *Virology,* 177, 768–771 (1990)) and LDV-P (Kuo et al, *Virus Res.,* 23, 55–72 (1992)); and EAV (Den Boon et al, *J. Virol.,* 65, 2910–2920 (1991)) (FIG. 18).

The amino acid sequences of the putative N gene are highly conserved among the seven U.S. PRRSV isolates (FIG. 18(B)), and displayed 96–100% amino acid sequence identity (Table 1). However, the putative N proteins of the U.S. PRRSV isolates shared only 57–59% amino acid sequence identity with those of the two European isolates (Table 1), suggesting that the U.S. and the European isolates may represent two different genotypes.

The putative M protein of each of the U.S. isolates was also highly conserved, and displayed higher sequence similarity with the M proteins of the two European isolates (FIG. 18(A)), ranging from 78 to 81% amino acid identity (see Table 2 below). The putative N gene of each of the U.S. PRRSV isolates shared 49–50% amino acid sequence identity with that of the LDV strains, whereas the two European PRRSV isolates shared only 40–41% amino acid identity with that of the LDV strains (Table 2).

Two regions of amino acid sequence deletions, “KKSTAPM” (SEQ ID NO:62) and “ASQG” (SEQ ID NO:63), were found in the putative N proteins of each of the seven U.S. PRRSV isolates, as well as the two LDV strains and EAV, when compared to the two European PRRSV isolates (FIG. 18(B)). These results indicated that the U.S. PRRSV isolates are more closely related to LDV than are the European PRRSV isolates, and that PRRSV may have undergone divergent evolution in the U.S. and in Europe before their association with PRRS was recognized in swine (Murtaugh, *Proc. Allen D. Leman Swine Conference*, Minneapolis, Minn., pp. 43–45 (1993)).

The European isolates may have diverged from LDV for a longer time than the U.S. isolates, and hence may have evolved first. However, the amino acid sequence identity of the putative M gene between U.S. PRRSV isolates and LDV strains was similar to that between the European PRRSV isolates and LDV strains (Table 2). The putative M and N genes of the U.S. and European isolates of PRRSV shared only 15–17% and 22–24% amino acid sequence identity with those of EAV, respectively.

The sequence homology of PRRSV with LDV and EAV suggests that these viruses are closely related and may have evolved from a common ancestor (Plagemann et al, supra; Murtaugh, supra). The high sequence conservation between LDV and PRRSV supported the hypothesis that PRRSV may have evolved from LDV and was rapidly adapted to a new host species (Murtaugh, supra). Asymptomatic LDV infection were found in all strains of mice (Murtaugh, supra; Kuo et al, supra). However, many pig forms are infested with wild rodents (Hooper et al, *J. Vet. Diagn. Invest.,* 6, 13–15 (1994)), so it is possible that PRRSV evolved from LDV-infected mice, and was rapidly adapted to a new host, swine.

Figure 19A:
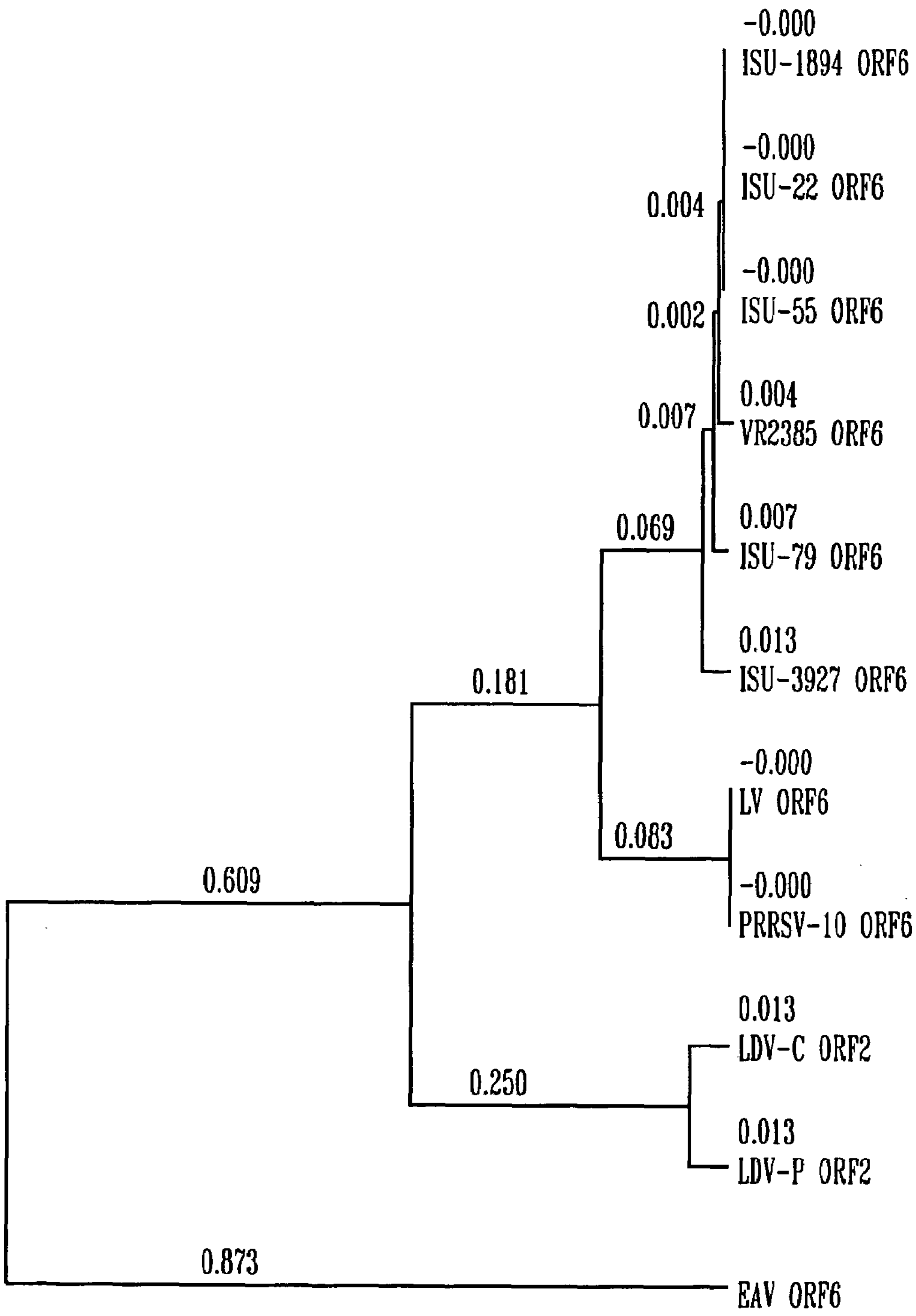
FIGS. 19(A)–(B) show phylogenetic trees based on the amino acid sequences of the putative M (FIG. 19(A)) and N genes (FIG. 19(B)) for the proposed arterivirus group.
Figure 19B:
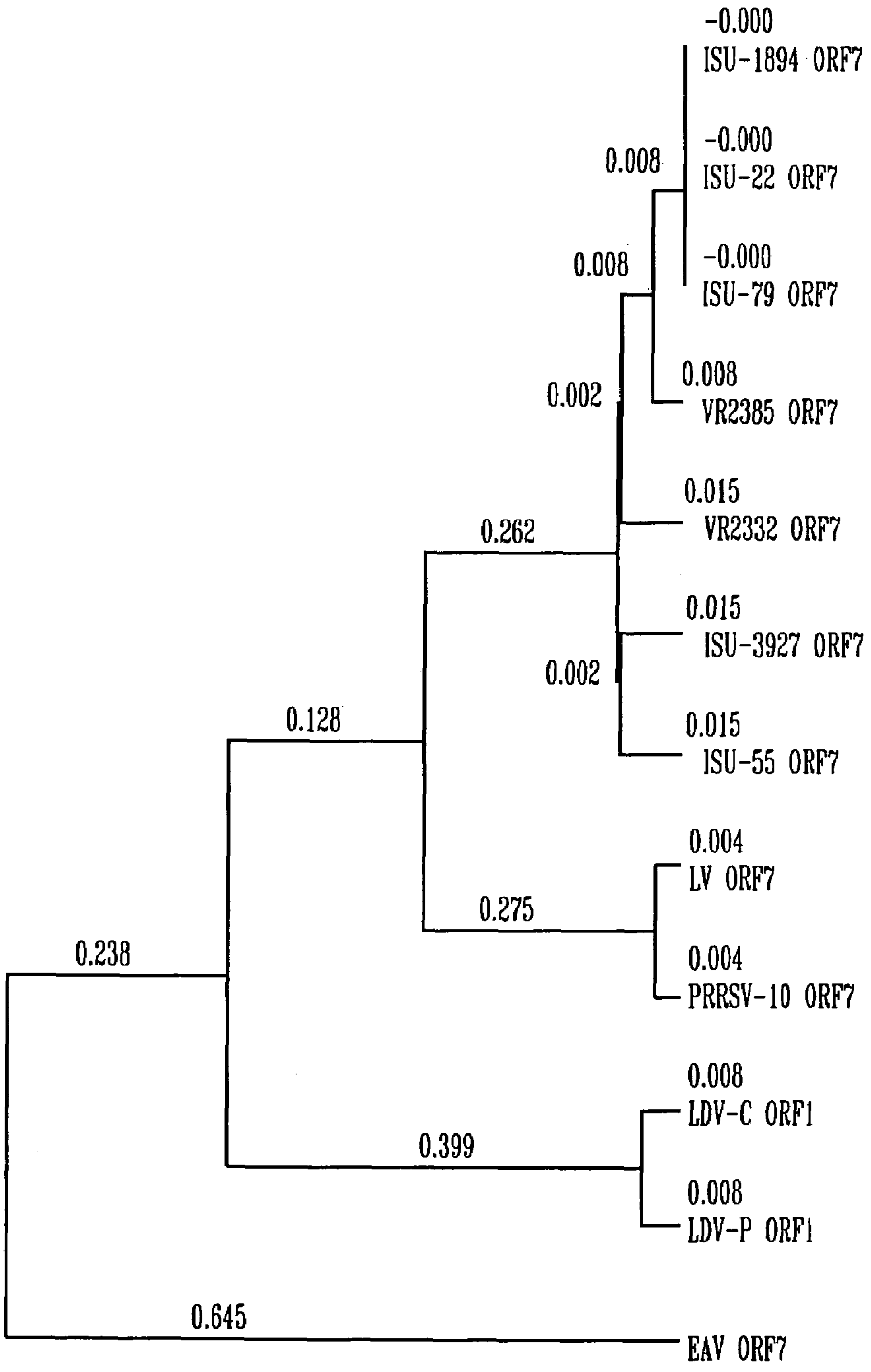

The evolutionary relationships of PRRSV with other members of the proposed arterivirus group were determined on the basis of the amino acid sequence of the putative M and N genes. FIG. 19 shows a phylogenetic tree of the

TABLE 2

Pairwise comparison of the amino acid sequences among the putative nucleocapsid and membrane proteins of the proposed arterivirus group

| | VIRUS | | | | | | | | | | | |
|---|---|---|---|---|---|---|---|---|---|---|---|---|
| Virus | VR2385 | ISU-22 | ISU-55 | ISU-79 | ISU-1894 | ISU-3927 | VR2332 | LV | PRRSV-10 | LDV-P | LDV-C | EAV |
| VR2385 | *** | 98 | 96 | 98 | 98 | 96 | 96 | 57 | 57 | 49 | 49 | 22 |
| ISU-22 | 99 | *** | 98 | 100 | 100 | 98 | 98 | 57 | 57 | 49 | 49 | 23 |
| ISU-55 | 99 | 100 | *** | 98 | 98 | 97 | 96 | 59 | 59 | 49 | 49 | 23 |
| ISU-79 | 98 | 99 | 99 | *** | 100 | 98 | 98 | 57 | 57 | 49 | 49 | 23 |
| ISU-1894 | 99 | 100 | 100 | 99 | *** | 98 | 98 | 57 | 57 | 49 | 49 | 23 |
| ISU-3927 | 96 | 97 | 97 | 97 | 97 | *** | 96 | 59 | 59 | 49 | 49 | 23 |
| VR2332 | N/A | N/A | N/A | N/A | N/A | N/A | *** | 57 | 57 | 50 | 49 | 22 |
| LV | 78 | 79 | 79 | 79 | 79 | 81 | N/A | *** | 99 | 41 | 40 | 23 |
| PRRSV-10 | 78 | 79 | 79 | 79 | 79 | 81 | N/A | 100 | *** | 41 | 40 | 23 |
| LDV-P | 50 | 51 | 51 | 51 | 51 | 51 | N/A | 53 | 53 | *** | 98 | 23 |
| LDV-C | 49 | 50 | 50 | 50 | 50 | 50 | N/A | 52 | 52 | 96 | *** | 24 |
| EAV | 16 | 16 | 16 | 16 | 16 | 15 | N/A | 17 | 17 | 16 | 17 | *** |

Note

[a]The values in the table are the percentage identity of amino acid sequences. N/A, not available.

[b]Nucleocapsid protein comparisons are presented in the upper right half and membrane protein comparisons are presented in the lower left half.

proposed arterivirus group based on the amino acid sequences of the putative M and N genes of this group. The phylogenetic tree for the N gene is essentially the same as that for the M gene. The length of the horizontal lines connecting one sequence to another is proportional to the estimated genetic distance between sequences, as indicated by the numbers given above each line. The UPGMA (unweighted pair group method with arithmetic mean) trees were constructed with a GENEWORKS program (IntelliGenetics, Inc.), which first clusters the two most similar sequences, then the average similarity of these two sequences is clustered with the next most similar sequences or subalignments, and the clustering continued in this manner until all sequences/isolates are located in the tree; both trees are unrooted.

The PRRSV isolates fall into two distinct groups. All the U.S. PRRSV isolates thus far sequenced are closely related and form one group. The two European PRRSV isolates are closely related and form another group. Both the U.S. and European PRRSV isolates are related to LDV strains and are distantly related to EAV (FIG. 19).

The evolution patterns for the putative N and M genes also suggest that PRRSV may be a variant of LDV. For example, the genetic distance of the U.S. PRRSV isolates is slightly closer to LDV than the European PRRSV isolates (FIG. 19), again suggesting that the U.S. and European PRRSV may have evolved from LDV at different time periods and existed separately before their association with PRRS was recognized in swine. European PRRSV may have evolved earlier than U.S. PRRSV. It is also possible that the U.S. and European PRRSV could have evolved separately from different LDV variants which existed separately in the U.S. and Europe.

A striking feature of RNA viruses is their rapid evolution, resulting in extensive sequence variation (Koonin et al, *Critical Rev. Biochem. Mol. Biol.*, 28, 375–430 (1993)). Direct evidence for recombination between different positive-strand RNA viruses has been obtained (Lai, *Microbiol. Rev.*, 56, 61–79 (1992)). Western equine encephalitis virus appears to be an evolutionally recent hybrid between Eastern equine encephalitis virus and another alphavirus closely related to Sindbis virus (Hahn et al, *Proc. Natl. Acad. Sci. USA*, 85, 5997–6001 (1988)). Accordingly, the emergence of PRRSV and its close relatedness to LDV and EAV is not surprising. Although the capsid or nucleocapsid protein has been used for construction of evolutionary trees of many positive-strand RNA viruses, proteins with conserved sequence motifs such as RNA-dependent RNA polymerase, RNA replicase, etc., are typically more suitable for phylogenetic studies (Koonin et al, supra).

EXPERIMENT IV

Cloning and Sequencing of cDNA Corresponding to ORF'S 2, 3 and 4 of PRRSV VR 2385.

The region including ORF's 2, 3, and 4 of the genome of the porcine reproductive and respiratory syndrome virus (PRRSV) isolate VR 2385 was cloned and analyzed. To clone the cDNA of PRRSV VR 2385, ATCC CRL 11171 cells were infected with the virus at a m.o.i. of 0.1, and total cellular RNA was isolated using an RNA Isolation Kit (Stratagene). The mRNA fraction was purified through a Poly(A) Quick column (Stratagene), and the purified mRNA was used to generate a cDNA library. A cDNA oligo dT library was constructed in Uni-ZAP XR λ vector using a ZAP-cDNA synthesis kit (Stratagene), according to the supplier's instructions. Recombinant clones were isolated after screening of the library with an ORF 4—specific hybridization probe (a 240 b.p. PCR product specific for the 3' end of ORF 4; SEQ ID NO:64). Recombinant pSK+ contained PRRSV-specific cDNA was excised in vivo from positive λ plaques according to the manufacturer's instructions.

Several recombinant plasmids with nested set of cDNA inserts with sizes ranging from 2.3 to 3.9 kb were sequenced from the 5' ends of the cloned fragments. The nucleotide sequence of SEQ ID NO:65 was determined on at least two independent cDNA clones and was 1800 nucleotides in length (FIG. 21). Computer analysis of the nucleotide and the deduced amino acid sequences was performed using GENEWORKS (IntelliGenetics, Inc.) and MACVECTOR (International Biotechnologies, Inc.) programs.

Three partially overlapping ORF's (ORF 2, ORF 3 and ORF 4) were identified in this region. ORF's 2, 3 and 4 comprised nucleotides 12–779 (SEQ ID NO:66), 635–1396 (SEQ ID NO:68) and 1180–1713 (SEQ ID NO:70), respectively, in the sequenced cDNA fragment.

A comparison of DNA sequences of ORF's 2, 3 and 4 of PRRSV VR 2385 with corresponding ORF's of LV virus (SEQ ID NOS:72, 74 and 76, respectively) is presented in FIG. 22. The level of nucleotide sequence identity (homology) was 65% for ORF 2, 64% for ORF 3 and 66% for ORF 4.

Figure 23:
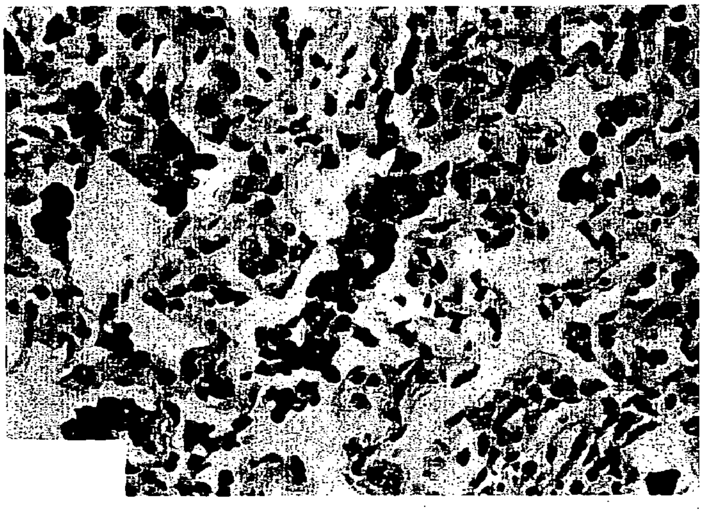
FIG. 23 shows an immunohistochemical stain of a lung tissue sample taken from a pig infected 9 days previously with PRRSV, in which positive ABC staining with hematoxylin counterstain is observed within the cytoplasm of macrophages and sloughed cells in the alveolar spaces.

The predicted amino acid sequences encoded by ORF's 2–4 of PRRSV VR 2385 (SEQ ID NOS:67, 69 and 71, respectively) and of LV (SEQ ID NOS:73, 75 and 77, respectively) are shown in FIG. 23. A comparison of PRRSV VR 2385 and LV shows a homology level of 58% for the protein encoded by ORF 2, 55% for the protein encoded by ORF 3 and 66% for the protein encoded by ORF 4 (see FIG. 23).

EXPERIMENT V

An Immunoperoxidase Method of Detecting PRRSV

Four 3-week-old colostrum-deprived PRRSV negative animals were inoculated intranasally with $10^{5.8}$ $TCID_{50}$ of PRRSV U.S. isolate ATCC VR 2386 propagated on ATCC CRL 11171 cells. These pigs were housed on elevated woven-wire decks and fed a commercial milk replacer. Two pigs were necropsied at 4 days post inoculation (DPI) and two at 8 DPI.

At the time of necropsy, the right and left lungs of each pig were separated and inflated via the primary bronchus with 45 ml of one of four fixatives and then immersion fixed for 24 hours. The fixatives used in this experiment included 10 neutral buffered formalin, Bouin's solution, HISTOCHOICE (available from Ambresco, Solon, Ohio), and a mixture containing 4% formaldehyde and 1% glutaraldehyde (4F:1G). The tissues fixed in Bouin's were rinsed in five 30-minute changes of 70% ethyl alcohol after 4 hours fixation in Bouin's. All the tissues were routinely processed in an automated tissue processor beginning in 70% ethyl alcohol. Tissues were processed to paraffin blocks within 48 hours of the necropsy.

Sections of 3 micron thickness were mounted on poly-1-lysine coated glass slides, deparaffinized with two changes of xylene and rehydrated through graded alcohol baths to distilled water. Endogenous peroxidase was removed by three 10-minute changes of 3% hydrogen peroxide. This was followed by a wash-bottle rinse with 0.05 M TRIS buffer (pH 7.6) followed by a 5-minute TRIS bath. Protease digestion was performed on all tissue sections except those fixed in HISTOCHOICE. Digestion was done in 0.05% protease (Protease XIV, available from Sigma Chem., St. Louis, Mo.) in TRIS buffer for 2 minutes at 37° C. Digestion was followed by a TRIS-buffer wash-bottle rinse and then a 5-minute cold TRIS buffer bath. Blocking for 20 minutes was done with a 5% solution of normal goat serum (available from Sigma Chem., St. Louis, Mo.).

The primary antibody used was the monoclonal antibody SDOW-17 (obtained from Dr. David Benfield, S. Dak. State Univ.), diluted 1:1000 in TRIS/PBS (1 part TRIS:9 parts PBS (0.01 M, pH 7.2)). The monoclonal antibody SDOW-17 recognizes a conserved epitope on the PRRSV nucleocapsid protein (Nelson et al, *J. Clin. Microbiol.,* 31:3184–3189). The tissue sections were flooded with primary antibody and incubated at 4° C. for 16 hours in a humidified chamber. The primary antibody incubation was then followed by a wash-bottle rinse with TRIS buffer, a 5-minute TRIS buffer bath, and then a 5-minute TRIS buffer bath containing 1% normal goat serum. The sections were flooded with biotinylated goat anti-mouse antisera (obtained from Dako Corporation, Carpintera, Calif.) for 30 minutes. The linking antibody incubation was followed by three rinses in TRIS buffer, as was done following primary antibody incubation. The sections were then treated with peroxidase-conjugated streptavidin, diluted 1:200 in TRIS/PBS, for 40 minutes, followed by a TRIS buffer wash-bottle rinse and a 5-minute TRIS buffer bath. The sections were then incubated with freshly-made 3,3'-diaminobenzidine tetrahydrochloride (DAB, obtained from Vector Laboratories Inc., Burlingame, Calif.) for 8–10 minutes at room temperature, and then rinsed in a distilled water bath for 5 minutes. Counterstaining was done in hematoxylin (available from Shandon, Inc., Pittsburgh, Pa.), and the sections were rinsed with Scott's Tap Water (10 g $MgSO_4$ and 2 g $NaHCO_3$ in 1 liter ultrapure water), then with distilled water. After dehydration, the sections were covered with mounting media, and then a coverslip was applied.

Two negative controls were included. Substitution of TRIS/PBS buffer in place of the primary antibody was done for one control. The other control was done by substituting uninfected, age-matched, gnotobiotic pig lungs for PRRSV-infected lungs.

Histological changes in infected tissues were characterized by moderate multifocal proliferative interstitial pneumonia with pronounced type 2 pneumocyte hypertrophy and hyperplasia, moderate infiltration of alveolar septa with mononuclear cells, and abundant accumulation of necrotic cell debris and mixed inflammatory cells in the alveolar spaces. No bronchial or bronchiolar epithelial damage was observed. However, there was necrotic cell debris in the smaller airway lumina.

Intense and specific staining in the cytoplasm of infected cells was observed in the formalin- and Bouin's-fixed tissues. Staining was less intense and specific in the 4F:1G-fixed tissues. There was poor staining, poor cellular detail, and moderate background staining in the HISTOCHOICE-fixed tissues. Background staining was negligible with the other fixatives. Cellular detail was superior in the formalin-fixed tissue sections and adequate in the Bouin's- and 4F:1G-fixed tissues.

Figure 24:
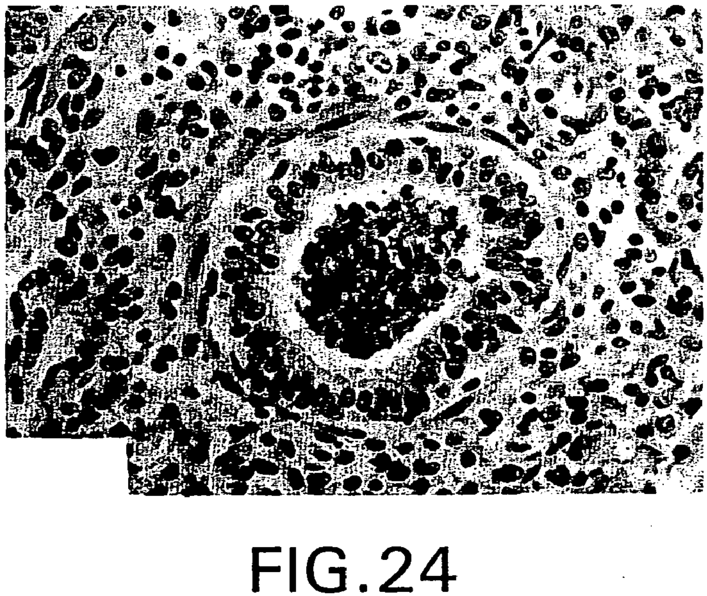
FIG. 24 shows an immunohistochemical stain of a lung tissue sample taken from a pig infected 4 days previously with PRRSV, in which positive ABC staining with hematoxylin counterstain is demonstrated within cellular debris in terminal airway lumina.
Figure 25:
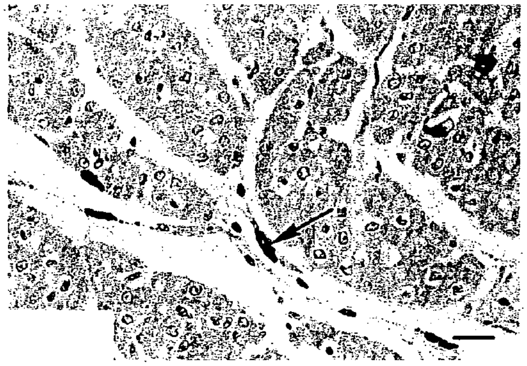
FIG. 25 shows a heart from a pig infected 9 days previously with PRRSV, in which positive staining is demonstrated within endothelial cells (arrow) and isolated macrophages by the present streptavidin-biotin complex method (with hematoxylin counterstain); the bar indicates a length of 21 microns.

The labeled antigen was primarily within the cytoplasm of sloughed cells and macrophages in the alveolar spaces (FIG. 24) and within cellular debris in terminal airway lumina (FIG. 25). When compared to sections from the same block stained with hematoxylin and eosin, it was determined that most of the labeled cells were macrophages, and some were likely sloughed pneumocytes. Lesser intensities of staining were observed in mononuclear cells within the alveolar septa and rarely in hypertrophied type 2 pneumocytes.

Using an immunoperoxidase technique on frozen sections, others were able to detect antigen in epithelial cells of brochioles and alveolar ducts as well as within cells in the alveolar septa and alveolar spaces (Pol et al, "Pathological, ultrastructural, and immunohistochemical changes caused by Lelystad virus in experimentally induced infections of mystery swine disease (synonym: porcine epidemic abortion and respiratory syndrome (PEARS))," Vet. O., 13:137–143). We were unable to detect antigen in brochiolar epithelium using the present immunoperoxidase method.

The present streptavidin-biotin complex (ABC) technique using a PRRSV monoclonal antibody can be modified as needed to identify PRRSV-infected porcine lungs. Both 10% neutral-buffered formalin and Bouin's solution are acceptable fixatives. Protease digestion enhances the antigen detection without destroying cellular detail. This technique is therefore quite useful for the diagnosis of PRRSV-induced pneumonia of pigs, and for detection of PRRSV in lung tissue samples.

EXPERIMENT VI

An Immunohistochemical Identification of Sites of Replication of PRRSV

SUMMARY

Four three-week-old caesarian-derived, colostrum-deprived (CDCD) pigs were inoculated intranasally with an isolate of porcine reproductive and respiratory syndrome virus. All inoculated pigs exhibited moderate respiratory disease. Two pigs were necropsied at 4 days post inoculation (PI) and two at 9 days PI. Moderate consolidation of the lungs and severe enlargement of the lymph nodes were noted at necropsy. Moderate perivascular lymphomacrophagic myocarditis was observed. Marked lymphoid follicular hyperplasia and necrosis was observed in the tonsil, spleen, and lymph nodes.

Porcine reproduction and respiratory syndrome virus antigen was detected by the present streptavidin-biotin immunoperoxidase method primarily within alveolar macrophages in the lung and in endothelial cells and macrophages in the heart. Macrophages and dendritic-like cells in the lymph nodes, spleen, tonsil, and thymus stained intensively positive for PRRSV nucleocapsid protein antigen as well.

Experimental section: Four pigs were snatched from the birth canal of a sow that was positive for PRRSV antibody by indirect immunofluorescent antibody (IFA) examination of serum. The pigs were taken to a different site, housed on elevated woven-wire decks and raised on commercial milk replacer. These pigs were bled at 0, 7, 14, and 21 days of age and found to be negative for PRRSV antibody by the IFA test. No PRRSV was isolated from the serum of the pigs or sow using MARC-145 cells (available from National Veterinary Services Laboratory, Ames, Iowa).

All four pigs were inoculated intranasally at 3 weeks of age with $10^{5.8}$ $TCID_{50}$ of PRRSV U.S. isolate ATCC VR 2385 propagated on ATCC CRL 11171 cells. Mild-to-moderate respiratory disease was observed from 3–9 days post inoculation (DPI). Two pigs were necropsied at 4 DPI and two at 9 DPI. At 4 DPI, one pig evidenced 31% and the other 36% tan-colored consolidation of the lungs. At 9 DPI, the remaining two pigs evidenced 37% and 46% consolidation of the lungs, respectively. Lymph nodes were moderately enlarged and edematous.

Lymphoid tissues collected at necropsy included the tonsil, thymus, spleen, tracheobronchial, mediastinal, and medial iliac lymph nodes. Lymphoid tissues were fixed by immersion for 24 hours in 10% neutral buffered formalin, processed routinely in an automated tissue processor, embedded in paraffin, sectioned at 6 microns and stained with hematoxylin and eosin. Additional sections (including the lung tissue sections above) were cut at 3 microns and mounted on poly-L-lysine coated slides for immunohistochemistry.

The immunoperoxidase assay described in Experiment VI above was repeated. Briefly, after endogenous peroxidase was removed with 3% hydrogen peroxide, primary monoclonal antibody ascites fluid diluted 1:1000 in TRIS/PBS was added for 16 hours at 4° C. in a humidified chamber. The monoclonal antibody SDOW-17 (obtained from Dr. David Benfield, S. Dak. State Univ.), which recognizes a conserved epitope of the PRRSV nucleocapsid protein, was used. Biotinylated goat anti-mouse linking antibody (obtained from Dako Corporation, Carpintera, Calif.) was added, followed by treatment with peroxidase-conjugated streptavidin (obtained from Zymed Laboratories, South San Francisco, Calif.) and incubation with 3,3'-diaminobenzidine tetrahydrochloride (obtained from Vector Laboratories Inc., Burlingame, Calif.). The incubated sample was finally counterstained in hematoxylin.

Microscopic lesions included interstitial pneumonia, myocarditis, tonsillitis, and lymphadenopathy. One section of lung from each lobe was examined. The interstitial pneumonic lesions were characterized by septal infiltration with mononuclear cells, hyperplasia and hypertrophy of type 2 pneumocytes, and accumulation of macrophages and necrotic cell debris in alveolar spaces. These lesions were moderate and multifocal by 4 DPI and severe and diffuse by 9 DPI. Bronchi and bronchiolar epithelium was unaffected. PRRSV antigen was readily detected by immunohistochemistry in alveolar macrophages. Large dark-brown PRRSV antigen-positive macrophages were often found in groups of 5–10 cells. A few PRRSV antigen-positive mononuclear cells were observed within the alveolar septa. PRRSV antigen was not detected in any tissues of the negative control pigs.

Figure 26:
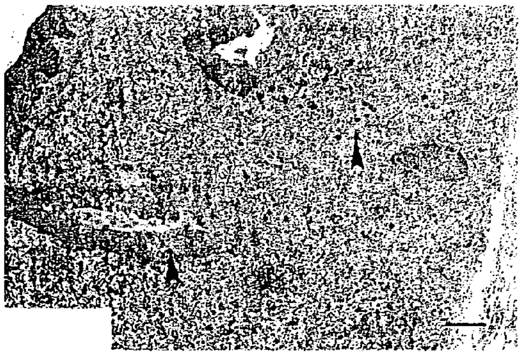
FIG. 26 shows a tonsil from a pig infected 9 days previously with PRRSV, in which positive staining cells (arrow heads) are demonstrated within follicles and in the crypt epithelium by the present streptavidin-biotin complex method (with hematoxylin counterstain); the bar indicates a length of 86 microns.

One section of left and one section of right ventricle were examined. At 4 DPI, there were small, randomly distributed, perivascular foci of lymphocytes and macrophages. There was moderate multifocal perivascular lymphoplasmacytic and histiocytic inflammation by 9 DPI. Moderate numbers or endothelial cells lining small capillaries of lymphatics throughout the myocardium stained strongly positive for PRRSV antigen (FIG. 26) at both 4 and 9 DPI. The PRRSV antigen-positive endothelial cells frequently were not surrounded by inflammatory cells at 4 DPI, but were in areas of inflammation at 9 DPI. A few macrophages between myocytes and in perivascular areolar tissue also stained strongly positive for PRRSV antigen.

Figure 27:
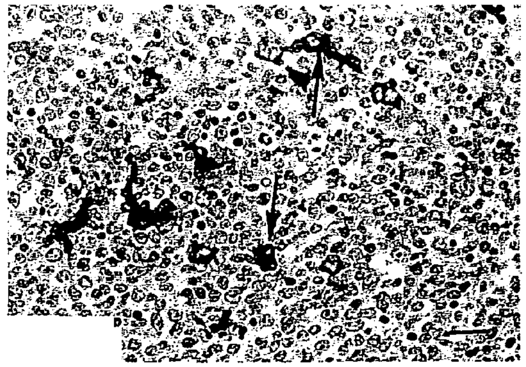
FIG. 27 shows a lymph node from a pig infected 9 days previously with PRRSV, in which positive staining is demonstrated within follicles by the present streptavidin-biotin complex method (with hematoxylin counterstain), and positive cells (arrows) resemble macrophages or dendritic cells; the bar indicates a length of 21 microns.

A mild tonsillitis with necrosis was observed. Necrotic foci of 1–10 cells with pyknosis and karyorrhexis were commonly observed in the center of prominent follicles and less often in the surrounding lymphoreticular tissue. Large numbers of lymphocytes and macrophages were observed within the crypt epithelium, and moderate amounts of necrotic cell debris were observed in crypts. PRRSV antigen was readily detected within cells in the center of hyperplastic follicles, in the surrounding lymphoreticular tissue, and within cells in the crypt epithelium (FIG. 27). Staining was also present amongst necrotic debris in the crypts. In all these sites, the PRRSV antigen-positive cells resembled macrophages or dendritic-like cells.

Thymic lesions were minimal. There were a few necrotic foci with pyknosis and karyorrhexis in the medulla. These foci tended to involve or be near thymic corpuscles. PRRSV antigen was frequently identified within macrophages near these necrotic areas and less often within large isolated macrophages in the cortex.

Necrotic foci and single necrotic cells were evident with germinal centers of lymphoid nodules and in periarteriolar lymphoid sheaths (PALS) of the spleen. PRRSV antigen positive staining cells were concentrated in the center of lymphoid follicles and scattered throughout PALS. The positive cells generally had large oval nuclei and abundant cytoplasm with prominent cytoplasmic projections, compatible with macrophages or dendritic cells. Lesser numbers of positive-staining fusiform-shaped cells in the marginal zone were observed. The size and location of these cells suggests that they are reticular cells.

The predominant lymph node changes were subcapsular edema, foci of necrosis in lymphoid follicles, and the presence of syncytial cells at the border of the central lymphoid tissue with the loose peripheral connective tissue. The high endothelial venules were unusually prominent and often swollen. The syncytial cells had 2–10 nuclei with multiple prominent nucleoli and moderate eosinophilic cytoplasm. These cells did not appear to contain PRRSV antigen. Intense and specific cellular cytoplasmic staining was observed in the follicles. The positive cells had large nuclei with abundant cytoplasm and prominent cytoplasmic processes (FIG. 27). These cells resembled macrophages or dendritic cells. Lesser numbers of positive cells were observed in the perifollicular lymphoid tissue.

The lesion severity and the amount of antigen detected within various tissues was generally similar at 4 and 9 DPI. The gross size of the lymph nodes and the number of syncytial cells in lymph nodes were more prominent at 9 DPI than at 4 DPI. The amount of antigen detected in the heart was also greater at 9 DPI.

Tissues from age-matched uninfected CDCD pigs were used for histologic and immunohistochemical controls. Other negative controls for immunohistochemistry included using the same protocol less the primary PRRSV antibody on the infected pig tissues. PRRSV antigen was not detected in any of the negative controls.

CONCLUSIONS

The immunohistochemical procedure described herein is useful for detecting PRRSV antigen in the lung, heart and lymphoid tissues of PRRSV-infected pigs. Severe interstitial pneumonia and moderate multifocal perivascular lymphohistiocytic myocarditis was observed. Marked lymphoid follicular hyperplasia and necrosis of individual or small clusters of cells in the tonsil, spleen, and lymph nodes was also observed. PRRSV antigen was readily detected in alveolar macrophages in the lung and in endothelial cells and macrophages in the heart. Macrophages and dendritic-like cells in tonsil, lymph nodes, thymus, and spleen stained intensely positive for viral antigen as well.

PRRSV may replicate in the tonsil with subsequent viremia and further replication, primarily within macrophages in the respiratory and lymphoid systems of the pig.

EXPERIMENT VII

Diagnosing PRRS:

The present streptavidin-biotin immunoperoxidase test for detection of PRRSV antigen in tissues is quite useful to confirm the presence of active infection. 26 pigs were experimentally inoculated with ATCC VR 2385 PRRSV in accordance with the procedure in Experiments V/VI above. One section of each of the lungs, tonsils, mediastinal lymph nodes, and tracheobronchial lymph nodes from each pig was examined. The virus was detected by the immunoperoxidase assay of Experiment V in 23/26 lungs, 26/26 tonsils, 15/26 mediastinal lymph nodes, and 14/26 tracheobronchial lymph nodes.

The pigs in this experiment were killed over a 28 day period post-inoculation. The virus was detected in at least one tissue in every pig necropsied up to 10 days post inoculation.

A complete technique for the streptavidin-biotin based immunoperoxidase technique for PRRSV antigen detection in porcine tissues is described in Experiment V infra. Briefly, after endogenous peroxidase removal by 3% hydrogen peroxide and digestion with 0.05% protease (Protease XIV, Sigma Chemical Company, St. Louis, Mo.), primary monoclonal antibody ascites fluid diluted 1:1000 in TRIS/PBS is added for 16 hours at 4° C. in a humidified chamber. The monoclonal antibody used was SDOW-17 (Dr. David Benfield, S. Dak. State Univ.), which recognizes a conserved epitope of the PRRSV nucleocapsid protein (Nelson et al, "Differentiation of U.S. and European isolates of porcine reproductive and respiratory syndrome virus by monoclonal antibodies," *J. Clin. Micro.,* 31:3184–3189 (1993)). Biotinylated goat anti-mouse linking antibody (Dako Corporation, Carpintera, Calif.) is then contacted with the tissue, followed by treatment with peroxidase-conjugated streptavidin (Zymed Laboratories, South San Francisco, Calif.), incubation with 3,3'-diaminobenzidine tetrahydrochloride (Vector Laboratories Inc., Burlingame, Calif.), and finally staining with hematoxylin.

Particularly when combined with one or more additional analytical techniques such as histopathology, virus isolation and/or serology, the present tissue immunoperoxidase antigen detection assay offers a rapid and reliable diagnosis of PRRSV infection.

EXPERIMENT VIII

The pathogenicity of PRRSV isolates in 4–8 week old pigs was determined. The isolates were divided into two groups: (1) phenotypes with high virulence (hv) and (2) phenotypes with low virulence (lv) (see Table 3 below). For example, the mean percentage of lung consolidation of groups of pigs inoculated with a PRRSV isolate is shown in Table 4 below. The pathogenicity of a number of PRRSV isolates at 10 DPI is shown in Table 5 below. The results in Table 5 were statistically analyzed to verify the difference between hv and lv phenotypes, as determined by percentage lung consolidation.

Isolates characterized as high virulence produce severe clinical disease with high fever and dyspnea. In general, hv isolates produce severe pneumonia characterized by proliferative interstitial pneumonia with marked type II pneumocyte proliferation, syncytial cell formation, alveolar exudate accumulation, mild septal infiltration with mononuclear cells, encephalitis and myocarditis (designated PRRS-B hereinafter). Isolates characterized as low virulence do not produce significant clinical disease and produce mild pneumonia characterized predominately by interstitial pneumonia with septal infiltration by mononuclear cells, typical of classical PRRS (designated PRRS-A hereinafter).

TABLE 3

Characteristics and Pathogenicity of PRRSV Isolates

| | | | | Microscopic Lesions** | | |
|---|---|---|---|---|---|---|
| Virus Isolate | No. of Subgenomic mRNAs | mRNA 4 | Severity of gross pneumonia* lesions | Lesion Type in Lung | Heart | Brain |
| | | | High Virulence (hv) | | | |
| VR 2385 | 6 | Normal | ++++ | B | ++++ | ++++ |
| VR 2429 | 8 | Normal | ++++ | B | ++++ | +++ |

TABLE 3-continued

Characteristics and Pathogenicity of PRRSV Isolates

| Virus Isolate | No. of Subge-nomic mRNAs | mRNA 4 | Severity of gross pneumonia* lesions | Microscopic Lesions** Lesion Type in Lung | Heart | Brain |
|---|---|---|---|---|---|---|
| ISU-28 | ND | ND | +++ | B | ++++ | ++++ |
| ISU-79 | 8 | Normal | ++++ | B | +++ | +++ |
| ISU-984 | ND | ND | +++ | B | +++ | +++ |
| | | Low Virulence (lv) | | | | |
| ISU-51 | ND | ND | + | A | + | + |
| VR 2430 | 8 | Normal | + | A/B | + | + |
| ISU-95 | ND | ND | + | A | + | + |
| ISU-1894 | 6 | Normal | + | A/B | + | + |
| VR 2431 | 6 | Deletion | + | A/B | – | – |
| Lelystad*** | 6 | Normal | + | A | +/– | +/– |

*(–) normal, (+) mild, (++) moderate, (+++) severe, (++++) very severe pneumonia.
**PRRSV isolates produce two types of microscopic lung lesions: Type A lesions include interstitial pneumonia with mild septal infiltration with mononuclear cells typical of PRRS as described by Collins et al (1992); Type B lesions include proliferation of type II pneumocytes, and are typical of those described as PIP (Halbur et al 1993).
*** Pol et al, (Vet. Quart., 13:137–143 (1991); Wensvoort et al, Antigenic comparison of Lelystad virus and swine infertility and respiratory syndrome virus. J. Vet. Diagn. Invest., 4:134–138 (1992); Meulenberg et al, Lelystad virus, the causative agent of porcine epidemic abortion and respiratory syndrome (PEARS), is related to LDV and EAV. Virology, 192: 62–72 (1993).

TABLE 4

| VIRUS ISOLATE | Mean % Lung Consolidation Score at DPI* 3 | 10 | 21 | 28 |
|---|---|---|---|---|
| VR-2385 | 29 | 77.3 | 37.3 | 6.0 |
| VR-2386pp | 20.5 | 77.5 | 25.0 | 0.0 |
| ISU-22 | 26.5 | 64.8 | 36.5 | 11.0 |
| ISU-984 | 7.25 | 76.0 | 21.0 | 0.5 |
| ISU-3927 | 13.5 | 10.5 | 0 | 0.0 |
| PSP-36 | 0 | 0 | 0 | 0.0 |
| UNINOC | 0 | 0 | 0 | 0.0 |

*Score range is from 0–100% consolidation of the lung tissue.

TABLE 5

| INOCULUM | NO. PIGS | Mean % Lung Consolidation at 10 DPI ± S.D. |
|---|---|---|
| Uninfected | 10 | 0 ± 0 |
| CRL 11171 Cell Line | 10 | 0 ± 0 |
| ISU-51 | 10 | 16.7 ± 9.0 |
| ISU-55 | 10 | 20.8 ± 15.1 |
| ISU-1894 | 10 | 27.4 ± 11.7 |
| ISU-79 | 10 | 51.9 ± 13.5 |
| VR-2386pp | 10 | 54.3 ± 9.8 |
| ISU-28 | 10 | 62.4 ± 20.9 |

*Pathogenicity of PRRSV isolates ISU-28, VR 2386pp and ISU-79 were not significantly different ($p > 0.05$) from each other, but were different from that of ISU-51, ISU-55, and ISU-1894 ($p < 0.001$). All PRRSV isolates were significantly different ($p < 0.001$) from controls.

The precise mechanisms important in pathogenesis of PRRSV infection have not been fully delineated. However, alveolar macrophages and epithelial cells lining bronchioli and alveolar ducts have been shown to contain viral antigen by immunocytochemistry on frozen sections (Pol et al: Pathological, ultrastructural, and immunohistochemical changes caused by Lelystad virus in experimentally induced infections of mystery swine disease (synonym: porcine epidermic abortion and respiratory syndrome (PEARS). *Veterinary Quarterly,* 13:137–143 (1991)).

The present immunocytochemistry test for the detection of PRRSV in formalin-fixed tissues (see Experiment VI supra) shows that PRRSV also replicates in alveolar epithelial cells and macrophages. The extent of virus replication and cell types infected by PRRSV isolates also appears to vary (see Experiment X below).

The role of different genes in virulence and replication is not precisely known. However, ORF's 4 and 5 appear to be important determinants of in vivo virulence and in vitro replication in PRRSV.

The results of cloning and sequencing ORF's 5, 6 and 7 of PRRSV isolate VR 2385 (see Experiment I supra) show that ORF 5 encodes a membrane protein (also see U.S. application Ser. No. 08/131,625). A comparison of ORF's 5–7 of VR 2385 with ORF's 5–7 of Lelystad virus shows that ORF 5 is the least-conserved of the three proteins analyzed (see Table 2 supra), thus indicating that ORF 5 may be important in determining virulence.

Based on Northern blot results, ORF 4 of lv isolate VR 2431 appears to have a deletion in mRNA 4 (also see Experiment V of U.S. application Ser. No. 08/131,625).

EXPERIMENTS IX–XI

PRRSV (ATCC VR 2386) was propagated in vitro in ATCC CRL 11171 cells by the method disclosed in Experiment III of U.S. application Ser. No. 08/131,625. The PRRSV isolate was biologically cloned by three rounds of plaque purification on CRL 11171 cells and characterized. The plaque-purified isolate (hereinafter "VR 2386 pp", which is equivalent to VR 2386, deposited at the ATCC, Rockville Md., on Oct. 29, 1992) replicated to about $10^6$–$10^7$ $TCID_{50}$/ml at the 11th cell culture passage in CRL 11171 cells. Viral antigens were also detected in the cytoplasm of infected cells using convalescent PRRSV serum. VR 2386 pp was shown to be antigenically related to VR 2332 by IFA using polyclonal and monoclonal antibodies to the nucleocapsid protein of VR 2332 (SDOW-17, obtained from Dr. David Benfield, S. Dak. State University).

Several other virus isolates (VR 2429 (ISU-22), ISU-28, VR 2428 (ISU-51), VR 2430 (ISU-55), ISU-79, ISU-984, ISU-1894, and VR 2431 (ISU-3927)) were isolated and plaque-purified on CRL 11171 cell line. Virus replication in the CRL 11171 cell line varied among PRRSV isolates (see Table 3 below). Isolate VR 2385 and plaque-purified isolates VR 2386 pp, VR 2430 and ISU-79 replicated to $10^{6-7}$ $TCID_{50}$/ml, and thus, have a high replication (hr) phenotype. Other isolates, such as ISU-984, ISU-1894 replicated to a titer of $10^{4-5}$ $TCID_{50}$/ml, corresponding to a moderate replication (mr) phenotype. Isolates ISU-3927 and ISU-984 replicated very poorly on CRL 11171 cell line and usually yielded a titer of $10^3$ $TCID_{50}$/ml, and thus have a low replication (lr) phenotype.

EXPERIMENT IX

The pathogenicity of several PRRSV isolates was compared in cesarean-derived colostrum-deprived (CDCD) pigs to determine if there was a correlation between in vitro replication and pathogenicity (also see Experiment V of application Ser. No. 08/131,625. Four plaque-purified PRRSV isolates (VR 2386 pp, VR 2429, ISU-984, and VR 2431), and one non-plaque-purified isolate (VR 2385) were used to inoculate pigs. An uninoculated group and an uninfected cell culture-inoculated group served as controls. Two pigs from each group were killed at 3, 7, 10, and 21 DPI. Three pigs were killed at 28 and 36 DPI. Biologically cloned PRRSV isolates VR 2386 pp, VR 2429, and ISU-984 induced severe respiratory disease in the 5 week-old CDCD pigs, whereas VR 2431 did not produce any significant disease. Gross lung lesion scores peaked at 10 DPI (see Table 4) and ranged from 10.5% consolidation (VR 2431) to 77% consolidation (VR 2385). Lesions were resolved by 36 DPI.

Microscopic lesions included interstitial pneumonia, encephalitis, and myocarditis (Table 3). The lv isolates also caused less severe myocarditis and encephalitis than the hv isolates.

Figure 28A:
FIGS. 28(A)–(C) are photomicrographs of lungs from pig inoculated with (A) culture fluid from an uninfected cell line, (B) culture fluid from a cell line infected with a low virulence PRRSV isolate (the lungs show PRRS-A type lesions), and (C) culture fluid from a cell line infected with a high virulence PRRSV isolate (the lungs show PRRS-B type lesions)
Figure 28B:
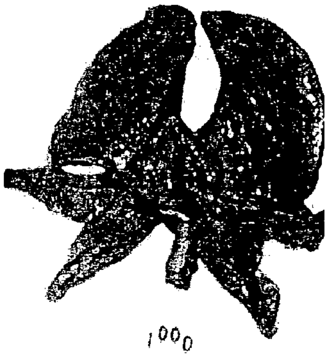
Figure 28C:

In FIGS. 28(A)–(C), photographs of lungs from pigs inoculated with (A) culture fluid from uninfected cell line CRL 11171, (B) culture fluids from cell line infected with lv isolate VR 2431, (C) or culture fluids from cell line infected with hv isolate VR 2386 pp. The lung in FIG. 28(B) has very mild pneumonia, whereas lung in FIG. 28(C) has severe consolidation.

EXPERIMENT X

An additional experiment was conducted using a larger number of pigs to further examine the pathogenicity of PRRSV isolates and to obtain more statistically significant data. Results are shown in Table 5. Collectively, the results show that PRRSV isolates can be divided into two groups based on pneumopathogenicity. Isolates VR 2385, VR 2429, ISU-28, and ISU-79 have a high virulence (hv) phenotype and produce severe pneumonia. Isolates ISU-51, VR 2430, ISU-1894 and VR 2431 have a low virulence (lv) phenotype (Table 4) and produce low grade pneumonia.

PRRSV isolates also produce two types of microscopic lesions in lungs. The first type found generally in lv isolates is designated as PRRS-A, and is characterized by interstitial pneumonia with septal infiltration with mononuclear cells typical of PRRS (as described by Collins et al, Isolation of swine infertility and respiratory syndrome virus (isolate ATCC VR-2332) in North America and experimental reproduction of the disease in gnotobiotic pigs. *J. Vet. Diagn. Invest.,* 4:117–126 (1992)). The second type of lesion, PRRS-B, is found in hv isolates and is characterized as proliferative interstitial pneumonia with marked type II pneumocyte proliferation, alveolar exudation and syncytial cell formation, as described in U.S. application Ser. No. 08/131,625 and by Halbur et al, An overview of porcine viral respiratory disease. *Proc. Central Veterinary Conference, pp.* 50–59 (1993). Examples of PRRS-A and PRRS-B type lesions are shown in FIGS. 28(A)–(C), in which FIG. 28(A) shows a normal lung, FIG. 28(B) are the lesions produced by PRRSV type A, and FIG. 28(C) shows the lesions produced by PRRSV type B.

Figure 29A:
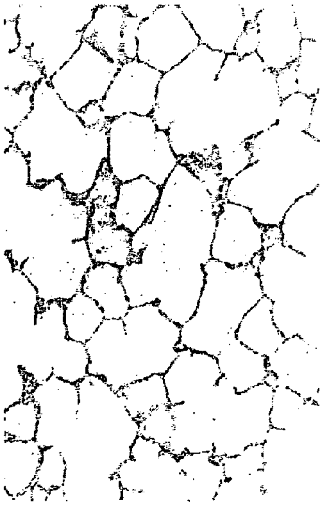
FIGS. 29(A)–(B) illustrate immunohistochemical staining with anti-PRRSV monoclonal antibody of a lung from a pig infected 9 days previously with PRRSV.

The immunoperoxidase assay of Experiment V using monoclonal antibodies to PRRSV was used to detect viral antigens in alveolar epithelial cells and macrophages (see FIG. 29(A)). This test is now being routinely used at the Iowa State University Veterinary Diagnostic Laboratory to detect PRRSV antigen in tissues.

Figure 29B:
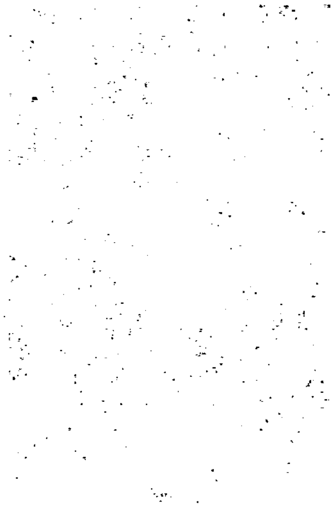
Figure 29C:
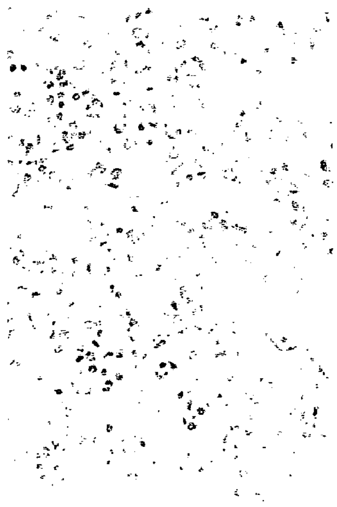

In FIGS. 29(A)–(B), immunohistochemical staining with anti-PRRSV monoclonal antibody of lung from a pig infected 9 days previously with VR 2385. A streptavidin-biotin complex (ABC) immunoperoxidase technique coupled with hematoxylin counterstaining were used. Positive staining within the cytoplasm of macrophages and sloughed cells in the alveolar spaces is clearly shown in FIG. 29(A), and within cellular debris in terminal airway lumina in FIG. 29(B).

EXPERIMENT XI

To determine if there was a correlation between biological phenotypes and genetic changes in PRRSV isolates, Northern blot analyses were performed on 6 PRRSV isolates.

Total intracellular RNA's from the VR 2386 pp virus-infected CRL 11171 cells were isolated by the guanidine isothiocyanate method, separated on 1% glyoxal/DMSO agarose gel and blotted onto nylon membranes. A cDNA probe was generated by PCR with a set of primers flanking the extreme 3' terminal region of the viral genome. The probe contained 3' noncoding sequence and most of the ORF-7 sequence (see U.S. application Ser. No. 08/131,625).

Figure 30B:
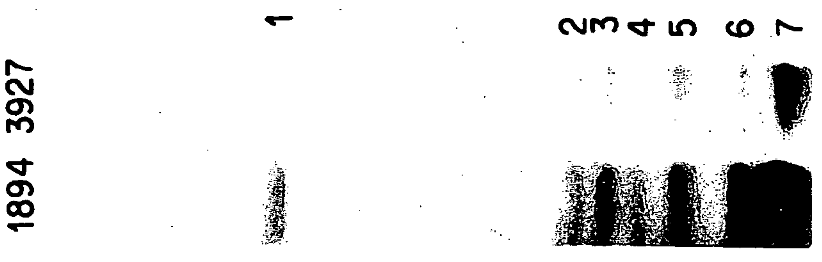
FIGS. 30(A)–(B) show Northern blots of PRRSV isolates VR 2385 pp (designated as "12"), VR 2429 (ISU-22, designated as "22"), VR 2430, designated as "55"), ISU-79 (designated as "79"), ISU-1894 (designated as "1894"), and VR 2431, designated as "3927").
Figure 30A:
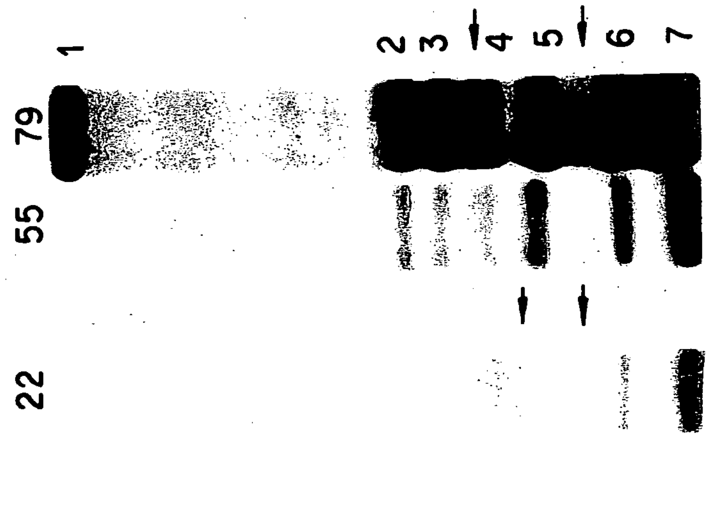

Northern blot hybridization revealed a nested set of 6 subgenomic mRNA species (FIG. 30). The size of VR 2386 pp viral genomic RNA (14.7 kb) and the six subgenomic mRNA's, mRNA 2 (3.3 kb), mRNA 3 (2.8 kb), mRNA 4 (2.3 kb), mRNA 5 (1.9 kb), mRNA 6 (1.4 kb) and mRNA 7 (0.9 kb), resembled those of LV, although there were slight differences in the estimated sizes of the genome and subgenomic mRNA's (Conzelmann et al, *Virology,* 193, 329–339 (1993), Meulenberg et al, *Virology,* 192, 62–72 (1993). The mRNA 7 of the VR 2386 pp was the most abundant subgenomic mRNA (see FIG. 30 and Experiment I above). The total numbers of subgenomic mRNA's and their relative sizes were also compared. The subgenomic mRNA's of three isolates had 6 subgenomic mRNA's, similar to that described for Lelystad virus. In contrast, three isolates had 8 subgenomic mRNA's (FIG. 30). The exact origin of the two additional species of mRNA's is not known, but they are located between subgenomic mRNA's 3 and 6 and were observed repeatedly in cultures infected at low MOI. Interestingly, an additional subgenomic mRNA has been detected in LDV isolates propagated in macrophage cultures (Kuo et al, 1992). We speculate that the additional mRNA's in cells infected with some PRRSV isolates are derived from gene 4 and 5 possibly transcribed from an alternate transcriptional start site. Additional studies are needed to determine the origin of these RNA's and their significance in pathogenesis of PRRSV infections.

FIG. 30 shows Northern blots of PRRSV isolates VR 2386 pp (designated as "12"), VR 2429 (ISU-22, designated as "122"), VR 2430, designated as "55"), ISU-79 (designated as "79"), ISU-1894 (designated as "1894"), and VR 2431, designated as "3927"). This data represents results from four separate Northern blot hybridization experiments. The VR 2386 pp isolate (12) was run in one gel, ISU-1894 and VR 2431 were run in a second gel, VR 2430 and ISU-79 were run in a third gel, and ISU-22 was run in a fourth gel. Two additional mRNA's are evident in isolates VR 2429, VR 2430, and ISU-79.

The subgenomic mRNA 4 of VR 2431 (ISU-3927) migrates faster than that of other isolates in Northern blotting, suggesting a deletion. Interestingly, the isolate VR 2431 has lv and lr phenotypes and is the least virulent PRRSV isolate of the Iowa strains described herein. This suggests that gene 4 may be important in virulence and replication. As described above, genes 6 and 7 are less likely to play a role in expression of virulence and replication phenotypes.

In summary, PRRSV isolates vary in pathogenicity and the extent of replication in cell cultures. The number of subgenomic mRNA's and the amount of mRNA's also varies among U.S. PRRSV isolates. More significantly, one of the isolates, VR 2431, which replicates to low titer (lr phenotype) and which is the least virulent isolate (lv phenotype) among the Iowa strain PRRSV isolates described herein, appears to have a faster migrating subgenomic mRNA 4, thus suggesting that a deletion exists in its ORF 4.

EXPERIMENT XII

Comparison of the Pathogenicity and Antigen Distribution of two U.S. Porcine Reproductive and Respiratory Syndrome Virus Isolates with the Lelystad Virus PRRSV-induced respiratory disease with secondary bacterial pneumonia, septicemia and enteritis are frequently observed in 2–10-week-old pigs (Halbur et al., "Viral contributions to the porcine respiratory disease complex," *Proc. Am. Assoc. Swine Pract*., pp. 343–350 (1993); Zeman et al., *J. Vet. Diagn. Invest*. (1993)). Outbreaks may last from 1–4 months or become an ongoing problem on some farms where pig-flow through the unit is appropriate for shedding of the virus from older stock to younger susceptible animals that have lost passive antibody protection.

The severity and duration of outbreaks is quite variable. In fact, some herds are devastated by the high production losses (Polson et al., "Financial Impact of Porcine Epidemic Abortion and Respiratory Syndrome (PEARS)," *Proc. 12th Inter. Pig Vet. Soc*., p. 132 (1992); Polson et al, "An evaluation of the financial impact of porcine reproductive and respiratory syndrome (PRRS) in nursery pigs," *Proc. 13th Inter. Pig Vet. Soc*., p. 436 (1994)), while other herds have no apparent losses due to infection with PRRSV. This may be due to a number of possibilities, including virus strain differences, pig genetic susceptibility differences, environmental or housing differences, or production style (pig flow) of the unit.

This experiment compares the pathogenicity and antigen distribution of two U.S. strains (ISU-12 [VR 2385], ISU-3927 [VR 2431]) and a European strain (Lelystad virus, obtained from the National Veterinary Services Laboratory, P.O. Box 844, Ames, Iowa, 50010) in a common pig model to document similarities and differences that may explain the differences in severity of field outbreaks of PRRSV and help to better understand the pathogenesis of disease induced by PRRSV. (In the following experimental descriptions, "x/y" refers to the number of pigs "x" out of a particular group of pigs having "y" members.)

MATERIALS AND METHODS

Experimental Design

One hundred caesarian-derived-colostrum-deprived (CDCD) pigs of 4 weeks of age were randomly divided into 4 large groups of 25 pigs each and assigned to one of four isolated buildings. Within each building, the pigs were further divided into 3 separate rooms (11 pigs, 11 pigs, and 3 pigs per room). Each room within the buildings had separate, automated ventilation systems. The pigs were housed on raised woven wire decks and fed a complete 18% protein corn and soybean meal based ration. Following challenge with a virus inoculum, the pigs were necropsied as detailed in Table 6 below at 1, 2, 3, 5, 7, 10, 15, 21 and 28 days post inoculation (DPI).

Virus Inocula Preparation:

Each virus was plaque-purified three times. Challenge doses were $10^{5.8}$ for VR 2385 and $10^{5.8}$ for VR 2431. The challenge dose of Lelystad virus was $10^{5.8}$.

Pigs were challenged intranasally by sitting them on their buttocks perpendicular to the floor and extending their neck fully back. The inocula was slowly dripped into both nostrils of the pigs, taking approximately 2–3 minutes per pig. Control pigs were given 5 mL of uninfected cell culture media in the same manner.

Clinical Evaluation

Rectal temperatures were taken and recorded daily from −2 DPI through 10 DPI. A clinical respiratory disease score was given to each pig daily from day 0 to 10 DPI, in accordance with the following 0–6 score range, similar to the respiratory distress analysis described above:

0=normal
1=mild dyspnea and/or tachypnea when stressed
2=mild dyspnea and/or tachypnea when not stressed
3=moderate dyspnea and/or tachypnea when stressed
4=moderate dyspnea and/or tachypnea when not stressed
5=severe dyspnea and/or tachypnea when stressed
6=severe dyspnea and/or tachypnea when not stressed A pig was considered "stressed" by the pig handler after holding the pig under his/her arm and taking the pig's rectal temperature for approximately 30–60 seconds. Other relevant clinical observations like coughing, diarrhea, inappe-

TABLE 6

| | | Necropsy Schedule | | | | | | | | | |
|---|---|---|---|---|---|---|---|---|---|---|---|
| Isolate | Room | 1 DPI | 2 DPI | 3 DPI | 5 DPI | 7 DPI | 10 DPI | 15 DPI | 21 DPI | 28 DPI | Total |
| Lelystad | 1 | 1 | 1 | 1 | 1 | 1 | 3 | 1 | 1 | 1 | 11 |
| Lelystad | 2 | 1 | 1 | 1 | 1 | 1 | 3 | 1 | 1 | 1 | 11 |
| Lelystad | 3 | | | | | | 3 | | | | 3 |
| VR 2385 | 4 | 1 | 1 | 1 | 1 | 1 | 3 | 1 | 1 | 1 | 11 |
| VR 2385 | 5 | 1 | 1 | 1 | 1 | 1 | 3 | 1 | 1 | 1 | 11 |
| VR 2385 | 6 | | | | | | 3 | | | | 3 |
| Control | 7 | 1 | 1 | 1 | 1 | 1 | 3 | 1 | 1 | 1 | 11 |
| Control | 8 | 1 | 1 | 1 | 1 | 1 | 3 | 1 | 1 | 1 | 11 |
| Control | 9 | | | | | | 3 | | | | 3 |
| VR 2431 | 10 | 1 | 1 | 1 | 1 | 1 | 3 | 1 | 1 | 1 | 11 |
| VR 2431 | 11 | 1 | 1 | 1 | 1 | 1 | 3 | 1 | 1 | 1 | 11 |
| VR 2431 | 12 | | | | | | 3 | | | | 3 |

tence or lethargy were noted separately, and are not reflected in the respiratory disease score.

Pathologic Examination:

Complete necropsies were performed on all pigs. Macroscopic lung lesions were given a score to estimate the percent consolidation of the lung. Each lung lobe was assigned a number to reflect the approximate volume of entire lung represented by that lobe. Ten (10) possible assigned to each of the right anterior lobe, right middle lobe, anterior part of the left anterior lobe, and caudal part of the left anterior lobe of the lung. The accessory lobe was assigned five (5) points. Twenty-seven and one-half (27.5) points were assigned to each of the right and left caudal lobes to reach a total of 100 points. Gross lung lesion scores were estimated, and a score was given to reflect the amount of consolidation in each lobe. The total for all the lobes was an estimate of the percent consolidation of the entire lung for each pig.

Sections were taken from all lung lobes, nasal turbinates, cerebrum, thalamus, hypothalamus, pituitary gland, brain stem, choroid plexus, cerebellum, heart, pancreas, ileum, tonsil, mediastinal lymph node, middle iliac lymph node, mesenteric lymph node, thymus, liver, kidney, and adrenal gland for histopathologic examination. Tissues were fixed in 10% neutral-buffered formalin for 1–7 days and routinely processed to paraffin blocks in an automated tissue processor. Sections were cut at 6 μm and stained with hematoxylin and eosin.

Immunohistochemistry:

Immunohistochemical staining was performed as described in Experiment VI above. Sections were cut at 3 μm and mounted on poly-L-lysine coated slides. Endogenous peroxidase was removed by three 10-minute changes of 3% hydrogen peroxide. This was followed by a TRIS bath, and then digestion with 0.05% protease (Protease XIV, Sigma Chemical company, St. Louis, Mo.) in TRIS buffer for 2 minutes at 37° C. After another TRIS buffer bath, blocking was done for 20 minutes with a 5% solution of normal goat serum. Primary monoclonal antibody ascites fluid (SDOW-17, obtained from Dr. David Benfield, South Dakota State Univ.) diluted 1:1000 in TRIS/PBS was added for 16 hours at 4° C. in a humidified chamber. After primary antibody incubation and a subsequent 5 minute TRIS bath containing 1% normal goat serum, the slides were flooded with biotinylated goat anti-mouse linking antibody (Dako Corporation, Carpintera, Calif.) for 30 minutes. The sections were washed with TRIS and treated with peroxidase-conjugated streptavidin (Zymed Laboratories, South San Francisco, Calif.) for 40 minutes, then incubated with 3,3'-diaminobenzidine tetrahydrochloride (Vector Laboratories Inc., Burlingame, Calif.) for 8–10 minutes. Sections were then stained with hematoxylin.

Immunohistochemical controls substituted TBS for the primary antibody on all lung and lymphoid tissue sections. The same was done on other sections of other tissues interpreted as possibly positive. Uninfected control pigs also served as negative controls. No staining was detected in any of the control pig tissues. The amount of antigen was estimated according to the following scale: (0)=negative (no positive cells), (1)=isolated or rare positive staining cells (about 1–5 positive cells per histologic section), (2)=a relatively low number of positive cells, yet more abundant than isolated cells (for example, about 10–20 positive cells per histologic section), (3)=a moderate number of positive cells (for example, about 40–80 positive cells per histologic section), and (4)=a relatively large number of positive cells (more than about 100 positive cells per histologic section).

Virus Isolation:

The same tissues from each of two pigs necropsied from each challenge group were pooled at 1, 2, 3, 5, 7, 14, 21, and 28 DPI. At 10 DPI, nine pigs were necropsied from each To group, so three pools of the same tissues from three pigs were made from each challenge group. Serum was also similarly pooled.

Results

Clinical Disease:

The mean clinical respiratory disease score for each group is summarized in Table 7. Control pigs remained normal. Respiratory disease was minimal, and symptoms and histopathology were similar in the groups of pigs infected with Lelystad virus and VR 2431. By 2 DPI, a few pigs in each of these groups demonstrated mild dyspnea and tachypnea after being stressed by handling. From 5–10 DPI, more of the pigs in these groups demonstrated mild respiratory disease, and a couple pigs evidenced moderate, but transient, labored abdominal respiration. By 14 DPI, all pigs in the Lelystad virus (LV) and VR 2431 groups had recovered. Other transient clinical disease noted in a few pigs in these groups included chemosis, reddened conjunctiva, ear drooping, and patchy cyanosis of skin when stressed by handling. Coughing was not observed.

By 2 DPI, the VR 2385-challenged group demonstrated mild respiratory disease without having been stressed. By 5 DPI, all of the pigs in this group demonstrated moderate respiratory disease characterized by labored abdominal respiration and dyspnea when stressed. Some of the pigs in this group received respiratory distress scores of 5 or 6 for a 2- to 5-day period, and the mean clinical respiratory disease score peaked at 3.5/6 at 7 DPI. Respiratory disease was characterized by severe tachypnea and labored abdominal respiration, but no coughing was observed. The VR 2385 pigs generally were moderately lethargic and anorexic from 4–10 DPI. Other transient clinical signs included chemosis,

TABLE 7

| | Mean Clinical Respiratory Disease Score | | | | | | | | | | |
|---|---|---|---|---|---|---|---|---|---|---|---|
| GROUP | 0 DPI | 1 DPI | 2 DPI | 3 DPI | 4 DPI | 5 DPI | 6 DPI | 7 DPI | 8 DPI | 9 DPI | 10 DPI |
| Control | 0 | 0 | 0 | 0 | 0 | 0 | 0 | 0.1 | 0 | 0.1 | 0 |
| Lelystad | 0 | 0.2 | 0.1 | 0.2 | 0.5 | 0.6 | 0.8 | 1.0 | 0.9 | 0.3 | 0.3 |
| VR 2431 | 0 | 0 | 0.3 | 0.2 | 0.4 | 0.6 | 0.3 | 1.3 | 0.7 | 0.5 | 0.5 |
| VR 2385 | 0 | 0.4 | 1.5 | 1.8 | 2.2 | 3.2 | 3.4 | 3.5 | 3.3 | 3.4 | 3.0 |

roughed hair coats, lethargy, and anorexia. It took up to 21 DPI for the majority of the pigs in this group to fully recover.

Gross Lesions

Table 8 summarizes the estimated percent consolidation of the lungs for pigs in each group. Lung lesions in the Lelystad group and VR 2431 group were similar in type and extent. Lesions were first observed at 5 DPI for both groups, and peaked at 15 DPI for the Lelystad challenged group and at 7 DPI for VR 2431 challenged group. Individual scores ranged from 0–31 percent consolidation for the Lelystad group and 0–27 percent for the VR 2431 group. The mean estimated percent consolidation of the lung for the nine pigs necropsied at 10 DPI was 6.8 percent for Lelystad virus challenged pigs and 9.7 percent for the VR 2431 challenged pigs. The lesions were predominately in the cranial, middle and accessory lobes and in the ventromedial portion of the diaphragmatic lobes. The consolidation was characterized by multifocal, tan-mottled areas with irregular, indistinct borders.

TABLE 8

Estimated Percent Consolidation of Lungs (0–100%)

| GROUP | 1 DPI | 2 DPI | 3 DPI | 5 DPI | 7 DPI | 10 DPI | 15 DPI | 21 DPI | 28 DPI |
|---|---|---|---|---|---|---|---|---|---|
| Control | 0 | 0 | 0 | 0 | 0 | 0 | 0 | 0 | 0 |
| Lelystad | 0 | 0 | 0 | 4.8 | 2.3 | 6.8 | 8.8 | 1.8 | 0 |
| VR 2431 | 0 | 0 | 0 | 2.5 | 8.5 | 9.7 | 7.5 | 0 | 0 |
| VR 2385 | 0 | 4.3 | 10.5 | 15.3 | 46.5 | 54.2 | 12.5 | 6.0 | 0 |

Gross lymphoid lesions were more common than lung lesions with both VR 2431 and LV. Lymphadenopathy was consistently observed in the mediastinal and middle iliac lymph nodes. These lymph nodes were tan in color, and from 5–28 DPI, were enlarged to 2–10 times their normal size. There often was at least one 1–5 mm fluid-filled cyst in each of these lymph nodes. No other gross lesions were observed in the LV or VR 2431 groups.

The VR 2385 group had considerably more severe lung consolidation. The distribution of lung consolidation was similar to pigs infected with VR 2431 and LV, but either the entire cranioventral lobes or large coalescing portions of the cranial, middle, accessory and ventromedial diaphragmatic lobes were consolidated. There was no pleuritis and no grossly visible pus in airways. Estimated percent consolidation of the lung 7–10 DPI ranged from 28% to 71%. The estimated mean score of the nine pigs necropsied at 10 DPI was 54.2% consolidation.

Lymphoid lesions in the VR 2385 group were generally similar to those observed in the other groups. Additionally, lymph nodes along the thoracic aorta and in the cervical region were often 2–5 times the normal size. Spleens were also slightly enlarged and meaty in texture.

Several pigs in the VR 2385 group had moderately enlarged and rounded hearts with 10–30 mL of clear fluid in the pericardial space. Some of these pigs also had 50–200 mL of similar fluid in the abdominal cavity. There was no visible exudate or fibrin in the fluid.

Microscopic Lesions:

Heart: Control pigs necropsied up to 10 DPI had no evidence of myocardial inflammation. Several pigs throughout the study had randomly distributed discrete foci of hematopoietic cells in the endocardium and myocardium.

These hematopoietic cells (i) were observed in clumps of 10–30 cells, (ii) ranged in size from 8–20 microns, and (iii) had large round-oval, dark staining nuclei with dense, clumped chromatin, multiple small nucleoli and scant amphophilic cytoplasm. At 10 DPI, 2/9 control pigs had mild multifocal perivascular lymphohistiocytic myocarditis. This was also observed in ½ pigs necropsied at 15 and 21 DPI, respectively.

VR 2431 inoculated pigs also had evidence of myocardial extramedullary hematopoiesis, similar to the controls. Myocarditis was first observed at 7 DPI, and was seen in 16/18 pigs necropsied from 7–28 DPI. The myocarditis was mild, multifocal, usually perivascular and peripurkinje, and lymphohistiocytic. Inflammation was consistently found in the endocardium, often around or involving purkinje fibers. Inflammation in the epicardium and myocardium was most consistently either around vessels or randomly distributed between muscle fibers. Myocardial degeneration, necrosis, or fibrosis was not evident. Low numbers of eosinophils were observed in the perivascular infiltrates in a 4/9 pigs at 9 DPI.

In the LV inoculated pigs, mild multifocal extramedullary hematopoiesis was evident in most pigs up to 7 DPI. Mild myocarditis was first observed at 2 DPI and was inconsistent and mild in pigs posted from 3–10 DPI. The pigs necropsied at 15 and 21 DPI had moderate multifocal myocarditis. The myocarditis was much less severe by 28 DPI. In all, 13/17 LV inoculated pigs necropsied from 7–28 DPI had lymphohistiocytic myocarditis, which was mild-moderate, perivascular, peripurkinje or random in distribution. Fewer numbers of plasma cells and eosinophils were found in areas of inflammation from 10–28 DPI.

Moderate multifocal lymphohistiocytic myocarditis was observed beginning at 10 DPI in all of the VR 2385 inoculated pigs. Severe myocarditis was observed in 2/9 pigs killed at 10 DPI and in 1/2 pigs killed at each of 15, 21, and 28 DPI, respectively. The more severe cases were characterized by multifocal-to-diffuse, lymphoplasmacytic and histiocytic infiltrates that were most intense in the perivascular, peripurkinje, and endocardial regions. Lesser numbers of eosinophils and unidentifiable pyknotic cells were also observed in association with the inflammation. Myocardial degeneration, necrosis and fibrosis were not evident.

Lung: Very mild lung lesions were observed in 2/25 of the control pigs. One pig necropsied at 5 DPI had mild multifocal septal thickening with lymphocytes, macrophages, and neutrophils. At 10 DPI, one pig had mild peribronchiolar and perivascular lymphohistiocytic cuffing and a mild increased number of macrophages and neutrophils in the alveolar spaces.

In the VR 2431 inoculated pigs, microscopic lung lesions were first detected at 2 DPI and were present in 20/25 of the pigs. All pigs necropsied on or after 7 DPI had microscopic lung lesions. The lesions, when present, were multifocal, mild (12/25) to moderate (8/25), generally most severe at 10 DPI and nearly resolved at 28 DPI. The multifocal interstitial pneumonia was characterized by three primary changes: septal thickening with mononuclear cells, type 2 pneumocyte hypertrophy and hyperplasia, and accumulation of normal and necrotic macrophages in alveolar spaces. These changes were present throughout the 28-day period. Mild-to-moderate peribronchiolar and perivascular lymphohistiocytic cuffing was observed in most pigs examined at 10–15 DPI but had apparently resolved by 28 DPI. Lung lesions were seldom observed in sections taken from the caudal lung lobe.

The LV inoculated pigs had microscopic lung lesions very similar to those of VR 2431 in distribution, type, and severity. Microscopic lung lesions were observed in 21/25 of the LV pigs. Lesions were first observed at 2 DPI and persisted throughout the 28 day period. The most severe lesions were seen in a few of the pigs necropsied at 10 DPI and in most of those necropsied at 15 and 21 DPI. The interstitial pneumonia was characterized mainly by septal thickening with mononuclear cells, peribronchiolar and perivascular lymphohistiocytic cuffing, and accumulation of macrophages and necrotic debris in alveolar spaces. Type 2 pneumocyte hyperplasia and hypertrophy was less consistent and less severe than that observed in the VR 2431 inoculated pigs. Lung lesions were seldom seen in sections taken from the caudal lung lobe.

Every pig that was inoculated with VR 2385 and necropsied on or after 5 DPI had moderate-to-severe interstitial pneumonia. Mild multifocal lesions were observed at 2 DPI. The lesions became moderate and multifocal by 5 DPI, severe and diffuse from 7–10 DPI, and still moderate but patchy at 21 and 28 DPI. The interstitial pneumonia at all stages was also characterized by three primary changes (septal thickening with mononuclear cells, type 2 pneumocyte hypertrophy and hyperplasia, and accumulation of normal and necrotic macrophages in alveolar spaces). Of these three changes, the pneumocyte hypertrophy was most prominent and characteristic of VR 2385 inoculation. Peribronchiolar and perivascular lymphomacrophagic cuffing was mild by 5 DPI, moderate by 10 DPI, and nearly resolved by 28 DPI.

Immunohistochemistrv

Both adrenal glands were examined from all pigs. Adrenal gland lesions were not observed in any of the control, VR 2431 or LV inoculated pigs. In the VR 2385 inoculated pigs, 9/25 pigs had mild multifocal lymphoplasmacytic and histiocytic adrenalitis. Inflammation was usually observed in the medulla. Pyknotic cells and karryhectic debris were also observed amongst the inflammatory cells. Lymphoplasmacytic vasculitis and neuritis were also observed in the adrenal artery and nerve, respectively, in 3/28 of the VR 2385 inoculated pigs.

Nasal turbinate lesions were similar in type but differed in severity and frequency in the 4 groups of pigs. A low number (5/25) of the control and LV (5/25) inoculated pigs had mild rhinitis, observed at 10–21 DPI. The rhinitis was characterized by patchy dysplasia of the epithelium, with loss of cilia and mild multifocal subepithelial lymphohistiocytic and suppurative inflammation, with slight edema and congestion.

More of the VR 2431 inoculated pigs (17/25) had rhinitis. Lesions were mild at 5 DPI but moderate by 10 DPI. Epithelial dysplasia with intercellular edema, a blebbed or “tombstone” appearance of swollen superficial epithelial cells becoming pyknotic and apparently sloughing into the nasal cavity, and complete or partial loss of cilia on large patches of epithelium were observed. There was moderate diffuse subepithelial edema, dilated and congested veins, and multifocal infiltrates of lymphocytes, plasma cells, macrophages and neutrophils. The inflammation was most intense near the locations where the ducts of submucosal mucous glands extended to the surface. Leukocytic exocytosis, especially of neutrophils, were frequently observed in dysplastic surface epithelium and along mucous ducts. By 21 DPI, the lesions had become mild, and were resolved by 28 DPI.

Rhinitis was first observed at 5 DPI in the VR 2385 inoculated pigs. A total of 20/25 pigs, and all 17 pigs necropsied on or after 7 DPI, had rhinitis similar to that observed in the ISU-3927 group, except that the lesion persisted throughout the 28 day period.

Tables 9, 10, and 11 summarize and compare the number of different tissues in which PRRSV antigen was detected for each of the challenge groups. No antigen was detected in the control pigs. Table 12 summarizes the estimated amount of antigen in some of the tissues that were tested.

Virus Isolation

Virus isolation from various tissues is summarized in Table 13, where “Lg” refers to lungs, “LN” refers to lymph nodes, “Ht” refers to the heart, “Ser” refers to serum, “Tons” refers to tonsils, “Spln” refers to the spleen, “SI” refers to small intestine, and “Brn” refers to the brain.

TABLE 9

Immunohistochemistry for VR 2385

| Tissue | 1 DPI | 2 DPI | 3 DPI | 5 DPI | 7 DPI | 10 DPI | 15 DPI | 21 DPI | 28 DPI | Total |
|---|---|---|---|---|---|---|---|---|---|---|
| Lung | 0/2 | 1/2 | 2/2 | 2/2 | 2/2 | 9/9 | 2/2 | 2/2 | 2/2 | 22/25 |
| TBLN | 1/2 | 2/2 | 2/2 | 2/2 | 2/2 | 3/9 | 0/2 | 1/2 | 0/2 | 13/25 |
| Med LN | 0/2 | 2/2 | 2/2 | 2/2 | 2/2 | 4/9 | 0/2 | 0/2 | 2/2 | 14/25 |
| Iliac LN | 1/2 | 2/2 | 2/2 | 2/2 | 2/2 | 5/9 | 0/2 | 0/2 | 0/2 | 14/25 |
| Tonsil | 2/2 | 2/2 | 2/2 | 2/2 | 2/2 | 9/9 | 2/2 | 2/2 | 2/2 | 25/25 |
| Thymus | 0/2 | 1/2 | 2/2 | 2/2 | 2/2 | 2/9 | 0/2 | 0/2 | 0/2 | 9/25 |
| Spleen | 0/2 | 2/2 | 2/2 | 2/2 | 0/2 | 3/9 | 0/2 | 1/2 | 0/2 | 10/25 |
| # pos | 2/2 | 2/2 | 2/2 | 2/2 | 2/2 | 9/9 | 2/2 | 2/2 | 2/2 | 25/25 |

TABLE 10

Immunohistochemistry for VR 2431

| Tissue | 1 DPI | 2 DPI | 3 DPI | 5 DPI | 7 DPI | 10 DPI | 15 DPI | 21 DPI | 28 DPI | Total |
|---|---|---|---|---|---|---|---|---|---|---|
| Lung | 1/2 | 1/2 | 0/2 | 1/2 | 0/2 | 7/9 | 2/2 | 0/2 | 2/2 | 14/25 |

TABLE 10-continued

Immunohistochemistry for VR 2431

| Tissue | 1 DPI | 2 DPI | 3 DPI | 5 DPI | 7 DPI | 10 DPI | 15 DPI | 21 DPI | 28 DPI | Total |
|---|---|---|---|---|---|---|---|---|---|---|
| TBLN | 0/2 | 2/2 | 1/2 | 2/2 | 2/2 | 1/9 | 0/2 | 0/2 | 0/2 | 8/25 |
| Med LN | 0/2 | 2/2 | 2/2 | 2/2 | 1/2 | 1/9 | 0/2 | 0/2 | 2/2 | 10/25 |
| Iliac LN | 0/2 | 2/2 | 2/2 | 2/2 | 1/2 | 1/9 | 0/2 | 0/2 | 0/2 | 8/25 |
| Tonsil | 1/2 | 1/2 | 1/2 | 2/2 | 1/2 | 9/9 | 2/2 | 2/2 | 2/2 | 21/25 |
| Thymus | 0/2 | 0/2 | 2/2 | 1/2 | 1/2 | 0/9 | 0/2 | 2/2 | 0/2 | 6/25 |
| Spleen | 0/2 | 0/2 | 0/2 | 0/2 | 0/2 | 0/9 | 0/2 | 0/2 | 1/2 | 1/25 |
| # pos | 1/2 | 2/2 | 2/2 | 2/2 | 2/2 | 9/9 | 2/2 | 2/2 | 2/2 | 25/25 |

TABLE 11

Immunohistochemistry for Lelystad virus

| Tissue | 1 DPI | 2 DPI | 3 DPI | 5 DPI | 7 DPI | 10 DPI | 15 DPI | 21 DPI | 28 DPI | Total |
|---|---|---|---|---|---|---|---|---|---|---|
| Lung | 0/2 | 1/2 | 1/2 | 1/2 | 1/2 | 5/9 | 2/2 | 2/2 | 1/2 | 14/25 |
| TBLN | 1/2 | 1/2 | 1/2 | 0/2 | 1/2 | 5/9 | 0/2 | 0/2 | 0/2 | 9/25 |
| Med LN | 1/2 | 1/2 | 2/2 | 1/2 | 1/2 | 2/9 | 0/2 | 1/2 | 1/2 | 10/25 |
| Iliac LN | 0/2 | 1/2 | 2/2 | 0/2 | 1/2 | 0/9 | 0/2 | 0/2 | 0/2 | 4/25 |
| Tonsil | 2/2 | 2/2 | 2/2 | 2/2 | 2/2 | 7/9 | 2/2 | 2/2 | 2/2 | 23/25 |
| Thymus | 0/2 | 0/2 | 0/2 | 2/2 | 0/2 | 0/9 | 0/2 | 0/2 | 0/2 | 2/25 |
| Spleen | 1/2 | 1/2 | 0/2 | 0/2 | 0/2 | 4/9 | 0/2 | 0/2 | 1/2 | 7/25 |
| # pos | 2/2 | 2/2 | 2/2 | 2/2 | 2/2 | 8/9 | 2/2 | 2/2 | 2/2 | 25/25 |

Serology

All pigs challenged with LV virus were negative prechallenge and remained <1:20 through 7 DPI. By 10 DPI, 6/9 of the pigs necropsied were seropositive with titers ranging from 1:20 to 1:1280. Only 2/10 pigs had titers >1:20 (both were 1:1280). By 15 DPI, all pigs were positive and 5/6 were >1:320. By 21 DPI, titers of 1:1280 or 1:5120 were most common. The VR 2431 antibody titers were similar to those levels seen with the LV virus. With VR 2385, however, 9/9 were positive by 10 DPI and 7/9 were ≧1:320. No PRRSV serum antibody was detected in control pigs.

Discussion

This Experiment clearly demonstrates differences in pathogenicity between PRRSV isolates, differences in PRRSV antigen distribution, and differences in the amount of PRRSV antigen in selected tissues. The low virulence Iowa strain isolate VR 2431 and the low virulence Lelystad virus were similar in these criteria. The Iowa strain VR 2385 isolate was considerably more virulent, and PRRSV antigen was detected in more tissues and in greater amounts as compared to LV and VR 2431.

The pattern of antigen distribution over time (Table 12) suggests that when pigs are infected oronasally, initial and continual replication of the virus may be in

TABLE 12

Mean score for intensity/amount of PRRSV antigen detected by immunohistochemistry

| DPI | CrVn Lung | Mid Lung | TBLN | Med LN | Iliac LN | Tonsil |
|---|---|---|---|---|---|---|
| VR 2385 | | | | | | |

TABLE 12-continued

Mean score for intensity/amount of PRRSV antigen detected by immunohistochemistry

| DPI | CrVn Lung | Mid Lung | TBLN | Med LN | Iliac LN | Tonsil |
|---|---|---|---|---|---|---|
| 1 | 0 | 0 | 1.5 | 0 | 0.5 | 1.0 |
| 2 | 0.5 | 1.0 | 2.0 | 1.5 | 2.0 | 1.5 |
| 3 | 2.0 | 2.5 | 3.0 | 3.0 | 3.0 | 3.0 |
| 5 | 2.0 | 2.0 | 3.0 | 3.0 | 2.5 | 3.0 |
| 7 | 2.5 | 1.5 | 1.0 | 1.5 | 2.0 | 1.0 |
| 10 | 2.0 | 1.6 | 0.5 | 0.6 | 0.7 | 1.2 |
| 15 | 1.0 | 0 | 0 | 0 | 0 | 1.0 |
| 21 | 2.0 | 0.5 | 0.5 | 0 | 0 | 2.5 |
| 28 | 1.0 | 0 | 0 | 1 | 0 | 1.5 |
| VR 2431 | | | | | | |
| 1 | 0.5 | 0 | 0 | 0 | 0 | 0.5 |
| 2 | 0.5 | 0 | 2.0 | 1.0 | 2.5 | 0.5 |
| 3 | 0 | 0 | 1.0 | 1.5 | 2.5 | 0.5 |
| 5 | 0.5 | 1 | 2.0 | 2.0 | 2.0 | 1.0 |
| 7 | 0 | 2 | 1.0 | 1.0 | 0.5 | 0.5 |
| 10 | 1.1 | 0.9 | 0.1 | 0.1 | 0.1 | 1.1 |
| 15 | 2.0 | 0.5 | 0 | 0 | 0 | 1.0 |
| 21 | 0 | 0 | 0 | 0 | 0 | 1.0 |
| 28 | 1.3 | 0 | 0 | 1.3 | 0 | 2.0 |
| Lelystad Virus | | | | | | |
| 1 | 0 | 0 | 0.5 | 0.5 | 0 | 1.0 |
| 2 | 0.5 | 0.5 | 1.0 | 1.0 | 1.0 | 1.0 |
| 3 | 0.5 | 0.5 | 1.0 | 1.5 | 2.0 | 1.0 |
| 5 | 1.0 | 0.5 | 0 | 0.5 | 0 | 1.0 |
| 7 | 1.0 | 0 | 1.0 | 0.5 | 0.5 | 1.0 |
| 10 | 0.3 | 0.4 | 0.6 | 0.2 | 0 | 0.8 |
| 15 | 0.5 | 0.5 | 0 | 0 | 0 | 1.0 |
| 21 | 1.0 | 0 | 0 | 0.5 | 0 | 1.5 |
| 28 | 0.5 | 0 | 0 | 0.5 | 0 | 1.0 |

TABLE 12-continued

| Mean score for intensity/amount of PRRSV antigen detected by immunohistochemistry | | | | | | |
|---|---|---|---|---|---|---|
| DPI | CrVn Lung | Mid Lung | TBLN | Med LN | Iliac LN | Tonsil |

Antigen amount was estimated and scored as follows: (0) = negative, (1) = isolated or rare positive staining cells, (2) = low number of positive cells, (3) moderate number of positive cells, and (4) = large number of positive cells.
CrVn = Cranioventral lung lobe; Mid = middle lung lobe; TBLN = tracheobronchial lymph node; Med LN = mediastinal lymph node.

TABLE 13

| Virus isolation | | | | | | | | |
|---|---|---|---|---|---|---|---|---|
| DPI | Lg | LN | Ht | Ser | Tons | Spln | SI | Brn |
| VR 2385 | | | | | | | | |
| 1 | + | + | − | + | − | − | + | − |
| 2 | + | + | + | + | + | + | + | + |
| 3 | + | + | + | + | + | + | + | + |
| 5 | + | + | + | + | + | + | + | + |
| 7 | + | + | + | + | + | + | + | + |
| 10 | + | + | + | + | + | + | + | − |
| 10 | + | + | − | + | + | + | + | − |
| 10 | + | + | + | + | + | + | + | + |
| 15 | + | + | + | + | + | + | + | − |
| 21 | + | + | + | + | + | + | + | − |
| 28 | + | + | − | + | + | − | − | − |
| VR 2431 | | | | | | | | |
| 1 | + | − | − | + | + | − | + | − |
| 2 | + | + | + | + | + | + | + | − |
| 3 | + | + | + | + | + | + | + | − |
| 5 | + | + | + | + | + | + | − | + |
| 7 | + | + | + | + | + | + | − | + |
| 10 | + | + | + | + | + | + | − | + |
| 10 | + | + | + | + | + | + | − | − |
| 10 | + | − | + | + | + | + | − | + |
| 15 | + | + | + | + | + | + | − | − |
| 21 | + | − | − | + | + | − | − | − |
| 28 | + | − | + | + | + | − | − | − |
| Lelystad Virus | | | | | | | | |
| 1 | − | − | − | + | + | − | − | − |
| 2 | + | + | + | + | + | + | + | − |
| 3 | + | + | + | + | + | + | + | − |
| 5 | + | + | − | + | + | + | + | − |
| 7 | + | + | + | + | + | + | + | − |
| 10 | + | + | + | + | + | + | + | − |
| 10 | + | + | + | + | + | + | + | − |
| 10 | + | + | + | + | + | + | − | + |
| 15 | + | + | + | + | + | + | − | − |
| 21 | + | − | + | + | + | − | − | − |
| 28 | + | − | + | + | + | − | − | − |

the tonsil and upper respiratory tract lymphoid tissues, with subsequent viremia by 24 hours PI. A small amount of antigen is detected in the lung by 24 hours PI and peaks by 5–7 DPI, but persists there for up to 28 days. Antigen is present in lymphoid tissues generally from 2–21 DPI.

Antigen is detected primarily within the macrophages and dendritic-like cells in lung, lymph nodes, tonsil, thymus and spleen.

EXPERIMENT XIII

Comparative Pathogenicity of Nine U.S. PRRSV Isolates in a 5 Week Old CDCD Pig Model Part (A) of this experiment demonstrates a consistent model to study PRRSV-induced respiratory and systemic 1 disease in piglets (e.g., about 5 weeks old) and to characterize gross and microscopic lesions associated with the course of PRRSV-induced disease. Part (B) of this experiment uses the model to statistically compare the virulence of PRRSV isolates from herds with differing disease severity, and to specifically determine if these differences may be due to virus virulence characteristics.

Materials and Methods

Source of PRRSV isolates:

Live pigs or fresh tissues were received from 61 herds over a 3-year period from 1991–1993. All cases were submitted for etiologic diagnosis of respiratory disease in pigs from 1–16 weeks of age. Some of the herds had concurrent reproductive failure, and some did not. The nine selected herds differed in size, production style, age of diseased pigs, time since initial disease was observed, and severity of the current disease outbreak. The clinical information from the selected farms is summarized in Table 14.

TABLE 14

| PRRSV Herd Profiles | | | | |
|---|---|---|---|---|
| Isolate | Herd Size | Production Style | Age of Disease | Type of Disease |
| VR 2385 | 180 sows | F-Fin/CF | ALL | severe PRRS |
| ISU-79 | 40 sows | F-Fin/AIAO | ALL | severe PRRS |
| ISU-28 | 150 sows | F-Fin/CF | ALL | severe PRRS |
| ISU-1894 | 600 sows | F-FRP/CF | 3–8 weeks | severe resp. |
| VR 2428 | 900 sows | F-FRP/AIAO | 3–8 weeks | severe resp. |
| VR 2429 | 100 sows | F-Fin/CF | 1–8 weeks | moderate resp. |
| ISU-984 | 600 sows | F-FRP/AIAO | 3–6 weeks | moderate resp. |
| VR 2430 | 150 sows | F-Fin/CF | 3–6 weeks | mild resp. |
| VR 2431 | 60 sows | F-Fin/AIAO | 1–4 weeks | mild resp. |

F-Fin = Farrow-to-Finish
F-FRP = Farrow-to-Feeder Pig
CF = Continuous Flow
AIAC = All-in-All-out Inocula Preparation PRRSV isolates were plaque purified 3 times in accordance with the procedure described in Experiment I, section (I) (A) above.

Experimental Pigs:

Four-week-old caesarean-derived-colostrum-deprived (CDCD) pigs were initially fed a commercial 22% protein pig starter containing spray-dried plasma protein for 7 days, then were switched to a second stage 18% protein corn-soybean meal based ration for the duration of the experiment. Pigs were housed in 10 feet×12 feet concrete-floored, individually power-ventilated rooms.

Part (A): CDCD Pig Model:

Ninety-eight 4-week-old CDCD pigs were randomly divided into 7 rooms of 14 pigs each. The rooms were randomly assigned one of seven treatments as shown in Table 15. The treatment consisted of intranasal inoculation of $10^{5.7}$ $TCID_{50}$ of a PRRSV isolate (selected from plaque-purified PRRSV isolates VR 2385, VR 2428 [ISU-22], VR 2431 or ISU-984, unplaque-purified isolate ISU-12 [VR 2386]), intranasal inoculation of uninfected cell culture and media, or no treatment. Two pigs from each group were necropsied at DPI 3, 7, 20 and 21, and 3 pigs were necropsied from each group at DPI 28 and 36. Rectal temperatures were recorded daily from DPI −2 though DPI+14. A clinical respiratory disease score was given from DPI −2 through DPI 14. Scores range from 0–6, in accordance with the respiratory distress scale recited in Experiment XII. A piglet was considered "stressed" by the pig handler when holding the pig under his/her arm and taking the rectal temperature for approximately 30–60 seconds. Other relevant clinical observations (e.g., coughing, diarrhea, inappetence or lethargy) were noted separately as observed. Additional clinical observations had no impact on the clinical respiratory score. Weights were recorded an DPI 0, 7, 14, 21 and 28.

TABLE 15

Part (A) Experimental Design

| Inoculum | 3 DPI | 7 DPI | 10 DPI | 21 DPI | 28 DPI | 36 DPI | Total Pigs |
|---|---|---|---|---|---|---|---|
| VR 2385 | 2 | 2 | 2 | 2 | 3 | 3 | 14 |
| ISU-984 | 2 | 2 | 2 | 2 | 3 | 3 | 14 |
| VR 2428 | 2 | 2 | 2 | 2 | 3 | 3 | 14 |
| VR 2431 | 2 | 2 | 2 | 2 | 3 | 3 | 14 |
| VR 2386 | 2 | 2 | 2 | 2 | 3 | 3 | 14 |
| Uninoculated Control | 2 | 2 | 2 | 2 | 3 | 3 | 14 |
| PSP-36 Cell Culture | 2 | 2 | 2 | 2 | 3 | 3 | 14 |

Part (B): Comparative Pathogenicity:

Results from Part (A) established that gross lung lesions were most severe at 10 DPI for 4 of 5 PRRSV isolates. Part (B) was designed to collect and compare data from a larger number of pigs necropsied at 10 DPI. In this experiment, 105 4-week-old crossbred CDCD pigs were randomly divided into seven rooms, each with 15 pigs. Each room was randomly assigned a treatment. Treatments consisted of intranasal challenge with $10^{5.8}$ $TCID_{50}$ of one of six plaque-purified PRRSV isolates (VR 2429 [ISU-51], ISU-79, VR 2430 [ISU-55], ISU-1894, ISU-28 or VR 2385) or PSP-36 uninfected cell culture and media. Ten pigs from each group were necropsied at 10 DPI, and 5 pigs from each group were necropsied at 28 DPI. Rectal temperatures were recorded from −2 DPI to +10 DPI, and weights were recorded at 0, 10 and 28 DPI. Clinical respiratory disease scores and other clinical signs were recorded as in Part (A) above.

Serology:

Part (A): Pigs were bled at 0, 10 and 28 DPI. The presence of PRRSV serum antibody was detected by the immunofluorescent antibody technique (IFA) as described by Benfield et al (*J. Vet. Diagn. Invest.,* 4:127–133 (1992)).

Part (B): Pigs were bled at 0, 3, 10, 16 and 28 DPI and tested by the IFA procedure of Part (A) for the presence of PRRSV serum antibody.

Virus Isolation:

Virus isolation was attempted from lung homogenates of all pigs killed at 3, 7, 10, 21 and 28 DPI (Part (A)). Virus isolation was also attempted from lung and from serum of all pigs separately in two-pig pools using CRL 11171 (PSP 36) cells (Part (B)).

Gross Pathology:

Complete necropsies were performed on all pigs. All organ systems were examined. An estimated percent consolidation of the lung of each pig was calculated based on the scoring system described in Experiment XII above, in which each lung lobe was assigned a number to reflect the approximate volume of entire lung represented by that lobe. Other lesions were noted accordingly.

Microscopic Pathology:

Sections were taken from all lung lobes described above, as well as from nasal turbinates, cerebrum, thalamus, hypothalamus, pituitary gland, brain stem, choroid plexus, cerebellum, heart, pancreas, ileum, tonsil, mediastinal lymph node, middle iliac lymph node, mesenteric lymph node, thymus, liver, kidney, and adrenal gland for histopathologic examination. Tissues were fixed in 10% neutral buffered formalin for 1–7 days and routinely processed to paraffin blocks in an automated tissue processor. Sections were cut at 6 μm and stained with hematoxylin and eosin. Lesions in several tissues were graded in accordance with the following scale: (−)=normal, (+)=mild, (++)=moderate, (+++)=severe, and (++++)=very severe (see Table 19).

Results

Clinical Disease—Part (A), CDCD Pig Model:

VR 2385 challenged pigs demonstrated the most severe clinical respiratory disease, with scores above 2.5/6.0 on 7–9 DPI (Table 16). The onset of respiratory disease was noted on 3 DPI, and symptoms and lesions continued through 14 DPI. Respiratory disease was characterized by labored and accentuated abdominal respirations and tachypnea. There was no coughing. The pigs became lethargic by 3 DPI, were anorexic by 5 DPI, and did not return to full feed and activity until after 14 DPI. Eyelid edema was noted in two pigs on 6 and 7 DPI.

VR 2428-challenged pigs had a later onset of respiratory disease (5 DPI), but severe respiratory disease occurred more quickly and for a longer duration than in ISU-12-inoculated pigs. VR 2428 produced respiratory scores greater than 3.0/6.0 on 7–13 DPI. The pigs were off feed and lethargic at 6–14 DPI. No other clinical signs were noted.

ISU-984-challenged pigs produced moderate-to-severe respiratory disease with gradual onset starting at 4 DPI. The pigs were scored 2–2.5/6.0 for respiratory disease from 7–10 DPI, and greater than 3.0/6.0 with a few scores of 4–5/6.0 on 11–14 DPI. Other clinical signs included lethargy, eyelid edema, and blotchy-purple transient discoloration of skin.

VR 2431-challenged pigs produced mild respiratory disease. Disease onset occurred at 5 DPI with the most severe respiratory clinical disease scores between 2 and 2.5/6.0 in some pigs at 7–8 DPI. The pigs appeared considerably better by 10 DPI and were completely normal by 14 DPI. Lethargy and anorexia were observed on 7–8 DPI.

Mean rectal temperatures were greater than 104° F. for all challenged groups by 7 DPI, and remained above 104° F. until after 10 DPI. This coincided with the period of most severe clinical respiratory disease. The control pigs remained clinically normal throughout the experiment.

Clinical Disease—Part (B), Comparative Pathogenicity:

Clinical respiratory disease scores and rectal temperatures are summarized in Table 17. VR 2429 produced very mild respiratory disease and the pigs appeared near normal through 10 DPI. VR 2430 induced mild dyspnea and tachypnea from 4–10 DPI, as well as lethargy and anorexia from 4–6 DPI. At 5–8 DPI, ISU-1894 produced moderate respiratory disease of short duration, and the pigs were generally recovered by 10 DPI. ISU-1894-inoculated pigs were also transiently lethargic and anorexic from 4–7 DPI. ISU-79 induced severe respiratory disease with labored respirations of increased frequency, accompanied by lethargy and anorexia from 4 DPI to 15 DPI. ISU-12 induced moderate tachypnea and dyspnea of long duration (4–28

DPI). These pigs were also moderately lethargic and mildly anorexic over that time period.

Pigs in three groups (ISU-12, ISU-79, ISU-28) frequently exhibited transient, blue-purple discoloration of the skin when stressed by handling. ISU-28 produced severe respiratory disease similar to ISU-79, but had a later onset (at 7 DPI) and only a 5-day duration. Controls remained normal through 10 DPI.

Gross Lesions—Part (A), CDCD Pig Model:

Gross lung lesions were scored and estimated as percent lung consolidation. Results are summarized in Table 16. The degree of consolidation ranged from 7.3% (ISU-984) to 29% (VR 2386) at 3 DPI, 20% (VR 2431) to 56.3% (VR 2386) at 7 DPI, 10.5% (VR 2431) to 77.5% (VR 2385) at DPI, 0% (VR 2431) to 37.3% at 21 DPI, and 0% (VR 2431, VR 2385) to 11% (VR 2428) at 28 DPI. No grossly detectable lesions remained in any group at 36 DPI. No gross lung lesions were observed at any time in the control group.

The affected lung lobes were primarily in the anterior, middle, accessory, and ventromedial portion of the caudal lobes. The consolidated areas were not well demarcated. These areas were multifocal within in each lobe and had irregular and indistinct borders, giving the affected lobes a tan-mottled appearance.

TABLE 16

Part (A) Mean Gross Lung Consolidation

| Isolate | Clin. Score | Gross Lung |
|---|---|---|
| | 3 DPI | |
| VR 2386 | 0.5 | 29 |
| VR 2385 | 0.5 | 20.5 |
| VR 2428 | 0 | 26.5 |
| ISU-984 | 0.5 | 7.3 |
| VR 2431 | 0 | 13.5 |
| PSP-36 | 0 | 0 |
| Uninoc. | 0 | 0 |
| | 7 DPI | |
| VR 2386 | 3.1 | 56.3 |
| VR 2385 | 2.3 | 35.5 |
| VR 2428 | 2.4 | 35.0 |
| ISU-984 | 2.3 | 21.8 |
| VR 2431 | 2.3 | 20.0 |
| PSP-36 | 0 | 0 |
| Uninoc. | 0 | 0 |
| | 10 DPI | |
| VR 2386 | 3.5 | 77.3 |
| VR 2385 | 2.0 | 77.5 |
| VR 2428 | 3.5 | 64.8 |
| ISU-984 | 3.5 | 76.0 |
| VR 2431 | 1.5 | 10.5 |
| PSP-36 | 0 | 0 |
| Uninoc. | 0 | 0 |
| | 21 DPI | |
| VR 2386 | 2.0 | 37.3 |
| VR 2385 | 0.5 | 25.0 |
| VR 2428 | 2.0 | 36.5 |
| ISU-984 | 2.0 | 21.0 |
| VR 2431 | 0 | 0 |
| PSP-36 | 0 | 0 |
| Uninoc. | 0 | 0 |
| | 28 DPI | |
| VR 2386 | 0.5 | 6.0 |
| VR 2385 | 0 | 0.0 |
| VR 2428 | 2.5 | 11.0 |
| ISU-984 | 0 | 0.5 |
| VR 2431 | 0 | 0.0 |

TABLE 16-continued

Part (A) Mean Gross Lung Consolidation

| Isolate | Clin. Score | Gross Lung |
|---|---|---|
| PSP-36 | 0 | 0.0 |
| Uninoc. | 0 | 0.0 |

Gross Lesions—Part (B), Comparative Pathogenicity:

Gross lung lesions were estimated by percent lung consolidation, and are shown in Table 18.

Microscopic Lesions—Part (A), CDCD Pig Model:

Results are shown in Table 19. VR 2385, VR 2386, VR 2428 and ISU-984 all induced similar microscopic lung lesions. They produced moderate-severe interstitial pneumonia, characterized by: (i) type II pneumocyte proliferation, (ii) septal thickening with mononuclear cells, and (iii) accumulation of mixed alveolar exudate. VR 2431 induced only mild interstitial pneumonia with septal thickening by mononuclear cells. Myocarditis was observed only in the VR 2386 inoculated pigs.

Virus Isolation—Part (A). CDCD Pig Model:

PRRSV was recovered from the lungs of all 11 pigs inoculated with VR 2386, from 9 of 11 pigs inoculated with VR 2385, from 6 of 11 pigs inoculated with ISU-984, from 9 of 11 pigs inoculated with VR 2431, from 0 of 11 pigs inoculated with cell culture controls, and from 0 of 11 uninoculated control pigs up to 28 DPI.

Seroloy—Part (A), CDCD Pig Model:

All of the PRRSV inoculated pigs had detectable PRRSV antibody titer of ≧640 by 10 DPI. None of the control pigs had detectable PRRSV antibody. Most of the PRRSV-inoculated pigs had titers of ≧2560 by 28 DPI.

Serology—Part (B). Comparative Pathogenicity:

All of the PRRSV-inoculated pigs had PRRSV antibody titers of ≧64 by 10 DPI. Control pigs did not have detectable PRRSV antibody.

Discussion

The 5-week-old CDCD pigs inoculated intranasally with $10^{5.8}$ $TCID_{50}$ of PRRSV provide an excellent model to study and compare PRRSV-induced respiratory and systemic disease. Significant differences ($p<0.05$) were observed in the pneumopathogenicity data reported in Table 18. Based on the results herein and in Experiment XI above, the isolates could be grouped into high and low virulence groups as follows:

high virulence: VR 2385, VR 2386, VR 2429 (ISU-22), ISU-28, ISU-984, ISU-79 low virulence: VR 2431, VR 2428 (ISU-51), VR 2430, ISU-1894, LV

A PRRSV isolate may be considered to be a "high virulence" phenotype if it results in one or more of the following:

(a) a mean gross lung consolidation at 10 DPI of at least 30%, and preferably, at least 40%;

(b) moderate-to-very severe type II pneumocyte hypertrophy and hyperplasia, moderate-to-very severe interstitial thickening, moderate-to-very severe alveolar exudate, and the presence of syncytia; or (c) a mean respiratory distress score of at least 2.0 at some point in time from 10–21 DPI.

Where an isolate does not meet any of the above criteria, it may be considered a "low virulence" phenotype.

Obviously, numerous modifications and variations of the present invention are possible in light of the above teachings. It is therefore to be understood that within the scope of the appended claims, the invention may be practiced otherwise than as specifically described herein.

TABLE 17

Part (B) Mean Respiratory Distress Scores and Mean Rectal Temperature (° F.)

| Isolate | 3 DPI | 5 DPI | 7 DPI | 10 DPI | 15 DPI | 21 DPI | 28 DPI |
|---|---|---|---|---|---|---|---|
| Mean Respiratory Distress Score | | | | | | | |
| PSP-36 | 0 | 0 | 0 | 0 | 0 | 0 | 0 |
| VR 2429 | 0 | 0.1 | 0.7 | 0.2 | 0 | 0.2 | 0 |
| VR 2430 | 0 | 1.1 | 0.8 | 1.5 | 0 | 0 | 0 |
| ISU-1894 | 0 | 2.5 | 1.5 | 1.1 | 0.5 | 0 | 0 |
| ISU-79 | 0 | 3.5 | 3.8 | 2.9 | 1.5 | 0.5 | 1.0 |
| VR 2385 | 0.2 | 1.5 | 1.4 | 1.4 | 1.0 | 2.4 | 0.8 |
| ISU-28 | 0 | 1.0 | 1.3 | 3.1 | 0 | 0 | 0 |
| Mean Rectal Temperature | | | | | | | |
| PSP-36 | 102.7 | 102.6 | 103.3 | 103.7 | 103.1 | 103.5 | 103.8 |
| VR 2429 | 102.6 | 103.7 | 104.2 | 103.2 | 104.5 | 103.6 | 104.2 |
| VR 2430 | 102.8 | 103.7 | 104.1 | 103.8 | 103.5 | 104.6 | 104.1 |
| ISU-1894 | 102.7 | 104.4 | 104.3 | 103.3 | 103.9 | 104.4 | 103.9 |
| ISU-79 | 103.6 | 104.9 | 104.6 | 103.7 | 103.4 | 103.5 | 103.8 |
| VR 2385 | 102.2 | 104.3 | 103.9 | 103.5 | 103.7 | 104.2 | 103.8 |
| ISU-28 | 102.6 | 104.2 | 104.0 | 104.8 | 104.0 | 103.8 | 103.9 |

TABLE 18

Part (B), Mean Gross Lung Consolidation and Standard Deviation

| Inocula | Number of Pigs | Mean gross lung score 10 DPI | SD |
|---|---|---|---|
| PSP-36 | 10 | 0.0 | 0.0 |
| ISU-28 | 10 | 62.4 | 20.9 |
| VR 2385 | 10 | 54.3 | 9.8 |
| ISU-79 | 10 | 51.9 | 13.5 |
| ISU-1894 | 10 | 27.4 | 11.7 |
| VR 2430 | 10 | 20.8 | 15.1 |
| VR 2429 | 10 | 16.7 | 9.0 |

TABLE 19

Experiment XIII, part (A), CDCD pig model: Microscopic Lesion Summary at 10 DPI

| Lesion | VR 2386 | VR 2385 | VR 2428 | ISU-984 | VR 2431 | PSP-36 control |
|---|---|---|---|---|---|---|
| Type II pneumo-cyte proliferation | ++++ | +++ | +++ | +++ | + | − |
| Syncytia | ++ | ++ | ++ | ++ | − | − |
| Interstitial thickening | ++++ | +++ | +++ | +++ | + | − |
| alveolar exudate | +++ | +++ | +++ | +++ | + | − |
| myocarditis | + | − | − | − | − | − |
| encephalitis | + | − | − | − | − | − |

What is claimed as new and desired to be secured by Letters Patent of the United States is:

1. A diagnostic kit comprising:

(a) a first primer comprising a polynucleotide having a sequence of 10 to 50 nucleotides in length which hybridizes to a genomic polynucleic acid from a North American strain of PRRSV, wherein said North American strain is ISU-12 (VR 2385), at a temperature of 25 to 75° C., (b) a second primer comprising a polynucleotide having a sequence of 10 to 50 nucleotides in length which hybridizes to said genomic polynucleic acid from said North American strain of PRRSV at a temperature of 25 to 75° C. and being downstream from the sequence to which said first primer hybridizes, and (c) a reagent which enables detection of an amplified polynucleic acid, wherein said first and second primers selectively hybridize to said North American strain and at least one of said first and second primers does not hybridize to a European PRRSV strain, wherein said European strain is Lelystad, resulting in amplification of said North American strain but no amplification of said European strain.

2. The diagnostic kit of claim 1, wherein said reagent is an intercalating dye, the fluorescent properties of which change upon intercalation into double-stranded DNA.

* * * * *

SEQUENCE LISTING

```
(1) GENERAL INFORMATION:

   (iii) NUMBER OF SEQUENCES: 77


(2) INFORMATION FOR SEQ ID NO: 1:

     (i) SEQUENCE CHARACTERISTICS:
          (A) LENGTH: 22 base pairs
          (B) TYPE: nucleic acid
          (C) STRANDEDNESS: unknown
          (D) TOPOLOGY: linear

    (ii) MOLECULE TYPE: DNA (genomic)

    (xi) SEQUENCE DESCRIPTION: SEQ ID NO: 1:

CGGCCGTGTG GTTCTCGCCA AT                                      22


(2) INFORMATION FOR SEQ ID NO: 2:

     (i) SEQUENCE CHARACTERISTICS:
          (A) LENGTH: 22 base pairs
          (B) TYPE: nucleic acid
          (C) STRANDEDNESS: unknown
          (D) TOPOLOGY: linear

    (ii) MOLECULE TYPE: DNA (genomic)
```

-continued (xi) SEQUENCE DESCRIPTION: SEQ ID NO: 2:

CCCCATTTCC CTCTAGCGAC TG 22

(2) INFORMATION FOR SEQ ID NO: 3:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 3:

GCCGCGGAAC CATCAAGCAC 20

(2) INFORMATION FOR SEQ ID NO: 4:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 4:

CAACTTGACG CTATGTGAGC 20

(2) INFORMATION FOR SEQ ID NO: 5:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 5:

GCGGTCTGGA TTGACGACAG 20

(2) INFORMATION FOR SEQ ID NO: 6:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 6:

GACTGCTAGG GCTTCTGCAC 20

(2) INFORMATION FOR SEQ ID NO: 7:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 7:

GCCATTCAGC TCACATAGCG 20

-continued (2) INFORMATION FOR SEQ ID NO: 8:

(i) SEQUENCE CHARACTERISTICS:
(A) LENGTH: 19 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 8:

CTCGTCAAGT ATGGCCGGT 19

(2) INFORMATION FOR SEQ ID NO: 9:

(i) SEQUENCE CHARACTERISTICS:
(A) LENGTH: 19 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 9:

GCCATTCGCC TGACTGTCA 19

(2) INFORMATION FOR SEQ ID NO: 10:

(i) SEQUENCE CHARACTERISTICS:
(A) LENGTH: 19 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 10:

TTGACGAGGA CTTCGGCTG 19

(2) INFORMATION FOR SEQ ID NO: 11:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 11:

GCTCTACCTG CAATTCTGTG 20

(2) INFORMATION FOR SEQ ID NO: 12:

(i) SEQUENCE CHARACTERISTICS:
(A) LENGTH: 20 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 12:

GTGTATAGGA CCGGCAACCG 20

(2) INFORMATION FOR SEQ ID NO: 13:

(i) SEQUENCE CHARACTERISTICS:

-continued (A) LENGTH: 2062 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(xi) SEQUENCE DESCRIPTION: SEQ ID NO: 13:

```
GGCAGGCTTT GCTGTCCTCC AAGACATCAG TTGCCTTAGG CATCGCAACT CGGCCTCTGA     60

GGCGATTCGC AAAGTCCCTC AGTGCCGCAC GGCGATAGGG ACACCCGTGT ATATCACTGT    120

CACAGCCAAT GTTACCGATG AGAATTATTT GCATTCCTCT GATCTTCTCA TGCTTTCTTC    180

TTGCCTTTTC TATGCTTCTG AGATGAGTGA AAAGGGATTT AAGGTGGTAT TTGGCAATGT    240

GTCAGGCATC GTGGCAGTGT GCGTCAACTT CACCAGTTAC GTCCAACATG TCAAGGAATT    300

TACCCAACGT TCCTTGGTAG TTGACCATGT GCGGCTGCTC CATTTCATGA CGCCCGAGAC    360

CATGAGGTGG GCAACTGTTT TAGCCTGTCT TTTTGGCATT CTGTTGGCAA TTTGAATGTT    420

TAAGTATGTT GGGGAAATGC TTGACCGCGG GCTGTTGCTC GCAATTGCTT TTTTTGTGGT    480

GTATCGTGCC GTCTTGTTTT GTTGCGCTCG TCAGCGCCAA CGGGAACAGC GGCTCAAATT    540

TACAGCTGAT TTACAACTTG ACGCTATGTG AGCTGAATGG CACAGATTGG CTAGCTAATA    600

AATTTGACTG GGCAGTGGAG TGTTTTGTCA TTTTTCCTGT GTTGACTCAC ATTGTCTCTT    660

ATGGTGCCCT CACTACTAGC CATTTCCTTG ACACAGTCGG TCTGGTCACT GTGTCTACCG    720

CTGGGTTTGT TCACGGGCGG TATGTTCTGA GTAGCATGTA CGCGGTCTGT GCCCTGGCTG    780

CGTTGATTTG CTTCGTCATT AGGCTTGCGA AGAATTGCAT GTCCTGGCGC TACTCATGTA    840

CCAGATATAC CAACTTTCTT CTGGACACTA AGGGCAGACT CTATCGTTGG CGGTCGCCTG    900

TCATCATAGA GAAAAGGGGC AAAGTTGAGG TCGAAGGTCA CCTGATCGAC CTCAAAAGAG    960

TTGTGCTTGA TGGTTCCGCG GCTACCCCTG TAACCAGAGT TTCAGCGGAA CAATGGAGTC   1020

GTCCTTAGAT GACTTCTGTC ATGATAGCAC GGCTCCACAA AAGGTGCTCT TGGCGTTTTC   1080

TATTACCTAC ACGCCAGTGA TGATATATGC CCTAAAGGTG AGTCGCGGCC GACTGCTAGG   1140

GCTTCTGCAC CTTTTGGTCT TCCTGAATTG TGCTTTCACC TTCGGGTACA TGACATTCGT   1200

GCACTTTCAG AGTACAAATA AGGTCGCGCT CACTATGGGA GCAGTAGTTG CACTCCTTTG   1260

GGGGGTGTAC TCAGCCATAG AAACCTGGAA ATTCATCACC TCCAGATGCC GTTTGTGCTT   1320

GCTAGGCCGC AAGTACATTC TGGCCCCTGC CCACCACGTT GAAAGTGCCG CAGGCTTTCA   1380

TCCGATTGCG GCAAATGATA ACCACGCATT TGTCGTCCGG CGTCCCGGCT CCACTACGGT   1440

CAACGGCACA TTGGTGCCCG GGTTAAAAAG CCTCGTGTTG GGTGGCAGAA AAGCTGTTAA   1500

ACAGGGAGTG GTAAACCTTG TTAAATATGC CAAATAACAC CGGCAAGCAG CAGAAGAGAA   1560

AGAAGGGGGA TGGCCAGCCA GTCAATCAGC TGTGCCAGAT GCTGGGTAAG ATCATCGCTC   1620

ACCAAAACCA GTCCAGAGGC AAGGGACCGG GAAAGAAAAA TAAGAAGAAA AACCCGGAGA   1680

AGCCCCATTT CCCTCTAGCG ACTGAAGATG ATGTCAGACA TCACTTTACC CCTAGTGAGC   1740

GTCAATTGTG TCTGTCGTCA ATCCAGACCG CCTTTAATCA AGGCGCTGGG ACTTGCACCC   1800

TGTCAGATTC AGGGAGGATA AGTTACACTG TGGAGTTTAG TTTGCCTACG CATCATACTG   1860

TGCGCCTGAT CCGCGTCACA GCATCACCCT CAGCATGATG GGCTGGCATT CTTGAGGCAT   1920
```

-continued

```
CCCAGTGTTT GAATTGGAAG AATGCGTGGT GAATGGCACT GATTGACATT GTGCCTCTAA   1980

GTCACCTATT CAATTAGGGC GACCGTGTGG GGGTAAGATT TAATTGGCGA GAACCACACG   2040

GCCGAAATTA AAAAAAAAAA AA                                            2062
```

(2) INFORMATION FOR SEQ ID NO: 14:

(i) SEQUENCE CHARACTERISTICS:
(A) LENGTH: 603 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(ix) FEATURE:
(A) NAME/KEY: CDS
(B) LOCATION: 1..600

(xi) SEQUENCE DESCRIPTION: SEQ ID NO: 14:

```
ATG TTG GGG AAA TGC TTG ACC GCG GGC TGT TGC TCG CAA TTG CTT TTT       48
Met Leu Gly Lys Cys Leu Thr Ala Gly Cys Cys Ser Gln Leu Leu Phe
  1               5                  10                  15

TTG TGG TGT ATC GTG CCG TCT TGT TTT GTT GCG CTC GTC AGC GCC AAC       96
Leu Trp Cys Ile Val Pro Ser Cys Phe Val Ala Leu Val Ser Ala Asn
             20                  25                  30

GGG AAC AGC GGC TCA AAT TTA CAG CTG ATT TAC AAC TTG ACG CTA TGT      144
Gly Asn Ser Gly Ser Asn Leu Gln Leu Ile Tyr Asn Leu Thr Leu Cys
         35                  40                  45

GAG CTG AAT GGC ACA GAT TGG CTA GCT AAT AAA TTT GAC TGG GCA GTG      192
Glu Leu Asn Gly Thr Asp Trp Leu Ala Asn Lys Phe Asp Trp Ala Val
     50                  55                  60

GAG TGT TTT GTC ATT TTT CCT GTG TTG ACT CAC ATT GTC TCT TAT GGT      240
Glu Cys Phe Val Ile Phe Pro Val Leu Thr His Ile Val Ser Tyr Gly
 65                  70                  75                  80

GCC CTC ACT ACT AGC CAT TTC CTT GAC ACA GTC GGT CTG GTC ACT GTG      288
Ala Leu Thr Thr Ser His Phe Leu Asp Thr Val Gly Leu Val Thr Val
                 85                  90                  95

TCT ACC GCT GGG TTT GTT CAC GGG CGG TAT GTT CTG AGT AGC ATG TAC      336
Ser Thr Ala Gly Phe Val His Gly Arg Tyr Val Leu Ser Ser Met Tyr
            100                 105                 110

GCG GTC TGT GCC CTG GCT GCG TTG ATT TGC TTC GTC ATT AGG CTT GCG      384
Ala Val Cys Ala Leu Ala Ala Leu Ile Cys Phe Val Ile Arg Leu Ala
        115                 120                 125

AAG AAT TGC ATG TCC TGG CGC TAC TCA TGT ACC AGA TAT ACC AAC TTT      432
Lys Asn Cys Met Ser Trp Arg Tyr Ser Cys Thr Arg Tyr Thr Asn Phe
    130                 135                 140

CTT CTG GAC ACT AAG GGC AGA CTC TAT CGT TGG CGG TCG CCT GTC ATC      480
Leu Leu Asp Thr Lys Gly Arg Leu Tyr Arg Trp Arg Ser Pro Val Ile
145                 150                 155                 160

ATA GAG AAA AGG GGC AAA GTT GAG GTC GAA GGT CAC CTG ATC GAC CTC      528
Ile Glu Lys Arg Gly Lys Val Glu Val Glu Gly His Leu Ile Asp Leu
                165                 170                 175

AAA AGA GTT GTG CTT GAT GGT TCC GCG GCT ACC CCT GTA ACC AGA GTT      576
Lys Arg Val Val Leu Asp Gly Ser Ala Ala Thr Pro Val Thr Arg Val
            180                 185                 190

TCA GCG GAA CAA TGG AGT CGT CCT TAG                                  603
Ser Ala Glu Gln Trp Ser Arg Pro
```

```
        195                 200


(2) INFORMATION FOR SEQ ID NO: 15:

     (i) SEQUENCE CHARACTERISTICS:
          (A) LENGTH: 200 amino acids
          (B) TYPE: amino acid
          (D) TOPOLOGY: linear

    (ii) MOLECULE TYPE: protein

    (xi) SEQUENCE DESCRIPTION: SEQ ID NO: 15:

Met Leu Gly Lys Cys Leu Thr Ala Gly Cys Cys Ser Gln Leu Leu Phe
  1               5                  10                  15

Leu Trp Cys Ile Val Pro Ser Cys Phe Val Ala Leu Val Ser Ala Asn
             20                  25                  30

Gly Asn Ser Gly Ser Asn Leu Gln Leu Ile Tyr Asn Leu Thr Leu Cys
        35                  40                  45

Glu Leu Asn Gly Thr Asp Trp Leu Ala Asn Lys Phe Asp Trp Ala Val
     50                  55                  60

Glu Cys Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Val His Gly Arg Tyr Val Leu Ser Ser Met Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Ala Ala Thr Pro Val Thr Arg Val
            180                 185                 190

Ser Ala Glu Gln Trp Ser Arg Pro
        195                 200


(2) INFORMATION FOR SEQ ID NO: 16:

     (i) SEQUENCE CHARACTERISTICS:
          (A) LENGTH: 525 base pairs
          (B) TYPE: nucleic acid
          (C) STRANDEDNESS: unknown
          (D) TOPOLOGY: unknown

    (ii) MOLECULE TYPE: cDNA

    (vi) ORIGINAL SOURCE:
          (A) ORGANISM: porcine reproductive and respiratory syndrome
               virus
          (B) STRAIN: Iowa
          (C) INDIVIDUAL ISOLATE: ISU-12 (VR 2385/VR 2386)

    (ix) FEATURE:
          (A) NAME/KEY: CDS
          (B) LOCATION: 1..522

    (xi) SEQUENCE DESCRIPTION: SEQ ID NO: 16:

ATG GAG TCG TCC TTA GAT GAC TTC TGT CAT GAT AGC ACG GCT CCA CAA       48
Met Glu Ser Ser Leu Asp Asp Phe Cys His Asp Ser Thr Ala Pro Gln
  1               5                  10                  15
```

```
AAG GTG CTC TTG GCG TTT TCT ATT ACC TAC ACG CCA GTG ATG ATA TAT        96
Lys Val Leu Leu Ala Phe Ser Ile Thr Tyr Thr Pro Val Met Ile Tyr
             20                  25                  30

GCC CTA AAG GTG AGT CGC GGC CGA CTG CTA GGG CTT CTG CAC CTT TTG       144
Ala Leu Lys Val Ser Arg Gly Arg Leu Leu Gly Leu Leu His Leu Leu
         35                  40                  45

GTC TTC CTG AAT TGT GCT TTC ACC TTC GGG TAC ATG ACA TTC GTG CAC       192
Val Phe Leu Asn Cys Ala Phe Thr Phe Gly Tyr Met Thr Phe Val His
     50                  55                  60

TTT CAG AGT ACA AAT AAG GTC GCG CTC ACT ATG GGA GCA GTA GTT GCA       240
Phe Gln Ser Thr Asn Lys Val Ala Leu Thr Met Gly Ala Val Val Ala
 65                  70                  75                  80

CTC CTT TGG GGG GTG TAC TCA GCC ATA GAA ACC TGG AAA TTC ATC ACC       288
Leu Leu Trp Gly Val Tyr Ser Ala Ile Glu Thr Trp Lys Phe Ile Thr
                 85                  90                  95

TCC AGA TGC CGT TTG TGC TTG CTA GGC CGC AAG TAC ATT CTG GCC CCT       336
Ser Arg Cys Arg Leu Cys Leu Leu Gly Arg Lys Tyr Ile Leu Ala Pro
            100                 105                 110

GCC CAC CAC GTT GAA AGT GCC GCA GGC TTT CAT CCG ATT GCG GCA AAT       384
Ala His His Val Glu Ser Ala Ala Gly Phe His Pro Ile Ala Ala Asn
        115                 120                 125

GAT AAC CAC GCA TTT GTC GTC CGG CGT CCC GGC TCC ACT ACG GTC AAC       432
Asp Asn His Ala Phe Val Val Arg Arg Pro Gly Ser Thr Thr Val Asn
    130                 135                 140

GGC ACA TTG GTG CCC GGG TTA AAA AGC CTC GTG TTG GGT GGC AGA AAA       480
Gly Thr Leu Val Pro Gly Leu Lys Ser Leu Val Leu Gly Gly Arg Lys
145                 150                 155                 160

GCT GTT AAA CAG GGA GTG GTA AAC CTT GTT AAA TAT GCC AAA               522
Ala Val Lys Gln Gly Val Val Asn Leu Val Lys Tyr Ala Lys
                165                 170

TAA                                                                   525
```

(2) INFORMATION FOR SEQ ID NO: 17:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 17:

```
Met Glu Ser Ser Leu Asp Asp Phe Cys His Asp Ser Thr Ala Pro Gln
  1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
         35                  40                  45

Val Phe Leu Asn Cys Ala Phe Thr Phe Gly Tyr Met Thr Phe Val His
     50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125
```

-continued

```
Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170
```

(2) INFORMATION FOR SEQ ID NO: 18:

(i) SEQUENCE CHARACTERISTICS:
(A) LENGTH: 372 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(ix) FEATURE:
(A) NAME/KEY: CDS
(B) LOCATION: 1..369

(xi) SEQUENCE DESCRIPTION: SEQ ID NO: 18:

```
ATG CCA AAT AAC ACC GGC AAG CAG CAG AAG AGA AAG AAG GGG GAT GGC        48
Met Pro Asn Asn Thr Gly Lys Gln Gln Lys Arg Lys Lys Gly Asp Gly
  1               5                  10                  15

CAG CCA GTC AAT CAG CTG TGC CAG ATG CTG GGT AAG ATC ATC GCT CAC        96
Gln Pro Val Asn Gln Leu Cys Gln Met Leu Gly Lys Ile Ile Ala His
             20                  25                  30

CAA AAC CAG TCC AGA GGC AAG GGA CCG GGA AAG AAA AAT AAG AAG AAA       144
Gln Asn Gln Ser Arg Gly Lys Gly Pro Gly Lys Lys Asn Lys Lys Lys
         35                  40                  45

AAC CCG GAG AAG CCC CAT TTC CCT CTA GCG ACT GAA GAT GAT GTC AGA       192
Asn Pro Glu Lys Pro His Phe Pro Leu Ala Thr Glu Asp Asp Val Arg
     50                  55                  60

CAT CAC TTT ACC CCT AGT GAG CGT CAA TTG TGT CTG TCG TCA ATC CAG       240
His His Phe Thr Pro Ser Glu Arg Gln Leu Cys Leu Ser Ser Ile Gln
 65                  70                  75                  80

ACC GCC TTT AAT CAA GGC GCT GGG ACT TGC ACC CTG TCA GAT TCA GGG       288
Thr Ala Phe Asn Gln Gly Ala Gly Thr Cys Thr Leu Ser Asp Ser Gly
                 85                  90                  95

AGG ATA AGT TAC ACT GTG GAG TTT AGT TTG CCT ACG CAT CAT ACT GTG       336
Arg Ile Ser Tyr Thr Val Glu Phe Ser Leu Pro Thr His His Thr Val
            100                 105                 110

CGC CTG ATC CGC GTC ACA GCA TCA CCC TCA GCA TGA                       372
Arg Leu Ile Arg Val Thr Ala Ser Pro Ser Ala
        115                 120
```

(2) INFORMATION FOR SEQ ID NO: 19:

(i) SEQUENCE CHARACTERISTICS:
(A) LENGTH: 123 amino acids
(B) TYPE: amino acid
(D) TOPOLOGY: linear (ii) MOLECULE TYPE: protein (xi) SEQUENCE DESCRIPTION: SEQ ID NO: 19:

```
Met Pro Asn Asn Thr Gly Lys Gln Gln Lys Arg Lys Lys Gly Asp Gly
  1               5                  10                  15
```

-continued

```
Gln Pro Val Asn Gln Leu Cys Gln Met Leu Gly Lys Ile Ile Ala His
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

(2) INFORMATION FOR SEQ ID NO: 20:

(i) SEQUENCE CHARACTERISTICS:
(A) LENGTH: 606 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(C) INDIVIDUAL ISOLATE: Lelystad (ix) FEATURE:
(A) NAME/KEY: CDS
(B) LOCATION: 1..603

(xi) SEQUENCE DESCRIPTION: SEQ ID NO: 20:

```
ATG AGA TGT TCT CAC AAA TTG GGG CGT TTC TTG ACT CCG CAC TCT TGC       48
Met Arg Cys Ser His Lys Leu Gly Arg Phe Leu Thr Pro His Ser Cys
  1               5                  10                  15

TTC TGG TGG CTT TTT TTG CTG TGT ACC GGC TTG TCC TGG TCC TTT GCC       96
Phe Trp Trp Leu Phe Leu Leu Cys Thr Gly Leu Ser Trp Ser Phe Ala
            20                  25                  30

GAT GGC AAC GGC GAC AGC TCG ACA TAC CAA TAC ATA TAT AAC TTG ACG      144
Asp Gly Asn Gly Asp Ser Ser Thr Tyr Gln Tyr Ile Tyr Asn Leu Thr
        35                  40                  45

ATA TGC GAG CTG AAT GGG ACC GAC TGG TTG TCC AGC CAT TTT GGT TGG      192
Ile Cys Glu Leu Asn Gly Thr Asp Trp Leu Ser Ser His Phe Gly Trp
    50                  55                  60

GCA GTC GAG ACC TTT GTG CTT TAC CCG GTT GCC ACT CAT ATC CTC TCA      240
Ala Val Glu Thr Phe Val Leu Tyr Pro Val Ala Thr His Ile Leu Ser
65                  70                  75                  80

CTG GGT TTT CTC ACA ACA AGC CAT TTT TTT GAC GCG CTC GGT CTC GGC      288
Leu Gly Phe Leu Thr Thr Ser His Phe Phe Asp Ala Leu Gly Leu Gly
                85                  90                  95

GCT GTA TCC ACT GCA GGA TTT GTT GGC GGG CGG TAC GTA CTC TGC AGC      336
Ala Val Ser Thr Ala Gly Phe Val Gly Gly Arg Tyr Val Leu Cys Ser
            100                 105                 110

GTC TAC GGC GCT TGT GCT TTC GCA GCG TTC GTA TGT TTT GTC ATC CGT      384
Val Tyr Gly Ala Cys Ala Phe Ala Ala Phe Val Cys Phe Val Ile Arg
        115                 120                 125

GCT GCT AAA AAT TGC ATG GCC TGC CGC TAT GCC CGT ACC CGG TTT ACC      432
Ala Ala Lys Asn Cys Met Ala Cys Arg Tyr Ala Arg Thr Arg Phe Thr
    130                 135                 140
```

-continued

```
AAC TTC ATT GTG GAC GAC CGG GGG AGA GTT CAT CGA TGG AAG TCT CCA      480
Asn Phe Ile Val Asp Asp Arg Gly Arg Val His Arg Trp Lys Ser Pro
145                 150                 155                 160

ATA GTG GTA GAA AAA TTG GGC AAA GCC GAA GTC GAT GGC AAC CTC GTC      528
Ile Val Val Glu Lys Leu Gly Lys Ala Glu Val Asp Gly Asn Leu Val
                165                 170                 175

ACC ATC AAA CAT GTC GTC CTC GAA GGG GTT AAA GCT CAA CCC TTG ACG      576
Thr Ile Lys His Val Val Leu Glu Gly Val Lys Ala Gln Pro Leu Thr
            180                 185                 190

AGG ACT TCG GCT GAG CAA TGG GAG GCC TAG                              606
Arg Thr Ser Ala Glu Gln Trp Glu Ala
        195                 200
```

(2) INFORMATION FOR SEQ ID NO: 21:

(i) SEQUENCE CHARACTERISTICS:
(A) LENGTH: 201 amino acids
(B) TYPE: amino acid
(D) TOPOLOGY: linear (ii) MOLECULE TYPE: protein (xi) SEQUENCE DESCRIPTION: SEQ ID NO: 21:

```
Met Arg Cys Ser His Lys Leu Gly Arg Phe Leu Thr Pro His Ser Cys
  1               5                  10                  15

Phe Trp Trp Leu Phe Leu Leu Cys Thr Gly Leu Ser Trp Ser Phe Ala
             20                  25                  30

Asp Gly Asn Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
 65                  70                  75                  80

Leu Gly Phe Leu Thr Thr Ser His Phe Phe Asp Ala Leu Gly Leu Gly
                 85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200
```

(2) INFORMATION FOR SEQ ID NO: 22:

(i) SEQUENCE CHARACTERISTICS:
(A) LENGTH: 164 base pairs
(B) TYPE: nucleic acid
(C) STRANDEDNESS: unknown
(D) TOPOLOGY: unknown (ii) MOLECULE TYPE: cDNA (vi) ORIGINAL SOURCE:

-continued

```
          (A) ORGANISM: porcine reproductive and respiratory syndrome
               virus
          (B) STRAIN: Iowa
          (C) INDIVIDUAL ISOLATE: ISU-12 (VR 2385/VR 2386)

    (xi) SEQUENCE DESCRIPTION: SEQ ID NO: 22:

TGGGCTGGCA TTCTTGAGGC ATCCCAGTGT TTGAATTGGA AGAATGCGTG GTGAATGGCA      60

CTGATTGACA TTGTGCCTCT AAGTCACCTA TTCAATTAGG GCGACCGTGT GGGGGTAAGA     120

TTTAATTGGC GAGAACCACA CGGCCGAAAT TAAAAAAAAA AAAA                      164


(2) INFORMATION FOR SEQ ID NO: 23:

     (i) SEQUENCE CHARACTERISTICS:
          (A) LENGTH: 522 base pairs
          (B) TYPE: nucleic acid
          (C) STRANDEDNESS: unknown
          (D) TOPOLOGY: unknown

    (ii) MOLECULE TYPE: cDNA

    (vi) ORIGINAL SOURCE:
          (A) ORGANISM: porcine reproductive and respiratory syndrome
               virus
          (C) INDIVIDUAL ISOLATE: Lelystad

    (ix) FEATURE:
          (A) NAME/KEY: CDS
          (B) LOCATION: 1..519

    (xi) SEQUENCE DESCRIPTION: SEQ ID NO: 23:

ATG GGA GGC CTA GAC GAT TTT TGC AAC GAT CCT ATC GCC GCA CAA AAG        48
Met Gly Gly Leu Asp Asp Phe Cys Asn Asp Pro Ile Ala Ala Gln Lys
  1               5                  10                  15

CTC GTG CTA GCC TTT AGC ATC ACA TAC ACA CCT ATA ATG ATA TAC GCC        96
Leu Val Leu Ala Phe Ser Ile Thr Tyr Thr Pro Ile Met Ile Tyr Ala
             20                  25                  30

CTT AAG GTG TCA CGC GGC CGA CTC CTG GGG CTG TTG CAC ATC CTA ATA       144
Leu Lys Val Ser Arg Gly Arg Leu Leu Gly Leu Leu His Ile Leu Ile
         35                  40                  45

TTT CTG AAC TGT TCC TTT ACA TTC GGA TAC ATG ACA TAT GTG CAT TTT       192
Phe Leu Asn Cys Ser Phe Thr Phe Gly Tyr Met Thr Tyr Val His Phe
     50                  55                  60

CAA TCC ACC AAC CGT GTC GCA CTT ACC CTG GGG GCT GTT GTC GCC CTT       240
Gln Ser Thr Asn Arg Val Ala Leu Thr Leu Gly Ala Val Val Ala Leu
 65                  70                  75                  80

CTG TGG GGT GTT TAC AGC TTC ACA GAG TCA TGG AAG TTT ATC ACT TCC       288
Leu Trp Gly Val Tyr Ser Phe Thr Glu Ser Trp Lys Phe Ile Thr Ser
                 85                  90                  95

AGA TGC AGA TTG TGT TGC CTT GGC CGG CGA TAC ATT CTG GCC CCT GCC       336
Arg Cys Arg Leu Cys Cys Leu Gly Arg Arg Tyr Ile Leu Ala Pro Ala
            100                 105                 110

CAT CAC GTA GAA AGT GCT GCA GGT CTC CAT TCA ATC TCA GCG TCT GGT       384
His His Val Glu Ser Ala Ala Gly Leu His Ser Ile Ser Ala Ser Gly
        115                 120                 125

AAC CGA GCA TAC GCT GTG AGA AAG CCC GGA CTA ACA TCA GTG AAC GGC       432
Asn Arg Ala Tyr Ala Val Arg Lys Pro Gly Leu Thr Ser Val Asn Gly
    130                 135                 140

ACT CTA GTA CCA GGA CTT CGG AGC CTC GTG CTG GGC GGC AAA CGA GCT       480
Thr Leu Val Pro Gly Leu Arg Ser Leu Val Leu Gly Gly Lys Arg Ala
145                 150                 155                 160

GTT AAA CGA GGA GTG GTT AAC CTC GTC AAG TAT GGC CGG TAA               522
Val Lys Arg Gly Val Val Asn Leu Val Lys Tyr Gly Arg
                165                 170
```

-continued (2) INFORMATION FOR SEQ ID NO: 24:

(i) SEQUENCE CHARACTERISTICS:
(A) LENGTH: 173 amino acids
(B) TYPE: amino acid
(D) TOPOLOGY: linear (ii) MOLECULE TYPE: protein (xi) SEQUENCE DESCRIPTION: SEQ ID NO: 24:

```
Met Gly Gly Leu Asp Asp Phe Cys Asn Asp Pro Ile Ala Ala Gln Lys
  1               5                  10                  15

Leu Val Leu Ala Phe Ser Ile Thr Tyr Thr Pro Ile Met Ile Tyr Ala
             20                  25                  30

Leu Lys Val Ser Arg Gly Arg Leu Leu Gly Leu Leu His Ile Leu Ile
         35                  40                  45

Phe Leu Asn Cys Ser Phe Thr Phe Gly Tyr Met Thr Tyr Val His Phe
     50                  55                  60

Gln Ser Thr Asn Arg Val Ala Leu Thr Leu Gly Ala Val Val Ala Leu
 65                  70                  75                  80

Leu Trp Gly Val Tyr Ser Phe Thr Glu Ser Trp Lys Phe Ile Thr Ser
                 85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Ser Ile Ser Ala Ser Gly
        115                 120                 125

Asn Arg Ala Tyr Ala Val Arg Lys Pro Gly Leu Thr Ser Val Asn Gly
    130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170
```

(2) INFORMATION FOR SEQ ID NO: 25:

(i) SEQUENCE CHARACTERISTICS:
(A) LENGTH: 387 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(C) INDIVIDUAL ISOLATE: Lelystad (ix) FEATURE:
(A) NAME/KEY: CDS
(B) LOCATION: 1..384

(xi) SEQUENCE DESCRIPTION: SEQ ID NO: 25:

```
ATG GCC GGT AAA AAC CAG AGC CAG AAG AAA AAG AAA AGT ACA GCT CCG        48
Met Ala Gly Lys Asn Gln Ser Gln Lys Lys Lys Lys Ser Thr Ala Pro
  1               5                  10                  15

ATG GGG AAT GGC CAG CCA GTC AAT CAA CTG TGC CAG TTG CTG GGT GCA        96
Met Gly Asn Gly Gln Pro Val Asn Gln Leu Cys Gln Leu Leu Gly Ala
             20                  25                  30

ATG ATA AAG TCC CAG CGC CAG CAA CCT AGG GGA GGA CAG GCC AAA AAG       144
Met Ile Lys Ser Gln Arg Gln Gln Pro Arg Gly Gly Gln Ala Lys Lys
         35                  40                  45
```

-continued

```
AAA AAG CCT GAG AAG CCA CAT TTT CCC CTG GCT GCT GAA GAT GAC ATC      192
Lys Lys Pro Glu Lys Pro His Phe Pro Leu Ala Ala Glu Asp Asp Ile
     50                 55                  60

CGG CAC CAC CTC ACC CAG ACT GAA CGC TCC CTC TGC TTG CAA TCG ATC      240
Arg His His Leu Thr Gln Thr Glu Arg Ser Leu Cys Leu Gln Ser Ile
 65                 70                  75                  80

CAG ACG GCT TTC AAT CAA GGC GCA GGA ACT GCG TCG CTT TCA TCC AGC      288
Gln Thr Ala Phe Asn Gln Gly Ala Gly Thr Ala Ser Leu Ser Ser Ser
                85                  90                  95

GGG AAG GTC AGT TTT CAG GTT GAG TTT ATG CTG CCG GTT GCT CAT ACA      336
Gly Lys Val Ser Phe Gln Val Glu Phe Met Leu Pro Val Ala His Thr
            100                 105                 110

GTG CGC CTG ATT CGC GTG ACT TCT ACA TCC GCC AGT CAG GGT GCA AGT      384
Val Arg Leu Ile Arg Val Thr Ser Thr Ser Ala Ser Gln Gly Ala Ser
        115                 120                 125

TAA                                                                  387
```

(2) INFORMATION FOR SEQ ID NO: 26:

(i) SEQUENCE CHARACTERISTICS:
(A) LENGTH: 128 amino acids
(B) TYPE: amino acid
(D) TOPOLOGY: linear (ii) MOLECULE TYPE: protein (xi) SEQUENCE DESCRIPTION: SEQ ID NO: 26:

```
Met Ala Gly Lys Asn Gln Ser Gln Lys Lys Lys Lys Ser Thr Ala Pro
  1               5                  10                  15

Met Gly Asn Gly Gln Pro Val Asn Gln Leu Cys Gln Leu Leu Gly Ala
            20                  25                  30

Met Ile Lys Ser Gln Arg Gln Gln Pro Arg Gly Gly Gln Ala Lys Lys
        35                  40                  45

Lys Lys Pro Glu Lys Pro His Phe Pro Leu Ala Ala Glu Asp Asp Ile
     50                 55                  60

Arg His His Leu Thr Gln Thr Glu Arg Ser Leu Cys Leu Gln Ser Ile
 65                 70                  75                  80

Gln Thr Ala Phe Asn Gln Gly Ala Gly Thr Ala Ser Leu Ser Ser Ser
                85                  90                  95

Gly Lys Val Ser Phe Gln Val Glu Phe Met Leu Pro Val Ala His Thr
            100                 105                 110

Val Arg Leu Ile Arg Val Thr Ser Thr Ser Ala Ser Gln Gly Ala Ser
        115                 120                 125
```

(2) INFORMATION FOR SEQ ID NO: 27:

(i) SEQUENCE CHARACTERISTICS:
(A) LENGTH: 127 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(C) INDIVIDUAL ISOLATE: Lelystad (xi) SEQUENCE DESCRIPTION: SEQ ID NO: 27:

```
TTTGACAGTC AGGTGAATGG CCGCGATTGG CGTGTGGCCT CTGAGTCACC TATTCAATTA     60

GGGCGATCAC ATGGGGGTCA TACTTAATCA GGCAGGAACC ATGTGACCGA AATTAAAAAA    120
```

-continued

AAAAAAA 127

(2) INFORMATION FOR SEQ ID NO: 28:

(i) SEQUENCE CHARACTERISTICS:
(A) LENGTH: 26 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 28:

GGGGATCCGG TATTTGGCAA TGTGTC 26

(2) INFORMATION FOR SEQ ID NO: 29:

(i) SEQUENCE CHARACTERISTICS:
(A) LENGTH: 28 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 29:

GGTGTTTTCC ACGAGAACCG CTTAAGGG 28

(2) INFORMATION FOR SEQ ID NO: 30:

(i) SEQUENCE CHARACTERISTICS:
(A) LENGTH: 21 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 30:

GGGGATCCAG AGTTTCAGCG G 21

(2) INFORMATION FOR SEQ ID NO: 31:

(i) SEQUENCE CHARACTERISTICS:
(A) LENGTH: 25 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 31:

CAGTTAGTCG ACACGGTCTT AAGGG 25

(2) INFORMATION FOR SEQ ID NO: 32:

(i) SEQUENCE CHARACTERISTICS:
(A) LENGTH: 22 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 32:

GGGGATCCTT GTTAAATATG CC 22

-continued (2) INFORMATION FOR SEQ ID NO: 33:

(i) SEQUENCE CHARACTERISTICS:
(A) LENGTH: 19 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 33:

CTTACGCACC ACTTAAGGG 19

(2) INFORMATION FOR SEQ ID NO: 34:

(i) SEQUENCE CHARACTERISTICS:
(A) LENGTH: 16 base pairs
(B) TYPE: nucleic acid
(C) STRANDEDNESS: unknown
(D) TOPOLOGY: linear (ii) MOLECULE TYPE: DNA (genomic)

(xi) SEQUENCE DESCRIPTION: SEQ ID NO: 34:

AATGGGGCTT CTCCGG 16

(2) INFORMATION FOR SEQ ID NO: 35:

(i) SEQUENCE CHARACTERISTICS:
(A) LENGTH: 886 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(xi) SEQUENCE DESCRIPTION: SEQ ID NO: 35:

ATGGAGTCGT CCTTAGATGA CTTCTGTCAT GATAGCACGG CTCCACAAAA GGTGCTCTTG 60

GCGTTTTCTA TTACCTACAC GCCAGTGATG ATATATGCCC TAAAGGTGAG TCGCGGCCGA 120

CTGCTAGGGC TTCTGCACCT TTTGGTCTTC CTGAATTGTG CTTTCACCTT CGGGTACATG 180

ACATTCGTGC ACTTTCAGAG TACAAATAAG GTCGCGCTCA CTATGGGAGC AGTAGTTGCA 240

CTCCTTTGGG GGGTGTACTC AGCCATAGAA ACCTGGAAAT TCATCACCTC CAGATGCCGT 300

TTGTGCTTGC TAGGCCGCAA GTACATTCTG GCCCCTGCCC ACCACGTTGA AAGTGCCGCA 360

GGCTTTCATC CGATTGCGGC AAATGATAAC CACGCATTTG TCGTCCGGCG TCCCGGCTCC 420

ACTACGGTCA ACGGCACATT GGTGCCCGGG TTAAAAAGCC TCGTGTTGGG TGGCAGAAAA 480

GCTGTTAAAC AGGGAGTGGT AAACCTTGTT AAATATGCCA AATAACACCG GCAAGCAGCA 540

GAAGAGAAAG AAGGGGGATG GCCAGCCAGT CAATCAGCTG TGCCAGATGC TGGGTAAGAT 600

CATCGCTCAC CAAAACCAGT CCAGAGGCAA GGGACCGGGA AAGAAAAATA AGAAGAAAAA 660

CCCGGAGAAG CCCCATTTCC CTCTAGCGAC TGAAGATGAT GTCAGACATC ACTTTACCCC 720

TAGTGAGCGT CAATTGTGTC TGTCGTCAAT CCAGACCGCC TTTAATCAAG GCGCTGGGAC 780

TTGCACCCTG TCAGATTCAG GGAGGATAAG TTACACTGTG GAGTTTAGTT TGCCTACGCA 840

TCATACTGTG CGCCTGATCC GCGTCACAGC ATCACCCTCA GCATGA 886

-continued (2) INFORMATION FOR SEQ ID NO: 36:

(i) SEQUENCE CHARACTERISTICS:
(A) LENGTH: 886 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-1894

(xi) SEQUENCE DESCRIPTION: SEQ ID NO: 36:

```
ATGGGGTCGT CCTTAGATGA CTTCTGCCAT GATAGTACGG CTCCACAAAA GGTGCTTTTG     60

GCGTTTTCTA TTACCTACAC GCCAGTGATG ATATATGCCC TAAAGGTGAG TCGCGGCCGA    120

CTGCTAGGGC TTCTGCACCT TTTGATCTTC CTGAATTGTG CTTTCACCTT CGGGTACATG    180

ACATTCGTGC ACTTTCAGAG TACAAATAAG GTCGCGCTCA CTATGGGAGC AGTAGTTGCA    240

CTCCTTTGGG GGGTGTACTC AGCCATAGAA ACCTGGAAAT TCATCACCTC CAGATGCCGT    300

TTGTGCTTGC TAGGCCGCAA GTACATTCTG GCCCCTGCCC ACCACGTTGA AAGTGCCGCA    360

GGCTTTCATC CGATTGCGGC AAATGATAAC CACGCATTTG TCGTCCGGCG TCCCGGCTCC    420

ACTACGGTCA ACGGCACATT GGTGCCCGGG TTGAAAAGCC TCGTGTTGGG TGGCAGAAAA    480

GCTGTTAAAC AGGGAGTGGT AAACCTTGTC AAATATGCCA AATAACAACG GCAAGCAGCA    540

GAAGAGAAAG AAGGGGGATG GCCAGCCAGT CAATCAGCTG TGCCAGATGC TGGGTAAGAT    600

CATCGCTCAG CAAAACCAGT CCAGAGGCAA GGGACCGGGA AAGAAAAACA AGAAGAAAAA    660

CCCGGAGAAG CCCCATTTTC CTCTAGCGAC TGAAGATGAT GTCAGACATC ACTTCACCCC    720

TAGTGAGCGG CAATTGTGTC TGTCGTCAAT CCAGACCGCC TTTAATCAAG GCGCTGGGAC    780

TTGCACCCTG TCAGATTCAG GGAGGATAAG TTACACTGTG GAGTTTAGTT TGCCAACGCA    840

TCATACTGTG CGCTTGATCC GCGTCACAGC ATCACCCTCA GCATGA                   886
```

(2) INFORMATION FOR SEQ ID NO: 37:

(i) SEQUENCE CHARACTERISTICS:
(A) LENGTH: 886 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-22 (VR 2429)

(xi) SEQUENCE DESCRIPTION: SEQ ID NO: 37:

```
ATGGGGTCGT CCTTAGATGA CTTCTGTCAT GACAGCACGG CTCCACAAAA GGTGCTTTTG     60

GCGTTTTCTA TTACCTACAC GCCAGTGATG ATATATGCCC TGAAGGTGAG TCGCGGCCGA    120

CTGCTAGGGC TTCTGCACCT TTTGATCTTC CTGAATTGTG CTTTCACCTT CGGGTACATG    180

ACATTCGTGC ACTTTCAGAG TACAAATAAG GTCGCACTCA CTATGGGAGC AGTAGTTGCA    240

CTCCTTTGGG GGGTGTACTC AGCCATAGAA ACCTGGAAAT TCATCACCTC CAGATGCCGT    300

TTGTGCTTGC TAGGCCGCAA GTACATTCTG GCCCCTGCCC ACCACGTTGA AAGTGCCGCA    360
```

-continued

```
GGCTTTCATC CGATTGCGGC AAATGATAAC CACGCATTTG TCGTTCGGCG TCCCGGCTCC    420

ACTACGGTCA ACGGCACATT GGTGCCCGGG TTGAAAAGCC TCGTGTTGGG TGGCAGAAAA    480

GCTGTTAAAC AGGGAGTGGT AAACCTTGTC AAATATGCCA AATAACAACG GTAAGCAGCA    540

GAAGAGAAAG AAGGGGGATG GCCAGCCAGT CAATCAGCTG TGCCAGATGC TGGGCAAGAT    600

CATCGCTCAG CAAAATCAGT CCAGAGGCAA GGGACCGGGA AAGAAAAATA AGAAGAAAAA    660

CCCGGAGAAG CCCCATTTTC CTCTAGCGAC TGAAGATGAT GTCAGACATC ACTTTACCCC    720

TAGTGAGCGG CAATTGTGTC TGTCGTCAAT CCAGACCGCC TTTAATCAAG GCGCTGGGAC    780

TTGCACCCTG TCAGATTCAG GGAGGATAAG TTACACTGTG GAGTTTAGTT TGCCTACGCA    840

TCATACTGTG CGCCTGATCC GCGTCACAGC ATCACCCTCA GCATGA                   886
```

(2) INFORMATION FOR SEQ ID NO: 38:

(i) SEQUENCE CHARACTERISTICS:
(A) LENGTH: 886 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-79

(xi) SEQUENCE DESCRIPTION: SEQ ID NO: 38:

```
ATGGGGTCGT CCTTAGATGA CTTCTGTTAT GATAGTACGG CTCCACAAAA GGTGCTTTTG     60

GCATTTTCTA TTACCTACAC GCCAGTAATG ATATATGCCC TAAAGGTGAG TCGCGGCCGA    120

CTGCTAGGGC TTCTGCACCT TTTGATTTTC CTGAACTGTG CTTTCACCTT CGGGTACATG    180

ACATTCATGC ACTTTCAGAG TACAAATAAG GTCGCGCTCA CTATGGGAGC AGTAGTTGCA    240

CTCCTTTGGG GGGTGTACTC AGCCATAGAA ACCTGGAAAT TCATCACCTC CAGATGCCGT    300

TTGTGCTTGC TAGGCCGCAA GTACATTCTG GCCCCTGCCC ACCACGTTGA AAGTGCCGCA    360

GGCTTTCATC CGATTGCGGC AAATGATAAC CACGCATTTG TCGTCCGGCG TCCCGGCTCC    420

ACTACGGTCA ACGGCACATT GGTGCCCGGG TTGAAAAGCC TCGTGTTGGG TGGCAGAAAA    480

GCTGTTAAAC AGGGAGTGGT AAACCTTGTC AAATATGCCA AATAACAACG GCAAGCAGCA    540

GAAGAGAAAG AAGGGGGATG GCCAGCCAGT CAATCAGCTG TGCCAGATGC TGGGTAAGAT    600

CATCGCCCAG CAAAACCAGT CTAGAGGCAA GGGACCGGGA AAGAAAAATA AGAAGAAAAA    660

CCCGGAGAAG CCCCATTTTC CTCTAGCGAC TGAAGATGAT GTCAGACATC ACTTTACCCC    720

TAGTGAGCGG CAATTGTGTC TGTCGTCAAT CCAAACTGCC TTTAATCAAG GCGCTGGGAC    780

TTGCACCCTG TCAGATTCAG GGAGGATAAG TTACACTGTG GAGTTTAGTT TGCCTACGCA    840

TCATACTGTG CGCTTGATCC GCGTCACAGC ATCACCCTCA GCATGA                   886
```

(2) INFORMATION FOR SEQ ID NO: 39:

(i) SEQUENCE CHARACTERISTICS:
(A) LENGTH: 886 base pairs
(B) TYPE: nucleic acid
(C) STRANDEDNESS: unknown
(D) TOPOLOGY: unknown (ii) MOLECULE TYPE: cDNA (vi) ORIGINAL SOURCE:

-continued (A) ORGANISM: porcine reproductive and respiratory syndrome virus
(B) STRAIN: Iowa
(C) INDIVIDUAL ISOLATE: ISU-55 (VR 2430)

(xi) SEQUENCE DESCRIPTION: SEQ ID NO: 39:

```
ATGGGGTCGT CCTTAGATGA CTTCTGCCAT GATAGCACGG CTCCACAAAA GGTGCTTTTG     60
GCGTTCTCTA TTACCTACAC GCCAGTGATG ATATATGCCC TAAAAGTAAG TCGCGGCCGA    120
CTGCTAGGGC TTCTGCACCT TTTGATCTTC CTAAATTGTG CTTTCACCTT CGGGTACATG    180
ACATTCGTGC ACTTTCAGAG CACAAACAAG GTCGCGCTCA CTATGGGAGC AGTAGTTGCA    240
CTCCTTTGGG GGTGTACTCC AGCCATAGAA ACCTGGAAAT TCATCACCTC CAGATGCCGT    300
TTGTGCTTGC TAGGCCGCAA GTACATTTTG GCCCCTGCCC ACCACGTTGA AAGTGCCGCA    360
GGCTTTCATC CGATAGCGGC AAATGATAAC CACGCATTTG TCGTCCGGCG TCCCGGCTCC    420
ACTACGGTTA ACGGCACATT GGTGCCCGGG TTGAAAAGCC TCGTGTTGGG TGGCAGAAAA    480
GCTGTCAAAC AGGGAGTGGT AAACCTTGTT AAATATGCCA AATAACAACG GCAAGCAGCA    540
GAAGAAAAAG AAGGGGGATG GCCAGCCAGT CAATCAGCTG TGCCAGATGC TGGGTAAGAT    600
CATCGCTCAG CAAAACCAGT CCAGAGGCAA GGGACCGGGA AAGAAAAACA AGAAGAAAAA    660
CCCGGAGAAG CCCCATTTTC CTCTAGCGAC TGAAGATGAT GTCAGACATC ACTTCACCTC    720
TGGTGAGCGG CAATTGTGTC TGTCGTCAAT CCAGACAGCC TTTAATCAAG GCGCTGGAAC    780
TTGTACCCTG TCAGATTCAG GGAGGATAAG TTACACTGTG GAGTTTAGTT TGCCGACGCA    840
TCATACTGTG CGCTTGATCC GCGTCACAGC GTCACCCTCA GCATGA                   886
```

(2) INFORMATION FOR SEQ ID NO: 40:

(i) SEQUENCE CHARACTERISTICS:
(A) LENGTH: 886 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-3927 (VR 2431)

(xi) SEQUENCE DESCRIPTION: SEQ ID NO: 40:

```
ATGGGGTCGT CCCTAGACGA CTTTTGCAAT GATAGCACGG CTCCACAAAA GGTGCTTTTG     60
GCGTTTTCTA TTACCTACAC GCCGGTGATG ATATATGCTC TAAAGGTAAG TCGCGGCCGA    120
CTGCTAGGGC TTCTGCACCT TTTGATTTTT CTGAATTGTG CTTTTACTTT CGGGTACATG    180
ACATTCGTGC ACTTTGAGAG CACAAATAGG GTCGCGCTCA CTATGGGAGC AGTAGTCGCA    240
CTTCTCTGGG GGTGTACTCC AGCCATAGAA ACCTGGAAAT TCATCACCTC CAGATGCCGT    300
TTGTGCTTGC TAGGCCGCAA GTACATTCTG GCCCCTGCCC ACCACGTTGA GAGTGCCGCA    360
GGCTTTCATC CGATTGCGGC AAATGATAAC CACGCATTTG TCGTCCGGCG TCCCGGCTCC    420
ACTACGGTTA ACGGCACATT GGTGCCCGGG TTGAGAAGCC TCGTGTTGGG TGGCAAAAAA    480
GCTGTTAAGC AGGGAGTGGT AAACCTTGTT AAATATGCCA AATAACAACG GCAAGCAGCA    540
GAAGAAAAAG AAGGGGGATG GCCAGCCAGT CAATCAGCTC TGCCAAATGC TGGGTAAGAT    600
CATCGCCCAG CAAAACCAGT CCAGAGGTAA GGGACCGGGA AAGAAAAATA AGAAGAAAAA    660
CCCGGAGAAG CCCCATTTTC CTCTAGCGAC TGAAGATGAT GTCAGACATC ACTTCACCCC    720
```

-continued

CAGTGAGCGG CAATTGTGTC TGTCGTCAAT CCAGACTGCC TTTAATCAGG GCGCTGGGAC 780

CTGTATCCTA TCAGATTCAG GGAGGATAAG TTACACTGTG GAGTTTAGTT TGCCGACGCA 840

TCATACTGTG CGCCTGATTC GCGTCACGGC ACCACCCTCA GCATGA 886

(2) INFORMATION FOR SEQ ID NO: 41:

(i) SEQUENCE CHARACTERISTICS:
(A) LENGTH: 898 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(C) INDIVIDUAL ISOLATE: Lelystad (xi) SEQUENCE DESCRIPTION: SEQ ID NO: 41:

ATGGGAGGCC TAGACGATTT TTGCAACGAT CCTATCGCCG CACAAAAGCT CGTGCTAGCC 60

TTTAGCATCA CATACACACC TATAATGATA TACGCCCTTA AGGTGTCACG CGGCCGACTC 120

CTGGGGCTGT TGCACATCCT AATATTTCTG AACTGTTCCT TTACATTCGG ATACATGACA 180

TATGTGCATT TTCAATCCAC CAACCGTGTC GCACTTACCC TGGGGGCTGT TGTCGCCCTT 240

CTGTGGGGTG TTTACAGCTT CACAGAGTCA TGGAAGTTTA TCACTTCCAG ATGCAGATTG 300

TGTTGCCTTG GCCGGCGATA CATTCTGGCC CCTGCCCATC ACGTAGAAAG TGCTGCAGGT 360

CTCCATTCAA TCTCAGCGTC TGGTAACCGA GCATACGCTG TGAGAAAGCC CGGACTAACA 420

TCAGTGAACG GCACTCTAGT ACCAGGACTT CGGAGCCTCG TGCTGGGCGG CAAACGAGCT 480

GTTAAACGAG GAGTGGTTAA CCTCGTCAAG TATGGCCGGT AAAAACCAGA GCCAGAAGAA 540

AAAGAAAAGT ACAGCTCCGA TGGGGAATGG CCAGCCAGTC AATCAACTGT GCCAGTTGCT 600

GGGTGCAATG ATAAAGTCCC AGCGCCAGCA ACCTAGGGGA GGACAGGCCA AAAAGAAAAA 660

GCCTGAGAAG CCACATTTTC CCCTGGCTGC TGAAGATGAC ATCCGGCACC ACCTCACCCA 720

GACTGAACGC TCCCTCTGCT TGCAATCGAT CCAGACGGCT TTCAATCAAG GCGCAGGAAC 780

TGCGTCGCTT TCATCCAGCG GGAAGGTCAG TTTTCAGGTT GAGTTTATGC TGCCGGTTGC 840

TCATACAGTG CGCCTGATTC GCGTGACTTC TACATCCGCC AGTCAGGGTG CAAGTTAA 898

(2) INFORMATION FOR SEQ ID NO: 42:

(i) SEQUENCE CHARACTERISTICS:
(A) LENGTH: 525 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-1894

(ix) FEATURE:
(A) NAME/KEY: CDS
(B) LOCATION: 1..522

(xi) SEQUENCE DESCRIPTION: SEQ ID NO: 42:

ATG GGG TCG TCC TTA GAT GAC TTC TGC CAT GAT AGT ACG GCT CCA CAA 48

-continued

```
Met Gly Ser Ser Leu Asp Asp Phe Cys His Asp Ser Thr Ala Pro Gln
  1               5                  10                  15

AAG GTG CTT TTG GCG TTT TCT ATT ACC TAC ACG CCA GTG ATG ATA TAT        96
Lys Val Leu Leu Ala Phe Ser Ile Thr Tyr Thr Pro Val Met Ile Tyr
             20                  25                  30

GCC CTA AAG GTG AGT CGC GGC CGA CTG CTA GGG CTT CTG CAC CTT TTG       144
Ala Leu Lys Val Ser Arg Gly Arg Leu Leu Gly Leu Leu His Leu Leu
         35                  40                  45

ATC TTC CTG AAT TGT GCT TTC ACC TTC GGG TAC ATG ACA TTC GTG CAC       192
Ile Phe Leu Asn Cys Ala Phe Thr Phe Gly Tyr Met Thr Phe Val His
     50                  55                  60

TTT CAG AGT ACA AAT AAG GTC GCG CTC ACT ATG GGA GCA GTA GTT GCA       240
Phe Gln Ser Thr Asn Lys Val Ala Leu Thr Met Gly Ala Val Val Ala
 65                  70                  75                  80

CTC CTT TGG GGG GTG TAC TCA GCC ATA GAA ACC TGG AAA TTC ATC ACC       288
Leu Leu Trp Gly Val Tyr Ser Ala Ile Glu Thr Trp Lys Phe Ile Thr
                 85                  90                  95

TCC AGA TGC CGT TTG TGC TTG CTA GGC CGC AAG TAC ATT CTG GCC CCT       336
Ser Arg Cys Arg Leu Cys Leu Leu Gly Arg Lys Tyr Ile Leu Ala Pro
            100                 105                 110

GCC CAC CAC GTT GAA AGT GCC GCA GGC TTT CAT CCG ATT GCG GCA AAT       384
Ala His His Val Glu Ser Ala Ala Gly Phe His Pro Ile Ala Ala Asn
        115                 120                 125

GAT AAC CAC GCA TTT GTC GTC CGG CGT CCC GGC TCC ACT ACG GTC AAC       432
Asp Asn His Ala Phe Val Val Arg Arg Pro Gly Ser Thr Thr Val Asn
    130                 135                 140

GGC ACA TTG GTG CCC GGG TTG AAA AGC CTC GTG TTG GGT GGC AGA AAA       480
Gly Thr Leu Val Pro Gly Leu Lys Ser Leu Val Leu Gly Gly Arg Lys
145                 150                 155                 160

GCT GTT AAA CAG GGA GTG GTA AAC CTT GTC AAA TAT GCC AAA               522
Ala Val Lys Gln Gly Val Val Asn Leu Val Lys Tyr Ala Lys
                165                 170

TAA                                                                   525
```

(2) INFORMATION FOR SEQ ID NO: 43:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 43:

```
Met Gly Ser Ser Leu Asp Asp Phe Cys His Asp Ser Thr Ala Pro Gln
  1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
         35                  40                  45

Ile Phe Leu Asn Cys Ala Phe Thr Phe Gly Tyr Met Thr Phe Val His
     50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
```

-continued

```
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170


(2) INFORMATION FOR SEQ ID NO: 44:

     (i) SEQUENCE CHARACTERISTICS:
          (A) LENGTH: 525 base pairs
          (B) TYPE: nucleic acid
          (C) STRANDEDNESS: unknown
          (D) TOPOLOGY: linear

    (ii) MOLECULE TYPE: cDNA

    (vi) ORIGINAL SOURCE:
          (A) ORGANISM: porcine reproductive and respiratory syndrome
               virus
          (B) STRAIN: Iowa
          (C) INDIVIDUAL ISOLATE: ISU-22 (VR 2429)

    (ix) FEATURE:
          (A) NAME/KEY: CDS
          (B) LOCATION: 1..522

    (xi) SEQUENCE DESCRIPTION: SEQ ID NO: 44:

ATG GGG TCG TCC TTA GAT GAC TTC TGT CAT GAC AGC ACG GCT CCA CAA       48
Met Gly Ser Ser Leu Asp Asp Phe Cys His Asp Ser Thr Ala Pro Gln
  1               5                  10                  15

AAG GTG CTT TTG GCG TTT TCT ATT ACC TAC ACG CCA GTG ATG ATA TAT       96
Lys Val Leu Leu Ala Phe Ser Ile Thr Tyr Thr Pro Val Met Ile Tyr
             20                  25                  30

GCC CTG AAG GTG AGT CGC GGC CGA CTG CTA GGG CTT CTG CAC CTT TTG      144
Ala Leu Lys Val Ser Arg Gly Arg Leu Leu Gly Leu Leu His Leu Leu
         35                  40                  45

ATC TTC CTG AAT TGT GCT TTC ACC TTC GGG TAC ATG ACA TTC GTG CAC      192
Ile Phe Leu Asn Cys Ala Phe Thr Phe Gly Tyr Met Thr Phe Val His
     50                  55                  60

TTT CAG AGT ACA AAT AAG GTC GCA CTC ACT ATG GGA GCA GTA GTT GCA      240
Phe Gln Ser Thr Asn Lys Val Ala Leu Thr Met Gly Ala Val Val Ala
 65                  70                  75                  80

CTC CTT TGG GGG GTG TAC TCA GCC ATA GAA ACC TGG AAA TTC ATC ACC      288
Leu Leu Trp Gly Val Tyr Ser Ala Ile Glu Thr Trp Lys Phe Ile Thr
                 85                  90                  95

TCC AGA TGC CGT TTG TGC TTG CTA GGC CGC AAG TAC ATT CTG GCC CCT      336
Ser Arg Cys Arg Leu Cys Leu Leu Gly Arg Lys Tyr Ile Leu Ala Pro
            100                 105                 110

GCC CAC CAC GTT GAA AGT GCC GCA GGC TTT CAT CCG ATT GCG GCA AAT      384
Ala His His Val Glu Ser Ala Ala Gly Phe His Pro Ile Ala Ala Asn
        115                 120                 125

GAT AAC CAC GCA TTT GTC GTT CGG CGT CCC GGC TCC ACT ACG GTC AAC      432
Asp Asn His Ala Phe Val Val Arg Arg Pro Gly Ser Thr Thr Val Asn
    130                 135                 140

GGC ACA TTG GTG CCC GGG TTG AAA AGC CTC GTG TTG GGT GGC AGA AAA      480
Gly Thr Leu Val Pro Gly Leu Lys Ser Leu Val Leu Gly Gly Arg Lys
145                 150                 155                 160

GCT GTT AAA CAG GGA GTG GTA AAC CTT GTC AAA TAT GCC AAA              522
Ala Val Lys Gln Gly Val Val Asn Leu Val Lys Tyr Ala Lys
                165                 170

TAA                                                                  525
```

-continued (2) INFORMATION FOR SEQ ID NO: 45:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 45:

```
Met Gly Ser Ser Leu Asp Asp Phe Cys His Asp Ser Thr Ala Pro Gln
  1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
         35                  40                  45

Ile Phe Leu Asn Cys Ala Phe Thr Phe Gly Tyr Met Thr Phe Val His
     50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170
```

(2) INFORMATION FOR SEQ ID NO: 46:

(i) SEQUENCE CHARACTERISTICS:
(A) LENGTH: 525 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-79

(ix) FEATURE:
(A) NAME/KEY: CDS
(B) LOCATION: 1..522

(xi) SEQUENCE DESCRIPTION: SEQ ID NO: 46:

```
ATG GGG TCG TCC TTA GAT GAC TTC TGT TAT GAT AGT ACG GCT CCA CAA       48
Met Gly Ser Ser Leu Asp Asp Phe Cys Tyr Asp Ser Thr Ala Pro Gln
  1               5                  10                  15

AAG GTG CTT TTG GCA TTT TCT ATT ACC TAC ACG CCA GTA ATG ATA TAT       96
Lys Val Leu Leu Ala Phe Ser Ile Thr Tyr Thr Pro Val Met Ile Tyr
             20                  25                  30

GCC CTA AAG GTG AGT CGC GGC CGA CTG CTA GGG CTT CTG CAC CTT TTG      144
Ala Leu Lys Val Ser Arg Gly Arg Leu Leu Gly Leu Leu His Leu Leu
```

-continued

```
        35                  40                  45

ATT TTC CTG AAC TGT GCT TTC ACC TTC GGG TAC ATG ACA TTC ATG CAC       192
Ile Phe Leu Asn Cys Ala Phe Thr Phe Gly Tyr Met Thr Phe Met His
     50                  55                  60

TTT CAG AGT ACA AAT AAG GTC GCG CTC ACT ATG GGA GCA GTA GTT GCA       240
Phe Gln Ser Thr Asn Lys Val Ala Leu Thr Met Gly Ala Val Val Ala
 65                  70                  75                  80

CTC CTT TGG GGG GTG TAC TCA GCC ATA GAA ACC TGG AAA TTC ATC ACC       288
Leu Leu Trp Gly Val Tyr Ser Ala Ile Glu Thr Trp Lys Phe Ile Thr
                 85                  90                  95

TCC AGA TGC CGT TTG TGC TTG CTA GGC CGC AAG TAC ATT CTG GCC CCT       336
Ser Arg Cys Arg Leu Cys Leu Leu Gly Arg Lys Tyr Ile Leu Ala Pro
            100                 105                 110

GCC CAC CAC GTT GAA AGT GCC GCA GGC TTT CAT CCG ATT GCG GCA AAT       384
Ala His His Val Glu Ser Ala Ala Gly Phe His Pro Ile Ala Ala Asn
        115                 120                 125

GAT AAC CAC GCA TTT GTC GTC CGG CGT CCC GGC TCC ACT ACG GTC AAC       432
Asp Asn His Ala Phe Val Val Arg Arg Pro Gly Ser Thr Thr Val Asn
    130                 135                 140

GGC ACA TTG GTG CCC GGG TTG AAA AGC CTC GTG TTG GGT GGC AGA AAA       480
Gly Thr Leu Val Pro Gly Leu Lys Ser Leu Val Leu Gly Gly Arg Lys
145                 150                 155                 160

GCT GTT AAA CAG GGA GTG GTA AAC CTT GTC AAA TAT GCC AAA               522
Ala Val Lys Gln Gly Val Val Asn Leu Val Lys Tyr Ala Lys
                165                 170

TAA                                                                   525
```

(2) INFORMATION FOR SEQ ID NO: 47:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 47:

```
Met Gly Ser Ser Leu Asp Asp Phe Cys Tyr Asp Ser Thr Ala Pro Gln
  1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Met His
     50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
```

-continued

```
              165                 170
```

(2) INFORMATION FOR SEQ ID NO: 48:

(i) SEQUENCE CHARACTERISTICS:
(A) LENGTH: 525 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-55 (VR 2430)

(ix) FEATURE:
(A) NAME/KEY: CDS
(B) LOCATION: 1..522

(xi) SEQUENCE DESCRIPTION: SEQ ID NO: 48:

```
ATG GGG TCG TCC TTA GAT GAC TTC TGC CAT GAT AGC ACG GCT CCA CAA       48
Met Gly Ser Ser Leu Asp Asp Phe Cys His Asp Ser Thr Ala Pro Gln
  1               5                  10                  15

AAG GTG CTT TTG GCG TTC TCT ATT ACC TAC ACG CCA GTG ATG ATA TAT       96
Lys Val Leu Leu Ala Phe Ser Ile Thr Tyr Thr Pro Val Met Ile Tyr
             20                  25                  30

GCC CTA AAA GTA AGT CGC GGC CGA CTG CTA GGG CTT CTG CAC CTT TTG      144
Ala Leu Lys Val Ser Arg Gly Arg Leu Leu Gly Leu Leu His Leu Leu
         35                  40                  45

ATC TTC CTA AAT TGT GCT TTC ACC TTC GGG TAC ATG ACA TTC GTG CAC      192
Ile Phe Leu Asn Cys Ala Phe Thr Phe Gly Tyr Met Thr Phe Val His
     50                  55                  60

TTT CAG AGC ACA AAC AAG GTC GCG CTC ACT ATG GGA GCA GTA GTT GCA      240
Phe Gln Ser Thr Asn Lys Val Ala Leu Thr Met Gly Ala Val Val Ala
 65                  70                  75                  80

CTC CTT TGG GGG GTG TAC TCA GCC ATA GAA ACC TGG AAA TTC ATC ACC      288
Leu Leu Trp Gly Val Tyr Ser Ala Ile Glu Thr Trp Lys Phe Ile Thr
                 85                  90                  95

TCC AGA TGC CGT TTG TGC TTG CTA GGC CGC AAG TAC ATT TTG GCC CCT      336
Ser Arg Cys Arg Leu Cys Leu Leu Gly Arg Lys Tyr Ile Leu Ala Pro
            100                 105                 110

GCC CAC CAC GTT GAA AGT GCC GCA GGC TTT CAT CCG ATA GCG GCA AAT      384
Ala His His Val Glu Ser Ala Ala Gly Phe His Pro Ile Ala Ala Asn
        115                 120                 125

GAT AAC CAC GCA TTT GTC GTC CGG CGT CCC GGC TCC ACT ACG GTT AAC      432
Asp Asn His Ala Phe Val Val Arg Arg Pro Gly Ser Thr Thr Val Asn
    130                 135                 140

GGC ACA TTG GTG CCC GGG TTG AAA AGC CTC GTG TTG GGT GGC AGA AAA      480
Gly Thr Leu Val Pro Gly Leu Lys Ser Leu Val Leu Gly Gly Arg Lys
145                 150                 155                 160

GCT GTC AAA CAG GGA GTG GTA AAC CTT GTT AAA TAT GCC AAA              522
Ala Val Lys Gln Gly Val Val Asn Leu Val Lys Tyr Ala Lys
                165                 170

TAA                                                                  525
```

(2) INFORMATION FOR SEQ ID NO: 49:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 49:

```
Met Gly Ser Ser Leu Asp Asp Phe Cys His Asp Ser Thr Ala Pro Gln
  1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
         35                  40                  45

Ile Phe Leu Asn Cys Ala Phe Thr Phe Gly Tyr Met Thr Phe Val His
     50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170
```

(2) INFORMATION FOR SEQ ID NO: 50:

(i) SEQUENCE CHARACTERISTICS:
(A) LENGTH: 525 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-3927 (VR 2431)

(ix) FEATURE:
(A) NAME/KEY: CDS
(B) LOCATION: 1..522

(xi) SEQUENCE DESCRIPTION: SEQ ID NO: 50:

```
ATG GGG TCG TCC CTA GAC GAC TTT TGC AAT GAT AGC ACG GCT CCA CAA       48
Met Gly Ser Ser Leu Asp Asp Phe Cys Asn Asp Ser Thr Ala Pro Gln
  1               5                  10                  15

AAG GTG CTT TTG GCG TTT TCT ATT ACC TAC ACG CCG GTG ATG ATA TAT       96
Lys Val Leu Leu Ala Phe Ser Ile Thr Tyr Thr Pro Val Met Ile Tyr
             20                  25                  30

GCT CTA AAG GTA AGT CGC GGC CGA CTG CTA GGG CTT CTG CAC CTT TTG      144
Ala Leu Lys Val Ser Arg Gly Arg Leu Leu Gly Leu Leu His Leu Leu
         35                  40                  45

ATT TTT CTG AAT TGT GCT TTT ACT TTC GGG TAC ATG ACA TTC GTG CAC      192
Ile Phe Leu Asn Cys Ala Phe Thr Phe Gly Tyr Met Thr Phe Val His
     50                  55                  60

TTT GAG AGC ACA AAT AGG GTC GCG CTC ACT ATG GGA GCA GTA GTC GCA      240
Phe Glu Ser Thr Asn Arg Val Ala Leu Thr Met Gly Ala Val Val Ala
 65                  70                  75                  80
```

-continued

```
CTT CTC TGG GGG GTG TAC TCA GCC ATA GAA ACC TGG AAA TTC ATC ACC      288
Leu Leu Trp Gly Val Tyr Ser Ala Ile Glu Thr Trp Lys Phe Ile Thr
                 85                  90                  95

TCC AGA TGC CGT TTG TGC TTG CTA GGC CGC AAG TAC ATT CTG GCC CCT      336
Ser Arg Cys Arg Leu Cys Leu Leu Gly Arg Lys Tyr Ile Leu Ala Pro
            100                 105                 110

GCC CAC CAC GTT GAG AGT GCC GCA GGC TTT CAT CCG ATT GCG GCA AAT      384
Ala His His Val Glu Ser Ala Ala Gly Phe His Pro Ile Ala Ala Asn
        115                 120                 125

GAT AAC CAC GCA TTT GTC GTC CGG CGT CCC GGC TCC ACT ACG GTT AAC      432
Asp Asn His Ala Phe Val Val Arg Arg Pro Gly Ser Thr Thr Val Asn
    130                 135                 140

GGC ACA TTG GTG CCC GGG TTG AGA AGC CTC GTG TTG GGT GGC AAA AAA      480
Gly Thr Leu Val Pro Gly Leu Arg Ser Leu Val Leu Gly Gly Lys Lys
145                 150                 155                 160

GCT GTT AAG CAG GGA GTG GTA AAC CTT GTT AAA TAT GCC AAA              522
Ala Val Lys Gln Gly Val Val Asn Leu Val Lys Tyr Ala Lys
                165                 170

TAA                                                                  525
```

(2) INFORMATION FOR SEQ ID NO: 51:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 51:

```
Met Gly Ser Ser Leu Asp Asp Phe Cys Asn Asp Ser Thr Ala Pro Gln
  1               5                  10                  15

Lys Val Leu Leu Ala Phe Ser Ile Thr Tyr Thr Pro Val Met Ile Tyr
             20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Val His
     50                  55                  60

Phe Glu Ser Thr Asn Arg Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Arg Ser Leu Val Leu Gly Gly Lys Lys
145                 150                 155                 160

Ala Val Lys Gln Gly Val Val Asn Leu Val Lys Tyr Ala Lys
                165                 170
```

(2) INFORMATION FOR SEQ ID NO: 52:

(i) SEQUENCE CHARACTERISTICS:
(A) LENGTH: 372 base pairs
(B) TYPE: nucleic acid
(C) STRANDEDNESS: unknown -continued (D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-1894

(ix) FEATURE:
(A) NAME/KEY: CDS
(B) LOCATION: 1..369

(xi) SEQUENCE DESCRIPTION: SEQ ID NO: 52:

```
ATG CCA AAT AAC AAC GGC AAG CAG CAG AAG AGA AAG AAG GGG GAT GGC       48
Met Pro Asn Asn Asn Gly Lys Gln Gln Lys Arg Lys Lys Gly Asp Gly
  1               5                  10                  15

CAG CCA GTC AAT CAG CTG TGC CAG ATG CTG GGT AAG ATC ATC GCT CAG       96
Gln Pro Val Asn Gln Leu Cys Gln Met Leu Gly Lys Ile Ile Ala Gln
             20                  25                  30

CAA AAC CAG TCC AGA GGC AAG GGA CCG GGA AAG AAA AAC AAG AAG AAA      144
Gln Asn Gln Ser Arg Gly Lys Gly Pro Gly Lys Lys Asn Lys Lys Lys
         35                  40                  45

AAC CCG GAG AAG CCC CAT TTT CCT CTA GCG ACT GAA GAT GAT GTC AGA      192
Asn Pro Glu Lys Pro His Phe Pro Leu Ala Thr Glu Asp Asp Val Arg
     50                  55                  60

CAT CAC TTC ACC CCT AGT GAG CGG CAA TTG TGT CTG TCG TCA ATC CAG      240
His His Phe Thr Pro Ser Glu Arg Gln Leu Cys Leu Ser Ser Ile Gln
 65                  70                  75                  80

ACC GCC TTT AAT CAA GGC GCT GGG ACT TGC ACC CTG TCA GAT TCA GGG      288
Thr Ala Phe Asn Gln Gly Ala Gly Thr Cys Thr Leu Ser Asp Ser Gly
                 85                  90                  95

AGG ATA AGT TAC ACT GTG GAG TTT AGT TTG CCA ACG CAT CAT ACT GTG      336
Arg Ile Ser Tyr Thr Val Glu Phe Ser Leu Pro Thr His His Thr Val
            100                 105                 110

CGC TTG ATC CGC GTC ACA GCA TCA CCC TCA GCA TGA                      372
Arg Leu Ile Arg Val Thr Ala Ser Pro Ser Ala
        115                 120
```

(2) INFORMATION FOR SEQ ID NO: 53:

(i) SEQUENCE CHARACTERISTICS:
(A) LENGTH: 123 amino acids
(B) TYPE: amino acid
(D) TOPOLOGY: linear (ii) MOLECULE TYPE: protein (xi) SEQUENCE DESCRIPTION: SEQ ID NO: 53:

```
Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
```

```
            100                 105                 110

Arg Leu Ile Arg Val Thr Ala Ser Pro Ser Ala
        115                 120
```

(2) INFORMATION FOR SEQ ID NO: 54:

(i) SEQUENCE CHARACTERISTICS:
(A) LENGTH: 372 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-22 (VR 2429)

(ix) FEATURE:
(A) NAME/KEY: CDS
(B) LOCATION: 1..369

(xi) SEQUENCE DESCRIPTION: SEQ ID NO: 54:

```
ATG CCA AAT AAC AAC GGT AAG CAG CAG AAG AGA AAG AAG GGG GAT GGC       48
Met Pro Asn Asn Asn Gly Lys Gln Gln Lys Arg Lys Lys Gly Asp Gly
  1               5                  10                  15

CAG CCA GTC AAT CAG CTG TGC CAG ATG CTG GGC AAG ATC ATC GCT CAG       96
Gln Pro Val Asn Gln Leu Cys Gln Met Leu Gly Lys Ile Ile Ala Gln
             20                  25                  30

CAA AAT CAG TCC AGA GGC AAG GGA CCG GGA AAG AAA AAT AAG AAG AAA      144
Gln Asn Gln Ser Arg Gly Lys Gly Pro Gly Lys Lys Asn Lys Lys Lys
         35                  40                  45

AAC CCG GAG AAG CCC CAT TTT CCT CTA GCG ACT GAA GAT GAT GTC AGA      192
Asn Pro Glu Lys Pro His Phe Pro Leu Ala Thr Glu Asp Asp Val Arg
     50                  55                  60

CAT CAC TTT ACC CCT AGT GAG CGG CAA TTG TGT CTG TCG TCA ATC CAG      240
His His Phe Thr Pro Ser Glu Arg Gln Leu Cys Leu Ser Ser Ile Gln
 65                  70                  75                  80

ACC GCC TTT AAT CAA GGC GCT GGG ACT TGC ACC CTG TCA GAT TCA GGG      288
Thr Ala Phe Asn Gln Gly Ala Gly Thr Cys Thr Leu Ser Asp Ser Gly
                 85                  90                  95

AGG ATA AGT TAC ACT GTG GAG TTT AGT TTG CCT ACG CAT CAT ACT GTG      336
Arg Ile Ser Tyr Thr Val Glu Phe Ser Leu Pro Thr His His Thr Val
            100                 105                 110

CGC CTG ATC CGC GTC ACA GCA TCA CCC TCA GCA TGA                      372
Arg Leu Ile Arg Val Thr Ala Ser Pro Ser Ala
        115                 120
```

(2) INFORMATION FOR SEQ ID NO: 55:

(i) SEQUENCE CHARACTERISTICS:
(A) LENGTH: 123 amino acids
(B) TYPE: amino acid
(D) TOPOLOGY: linear (ii) MOLECULE TYPE: protein (xi) SEQUENCE DESCRIPTION: SEQ ID NO: 55:

```
Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
```

-continued

```
        35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

(2) INFORMATION FOR SEQ ID NO: 56:

(i) SEQUENCE CHARACTERISTICS:
(A) LENGTH: 372 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-79

(ix) FEATURE:
(A) NAME/KEY: CDS
(B) LOCATION: 1..369

(xi) SEQUENCE DESCRIPTION: SEQ ID NO: 56:

```
ATG CCA AAT AAC AAC GGC AAG CAG CAG AAG AGA AAG AAG GGG GAT GGC       48
Met Pro Asn Asn Asn Gly Lys Gln Gln Lys Arg Lys Lys Gly Asp Gly
  1               5                  10                  15

CAG CCA GTC AAT CAG CTG TGC CAG ATG CTG GGT AAG ATC ATC GCC CAG       96
Gln Pro Val Asn Gln Leu Cys Gln Met Leu Gly Lys Ile Ile Ala Gln
            20                  25                  30

CAA AAC CAG TCT AGA GGC AAG GGA CCG GGA AAG AAA AAT AAG AAG AAA      144
Gln Asn Gln Ser Arg Gly Lys Gly Pro Gly Lys Lys Asn Lys Lys Lys
        35                  40                  45

AAC CCG GAG AAG CCC CAT TTT CCT CTA GCG ACT GAA GAT GAT GTC AGA      192
Asn Pro Glu Lys Pro His Phe Pro Leu Ala Thr Glu Asp Asp Val Arg
     50                  55                  60

CAT CAC TTT ACC CCT AGT GAG CGG CAA TTG TGT CTG TCG TCA ATC CAA      240
His His Phe Thr Pro Ser Glu Arg Gln Leu Cys Leu Ser Ser Ile Gln
 65                  70                  75                  80

ACT GCC TTT AAT CAA GGC GCT GGG ACT TGC ACC CTG TCA GAT TCA GGG      288
Thr Ala Phe Asn Gln Gly Ala Gly Thr Cys Thr Leu Ser Asp Ser Gly
                 85                  90                  95

AGG ATA AGT TAC ACT GTG GAG TTT AGT TTG CCT ACG CAT CAT ACT GTG      336
Arg Ile Ser Tyr Thr Val Glu Phe Ser Leu Pro Thr His His Thr Val
            100                 105                 110

CGC TTG ATC CGC GTC ACA GCA TCA CCC TCA GCA TGA                      372
Arg Leu Ile Arg Val Thr Ala Ser Pro Ser Ala
        115                 120
```

(2) INFORMATION FOR SEQ ID NO: 57:

(i) SEQUENCE CHARACTERISTICS:
(A) LENGTH: 123 amino acids
(B) TYPE: amino acid
(D) TOPOLOGY: linear -continued (ii) MOLECULE TYPE: protein (xi) SEQUENCE DESCRIPTION: SEQ ID NO: 57:

```
Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

(2) INFORMATION FOR SEQ ID NO: 58:

(i) SEQUENCE CHARACTERISTICS:
(A) LENGTH: 372 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-55 (VR 2430)

(ix) FEATURE:
(A) NAME/KEY: CDS
(B) LOCATION: 1..369

(xi) SEQUENCE DESCRIPTION: SEQ ID NO: 58:

```
ATG CCA AAT AAC AAC GGC AAG CAG CAG AAG AAA AAG AAG GGG GAT GGC       48
Met Pro Asn Asn Asn Gly Lys Gln Gln Lys Lys Lys Lys Gly Asp Gly
  1               5                  10                  15

CAG CCA GTC AAT CAG CTG TGC CAG ATG CTG GGT AAG ATC ATC GCT CAG       96
Gln Pro Val Asn Gln Leu Cys Gln Met Leu Gly Lys Ile Ile Ala Gln
             20                  25                  30

CAA AAC CAG TCC AGA GGC AAG GGA CCG GGA AAG AAA AAC AAG AAG AAA      144
Gln Asn Gln Ser Arg Gly Lys Gly Pro Gly Lys Lys Asn Lys Lys Lys
         35                  40                  45

AAC CCG GAG AAG CCC CAT TTT CCT CTA GCG ACT GAA GAT GAT GTC AGA      192
Asn Pro Glu Lys Pro His Phe Pro Leu Ala Thr Glu Asp Asp Val Arg
     50                  55                  60

CAT CAC TTC ACC TCT GGT GAG CGG CAA TTG TGT CTG TCG TCA ATC CAG      240
His His Phe Thr Ser Gly Glu Arg Gln Leu Cys Leu Ser Ser Ile Gln
 65                  70                  75                  80

ACA GCC TTT AAT CAA GGC GCT GGA ACT TGT ACC CTG TCA GAT TCA GGG      288
Thr Ala Phe Asn Gln Gly Ala Gly Thr Cys Thr Leu Ser Asp Ser Gly
                 85                  90                  95

AGG ATA AGT TAC ACT GTG GAG TTT AGT TTG CCG ACG CAT CAT ACT GTG      336
Arg Ile Ser Tyr Thr Val Glu Phe Ser Leu Pro Thr His His Thr Val
            100                 105                 110
```

-continued

```
CGC TTG ATC CGC GTC ACA GCG TCA CCC TCA GCA TGA                    372
Arg Leu Ile Arg Val Thr Ala Ser Pro Ser Ala
        115                 120
```

(2) INFORMATION FOR SEQ ID NO: 59:

(i) SEQUENCE CHARACTERISTICS:
(A) LENGTH: 123 amino acids
(B) TYPE: amino acid
(D) TOPOLOGY: linear (ii) MOLECULE TYPE: protein (xi) SEQUENCE DESCRIPTION: SEQ ID NO: 59:

```
Met Pro Asn Asn Asn Gly Lys Gln Gln Lys Lys Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Ser Gly Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

(2) INFORMATION FOR SEQ ID NO: 60:

(i) SEQUENCE CHARACTERISTICS:
(A) LENGTH: 372 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-3927 (VR 2431)

(ix) FEATURE:
(A) NAME/KEY: CDS
(B) LOCATION: 1..369

(xi) SEQUENCE DESCRIPTION: SEQ ID NO: 60:

```
ATG CCA AAT AAC AAC GGC AAG CAG CAG AAG AAA AAG AAG GGG GAT GGC       48
Met Pro Asn Asn Asn Gly Lys Gln Gln Lys Lys Lys Lys Gly Asp Gly
  1               5                  10                  15

CAG CCA GTC AAT CAG CTC TGC CAA ATG CTG GGT AAG ATC ATC GCC CAG       96
Gln Pro Val Asn Gln Leu Cys Gln Met Leu Gly Lys Ile Ile Ala Gln
             20                  25                  30

CAA AAC CAG TCC AGA GGT AAG GGA CCG GGA AAG AAA AAT AAG AAG AAA      144
Gln Asn Gln Ser Arg Gly Lys Gly Pro Gly Lys Lys Asn Lys Lys Lys
         35                  40                  45

AAC CCG GAG AAG CCC CAT TTT CCT CTA GCG ACT GAA GAT GAT GTC AGA      192
Asn Pro Glu Lys Pro His Phe Pro Leu Ala Thr Glu Asp Asp Val Arg
     50                  55                  60
```

-continued

```
CAT CAC TTC ACC CCC AGT GAG CGG CAA TTG TGT CTG TCG TCA ATC CAG      240
His His Phe Thr Pro Ser Glu Arg Gln Leu Cys Leu Ser Ser Ile Gln
 65                  70                  75                  80

ACT GCC TTT AAT CAG GGC GCT GGG ACC TGT ATC CTA TCA GAT TCA GGG      288
Thr Ala Phe Asn Gln Gly Ala Gly Thr Cys Ile Leu Ser Asp Ser Gly
                 85                  90                  95

AGG ATA AGT TAC ACT GTG GAG TTT AGT TTG CCG ACG CAT CAT ACT GTG      336
Arg Ile Ser Tyr Thr Val Glu Phe Ser Leu Pro Thr His His Thr Val
            100                 105                 110

CGC CTG ATT CGC GTC ACG GCA CCA CCC TCA GCA TGA                      372
Arg Leu Ile Arg Val Thr Ala Pro Pro Ser Ala
        115                 120
```

(2) INFORMATION FOR SEQ ID NO: 61:

(i) SEQUENCE CHARACTERISTICS:
(A) LENGTH: 123 amino acids
(B) TYPE: amino acid
(D) TOPOLOGY: linear (ii) MOLECULE TYPE: protein (xi) SEQUENCE DESCRIPTION: SEQ ID NO: 61:

```
Met Pro Asn Asn Asn Gly Lys Gln Gln Lys Lys Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Ile Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Pro Pro Ser Ala
        115                 120
```

(2) INFORMATION FOR SEQ ID NO: 62:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO: 62:

```
Lys Lys Ser Thr Ala Pro Met
1               5
```

(2) INFORMATION FOR SEQ ID NO: 63:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO: 63:

-continued

Ala Ser Gln Gly
1

(2) INFORMATION FOR SEQ ID NO: 64:

(i) SEQUENCE CHARACTERISTICS:
(A) LENGTH: 240 base pairs
(B) TYPE: nucleic acid
(C) STRANDEDNESS: single
(D) TOPOLOGY: linear (ii) MOLECULE TYPE: Other nucleic acid;
(A) DESCRIPTION: DNA (synthetic)

(vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(xi) SEQUENCE DESCRIPTION: SEQ ID NO: 64:

```
TCTTCTTGCC TTTTCTATGC TTCTGAGATG AGTGAAAAGG GATTTAAGGT GGTATTTGGC     60

AATGTGTCAG GCATCGTGGC AGTGTGCGTC AACTTCACCA GTTACGTCCA ACATGTCAAG    120

GAATTTACCC AACGTTCCTT GGTAGTTGAC CATGTGCGGC TGCTCCATTT CATGACGCCC    180

GAGACCATGA GGTGGGCAAC TGTTTTAGCC TGTCTTTTTA CCATTCTGTT GGCAATTTGA    240
```

(2) INFORMATION FOR SEQ ID NO: 65:

(i) SEQUENCE CHARACTERISTICS:
(A) LENGTH: 1799 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(xi) SEQUENCE DESCRIPTION: SEQ ID NO: 65:

```
CCTGAATTGA GATGAAATGG GGTCTATGCA AAGCCTTTTT GACAAAATTG GCCAACTTTT     60

TGTGGATGCT TTCACGGAGT TCTTGGTGTC CATTGTTGAT ATCATTATAT TTTTGGCCAT    120

TTTGTTTGGC TTCACCATCG CAGGTTGGCT GGTGGTCTTT TGCATCAGAT TGGTTTGCTC    180

CGCGATACTC CGTGCGCGCC CTGCCATTCA CTCTGAGCAA TTACAGAAGA TCCTATGAGG    240

CCTTTCTCTC TCAGTGCCAG GTGGACATTC CCACCTGGGG AACTAAACAT CCTTTGGGGA    300

TGCTTTGGCA CCATAAGGTG TCAACCCTGA TTGATGAAAT GGTGTCGCGT CGAATGTACC    360

GCATCATGGA AAAAGCAGGA CAGGCTGCCT GGAAACAGGT AGTGAGCGAG GCTACGCTGT    420

CTCGCATTAG TAGTTTGGAT GTGGTGGCTC ATTTTCAGCA TCTTGCCGCC ATTGAAGCCG    480

AGACCTGTAA ATATCTGGCC TCTCGGCTGC CCATGCTACA CCACCTGCGC ATGACAGGGT    540

CAAATGTAAC CATAGTGTAT AATAGTACTT TGAATCAGGT GTTTGCTGTT TTCCCAACCC    600

CTGGTTCCCG GCCAAAGCTT CATGATTTCC AGCAATGGCT AATAGCTGTA CATTCCTCTA    660

TATTTTCCTC TGTTGCAGCT TCTTGTACTC TTTTTGTTGT GCTGTGGTTG CGGGTTCCAA    720

TGCTACGTAC TGTTTTTGGT TTCCGCTGGT TAGGGGCAAT TTTTCTTTCG AACTCACGGT    780

GAATTACACG GTGTGCCCGC CTTGCCTCAC CCGGCAAGCA GCCGCAGAGG CCTACGAACC    840
```

-continued

```
CGGCAGGTCC CTTTGGTGCA GGATAGGGCA TGATCGATGT GGGGAGGACG ATCATGATGA    900

ACTAGGGTTT GTGGTGCCGT CTGGCCTCTC CAGCGAAGGC CACTTGACCA GTGCTTACGC    960

CTGGTTGGCG TCCCTGTCCT TCAGCTATAC GGCCCAGTTC CATCCCGAGA TATTCGGGAT   1020

AGGGAATGTG AGTCGAGTCT ATGTTGACAT CAAGCACCAA TTCATTTGCG CTGTTCATGA   1080

TGGGCAGAAC ACCACCTTGC CCCACCATGA CAACATTTCA GCCGTGCTTC AGACCTATTA   1140

CCAGCATCAG GTCGACGGGG GCAATTGGTT TCACCTAGAA TGGGTGCGTC CCTTCTTTTC   1200

CTCTTGGTTG GTTTTAAATG TCTCTTGGTT TCTCAGGCGT TCGCCTGCAA GCCATGTTTC   1260

AGTTCGAGTC TTTCAGACAT CAAGACCAAC ACCACCGCAG CGGCAGGCTT TGCTGTCCTC   1320

CAAGACATCA GTTGCCTTAG GCATCGCAAC TCGGCCTCTG AGGCGATTCG CAAAGTCCCT   1380

CAGTGCCGCA CGGCGATAGG GACACCCGTG TATATCACTG TCACAGCCAA TGTTACCGAT   1440

GAGAATTATT TGCATTCCTC TGATCTTCTC ATGCTTTCTT CTTGCCTTTT CTATGCTTCT   1500

GAGATGAGTG AAAAGGGATT TAAGGTGGTA TTTGGCAATG TGTCAGGCAT CGTGGCAGTG   1560

TGCGTCAACT TCACCAGTTA CGTCCAACAT GTCAAGGAAT TTACCCAACG TTCCTTGGTA   1620

GTTGACCATG TGCGGCTGCT CCATTTCATG ACGCCCGAGA CCATGAGGTG GGCAACTGTT   1680

TTAGCCTGTC TTTTTACCAT TCTGTTGGCA ATTTGAATGT TTAAGTATGT TGGGGAAATG   1740

CTTGACCGCG GGCTGTTGCT CGCAATTGCT TTTTTTATGG TGTATCGTGC CGTCTTGTT    1799
```

(2) INFORMATION FOR SEQ ID NO: 66:

(i) SEQUENCE CHARACTERISTICS:
(A) LENGTH: 771 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(ix) FEATURE:
(A) NAME/KEY: CDS
(B) LOCATION: 1..768

(xi) SEQUENCE DESCRIPTION: SEQ ID NO: 66:

```
ATG AAA TGG GGT CTA TGC AAA GCC TTT TTG ACA AAA TTG GCC AAC TTT       48
Met Lys Trp Gly Leu Cys Lys Ala Phe Leu Thr Lys Leu Ala Asn Phe
  1               5                  10                  15

TTG TGG ATG CTT TCA CGG AGT TCT TGG TGT CCA TTG TTG ATA TCA TTA       96
Leu Trp Met Leu Ser Arg Ser Ser Trp Cys Pro Leu Leu Ile Ser Leu
             20                  25                  30

TAT TTT TGG CCA TTT TGT TTG GCT TCA CCA TCG CAG GTT GGC TGG TGG      144
Tyr Phe Trp Pro Phe Cys Leu Ala Ser Pro Ser Gln Val Gly Trp Trp
         35                  40                  45

TCT TTT GCA TCA GAT TGG TTT GCT CCG CGA TAC TCC GTG CGC GCC CTG      192
Ser Phe Ala Ser Asp Trp Phe Ala Pro Arg Tyr Ser Val Arg Ala Leu
     50                  55                  60

CCA TTC ACT CTG AGC AAT TAC AGA AGA TCC TAT GAG GCC TTT CTC TCT      240
Pro Phe Thr Leu Ser Asn Tyr Arg Arg Ser Tyr Glu Ala Phe Leu Ser
 65                  70                  75                  80

CAG TGC CAG GTG GAC ATT CCC ACC TGG GGA ACT AAA CAT CCT TTG GGG      288
Gln Cys Gln Val Asp Ile Pro Thr Trp Gly Thr Lys His Pro Leu Gly
                 85                  90                  95
```

-continued

```
ATG CTT TGG CAC CAT AAG GTG TCA ACC CTG ATT GAT GAA ATG GTG TCG       336
Met Leu Trp His His Lys Val Ser Thr Leu Ile Asp Glu Met Val Ser
            100                 105                 110

CGT CGA ATG TAC CGC ATC ATG GAA AAA GCA GGA CAG GCT GCC TGG AAA       384
Arg Arg Met Tyr Arg Ile Met Glu Lys Ala Gly Gln Ala Ala Trp Lys
        115                 120                 125

CAG GTA GTG AGC GAG GCT ACG CTG TCT CGC ATT AGT AGT TTG GAT GTG       432
Gln Val Val Ser Glu Ala Thr Leu Ser Arg Ile Ser Ser Leu Asp Val
    130                 135                 140

GTG GCT CAT TTT CAG CAT CTT GCC GCC ATT GAA GCC GAG ACC TGT AAA       480
Val Ala His Phe Gln His Leu Ala Ala Ile Glu Ala Glu Thr Cys Lys
145                 150                 155                 160

TAT CTG GCC TCT CGG CTG CCC ATG CTA CAC CAC CTG CGC ATG ACA GGG       528
Tyr Leu Ala Ser Arg Leu Pro Met Leu His His Leu Arg Met Thr Gly
                165                 170                 175

TCA AAT GTA ACC ATA GTG TAT AAT AGT ACT TTG AAT CAG GTG TTT GCT       576
Ser Asn Val Thr Ile Val Tyr Asn Ser Thr Leu Asn Gln Val Phe Ala
            180                 185                 190

GTT TTC CCA ACC CCT GGT TCC CGG CCA AAG CTT CAT GAT TTC CAG CAA       624
Val Phe Pro Thr Pro Gly Ser Arg Pro Lys Leu His Asp Phe Gln Gln
        195                 200                 205

TGG CTA ATA GCT GTA CAT TCC TCT ATA TTT TCC TCT GTT GCA GCT TCT       672
Trp Leu Ile Ala Val His Ser Ser Ile Phe Ser Ser Val Ala Ala Ser
    210                 215                 220

TGT ACT CTT TTT GTT GTG CTG TGG TTG CGG GTT CCA ATG CTA CGT ACT       720
Cys Thr Leu Phe Val Val Leu Trp Leu Arg Val Pro Met Leu Arg Thr
225                 230                 235                 240

GTT TTT GGT TTC CGC TGG TTA GGG GCA ATT TTT CTT TCG AAC TCA CGG       768
Val Phe Gly Phe Arg Trp Leu Gly Ala Ile Phe Leu Ser Asn Ser Arg
                245                 250                 255

TGA                                                                   771
```

(2) INFORMATION FOR SEQ ID NO: 67:

(i) SEQUENCE CHARACTERISTICS:
(A) LENGTH: 256 amino acids
(B) TYPE: amino acid
(D) TOPOLOGY: linear (ii) MOLECULE TYPE: protein (xi) SEQUENCE DESCRIPTION: SEQ ID NO: 67:

```
Met Lys Trp Gly Leu Cys Lys Ala Phe Leu Thr Lys Leu Ala Asn Phe
  1               5                  10                  15

Leu Trp Met Leu Ser Arg Ser Ser Trp Cys Pro Leu Leu Ile Ser Leu
             20                  25                  30

Tyr Phe Trp Pro Phe Cys Leu Ala Ser Pro Ser Gln Val Gly Trp Trp
         35                  40                  45

Ser Phe Ala Ser Asp Trp Phe Ala Pro Arg Tyr Ser Val Arg Ala Leu
     50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Thr Trp Gly Thr Lys His Pro Leu Gly
                 85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
```

-continued

```
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His His Leu Arg Met Thr Gly
                165                 170                 175

Ser Asn Val Thr Ile Val Tyr Asn Ser Thr Leu Asn Gln Val Phe Ala
            180                 185                 190

Val Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Met Leu Arg Thr
225                 230                 235                 240

Val Phe Gly Phe Arg Trp Leu Gly Ala Ile Phe Leu Ser Asn Ser Arg
                245                 250                 255
```

(2) INFORMATION FOR SEQ ID NO: 68:

(i) SEQUENCE CHARACTERISTICS:
(A) LENGTH: 765 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(B) STRAIN: Iowa
(C) INDIVIDUAL ISOLATE: ISU-12 (VR 2385/VR 2386)

(ix) FEATURE:
(A) NAME/KEY: CDS
(B) LOCATION: 1..762

(xi) SEQUENCE DESCRIPTION: SEQ ID NO: 68:

```
ATG GCT AAT AGC TGT ACA TTC CTC TAT ATT TTC CTC TGT TGC AGC TTC       48
Met Ala Asn Ser Cys Thr Phe Leu Tyr Ile Phe Leu Cys Cys Ser Phe
  1               5                  10                  15

TTG TAC TCT TTT TGT TGT GCT GTG GTT GCG GGT TCC AAT GCT ACG TAC       96
Leu Tyr Ser Phe Cys Cys Ala Val Val Ala Gly Ser Asn Ala Thr Tyr
             20                  25                  30

TGT TTT TGG TTT CCG CTG GTT AGG GGC AAT TTT TCT TTC GAA CTC ACG      144
Cys Phe Trp Phe Pro Leu Val Arg Gly Asn Phe Ser Phe Glu Leu Thr
         35                  40                  45

GTG AAT TAC ACG GTG TGC CCG CCT TGC CTC ACC CGG CAA GCA GCC GCA      192
Val Asn Tyr Thr Val Cys Pro Pro Cys Leu Thr Arg Gln Ala Ala Ala
     50                  55                  60

GAG GCC TAC GAA CCC GGC AGG TCC CTT TGG TGC AGG ATA GGG CAT GAT      240
Glu Ala Tyr Glu Pro Gly Arg Ser Leu Trp Cys Arg Ile Gly His Asp
 65                  70                  75                  80

CGA TGT GGG GAG GAC GAT CAT GAT GAA CTA GGG TTT GTG GTG CCG TCT      288
Arg Cys Gly Glu Asp Asp His Asp Glu Leu Gly Phe Val Val Pro Ser
                 85                  90                  95

GGC CTC TCC AGC GAA GGC CAC TTG ACC AGT GCT TAC GCC TGG TTG GCG      336
Gly Leu Ser Ser Glu Gly His Leu Thr Ser Ala Tyr Ala Trp Leu Ala
            100                 105                 110

TCC CTG TCC TTC AGC TAT ACG GCC CAG TTC CAT CCC GAG ATA TTC GGG      384
Ser Leu Ser Phe Ser Tyr Thr Ala Gln Phe His Pro Glu Ile Phe Gly
        115                 120                 125

ATA GGG AAT GTG AGT CGA GTC TAT GTT GAC ATC AAG CAC CAA TTC ATT      432
```

-continued

```
Ile Gly Asn Val Ser Arg Val Tyr Val Asp Ile Lys His Gln Phe Ile
    130                 135                 140

TGC GCT GTT CAT GAT GGG CAG AAC ACC ACC TTG CCC CAC CAT GAC AAC      480
Cys Ala Val His Asp Gly Gln Asn Thr Thr Leu Pro His His Asp Asn
145                 150                 155                 160

ATT TCA GCC GTG CTT CAG ACC TAT TAC CAG CAT CAG GTC GAC GGG GGC      528
Ile Ser Ala Val Leu Gln Thr Tyr Tyr Gln His Gln Val Asp Gly Gly
                165                 170                 175

AAT TGG TTT CAC CTA GAA TGG GTG CGT CCC TTC TTT TCC TCT TGG TTG      576
Asn Trp Phe His Leu Glu Trp Val Arg Pro Phe Phe Ser Ser Trp Leu
            180                 185                 190

GTT TTA AAT GTC TCT TGG TTT CTC AGG CGT TCG CCT GCA AGC CAT GTT      624
Val Leu Asn Val Ser Trp Phe Leu Arg Arg Ser Pro Ala Ser His Val
        195                 200                 205

TCA GTT CGA GTC TTT CAG ACA TCA AGA CCA ACA CCA CCG CAG CGG CAG      672
Ser Val Arg Val Phe Gln Thr Ser Arg Pro Thr Pro Pro Gln Arg Gln
    210                 215                 220

GCT TTG CTG TCC TCC AAG ACA TCA GTT GCC TTA GGC ATC GCA ACT CGG      720
Ala Leu Leu Ser Ser Lys Thr Ser Val Ala Leu Gly Ile Ala Thr Arg
225                 230                 235                 240

CCT CTG AGG CGA TTC GCA AAG TCC CTC AGT GCC GCA CGG CGA              762
Pro Leu Arg Arg Phe Ala Lys Ser Leu Ser Ala Ala Arg Arg
                245                 250

TAG                                                                  765
```

(2) INFORMATION FOR SEQ ID NO: 69:

(i) SEQUENCE CHARACTERISTICS:
(A) LENGTH: 254 amino acids
(B) TYPE: amino acid
(D) TOPOLOGY: linear (ii) MOLECULE TYPE: protein (xi) SEQUENCE DESCRIPTION: SEQ ID NO: 69:

```
Met Ala Asn Ser Cys Thr Phe Leu Tyr Ile Phe Leu Cys Cys Ser Phe
  1               5                  10                  15

Leu Tyr Ser Phe Cys Cys Ala Val Val Ala Gly Ser Asn Ala Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Ala
     50                  55                  60

Glu Ala Tyr Glu Pro Gly Arg Ser Leu Trp Cys Arg Ile Gly His Asp
 65                  70                  75                  80

Arg Cys Gly Glu Asp Asp His Asp Glu Leu Gly Phe Val Val Pro Ser
                85                  90                  95

Gly Leu Ser Ser Glu Gly His Leu Thr Ser Ala Tyr Ala Trp Leu Ala
            100                 105                 110

Ser Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Phe Ile
    130                 135                 140

Cys Ala Val His Asp Gly Gln Asn Thr Thr Leu Pro His His Asp Asn
145                 150                 155                 160

Ile Ser Ala Val Leu Gln Thr Tyr Tyr Gln His Gln Val Asp Gly Gly
                165                 170                 175

Asn Trp Phe His Leu Glu Trp Val Arg Pro Phe Phe Ser Ser Trp Leu
```

-continued

```
          180                 185                 190

Val Leu Asn Val Ser Trp Phe Leu Arg Arg Ser Pro Ala Ser His Val
        195                 200                 205

Ser Val Arg Val Phe Gln Thr Ser Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Ala Arg Arg
                245                 250


(2) INFORMATION FOR SEQ ID NO: 70:

     (i) SEQUENCE CHARACTERISTICS:
          (A) LENGTH: 537 base pairs
          (B) TYPE: nucleic acid
          (C) STRANDEDNESS: unknown
          (D) TOPOLOGY: linear

    (ii) MOLECULE TYPE: cDNA

    (vi) ORIGINAL SOURCE:
          (A) ORGANISM: porcine reproductive and respiratory syndrome
               virus
          (B) STRAIN: Iowa
          (C) INDIVIDUAL ISOLATE: ISU-12 (VR 2385/VR 2386)

    (ix) FEATURE:
          (A) NAME/KEY: CDS
          (B) LOCATION: 1..534

    (xi) SEQUENCE DESCRIPTION: SEQ ID NO: 70:

ATG GGT GCG TCC CTT CTT TTC CTC TTG GTT GGT TTT AAA TGT CTC TTG       48
Met Gly Ala Ser Leu Leu Phe Leu Leu Val Gly Phe Lys Cys Leu Leu
  1               5                  10                  15

GTT TCT CAG GCG TTC GCC TGC AAG CCA TGT TTC AGT TCG AGT CTT TCA       96
Val Ser Gln Ala Phe Ala Cys Lys Pro Cys Phe Ser Ser Ser Leu Ser
             20                  25                  30

GAC ATC AAG ACC AAC ACC ACC GCA GCG GCA GGC TTT GCT GTC CTC CAA      144
Asp Ile Lys Thr Asn Thr Thr Ala Ala Ala Gly Phe Ala Val Leu Gln
        35                  40                  45

GAC ATC AGT TGC CTT AGG CAT CGC AAC TCG GCC TCT GAG GCG ATT CGC      192
Asp Ile Ser Cys Leu Arg His Arg Asn Ser Ala Ser Glu Ala Ile Arg
     50                  55                  60

AAA GTC CCT CAG TGC CGC ACG GCG ATA GGG ACA CCC GTG TAT ATC ACT      240
Lys Val Pro Gln Cys Arg Thr Ala Ile Gly Thr Pro Val Tyr Ile Thr
 65                  70                  75                  80

GTC ACA GCC AAT GTT ACC GAT GAG AAT TAT TTG CAT TCC TCT GAT CTT      288
Val Thr Ala Asn Val Thr Asp Glu Asn Tyr Leu His Ser Ser Asp Leu
                 85                  90                  95

CTC ATG CTT TCT TCT TGC CTT TTC TAT GCT TCT GAG ATG AGT GAA AAG      336
Leu Met Leu Ser Ser Cys Leu Phe Tyr Ala Ser Glu Met Ser Glu Lys
            100                 105                 110

GGA TTT AAG GTG GTA TTT GGC AAT GTG TCA GGC ATC GTG GCA GTG TGC      384
Gly Phe Lys Val Val Phe Gly Asn Val Ser Gly Ile Val Ala Val Cys
        115                 120                 125

GTC AAC TTC ACC AGT TAC GTC CAA CAT GTC AAG GAA TTT ACC CAA CGT      432
Val Asn Phe Thr Ser Tyr Val Gln His Val Lys Glu Phe Thr Gln Arg
    130                 135                 140

TCC TTG GTA GTT GAC CAT GTG CGG CTG CTC CAT TTC ATG ACG CCC GAG      480
Ser Leu Val Val Asp His Val Arg Leu Leu His Phe Met Thr Pro Glu
145                 150                 155                 160

ACC ATG AGG TGG GCA ACT GTT TTA GCC TGT CTT TTT ACC ATT CTG TTG      528
Thr Met Arg Trp Ala Thr Val Leu Ala Cys Leu Phe Thr Ile Leu Leu
```

-continued

```
                165                 170                 175

GCA ATT TGA                                                         537
Ala Ile
```

(2) INFORMATION FOR SEQ ID NO: 71:

(i) SEQUENCE CHARACTERISTICS:
(A) LENGTH: 178 amino acids
(B) TYPE: amino acid
(D) TOPOLOGY: linear (ii) MOLECULE TYPE: protein (xi) SEQUENCE DESCRIPTION: SEQ ID NO: 71:

```
Met Gly Ala Ser Leu Leu Phe Leu Leu Val Gly Phe Lys Cys Leu Leu
  1               5                  10                  15

Val Ser Gln Ala Phe Ala Cys Lys Pro Cys Phe Ser Ser Ser Leu Ser
             20                  25                  30

Asp Ile Lys Thr Asn Thr Thr Ala Ala Ala Gly Phe Ala Val Leu Gln
         35                  40                  45

Asp Ile Ser Cys Leu Arg His Arg Asn Ser Ala Ser Glu Ala Ile Arg
     50                  55                  60

Lys Val Pro Gln Cys Arg Thr Ala Ile Gly Thr Pro Val Tyr Ile Thr
 65                  70                  75                  80

Val Thr Ala Asn Val Thr Asp Glu Asn Tyr Leu His Ser Ser Asp Leu
                 85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Thr Ile Leu Leu
                165                 170                 175

Ala Ile
```

(2) INFORMATION FOR SEQ ID NO: 72:

(i) SEQUENCE CHARACTERISTICS:
(A) LENGTH: 750 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(C) INDIVIDUAL ISOLATE: Lelystad (ix) FEATURE:
(A) NAME/KEY: CDS
(B) LOCATION: 1..747

(xi) SEQUENCE DESCRIPTION: SEQ ID NO: 72:

```
ATG CAA TGG GGT CAC TGT GGA GTA AAA TCA GCC AGC TGT TCG TGG ACG       48
Met Gln Trp Gly His Cys Gly Val Lys Ser Ala Ser Cys Ser Trp Thr
  1               5                  10                  15

CCT TCA CTG AGT TCC TTG TTA GTG TGG TTG ATA TTG CCA TTT TCC TTG       96
```

-continued

```
Pro Ser Leu Ser Ser Leu Leu Val Trp Leu Ile Leu Pro Phe Ser Leu
            20                  25                  30

CCA TAC TGT TTG GGT TCA CCG TCG CAG GAT GGT TAC TGG TCT TTC TTC      144
Pro Tyr Cys Leu Gly Ser Pro Ser Gln Asp Gly Tyr Trp Ser Phe Phe
        35                  40                  45

TCA GAG TGG TTT GCT CCG CGC TTC TCC GTT CGC GCT CTG CCA TTC ACT      192
Ser Glu Trp Phe Ala Pro Arg Phe Ser Val Arg Ala Leu Pro Phe Thr
    50                  55                  60

CTC CCG AAC TAT CGA AGG TCC TAT GAA GGC TTG TTG CCC AAC TGC AGA      240
Leu Pro Asn Tyr Arg Arg Ser Tyr Glu Gly Leu Leu Pro Asn Cys Arg
65                  70                  75                  80

CCG GAT GTC CCA CAA TTT GCA GTC AAG CAC CCA TTG GGT ATG TTT TGG      288
Pro Asp Val Pro Gln Phe Ala Val Lys His Pro Leu Gly Met Phe Trp
                85                  90                  95

CAC ATG CGA GTT TCC CAC TTG ATT GAT GAG ATG GTC TCT CGT CGC ATT      336
His Met Arg Val Ser His Leu Ile Asp Glu Met Val Ser Arg Arg Ile
            100                 105                 110

TAC CAG ACC ATG GAA CAT TCA GGT CAA GCG GCC TGG AAG CAG GTG GTT      384
Tyr Gln Thr Met Glu His Ser Gly Gln Ala Ala Trp Lys Gln Val Val
        115                 120                 125

GGT GAG GCC ACT CTC ACG AAG CTG TCA GGG CTC GAT ATA GTT ACT CAT      432
Gly Glu Ala Thr Leu Thr Lys Leu Ser Gly Leu Asp Ile Val Thr His
    130                 135                 140

TTC CAA CAC CTG GCC GCA GTG GAG GCG GAT TCT TGC CGC TTT CTC AGC      480
Phe Gln His Leu Ala Ala Val Glu Ala Asp Ser Cys Arg Phe Leu Ser
145                 150                 155                 160

TCA CGA CTC GTG ATG CTA AAA AAT CTT GCC GTT GGC AAT GTG AGC CTA      528
Ser Arg Leu Val Met Leu Lys Asn Leu Ala Val Gly Asn Val Ser Leu
                165                 170                 175

CAG TAC AAC ACC ACG TTG GAC CGC GTT GAG CTC ATC TTC CCC ACG CCA      576
Gln Tyr Asn Thr Thr Leu Asp Arg Val Glu Leu Ile Phe Pro Thr Pro
            180                 185                 190

GGT ACG AGG CCC AAG TTG ACC GAT TTC AGA CAA TGG CTC ATC AGT GTG      624
Gly Thr Arg Pro Lys Leu Thr Asp Phe Arg Gln Trp Leu Ile Ser Val
        195                 200                 205

CAC GCT TCC ATT TTT TCC TCT GTG GCT TCA TCT GTT ACC TTG TTC ATA      672
His Ala Ser Ile Phe Ser Ser Val Ala Ser Ser Val Thr Leu Phe Ile
    210                 215                 220

GTG CTT TGG CTT CGA ATT CCA GCT CTA CGC TAT GTT TTT GGT TTC CAT      720
Val Leu Trp Leu Arg Ile Pro Ala Leu Arg Tyr Val Phe Gly Phe His
225                 230                 235                 240

TGG CCC ACG GCA ACA CAT CAT TCG AGC TGA                              750
Trp Pro Thr Ala Thr His His Ser Ser
                245
```

(2) INFORMATION FOR SEQ ID NO: 73:

(i) SEQUENCE CHARACTERISTICS:
(A) LENGTH: 249 amino acids
(B) TYPE: amino acid
(D) TOPOLOGY: linear (ii) MOLECULE TYPE: protein (xi) SEQUENCE DESCRIPTION: SEQ ID NO: 73:

```
Met Gln Trp Gly His Cys Gly Val Lys Ser Ala Ser Cys Ser Trp Thr
 1               5                  10                  15

Pro Ser Leu Ser Ser Leu Leu Val Trp Leu Ile Leu Pro Phe Ser Leu
            20                  25                  30

Pro Tyr Cys Leu Gly Ser Pro Ser Gln Asp Gly Tyr Trp Ser Phe Phe
        35                  40                  45
```

-continued

```
Ser Glu Trp Phe Ala Pro Arg Phe Ser Val Arg Ala Leu Pro Phe Thr
     50                  55                  60

Leu Pro Asn Tyr Arg Arg Ser Tyr Glu Gly Leu Leu Pro Asn Cys Arg
 65                  70                  75                  80

Pro Asp Val Pro Gln Phe Ala Val Lys His Pro Leu Gly Met Phe Trp
                 85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

(2) INFORMATION FOR SEQ ID NO: 74:

(i) SEQUENCE CHARACTERISTICS:
(A) LENGTH: 798 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(A) ORGANISM: porcine reproductive and respiratory syndrome virus
(C) INDIVIDUAL ISOLATE: Lelystad (ix) FEATURE:
(A) NAME/KEY: CDS
(B) LOCATION: 1..795

(xi) SEQUENCE DESCRIPTION: SEQ ID NO: 74:

```
ATG GCT CAT CAG TGT GCA CGC TTC CAT TTT TTC CTC TGT GGC TTC ATC       48
Met Ala His Gln Cys Ala Arg Phe His Phe Phe Leu Cys Gly Phe Ile
  1               5                  10                  15

TGT TAC CTT GTT CAT AGT GCT TTG GCT TCG AAT TCC AGC TCT ACG CTA       96
Cys Tyr Leu Val His Ser Ala Leu Ala Ser Asn Ser Ser Ser Thr Leu
             20                  25                  30

TGT TTT TGG TTT CCA TTG GCC CAC GGC AAC ACA TCA TTC GAG CTG ACC      144
Cys Phe Trp Phe Pro Leu Ala His Gly Asn Thr Ser Phe Glu Leu Thr
         35                  40                  45

ATC AAC TAC ACC ATA TGC ATG CCC TGT TCT ACC AGT CAA GCG GCT CGC      192
Ile Asn Tyr Thr Ile Cys Met Pro Cys Ser Thr Ser Gln Ala Ala Arg
     50                  55                  60

CAA AGG CTC GAG CCC GGT CGT AAC ATG TGG TGC AAA ATA GGG CAT GAC      240
```

-continued

```
Gln Arg Leu Glu Pro Gly Arg Asn Met Trp Cys Lys Ile Gly His Asp
 65                  70                  75                  80

AGG TGT GAG GAG CGT GAC CAT GAT GAG TTG TTA ATG TCC ATC CCG TCC      288
Arg Cys Glu Glu Arg Asp His Asp Glu Leu Leu Met Ser Ile Pro Ser
                 85                  90                  95

GGG TAC GAC AAC CTC AAA CTT GAG GGT TAT TAT GCT TGG CTG GCT TTT      336
Gly Tyr Asp Asn Leu Lys Leu Glu Gly Tyr Tyr Ala Trp Leu Ala Phe
            100                 105                 110

TTG TCC TTT TCC TAC GCG GCC CAA TTC CAT CCG GAG TTG TTC GGG ATA      384
Leu Ser Phe Ser Tyr Ala Ala Gln Phe His Pro Glu Leu Phe Gly Ile
        115                 120                 125

GGG AAT GTG TCG CGC GTC TTC GTG GAC AAG CGA CAC CAG TTC ATT TGT      432
Gly Asn Val Ser Arg Val Phe Val Asp Lys Arg His Gln Phe Ile Cys
    130                 135                 140

GCC GAG CAT GAT GGA CAC AAT TCA ACC GTA TCT ACC GGA CAC AAC ATC      480
Ala Glu His Asp Gly His Asn Ser Thr Val Ser Thr Gly His Asn Ile
145                 150                 155                 160

TCC GCA TTA TAT GCG GCA TAT TAC CAC CAC CAA ATA GAC GGG GGC AAT      528
Ser Ala Leu Tyr Ala Ala Tyr Tyr His His Gln Ile Asp Gly Gly Asn
                165                 170                 175

TGG TTC CAT TTG GAA TGG CTG CGG CCA CTC TTT TCT TCC TGG CTG GTG      576
Trp Phe His Leu Glu Trp Leu Arg Pro Leu Phe Ser Ser Trp Leu Val
            180                 185                 190

CTC AAC ATA TCA TGG TTT CTG AGG CGT TCG CCT GTA AGC CCT GTT TCT      624
Leu Asn Ile Ser Trp Phe Leu Arg Arg Ser Pro Val Ser Pro Val Ser
        195                 200                 205

CGA CGC ATC TAT CAG ATA TTG AGA CCA ACA CGA CCG CGG CTG CCG GTT      672
Arg Arg Ile Tyr Gln Ile Leu Arg Pro Thr Arg Pro Arg Leu Pro Val
    210                 215                 220

TCA TGG TCC TTC AGG ACA TCA ATT GTT TCC GAC CTC ACG GGG TCT CAG      720
Ser Trp Ser Phe Arg Thr Ser Ile Val Ser Asp Leu Thr Gly Ser Gln
225                 230                 235                 240

CAG CGC AAG AGA AAA TTT CCT TCG GAA AGT CGT CCC AAT GTC GTG AAG      768
Gln Arg Lys Arg Lys Phe Pro Ser Glu Ser Arg Pro Asn Val Val Lys
                245                 250                 255

CCG TCG GTA CTC CCC AGT ACA TCA CGA TAA                              798
Pro Ser Val Leu Pro Ser Thr Ser Arg
            260                 265
```

(2) INFORMATION FOR SEQ ID NO: 75:

(i) SEQUENCE CHARACTERISTICS:
(A) LENGTH: 265 amino acids
(B) TYPE: amino acid
(D) TOPOLOGY: linear (ii) MOLECULE TYPE: protein (xi) SEQUENCE DESCRIPTION: SEQ ID NO: 75:

```
Met Ala His Gln Cys Ala Arg Phe His Phe Phe Leu Cys Gly Phe Ile
  1               5                  10                  15

Cys Tyr Leu Val His Ser Ala Leu Ala Ser Asn Ser Ser Ser Thr Leu
             20                  25                  30

Cys Phe Trp Phe Pro Leu Ala His Gly Asn Thr Ser Phe Glu Leu Thr
         35                  40                  45

Ile Asn Tyr Thr Ile Cys Met Pro Cys Ser Thr Ser Gln Ala Ala Arg
     50                  55                  60

Gln Arg Leu Glu Pro Gly Arg Asn Met Trp Cys Lys Ile Gly His Asp
 65                  70                  75                  80

Arg Cys Glu Glu Arg Asp His Asp Glu Leu Leu Met Ser Ile Pro Ser
```

-continued

```
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Arg His Gln Phe Ile Cys
    130                 135                 140

Ala Glu His Asp Gly His Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
                245                 250                 255

Pro Ser Val Leu Pro Ser Thr Ser Arg
            260                 265
```

(2) INFORMATION FOR SEQ ID NO: 76:

(i) SEQUENCE CHARACTERISTICS:
(A) LENGTH: 552 base pairs
(B) TYPE: nucleic acid
(C) STRANDEDNESS: unknown
(D) TOPOLOGY: linear (ii) MOLECULE TYPE: cDNA (vi) ORIGINAL SOURCE:
(C) INDIVIDUAL ISOLATE: Lelystad (ix) FEATURE:
(A) NAME/KEY: CDS
(B) LOCATION: 1..549

(xi) SEQUENCE DESCRIPTION: SEQ ID NO: 76:

```
ATG GCT GCG GCC ACT CTT TTC TTC CTG GCT GGT GCT CAA CAT ATC ATG       48
Met Ala Ala Ala Thr Leu Phe Phe Leu Ala Gly Ala Gln His Ile Met
  1               5                  10                  15

GTT TCT GAG GCG TTC GCC TGT AAG CCC TGT TTC TCG ACG CAT CTA TCA       96
Val Ser Glu Ala Phe Ala Cys Lys Pro Cys Phe Ser Thr His Leu Ser
             20                  25                  30

GAT ATT GAG ACC AAC ACG ACC GCG GCT GCC GGT TTC ATG GTC CTT CAG      144
Asp Ile Glu Thr Asn Thr Thr Ala Ala Ala Gly Phe Met Val Leu Gln
         35                  40                  45

GAC ATC AAT TGT TTC CGA CCT CAC GGG GTC TCA GCA GCG CAA GAG AAA      192
Asp Ile Asn Cys Phe Arg Pro His Gly Val Ser Ala Ala Gln Glu Lys
     50                  55                  60

ATT TCC TTC GGA AAG TCG TCC CAA TGT CGT GAA GCC GTC GGT ACT CCC      240
Ile Ser Phe Gly Lys Ser Ser Gln Cys Arg Glu Ala Val Gly Thr Pro
 65                  70                  75                  80

CAG TAC ATC ACG ATA ACG GCT AAC GTG ACC GAC GAA TCA TAC TTG TAC      288
Gln Tyr Ile Thr Ile Thr Ala Asn Val Thr Asp Glu Ser Tyr Leu Tyr
                 85                  90                  95
```

-continued

```
AAC GCG GAC CTG CTG ATG CTT TCT GCG TGC CTT TTC TAC GCC TCA GAA      336
Asn Ala Asp Leu Leu Met Leu Ser Ala Cys Leu Phe Tyr Ala Ser Glu
            100                 105                 110

ATG AGC GAG AAA GGC TTC AAA GTC ATC TTT GGG AAT GTC TCT GGC GTT      384
Met Ser Glu Lys Gly Phe Lys Val Ile Phe Gly Asn Val Ser Gly Val
        115                 120                 125

GTT TCT GCT TGT GTC AAT TTC ACA GAT TAT GTG GCC CAT GTG ACC CAA      432
Val Ser Ala Cys Val Asn Phe Thr Asp Tyr Val Ala His Val Thr Gln
    130                 135                 140

CAT ACC CAG CAG CAT CAT CTG GTA ATT GAT CAC ATT CGG TTG CTG CAT      480
His Thr Gln Gln His His Leu Val Ile Asp His Ile Arg Leu Leu His
145                 150                 155                 160

TTC CTG ACA CCA TCT GCA ATG AGG TGG GCT ACA ACC ATT GCT TGT TTG      528
Phe Leu Thr Pro Ser Ala Met Arg Trp Ala Thr Thr Ile Ala Cys Leu
                165                 170                 175

TTC GCC ATT CTC TTG GCA ATA TGA                                      552
Phe Ala Ile Leu Leu Ala Ile
            180


(2) INFORMATION FOR SEQ ID NO: 77:

    (i) SEQUENCE CHARACTERISTICS:
        (A) LENGTH: 183 amino acids
        (B) TYPE: amino acid
        (D) TOPOLOGY: linear

   (ii) MOLECULE TYPE: protein

   (xi) SEQUENCE DESCRIPTION: SEQ ID NO: 77:

Met Ala Ala Ala Thr Leu Phe Phe Leu Ala Gly Ala Gln His Ile Met
  1               5                  10                  15

Val Ser Glu Ala Phe Ala Cys Lys Pro Cys Phe Ser Thr His Leu Ser
             20                  25                  30

Asp Ile Glu Thr Asn Thr Thr Ala Ala Ala Gly Phe Met Val Leu Gln
         35                  40                  45

Asp Ile Asn Cys Phe Arg Pro His Gly Val Ser Ala Ala Gln Glu Lys
     50                  55                  60

Ile Ser Phe Gly Lys Ser Ser Gln Cys Arg Glu Ala Val Gly Thr Pro
 65                  70                  75                  80

Gln Tyr Ile Thr Ile Thr Ala Asn Val Thr Asp Glu Ser Tyr Leu Tyr
                 85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Thr Gln
    130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
            180
```